US007943179B2

(12) United States Patent  
Little et al.

(10) Patent No.: US 7,943,179 B2  
(45) Date of Patent: *May 17, 2011

(54) PH TRIGGERABLE POLYMERIC PARTICLES

(75) Inventors: Steven R. Little, Somerville, MA (US); David M. Lynn, Middleton, WI (US); Daniel G. Anderson, Framingham, MA (US); Robert S. Langer, Newton, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 748 days.

This patent is subject to a terminal disclaimer.

(21) Appl. No.: 11/002,542

(22) Filed: Dec. 2, 2004

(65) Prior Publication Data

US 2005/0244504 A1 Nov. 3, 2005

Related U.S. Application Data

(63) Continuation-in-part of application No. 10/948,981, filed on Sep. 23, 2004.

(60) Provisional application No. 60/505,355, filed on Sep. 23, 2003, provisional application No. 60/526,481, filed on Dec. 2, 2003.

(51) Int. Cl.  
*A61K 9/16* (2006.01)

(52) U.S. Cl. ...................................................... 424/490

(58) Field of Classification Search .................... None  
See application file for complete search history.

(56) References Cited

U.S. PATENT DOCUMENTS

| | | | |
|---|---|---|---|
| 2,759,913 A | 8/1956 | Hulse | 260/89.7 |
| 3,963,771 A | 6/1976 | Robson et al. | 260/482 |
| 4,224,365 A | 9/1980 | Ali-Zaidi | 428/35 |
| 4,348,511 A | 9/1982 | Haug | 528/72 |
| 5,049,388 A | 9/1991 | Knight et al. | 424/450 |
| 5,180,424 A | 1/1993 | Hutter | 106/20 |
| 5,364,634 A | 11/1994 | Lew | 424/451 |
| 5,384,124 A | 1/1995 | Courteille et al. | |
| 5,462,990 A | 10/1995 | Hubbell et al. | 525/54.1 |
| 5,567,433 A | 10/1996 | Collins | 424/450 |
| 5,855,913 A | 1/1999 | Hanes et al. | 424/489 |
| 5,858,746 A | 1/1999 | Hubbell et al. | 435/177 |
| 5,874,064 A | 2/1999 | Edwards et al. | 424/46 |
| 5,904,927 A | 5/1999 | Amiji | 424/422 |
| 5,942,241 A | 8/1999 | Chasin et al. | 424/426 |
| 5,962,520 A | 10/1999 | Smith et al. | 514/529 |
| 5,985,309 A | 11/1999 | Edwards et al. | 424/426 |
| 5,985,985 A | 11/1999 | Weingart et al. | |
| 5,994,314 A | 11/1999 | Eljamal et al. | 514/44 |
| 5,994,318 A | 11/1999 | Gould-Fogerite et al. | 514/44 |
| 6,017,513 A | 1/2000 | Betbeder et al. | 424/1.73 |
| 6,031,007 A | 2/2000 | Brodin et al. | 514/716 |
| 6,046,187 A | 4/2000 | Berde et al. | 514/180 |
| 6,060,582 A | 5/2000 | Hubbell et al. | 528/354 |
| 6,071,959 A | 6/2000 | Rhodes et al. | 514/535 |
| 6,368,629 B1 | 4/2002 | Watanabe et al. | |
| 7,427,394 B2 * | 9/2008 | Anderson et al. | 424/78.37 |
| 2002/0131951 A1 | 9/2002 | Langer et al. | |
| 2002/0150621 A1 | 10/2002 | Kohane et al. | |
| 2003/0129131 A1 | 7/2003 | Inada et al. | |
| 2003/0185795 A1* | 10/2003 | Habberfield | 424/85.1 |
| 2003/0185796 A1 | 10/2003 | Wolin et al. | |
| 2004/0115254 A1* | 6/2004 | Niedzinski et al. | 424/450 |
| 2004/0260115 A1* | 12/2004 | Liu et al. | 560/155 |

FOREIGN PATENT DOCUMENTS

| | | |
|---|---|---|
| DE | 42 01 179 A1 | 7/1993 |
| EP | 0 959 092 A1 | 11/1999 |
| WO | WO 95/31187 | 11/1995 |
| WO | WO 98/06279 | 2/1998 |
| WO | WO 98/16202 | 4/1998 |
| WO | WO 98/41188 | 9/1998 |
| WO | WO 00/03660 | 1/2000 |
| WO | WO 02/09674 | 2/2002 |
| WO | WO 02/13767 | 2/2002 |
| WO | 02/31025 A2 | 4/2002 |
| WO | 02/32396 A3 | 4/2002 |
| WO | 2004/106411 | 12/2004 |

OTHER PUBLICATIONS

Ackerman, et al., "Early Phagosomes in Dendritic Cells Form a Cellular Compartment Sufficient for Cross Presentation of Exogenous Antigens", *Proc. Natl. Acad. Sci. USA*, 100: 12889-12894, 2003.  
Agrawal, et al., "Tuftsin-Bearing Liposomes in Treatment of Macrophage-Based Infections" *Adv. Drug. Deliv Rev*, 41: 135-146, 2000.  
Akinc, et al., "Parallel Synthesis and Biophysical Characaterization of a Degradable Polymer Library for Gene Delivery", *J. Am. Chem. Soc.*, 125: 5316-5323, 2003.  
Akinc, et al., "Measuring the pH Environment of DNA Delivered Using Nonviral Vectors: Implications for Lysosomal Trafficking", *Biotechnol Bioeng.*, 78(5): 503-508, 2002.  
Allison, "The Mode of Action of Immunological Adjuvants", *Dev. Biol. Stand*. 92: 3-11, 1998.  
Alves, et al., "EphA2 as Target of Anticancer Immunotherapy: Identification of HLA-A 0201-Restricted Epitopes", *Cancer Res*, 63: 8476-8480, 2003.  
Anderson, "Humen Gene Therapy" *Nature*, 392: 25-30, 1996.  
Anderson, et al., "In Vivo Biocompatibility of Implantable Delivery Systems and Biomaterials", *Eur. J. Pharm. Biopharm*. 40: 1-8, 1994.  
Anderson, "Biodegradation and Biocompatibility of PLA and PLGA Microspheres" *Adv. Drug Delivery Rev*. 28: 5-24, 1997.

(Continued)

*Primary Examiner* — Robert A Wax  
*Assistant Examiner* — Bethany Barham  
(74) *Attorney, Agent, or Firm* — Wolf, Greenfield & Sacks, P.C.; C. Hunter Baker

(57) ABSTRACT

A drug delivery system comprising pH triggerable particles is described. The pH triggerable particles comprise and agent(s) to be delivered, which is encapsulated in a matrix comprising a pH trigger agent and a polymer. Agents including nucleic acids may be delivered intracellularly using the inventive pH triggerable particles. Upon exposure to an acidic environment such as the endosome or phagosome of a cell, the particles dissolve or disrupt due to protonation or an increase in solubility of the pH triggering agent. Pharmaceutical compositions and methods of preparing and administering these particles are also described. These particles may be particularly useful in genetic vaccination.

24 Claims, 39 Drawing Sheets

OTHER PUBLICATIONS

Ando, et al., "PLGA Microspheres Containing Plasmid DNA: Preservation of Supercoiled DNA via Cryopreparation and Carbohydrate Stabilization", *J. Pharm. Sci.* 88: 126-130, 1999.

Arthur, et al., "A Comparison of Gene Transfer Methods in Human Dendritic Cells", *Cancer Gene Ther.*4: 17-25, 1997.

Athanasiou, et al., "Sterilization, Toxicity, Biocompatibility and Clinical Applications of Polylactic Acid/Polyglycolic Acid Copolymers", *Biomaterials*, 17:93-102, 1996.

Badovinac, et al., "Programmed Contraction of CD8+ T Cells after Infection", *Nat. Immunol.* 3: 619-626, 2002.

Banchereau, et al., "Dendritic Cells and the Control of Immunity", *Nature*, 392:245-252, 1998.

Barbucci, et al., "Thermodynamic and C n.m.r. Data on the Protonation of Polymeric Bases Whose Repeating Units Behave Independently Towards Protonation", *Polymer*, 21: 81-85, 1980.

Barbucci, et al., "Protonation Studies of Multifunctional Polymers with a Poly(Amido-Amine) Structure", *Polymer*, 19: 1329-1334, 1978.

Barbucci, et al., "Macroinorganics 7. Property-Structure Relationships for Polymeric Bases Whose Monomeric Units Behave Independently Toward Protonation", *Macromolecules*, 14: 1203-1209, 1981.

Barrera, et al., "Synthesis and RGD Peptide Modification of a New Biodegradable Copolymer: Poly (lactic acid-co-lysine)" *J. Am. Chem. Soc.* 115:11010-11011, 1993.

Behr, "Synthetic Gene-Transfer Vectors", *Acc. Chem. Res.* 26: 274-278, 1993.

Behr, "The Proton Sponge: a Trick to Enter Cells the Viruses Did Not Exploit", *Chimia*, 51: 34-36, 1997.

Benita, et al., "Characterization of Drug-Loaded Poly(d,1-Lactide) Microspheres", *J. Pharm. Sci.* 73: 1721-1724, 1984.

Ben-Jebria, et al., "Large Porous Particles for Sustained Protection from Carbachol-Induced Bronchoconstriction in Guinea Pigs" *Pharm. Res.* 16: 555-561, 1999.

Benns, et al., "pH-Sensitive Cationic Polymer Gene Delivery Vehicle: N-Ac-Poly(L-Histidine)-Graft-Poly(L-Lysine) Comb Shaped Polymer", *Bioconjugate Chem.* 11: 637-645, 2000.

Bevan, M.J., "Cross-Priming for a Secondary Cytotoxic Response to Minor H Antigens with H-2 Congenic Cells Which Do Not Cross-React in the Cytotoxic Assay", *J. Exp.Med.*, 143: 1283-1288, 1976.

Boedecker, et al., "Ultra-Long-Duration Local Anesthesia Produced by Injection of Lecithin-Coated Tetracaine Microcrystals", *J. Clin. Pharmacol.* 34: 699-702, 1994.

Bonifaz, et al., "In Vivo Targeting of Antigens to Maturing Dendritic Cells via the DEC-205 Receptor Improves T Cell Vaccination", *J. Exp. Med.* 199: 815-824, 2004.

Boussif, et al., "A Versatile Vector for Gene and Oligonucleotide Transfer into Cells in Culture and In Vivo: Polyethylenimine", *Prof. Natl. Acad. Sci. USA*, 92: 7297-7301, 1995.

Brazeau, et al., "Evaluation of PLGA Microspheres Size Effect on Myotoxicity Using the Isolaed Rodent Skeletal Muscle Model" *Pharm. Dev. Technol.* 1:279-283, 1996.

Brazeau, et al., "In Vitro Myotoxicity of Selected Cationic Macromolecules Used in Non-Viral Gene Delivery" *Pharm. Res.* 15: 680-684, 1998.

Brocchini, et al., "A Combinatorial Approach for Polymer Design", *J. Am. Chem. Soc.* 119: 4553-4554, 1997.

Brocchini, et al., "Combinatorial Chemistry and Biomedical Polymer Development", *Advanced Drug Delivery Reviews*, 53: 123-130, 2001.

Bullock, et al., "Antigen Density Presented by Dendritic Cells in Vivo Differentially Affects the Number and Avidity of a Primary, Memory, and Recall CD8+ T Cells", *J. Immunol.* 170: 1822-1829, 2003.

Caminschi, et al., "Molecular Cloning of F4/80-Like-Receptor, A Seven-Span Membrane Protein Expressed Differentially by Dendritic Cell and Monocyte-Macrophage Subpopulations", *J. Immunol.* 167: 3570-3576, 2001.

Capan, et al., "Preparation and Characterization of Poly (D,L-Lactide-Co-Glycolide) Microspheres for Controlled Release of Poly(L-Lysine) Complexed Plasmid DNA", *Pharm. Res.* 16: 509-513, 1999.

Casimiro, et al., "Vaccine-Induced Immunity in Baboons by Using DNA and Replication-Incompetent Adenovirus Type 5 Vectors Expressing a Human Immunodeficiency Virus Type 1 gag Gene", *J. Virol.* 77: 7663-7668, 2003.

Castillo, et al., "Glucocorticoids Prolong Rat Sciatic Nerve Blockade in Vivo from Bupivacaine Microspheres", *Anesthesiology*, 85: 1157-1166, 1996.

Chan, et al., "Triplex DNA: Fundamentals, Advances, and Potential Applications for Gene Therapy", *J. Mol. Med.* 75(4): 267-282, 1997.

Chen, H., "Recent Advances in Mucosal Vaccine Development", *J. Control. Release*, 67: 117-128, 2000.

Cho, et al., "A Proposed Mechanism for the Induction of Cytotoxic T Lymphocyte Production by Heat Shock Fusion Proteins", *Immunity*, 12: 263-272, 2000.

Cho, et al., "Homeostasis-Stimulated Proliferation Drives Naïve T Cells to Differentiate Directly into Memory T Cells", *J. Exp. Med.* 192: 549-556, 2000.

Choksakulnimitr et al., "In Vitro Cytotoxicity of Macromolecules in Different Cell Culture Systems" *Controlled Release*, 34: 233-241, 1995.

Clark, et al., "Gene Delivery of Vaccines for Infectious Disease", *Curr Opin Mol. Ther.* 3: 375-384, 2001.

Coombes, et al., "Dendritic Cell Discoveries Provide New Insight into the Cellular Immunobiology of DNA Vaccines", *Immunol. Lett.* 78: 103-111, 2001.

Cotton, et al., "Receptor-Mediated Transport of DNA into Eukaryotic Cells", *Methods Enzym*, 217: 618-644, 1993.

Cripps, et al., "Vaccines and Mucosal Immunisation", *Vaccine*, 19: 2513-2515, 2001.

Crooke, "Molecular Mechanisms of Action of Antisense Drugs", *Biochim. Biophys. Acta*, 1489(1): 31-44, 1999.

Crooke, "Evaluating the Mechanism of Action of Antiproliferative Antisense Drugs", Antisense Nucleic Acid Drug Dev. 10(2): 123-126, 2000.

Crystal, et al., "Transfer of Genes to Humans: Early Lessons and Ostacles to Success" *Science*, 270: 404-410, 1995.

Curley, et al., "Prolonged Regional Nerve Blockade. Injectable Biodegradable Bupivacaine/Polyester Microspheres", *Anesthesiology*, 84: 1401-1410, 1996.

Danusso, et al., "Synthesis of Tertiary Amine Polymers", *Polymer*, 11: 88-113, 1970.

Decco, et al., Nebulized Lidocaine in the Treatment of Severe Asthma in Children: A Pilot Study. *Ann Allergy Asthma Immunol.* 82: 29-32, 1999.

Demeneix, et al., In *Artificial Self-Assembling Systems for Gene Delivery* (Felgner, et al., Eds). American Chemical Society, Washington, D.C., 1996, 146-151.

Denis-Mize, et al., "Plasmid DNA Adsorbed onto Cationic Microparticles Mediates Target Gene Expression and Antigen Presentation by Dendritic Cells", *Gene. Ther.* 7: 2105-2112, 2000.

Deshmukh, et al., "Liposome and Polylysine Mediated Gene Transfer", *New J. Chem.* 21: 113-124, 1997.

De Smedt, et al., "Cationic Polymer Based Gene Delivery Systems", *Pharmaceutical Research*, 17(2): 113-126, 2000.

Drager, et al., "Prolonged Intercostal Nerve Blockade in Sheep Using Controlled Release Bupivacaine and Dexamethasone From Polyester Microspheres", *Anesthesiology*, 89: 969-979, 1998.

Dubensky, et al., "Delivery Systems for Gene-Based Vaccines", *Mol. Med.* 6: 723-732, 2000.

Edwards, et al., "Recent Advances in Pulmonary Drug Delivery Using Large Porous Inhaled Particles", *J. Appl. Physiol.* 85: 379-385, 1998.

Edwards, et al., "Large Porous Particles or Pulmunary Drug Delivery", *Science*, 276: 1868-1871, 1997.

Eldridge, "Biodegradable Microspheres as a Vaccine Delivery System" *Mol. Immunol.* 28: 287-294, 1991.

Estebe, et al., "Prolongation of Spinal Anesthesia with Bupivacaine-Loaded (DL-Lactide) Microspheres", *Anesth. Analg.* 81:99-103, 1995.

Faure, et al., "Inducible Hsp70 as Target of Anticancer Immunotherapy: Identification of HLA-A *0201-Restricted Epitopes":, *Int. J. Cancer*, 108: 863-870, 2004.

Ferruti, et al., "A Novel Modification of poly(L-lysine) Leading to a Soluble Cationic Polymer with Reduced Toxicity and with Potential as a Transfection Agent", *Macromol. Chem. Phys.* 199: 2565-2575, 1998.

Ferruti, et al., "Synthesis, Characterisation and Antitumour Activity of Platinum (II) Complexes of Novel Functionalised Poly(Amido Amine)s", *Advances in Polymer Science*, 58: 55-92, 1984.

Ferruti, et al., "Recent Results on Functional Polymers and Macromonomers of Interest as Biomaterials or for Biomaterial Modification", *Biomaterials*, 15: 1235-1241, 1994.

Ferruti, et al., "Synthesis, Characterisation and Antitumour Activity of Platinum (II) Complexes of Novel Functionalised Poly(Amido Amine)s", *Macromol. Chem. Phys.* 200: 1644-1654, 1999.

Ferruti, et al., "Synthesis, Physico-Chemical Properties and Biomedical Applications of Poly(Amido-Amine)s", Polymer, 26: 1336-1348, 1985.

Firat, et al., "H-2 Class I Knockout, HLA-A2.1-Transgenic Mice: a Versatile Animal Model for Preclinical Evaluation of Antitumor Immunotherapeutic Strategies", *Eur. J. Immunol*, 29: 3112-3121, 1999.

Fire, et al., "Potent and Specific Genetic Interference by Double-Stranded RNA in Caenorhabditis Elegans", *Nature*, 391: 806-811, 1998.

Fominaya, et al., "Target Cell-Specific DNA Transfer Mediated by A Chimeric Multidomain Protein", *Journal of Biological Chemistry*, 271: 10560-10568, 1996.

Francini, et al., "High-Affinity HLA-A (*)02.01 Peptides from Parathyroid Hormone-Related Protein Generate in Vitro and In Vivo Antitumor CTL Response without Autoimmune Side Effects", *J. Immunol.* 169: 4840-4849, 2002.

Friedman, et al., "Human Gene Therapy-An Immature Genie, but Certainly out of the Bottle" *Nature Med.* 2: 144-147, 1996.

Fritz, et al., "Gene Transfer into Mammalian Cells Using Histone-Condensed Plasmid DNA", *Hum Gene Ther*, 7(12): 1395-1404, 1996.

Fu, et al., "Visual Evidence of Acidic Environment Within Degrading Poly(Lactic-co-Glycolic Acid) (PLGA) Microspheres", *Pharm. Res.* 17: 100-10, 2000.

Garg, et al., "Genetic Tagging Shows Increased Frequency and Longevity of Antigen-Presenting, Skin-Derived Dendritic Cells in Vivo", *Nature Immunology*, 4: 907-912, 2003.

Gebhart, et al., "Evaluation of Polyplexes as Gene Transfer Agents", *Journal of Controlled Release*, 73: 401-416, 2001.

Gerasimov, et al., "Cytosolic Drug Delivery Using pH- and Light-Sensitive Liposomes", *Adv. Drug Deliv. Rev*, 38: 317-338, 1999.

Gett, et al., T Cell Fitness Determined by Signal Strength, *Nat. Immunol.* 4: 355-360, 2003.

Gonzalez, et al., "New Class of Polymers for the Delivery of Macromolecular Therapeutics", *Bioconjugate Chem.* 10: 1068-1074, 1999.

Graff-Dubois, et al., "Generation of CTL Recognizing an HLA-A*0201-Restricted Epitope Shared by MAGE-A1, -A2, -A3, -A4, -A6, -A10, and —A12 Tumor Antigens: Implication in a Broad-Spectrum Tumor Immunotherapy", J. Immunol. 169: 575-580, 2002.

Grant, et al., "Prolonged Analgesia with Liposomal Bupivacaine in a Mouse Model", *Reg. Anesth.* 19(4): 264-269, 1994.

Groeben, et al., "Both Intravenous and Inhaled Lidocaine Attenuate Reflex Bronchoconstriction but at Different Plasma Concentrations", *Am. J. Respir. Crit. Care Med.* 159: 530-535, 1999.

Gross, et al., "High Vaccination Efficiency of Low-Affinity Epitopes in Antitumor Immunotherapy", *J. Clin. Invest.* 113: 425-433, 2004.

Guermonprez, et al., "ER-Phagosome Fusion Defines an MHC Class I Cross-Presentation Compartment in Dendritic Cells", *Nature*, 425: 397-406, 2003.

Gurunathan, et al., "DNA Vaccines: Immunology, Application, and Optimization", *Annu. Rev. Immunol.* 18: 927-974, 2000.

Hackam, et al., "Regulation of Phagosomal Acidification", *J. Biol. Chem.* 272: 29810-29820, 1997.

Haensler, et al., "Polyamidoamine Cascade Polymers Mediate Efficient Transfection of Cells in Culture". *Bioconjugate Chem.* 4: 372-379, 1993.

Hanes, et al., "New Advances in Microsphere-Based Single-Dose Vaccines" *Adv. Drug. Deliv Rev.* 28: 97-119, 1997.

Hanson, et al., "Re-Examination and Further Development of a Precise and Rapid Dye Method for Measuring Cell Growth/Cell Kill" *Immunol. Methods*, 119:203-210, 1989.

He, et al., "Experimental Investigation Into One-Step and Two-Steps Polymerization Via Michael Addition from Primary Amine", *Polymer Preprints*, 42(2): 335.

Heath, et al., "Cross-Presentation, Dendritic Cells, Tolerance and Immunity", *Annu. Rev. Immunol.* 19: 47-64, 2001.

Hedley, et al., "Microspheres Containing Plasmid-Encoded Antigens Elicit Cytotoxic T-Cell Responses", *Nat. Med.* 4: 365-368, 1998.

Hill, et al., "In Vitro Cytotoxicity of Poly(Amidoamine)s: Relevance to DNA Delivery" *Biochim. Biophys. Acta*, 1427: 161-174, 1999.

Hope, et al., "Cationic Lipids, Phosphatidylethanolamine and the Intracellular Delivery of Polymeric, Nucleic Acid-Based Drugs (Review)", *Molecular Membrane Technology*, 15: 1-14, 1998.

Houde, et al., "Phagosomes are Competent Organelles for Antigen Cross-Presentation", *Nature*, 425: 402-406, 2003.

Hsu, et al., "Comparison of Process Parameters for Microencapsulation of Plasmid DNA in Poly(D,L-Lactic-co-Glycolic) Acid Microspheres" *J. Drug Target*, 7: 313-323, 1999.

Hunt, et al., "Effect of Nebulized Lidocaine on Severe Glucocorticoid-Dependent Asthma", *Mayo Clin. Proc.* 71:361-368, 1996.

Hwang, et al., "Effects of Structure of β-Cyclodextrin-Containing Polymers on Gene Delivery", *Bioconjugate Chem.* 12: 280-290, 2001.

Ignatius, et al., "Presentation of Proteins Encapsulated in Sterically Stabilized Liposomes by Dendritic Cells Initiates $CD8^+$ T-Cell Responses in Vivo", *Blood*, 96: 3505-3513, 2000.

Jiang, et al., "Effect of Osmotic Pressure in the Solvent Extraction Phase on BSA Release Profile from PLGA Microspheres", *Pharm. Dev. Technol*, 7: 391-399, 2002.

Kabanov, et al., "DNA Complexes with Polycations for the Delivery of Genetic Material into Cells", *Bioconjugate Chem.* 6: 7-20, 1995.

Kabanov, "Taking Polycation Gene Delivery Systems from In Vitro to In Vivo" *Pharm. Sci. Technol. Today*, 2:365-372, 1999.

Kaech, et al., "Memory $CD8^+$ Cell Differentiation: Initial Antigen Encounter Triggers a Developmental Program in Naïve Cells", *Nat. Immunol.* 2: 415-422, 2001.

Kargina, et al., "Self-Splitted Water-Soluble Ionogenic Polymers" *Vysokomol. Soedin. Seriya A*, 28: 1139-1144, 1986.

Keane, et al., "Comparison of Nebulized and Sprayed Topical Anaesthesia for Fiberoptic Bronchoscopy", *Eur. Respir. J.* 5: 1123-1125, 1992.

Kempf, et al., "Improved Stimulation of Human Dendritic Cells by Receptor Engagement with Surface-Modified Microparticles", *J. Drug Target.* 11: 11-18, 2003.

Kirkpatrick, et al., "Long Duration Local Anesthesia with Lecithin-Coated Microdroplets of Methoxyflurane: Studies with Rat Skin" *Reg. Anesth.* 16: 164-172, 1991.

Kohane, et al., "Sciatic Nerve Blockade with Lipid-Protein-Sugar Particles Containing Bupivacaine", *Pharm. Res.* 17: 1243-1249, 2000.

Kohane, et al., "Lipid-Sugar Particles for Intracranial Drug Delivery: Safety and Biocompatibility", *Brain. Res.* 946: 206-213, 2002.

Kohane, et al., "Effectiveness of Muscimol-Containing Microparticles Against Pilocarpine-Induced Focal Seizures", *Epilepsia*, 43: 1462-1468, 2002.

Kohane, et al., "Biocompatibility of Lipid-Protein-Sugar Particles Containing Bupivacaine in the Epineurium", *J. Biomed. Mat. Res.* 59: 450-459, 2002.

Kohane, et a.l, "A Re-Examination of Tetrodotoxin for Prolonged Duration Local Anesthesia", *Anesthesiology*, 89: 119-131, 1998.

Kohane, et al., "pH-Triggered Release of Macromolecules from Spray-Dried Polymethacrylate Microparticles", *Pharm Res.* 20: 1533-1538, 2003.

Kovacsovics-Bankowski, et al., "Efficient Major Histocompatibility Complex Class I Presentation of Exogenous Antigen Upon Phagocytosis by Macrophages", *Proc. Natl Acad. Sci. USA*, 90: 4942-4946, 1993.

Kovacsovics-Bankowski, et al., "A Phagosome-to-Cytosol Pathway for Exogenous Antigens Presented on MHC Class I Molecules", *Science*, 267: 243-246, 1995.

Kukowska-Latallo, et al., "Efficient Transfer of Genetic Material into Mammalian Cells Using Starburst Polyamidoamine Dendrimers", *Proc. Natl. Acad. Sci. USA*, 93: 4897-4902, 1996.

Kwon, et al., "Pseudopoly (Amino Acids): A Study of the Synthesis and Characterization of Poly(trans-4-hydroxy-N-acyl-L-proline esters)" *Macromolecules*, 22: 3250-3255, 1989.

Langer, "New Methods of Drug Delivery" *Science*, 249: 1527-1533, 1990.

Langenkamp, et al., "T Cell Priming by Dendritic Cells: Thresholds for Proliferation, Differentiation and Death and Intraclonal Functional Diversification", *Eur. J. Immunol.* 32: 2046-2054, 2002.

Le Corre et al., "Preparation and Chacterization of Bupivicaine-Loaded Polylactide and Polylactide-Coglycolide Microspheres" *Int. J. Pharmaceut.* 107:41-49, 1994.

Le Corre, et al., "In Vitro Controlled Release Kinetics of Local Anaesthetics From Poly(D,L-Lactide) and Poly(Lactide-Co-Glycolide) Microspheres" *J. Microencaps*, 14: 243-255, 1997.

Ledley, et al., "Nonviral Gene Therapy: The Promise of Genes as Pharmaceutical Products", *Human Gene Therapy*, 6: 1129-1144, 1995.

Leitner, et al., "Alphavirus-Based DNA Vaccine Breaks Immunological Tolerance by Activating Innate Antiviral Pathways", *Nat. Med.* 9: 33-39,2003.

Leitner, et al., "Nucleic Acid for the Treatment of Cancer: Genetic Vaccines and DNA Adjuvants", *Curr. Pharm. Design*, 7: 1641-1667, 2001.

Lim, et al., "A Self-Destroying Polycationic Polymer: Biodegradable Poly(4-Hydroxy-L-Proline Ester)" *J. Am. Chem. Soc.*, 121: 5633-5639, 1999.

Lim, et al., "Development of a Safe Gene Delivery System Using Biodegradable Polymer, Poly ($\alpha$-(4-Aminobutyl)-L-Glycolic Acid)", *J. Am. Chem. Soc.* 122:6524-6525, 2000.

Lim, et al., "Cationic Hyperbranched Poly(Amino ester): A Novel Class of DNA Condensing Molecule with Cationic Surface, Biodegradable Three-Dimensional Structure, and Tertiary Amine Groups in the Interior" *J. Am. Chem. Soc.* 123: 2460-2461, 2001.

Lim, et al., "Biodegradable, Endosome Disruptive, and Cationic Network-Type Polymer as a Highly Efficient and Nontoxic Gene Delivery Carrier", *Bioconjugate Chemistry*, 13: 952-957, 2002.

Lim, et al., "Self-Assembled Ternary Complex of Cationic Dendrimer, Cucurbituril, and DNA: Noncovalent Strategy in Developing a Gene Delivery Carrier" *Bioconjug Chem.*, 13(6): 1181-1185, 2002.

Linhart, et al., "pH-Induced Fusion and Lysis of Phosphatidylcholine Vesicles by the Hydrophobic Polyelectrolyte Poly(2-ethylacrylic Acid)", *Langmuir*, 16: 122-127, 2000.

Linhardt, et al., "Free-Radical Synthesis of Poly(2-Ethylacrylic Acid) Fractions of Low Polydispersity: Effects of Molecular Weight and Polydispersity on the pH-Dependent Conformational Transition in Aqueous Solutions", *Macromolecules*, 32: 4457-4459, 1999.

Little, et al., "Poly-$\beta$ Amino Ester-Containing Microparticles Enhance the Activity of Nonviral Genetic Vaccines", *Proceedings of the National Academy of Sciences of the United States of America*, 101: 9534-9539, 2004.

Loan, et al., "Poly(Amido-Amine)s and Poly(Ester-Amine)s based on Aromatic Amines Containing Carboxyl Groups", *Macromolecular Chemistry and Physics*, 11: 3525-3533, 1995.

Luo, et al., "Synthetic DNA Delivery Systems", *Nat. Biotechnol*. 18: 33-37, 2000.

Luo, et al., "Plasmid DNA Encoding Human Carcinoembryonic Antigen (CEA) Adsorbed onto Cationic Microparticles Induces Protective Immunity Against Colon Cancer in CEA-Transgenic Mice", *Vaccine*, 21: 1938-1947, 2003.

Lynn, et al., "Degradable Poly($\beta$-Amino Esters): Synthesis, Characterization, and Self-Assembly with Plasmid DNA", *J. Am. Chem. Soc.* 122: 10761-10768, 2000.

Lynn, et al., "pH-Responsive Polymer Microspheres: Rapid Release of Encapsulated Material within the Range of Intracellular pH", *Angewandte Chemie-International Edition*, 40: 1707-1710, 2001.

Lynn, et al., "Accelerated Discovery of Synthetic Transfection Vectors: Parallel Synthesis and Screening of a Degradable Polymer Library" *J. Am. Chem. Soc*, 123: 8155-8156, 2001.

Masters, et al., "Prolonged Regional Nerve Blockade by Controlled Release of Local Anesthetic From a Biodegradable Polymer Matrix", *Anesthesiology*, 79:340-346, 1993.

Mathiowitz, et al., "Polyanhydride Microspheres. IV. Morphology and Characterization of Systems Made by Spray Drying", *J. Appl. Polymer. Sci.* 45: 125-134, 1992.

Mathiowitz, et al., "Morphology of Polyanhydride Microsphere Delivery Systems" *Scanning Microscropy*, 4: 329-340, 1990.

Mathiowitz, et al., "Polyanhydride Microspheres as Drug Carriers 1. Hot-Melt Microencapsulation", *J. Controlled Release*, 5: 13-22, 1987.

Mathiowitz, et al., "Novel Microcapsules for Delivery Systems", *Reactive Polymers*, 6: 275-283, 1987.

Mathiowitz, et al., "Polyanhydride Microspheres as Drug Carriers. II. Microencapsulation by Solvent Removal", *J. Appl. Polymer Sci.*, 35: 755-774, 1988.

McKeever, et al., "Protective Immune Responses Elicited in Mice by Immunization with Formulations of Poly(Lactide-co-Glyclolide) Microparticles" *Vaccine*, 20: 1524-1531, 2002.

McKenzie, et al., "Nucleic Acid Vaccines", *Immunol. Res.* 24: 225-244, 2001.

McKnight, et al., "Molecular Cloning of F4/80, a Murine Macrophage-Restricted Cell Surface Glycoprotein with Homology to the G-Protein-Linked Transmembrane 7 Hormone Receptor Family", *J. Biol. Chem.* 271: 486-489, 1996.

Midoux, et al., "Efficient Gene Transfer by Histidylated Polylysine/ pDNA Complexes" *Bioconjugate Chem.* 10: 406-411, 1999.

Miller, "Cationic Liposomes for Gene Therapy", *Angew. Chem. Int. Ed.* 37: 1768-1785, 1998.

Moore, et al., "Immunization with a Soluble Recombinant HIV Protein Entrapped in Biodegradable Microparticles Induces HIV-Specific $CD^{8+}$ Cytotoxic T Lymphocytes and $CD4^+$ Th1 Cells", *Vaccine*, 13: 1741-1749, 1995.

Mulligan, "The Basic Science of Gene Therapy", *Science*, 260: 926-932, 1993.

Murphy, et al., "A Combinatorial Approach to the Discovery of Efficient Cationic Peptoid Reagents for Gene Delivery", *Proceedings of the National Academy of Sciences of the United States of America*, 95: 1517-1522, 1998.

Nair, et al., "Role of Macrophages and Dendritic Cells in Primary Cytotoxic T Lymphocyte Responses", *Int. Immunol.* 7: 679-688, 1995.

Nixon, et al., "Synthetic Peptides Entrapped in Microparticles Can Elicit Cytotoxic T Cell Activity", *Vaccine*, 14: 1523-1530, 1996.

O'Donnell, et al., "Preparation of Microspheres by the Solvent Evaporation Technique", *Adv. Drug Delivery Rev.* 28: 25-42, 1997.

O'Hagan, et al., "Recent Developments in Adjuvants for Vaccines Against Infectious Diseases", *Biomol. Eng.* 18: 69-85, 2001.

O'Hagan, et al., "Poly(Lactide-Co-Glycolide) Microparticles for the Development of Single-Dose Controlled-Release Vaccines" *Adv. Drug. Deliv. Rev.* 32: 225-246, 1998.

O'Hagan, et al., "Induction of Potent Immune Responses by Cationic Microparticles with Adsorbed Human Immunodeficiency Virus DNa Vaccines", J. Virol., 75: 9037-9043, 2001.

Okada, *Adv.* "One-and Three-Month Release Injectable Microspheres of the LH-RH Superagonist Leuprorelin Acetate"*Drug Delivery Rev.* 28: 43-70, 1997.

Oussoren, et al., "Lymphatic Uptake and Biodistribution of Liposomes After Subcutaneous Injection. II. Influence of Liposomal Size, Lipid Composition and Lipid Dose", *Biochim. Biophys. Acta*, 1328: 261-272, 1997.

Pachuk, et al., "DNA Vaccines—Challenges in Delivery", *Curr. Opin. Mol. Ther.* 2: 188-198, 2000.

Pack, et al., "Design of Imidazole-Containing Endosomolytic Biopolymers for Gene Delivery", *Biotechnol. Bioeng.*, 67(2): 217-223, 2000.

Pardoll, "Spinning Molecular Immunology into Successful Immunotherapy", *Nature Reviews Immunology*, 2: 227-238, 2002.

Pascolo, et al., "HLA-A2.1-Restricted Education and Cytolytic Activity of $CD8^+$ T Lymphocytes from $\beta2$ Microglobulin ($\beta2m$) HLA-A2.1 Monochain Transgenic H-$2D^b$ $\beta2m$ Double Knockout Mice" *J. Exp. Med.* 185: 2043-2051, 1997.

Phillips, et al., "Enhanced Antibody Response to Liposome-Associated Protein Antigens: Preferential Stimulation of IgG2a/b Production", *Vaccine*, 10: 151-158, 1992.

Prabha, et al., "Size-Dependency of Nanoparticle-Mediated Gene Transfection: Studies with Fractionated Nanoparticles", *International Journal of Pharmaceutics*, 244(1-2): 105-115, 2002.

Plonquet, et al., "Peptides Derived from the Onconeural HuD Protein can Elicit Cytotoxic Responses in HHD Mouse and Human" *J. Neuroimmunol.* 142: 93-100, 2003.

Putnam, et al., "Poly(4-Hydroxy-L-Proline Ester): Low-Temperature Polycondensation and Plasmid DNA Complexation", *Macromolecules*, 32: 3658-3662, 1999.

Putnam, et al., "Polymer-Based Gene Delivery with Low Cytotoxicity by a Unique Balance of Side-Chain Termini" *Proc. Natl. Acad. Sci. USA*, 98: 1200-1205, 2001.

Rao, et al., "Poly(Butanediol Spermate): A Hydrolytically Labile Polyester-Based Nitric Oxide Carrier", *J. Bioactive and Compatible Polymers*, 14: 54-63, 1999.

Raychaudhuri, et al., "Fully Mobilizing Hose Defense: Building Better Vaccines", *Nat. Biotechnol.* 16: 1025-1031, 1998.

Reddy, et al., "pH Sensitive Liposomes Provide an Efficient Means of Sensitizing Target Cells to Class I Restricted CTL Recognition of a Soluble Protein", *J. Immunol. Methods*, 141: 157-163, 1991.

Reddy, et al., "In Vivo Cytotoxic T Lymphocyte Induction with Soluble Proteins Administered in Liposomes" *J. Immunol.* 148: 1585-1589, 1992.

Remy, et al., "Gene Transfer with Lipospermines and Polyethylenimines", *Advanced Drug Delivery Reviews*, 30: 85-95, 1998.

Roberts, et al., "Preliminary Biological Evaluation of Polyamidoamine (PAMAM) Starburst™ Dendrimers" *J. Biomed. Mater. Res.* 30: 53-65, 1996.

Rodriguez, et al., "Selective Transport of Internalized Antigens to the Cytosol for MHC Class I Presentation in Dendritic Cells", *Nat. Cell. Biol.*, 1: 362-368, 1999.

Romani, et al., "Proliferating Dendritic Cell Progenitors in Human Blood", *J. Exp. Med.* 180: 83-93, 1994.

Sahoo, et al., "Residual Polyvinyl Alcohol Associated with Poly (D,L-Lactide-Co-Glycolide) Nanoparticles Affects Their Physical Properties and Cellular Uptake", *J. Control. Release*, 82: 105-114, 2002.

Sanford, et al., "The Biolistic Process", *Trends Biotechnol.* 6: 288-302, 1988.

Savelyeva, et al., "Plant Viral Genes in DNA Idiotypic Vaccines Activate Linked CD4+ T-Cell Mediated Immunity Against B-Cell Malignancies", *Nat. Biotechnol.* 19: 760-764, 2001.

Schaffer, et al., "Vector Unpacking as a Potential Barrier for Receptor-Mediated Polyplex Gene Delivery", *Biotechnol. Bioeng.* 67: 598-606, 2000.

Schwartz, et al., "Peptide-Mediated Cellular Delivery", *Curr. Opin. Mol. Ther.* 2: 162-167, 2000.

Schweikl, et al., "Triethylene Glycol Dimethacrylate Induces Large Deletions in the Hprt of V79 Cells", *Mutation. Resource.* 438: P71-P78, 1999.

Shchori, Ehud, "Poly(Secondary Amine)s from Diacrylates and Diamines", *J. Polym. Sci. Polym*, 21:413-415, 1983.

Shen, et al., "Cloned Dendritic Cells Can Present Exogenous Antigens on Both MHC Class I and Class II Molecules", *J. Immunol.* 158: 2723-2730, 1997.

Shenderova, et al., "The Acidic Microclimate in Poly(Lactide-co-Glycolide) Microspheres Stabilizes Camptothecins", *Pharm Res.* 16: 241-248, 1999.

Shirai, et al., "CTL Responses of HLA-A2.1-Transgenic Mice Specific for Hepatitis C Viral Peptides Predict Epitopes for CTL of Humans Carrying HLA-A2.1", *J. Immunol.* 154: 2733-2742, 1995.

Singh, et al., "Cationic Microparticles: A Potent Delivery System for DNA Vaccines", *Proc. Natl. Acad. Sci. USA*, 97: 811-816, 2000.

Singh, et al., "Cationic Microparticles Are an Effective Delivery System for Immune Stimulatory CpG DNA", *Pharm. Res.* 18: 1476-1479, 2001.

Somia, et al., "Gene Therapy: Trials and Tribulations", *Nat. Rev. Genet.* 1:91-99, 2000.

Song, et al., "Dendritic Cells Genetically Modified with an Adenovirus Vector Encoding the cDNA for a Model Antigen Induce Protective and Therapeutic Antitumor Immunity", *J. Exp. Med.* 186: 1247-1256, 1997.

Steinman, et al., "Dendritic Cell Function in Vivo During the Steady State: A Role in Peripheral Tolerance", *Immune Mechanisms and Disease*, 987: 15-25, 2003.

Steinman, et al., "Tolerogenic Dendritic Cells" *Annu. Rev. Immunol.* 21: 685-711, 2003.

Stevceva, et al., "Targeting the Mucosa: Genetically Engineered Vaccines and Mucosal Immune Responses", *Genes Immun.* 1: 308-315, 2000.

Strong, et al., "A General Synthetic Route to Defined, Biologically Active Multivalent Arrays", *J. Am. Chem. Soc.* 121:6193-6196, 1999.

Tabata, et al., "Phagocytosis of Polymer Microspheres by Macrophages", *Adv. Polymer Sci.*, 94: 107-141, 1990.

Tang, et al., "In Vitro Gene Delivery by Degraded Polyamidoamine Dendrimers", *Bioconjugate Chem.* 7: 703-714, 1996.

Thalhammer, et al., "Neurologic Evaluation of the Rat During Sciatic Nerve Block with Lidocaine", *Anesthesiology*, 82: 1013-1025, 1995.

Thomas, et al., "Development of Polyamine Analogs as Cancer Therapeutic Agents" *Oncol. Res.* 13: 123-135, 2002.

Thomas, et al, "Microparticulate Formulations for the Controlled Release of Interleukin -2", *J. Pharm. Sci.* 93: 1100-1109, 2004.

Thumer, et al., "Generation of Large Numbers of Fully Mature and Stable Dendritic Cells from Leukapheresis Products for Clinical Application", *J. Immunol. Methods*, 223: 1-15, 1999.

Tuettenberg, et al., "Priming of T Cells with Ad-Transduced DC Followed by Expansion with Peptide-Pulsed DC Significantly Enhances the Induction of Tumor-Specific CD8+ T Cells: Implications for an Efficient Vaccination Strategy", *Gene Ther.* 10: 243-250, 2003.

Udaka, et al., "Self-MHC-Restricted Peptides Recognized by an Alloreactive T Lymphocyte Clone", *J. Immunol.* 157: 670-678, 1996.

Uhrich, "Hyperbranched Polymers for Drug Delivery" *Trends Polym. Sci.* 5: 388-393, 1997.

Unkeless, et al., "Structure and Function of Human and Murine Receptors for IgG", *Annu Rev. Immunol.* 6: 251-281, 1998.

van der Elst, et al., "Bone Tissue Response to Biodegradable Polymers Used for Intramedullary Fracture Fixation: A Long-Term In Vivo Study in Sheep Femora" *Biomaterials*, 20: 121-128, 1999.

van de Wetering, et al., "Structure-Activity Relationships of Water-Soluble Cationic Methacrylate/Methacrylamide Polymers for Nonviral Gene Delivery" *Bioconjugate Chem.* 10: 589-597, 1999.

Vitiello, et al., "Analysis of the HLA-Restricted Influenza-Specific Cytotoxic T Lymphocyte Response in Transgenic Mice Carrying a Chimeric Human-Mouse Class I Major Histocompatibility Complex". *Exp. Med.* 173: 1007-1015, 1991.

Von Bergwelt-Baildon, et al., "Human Primary and Memory Cytotoxic T Lymphocyte Responses are Efficiently Induced by Means of CD40-Activated B Cells as Antigens-Presenting Cells: Potential for Clinical Application", *Blood*, 99: 3319-3325,2002.

Wagner, et al., "Influenza Virus Hemagglutinin HA-2 N-Terminal Fusogenic Peptides Augment Gene Transfer by Transferrin-Polylysine-DNA Complexes: Toward a Synthetic Virus-Like Gene-Transfer Vehicle", *Proc. Natl. Sci. USA.*, 89(17): 7934-7938, 1992.

Wakiyama, et al., "Preparation and Evaluation in Vitro of Polylactic Acid Microspheres Containing Local Anesthetics" *Chem. Pharm. Bull.* 29: 3363-3368, 1981.

Wakiyama et al., "Preparation and Evaluation in Vitro and In Vivo of Polylactic Acid Microspheres Containing Dibucaine", *Chem. Pharm. Bull.* 30: 3719-3727, 1982.

Wall, et al., "Autotomy Following Peripheral Nerve Lesions: Experimental Anaesthesia Dolorosa", *Pain*, 7: 103-111, 1979.

Walter, et al., "Microparticle-Mediated Transfection of Non-Phagocytic Cells In Vitro", *J. Drug. Target.* 10: 11-21, 2002.

Walter, et al., "Gene Delivery Systems to Phagocytic Antigen-Presenting Cells", *STP Pharma Sci.* 11: 45-56, 2001.

Walter, et al., "Hydrophilic Poly (DL-Lactide-Co-Glycolide) Microspheres for the Delivery of DNA to Human-Derived Macrophages and Dendritic Cells", *J. Control. Release*, 76: 149-168, 2001.

Walter, et al., "Microencapsulation of DNA Using Poly (DL-Lactide-Co-Glycolide): Stability Issues and Release Characteristics", *J. Control. Release*, 61: 361-374, 1999.

Wang, et al., "Molecularly Engineered Poly(Ortho Ester) Microspheres for Enhanced Delivery of DNA Vaccines", *Nat. Mater.* 3: 190-196, 2004.

Watts, et al., Microencapsulation Using Emulsification/Solvent Evaporation: An Overview of Techniques and Applications. *Crit Rev. Ther. Drug. Carr. Sys.* 7:235-259, 1990.

Wentworth et al., "Differences and Similarities in the A2.1-Restricted Cytotoxic T Cell Repertoire in Humans and Human Leukocyte Antigen-Transgenic Mice" *Eur. J. Immunol.* 26: 97-101, 1996.

Wetering, et al., "Structure-Activity Relationships of Water-Soluble Cationic Methacrylate/Methacrylamide Polymers for Nonviral Gene Delivery", *Bioconjugate Chem.* 10:589-597, 1999.

Wherry, et al., "The Induction of Virus-Specific CTL as a Function of Increasing Epitope Expression: Responses Rise Steadily Until Excessively High Levels of Epitope are Attained", *J. Immunol.* 163: 3735-3745, 1999.

Wickham, et al., "Targeting Adenovirus", *Gene Ther.* 7: 110-114, 2000.

Wildsmith, et al., "Differential Nerve Blocking Activity of Amino-Ester Local Anaesthetics", *Br. J. Anaesth.* 57: 612-620, 1985.

Wiethoff, et al., "Barriers to Nonviral Gene Delivery", *Journal of Pharmaceutical Sciences*, 92(2): 203-217, 2003.

Wong, et al., "Recombinant Adenovirus Vaccine Encoding a Chimeric T-Cell Antigen Receptor Induces Protective Immunity Against a T-Cell Lymphoma", *Cancer Res.* 60: 2689-2695, 2000.

Yanez, et al., "Touch-Evoked Agitation Produced by Spinally Administered Phospholipid Emulsion and Liposomes in Rats" *Anesthesiology*, 82: 1189-1198, 1995.

Yang, et al., "A New Approach to Identifying Genotoxic Carcinogens: p53 Induction as an Indicator of Genotoxic Damage", *Carcinogenesis*, 19: P1117-P1125, 1998.

Zauner, et al., "Polylysine-Based Transfection Systems Utilizing Receptor-Mediated Delivery", *Adv. Drug. Del. Rev.* 30: 97-113, 1998.

Zhou, et al., "Preparation of Poly(L-serine ester): A Structural Analogue of Conventional Poly(L-serine)" *Macromolecules*, 23: 3399-3406, 1990.

International Search Report issued for corresponding PCT application PCT/US2004/016521.

International Search Report and Written Opinion for PCT/US2004/031173 mailed Feb. 23, 2005.

International Preliminary Report on Patentability for PCT/US2004/031173 mailed Apr. 6, 2006.

Choi et al., Low-pH-sensitive PEG-stabilized plasmid-lipid nanoparticles: preparation and characterization. Bioconjug Chem. Mar.-Apr. 2003;14(2):420-9.

Gregorius et al., In situ deprotection: a method for covalent immobilization of peptides with well-defined orientation for use in solid phase immunoassays such as enzyme-linked immunosorbent assay. Anal Biochem. Dec. 1, 2001;299(1):84-91.

Haining et al., pH-Triggered Microparticles Enhance Peptide Antigen Delivery to Dendritic Cells Implications for Tumor Vaccines. Blood. 2002;100(11):Abstract 2648.

Haining et al., pH-triggered microparticles for peptide vaccination. J Immunol. Aug. 15, 2004;173(4):2578-85.

Leckband et al., An approach for the stable immobilization of proteins. Biotechnol Bioeng. Feb. 5, 1991;37(3):227-37.

Little et al., Formulation and characterization of poly (beta amino ester) microparticles for genetic vaccine delivery. J Control Release. Oct. 20, 2005;107(3):449-62.

Rhaese et al., Human serum albumin-polyethylenimine nanoparticles for gene delivery. J Control Release. Sep. 19, 2003;92(1-2):199-208.

Rusmini et al., Protein immobilization strategies for protein biochips. Biomacromolecules. Jun. 2007;8(6):1775-89. Epub Apr. 20, 2007.

\* cited by examiner poly-1

| Polymer | Binding |
|---------|---------|
| A55 | + |
| F68 | + |
| E87 | + |
| U71 | + |
| U87 | + |
| S28 | + |
| D68 | + |
| E69 | + |
| L16 | (+/-) |
| U68 | + |
| D28 | + |
| U84 | + |
| B7 | (+/-) |
| F71 | + |
| U80 | + |
| S32 | + |
| D64 | + |
| E86 | + |
| F13 | (+/-) |
| P69 | + |
| U94 | + |
| D62 | + |
| JJ86 | + |
| F94 | + |
| LL32 | + |
| T94 | + |
| C94 | + |
| U36 | + |
| D65 | + |
| KK89 | - |
| LL74 | + |
| D61 | + |
| D86 | + |
| Z17 | + |
| AA28 | + |
| S20 | + |
| LL6 | + |
| O20 | + |
| LL8 | + |
| M17 | - |
| U86 | + |
| D24 | + |
| C36 | + |
| D36 | + |
| F28 | + |
| D60 | + |
| D25 | + |
| PP86 | + |
| D94 | + |

PH TRIGGERABLE POLYMERIC PARTICLES

RELATED APPLICATIONS

The present application claims priority under 35 U.S.C. §120 to and is a continuation-in-part of co-pending U.S. application Ser. No. 10/948,981, filed Sep. 23, 2004, entitled "pH-Triggered Microparticles," which claims priority under 35 U.S.C. §119(e) to U.S. provisional application, U.S. Ser. No. 60/505,355, filed Sep. 23, 2003, entitled "pH-Triggered Microparticles," the contents of each of which are incorporated herein by reference. The present application also claims priority under 35 U.S.C. §119(e) to U.S. provisional application, U.S. Ser. No. 60/526,481, filed Dec. 2, 2003, entitled "pH Triggerable Polymeric Particles," which is incorporated herein by reference.

The subject matter of the present application is also related to U.S. non-provisional applications U.S. Ser. No. 10/446,444, filed May 28, 2003, entitled "Biodegradable Poly(beta-amino esters) and Uses Thereof," and U.S. Ser. No. 09/969,431, filed Oct. 2, 2001, entitled "Biodegradable Poly(beta-amino esters) and Uses Thereof;" and U.S. provisional applications, U.S. Ser. No. 60/305,337, filed Jul. 13, 2001, and U.S. Ser. No. 60/239,330, filed Oct. 10, 2000, the contents of each of which are incorporated herein by reference.

GOVERNMENT SUPPORT

The work described herein was supported, in part, by grants from the National Science Foundation (Cooperative Agreement #ECC9843342 to the MIT Biotechnology Process Engineering Center), the National Institutes of Health (EB00244; GM26698; NRSA Fellowship # 1 F32 GM20227-01), and the Department of the Army (Cooperative Agreement # DAMD 17-99-2-9-001 to the Center for Innovative Minimally Invasive Therapy). The United States government may have certain rights in the invention.

BACKGROUND OF THE INVENTION

The treatment of human diseases through the administration of nucleic acid-based drugs such as DNA and RNA has the potential to revolutionize the field of medicine (Anderson *Nature* 392 (Suppl.):25-30, 1996; Friedman *Nature Med.* 2:144-147, 1996; Crystal *Science* 270:404-410, 1995; Mulligan *Science* 260:926-932, 1993; each of which is incorporated herein by reference). Thus far, the use of modified viruses as gene transfer vectors to introduce nucleic acids into cells has generally represented the most clinically successful approach to gene therapy. While viral vectors are currently the most efficient gene transfer agents, concerns surrounding the overall safety of viral vectors, which include the potential for unsolicited immune responses, have resulted in parallel efforts to develop non-viral alternatives (for leading references, see, Luo et al. *Nat. Biotechnol.* 18:33-37, 2000; Behr *Acc. Chem. Res.* 26:274-278, 1993; each of which is incorporated herein by reference). Current alternatives to viral vectors include polymeric delivery systems (Zauner et al. *Adv. Drug Del. Rev.* 30:97-113, 1998; Kabanov et al. *Bioconjugate Chem.* 6:7-20, 1995; each of which is incorporated herein by reference), liposomal formulations (Miller *Angew. Chem. Int. Ed.* 37:1768-1785, 1998; Hope et al. *Molecular Membrane Technology* 15:1-14, 1998; Deshmukh et al. *New J. Chem.* 21:113-124, 1997; each of which is incorporated herein by reference), and "naked" DNA injection protocols (Sanford *Trends Biotechnol.* 6:288-302, 1988; incorporated herein by reference). While these strategies have yet to achieve the clinical effectiveness of viral vectors, the potential safety, processing, and economic benefits offered by these methods (Anderson *Nature* 392 (Suppl.):25-30, 1996; incorporated herein by reference) have ignited interest in the continued development of non-viral approaches to gene therapy (Boussif et al. *Proc. Natl. Acad. Sci. USA* 92:7297-7301, 1995; Putnam et al. *Macromolecules* 32:3658-3662, 1999; Lim et al. *J. Am. Chem. Soc.* 121:5633-5639, 1999; Gonzalez et al. *Bioconjugate Chem.* 10:1068-1074, 1999; Kukowska-Latallo et al. *Proc. Natl. Acad. Sci. USA* 93:4897-4902, 1996; Tang et al. *Bioconjugate Chem.* 7:703-714, 1996; Haensler et al. *Bioconjugate Chem.* 4:372-379, 1993; each of which is incorporated herein by reference).

One form of gene therapy, genetic vaccination, has tremendous potential for treating or preventing numerous diseases for which traditional vaccination has been shown to be effective. Genetic vaccination also may prove effective in treating and preventing diseases for which traditional vaccines are ineffective (Gurunathan et al. DNA vaccines: Immunology, application, and optimization. *Annu. Rev. Immunol.* 18:927-974 (2000); McKenzie et al. Nucleic acid vaccines—Tasks and tactics. *Immunol. Res.* 24:225-244 (2001); each of which is incorporated herein by reference). However, this potential is largely unrealized due to the inability of current vaccine systems to safely cause an appropriate level of immunogenicity and target gene expression in antigen presenting cells (APC) (Arthur et al. A comparison of gene transfer methods in human dendritic cells. *Cancer Gene Ther.* 4:17-25 (1997); Dubensky, T. W., Jr., Liu, M. A. & Ulmer, J. B. Delivery systems for gene-based vaccines. *Mol Med* 6:723-732. (2000); Walter, E. & Merkle, H. P. Microparticle-mediated transfection of non-phagocytic cells in vitro. *J. Drug Target.* 10:11-21 (2002); Denis-Mize, K. S. et al. Plasmid DNA adsorbed onto cationic microparticles mediates target gene expression and antigen presentation by dendritic cells. *Gene Ther.* 7:2105-2112 (2000); each of which is incorporated herein by reference). This deficiency is a particularly important issue in non-viral genetic vaccine cancer therapies in which epitopes can be weakly antigenic, and tumors can down-regulate the ability of APCs to process and present antigen efficiently to T-cells in an activated state (Pardoll, Spinning molecular immunology into successful immunotherapy. *Nature Reviews Immunology* 2:227-238 (2002); incorporated herein by reference). Viral vectors, such as adenovirus, have been shown to transfect dendritic cells in vitro and elicit strong, antigen-specific immune responses in vivo (Walter, E., Thiele, L. & Merkle, H. P. Gene delivery systems to phagocytic antigen-presenting cells. *STP Pharma Sci.* 11:45-56 (2001); Casimiro, D. R. et al. Vaccine-induced immunity in baboons by using DNA and replication-incompetent adenovirus type 5 vectors expressing a human immunodeficiency virus type 1 gag gene. *J. Virol.* 77:7663-7668 (2003); Song, W. et al. Dendritic cells genetically modified with an adenovirus vector encoding the CDNA for a model antigen induce protective and therapeutic antitumor immunity. *J. Exp. Med.* 186:1247-1256 (1997); Wong, C. P. & Levy, R. Recombinant adenovirus vaccine encoding a chimeric T-cell antigen receptor induces protective immunity against a T-cell lymphoma. *Cancer Res.* 60:2689-2695 (2000); each of which is incorporated herein by reference); however, as mentioned above, there are concerns related to the safety, manufacturability, immunological rejection, and payload size constraints inherent to viral gene delivery (Wickham, T. J. Targeting adenovirus. *Gene Ther.* 7:110-114 (2000); Tuettenberg et al. Priming of T cells with ad-transduced DC followed by expansion with peptide-pulsed DC significantly enhances the induction, of tumor-specific CD8(+) T cells: implications for an efficient vaccination strategy. *Gene Ther.* 10:243-250 (2003); Luo, D. & Saltzman, W. M. Synthetic DNA delivery systems. *Nat. Biotechnol.* 18:33-37 (2000); Clark et al. Gene delivery of vaccines for infectious disease. *Curr Opin Mol Ther* 3:375-384. (2001); each of which is incorporated herein by reference). Current non-viral vaccine systems are not designed to activate APCs (McKeever et al. Protective immune responses elicited in mice by immunization with formulations of poly(lactide-co-glycolide) microparticles. *Vaccine* 20:1524-1531 (2002); incorporated herein by reference), and lack the gene delivery capacity of viral vectors. In an attempt to increase immunogenicity of non-viral systems, focus has shifted towards exploring the use of adjuvants, cytokines, and self-replicating RNA systems (Leitner, W. W. et al. Alphavirus-based DNA vaccine breaks immunological tolerance by activating innate antiviral pathways. *Nat. Med.* 9:33-39 (2003); Pachuk, C. J., McCallus, D. E., Weiner, D. B. & Satishchandran, C. DNA vaccines—challenges in delivery. *Curr. Opin. Mol. Ther.* 2:188-198 (2000); Leitner, W. W., Hammerl, P. & Thalhamer, J. Nucleic acid for the treatment of cancer: Genetic vaccines and DNA adjuvants. *Curr. Pharm. Design* 7:1641-1667 (2001); O'Hagan, D. T., MacKichan, M. L. & Singh, M. Recent developments in adjuvants for vaccines against infectious diseases. *Biomol Eng* 18:69-85. (2001); each of which is incorporated herein by reference). The ideal non-viral genetic vaccine delivery system would be virus-like in function (Luo, D. & Saltzman, W. M. Synthetic DNA delivery systems. *Nat. Biotechnol.* 18:33-37 (2000); incorporated herein by reference), i.e., capable of mediating efficient intracellular delivery of antigen-encoding DNA while enhancing the immogenicity of the delivery system.

A promising method of non-viral delivery for genetic vaccines is microparticulate DNA delivery systems formulated with a biodegradable polymers such as poly lactic-co-glycolic acid (PLGA), as these particles take advantage of size-based immunogenicity and APC targeting (O'Hagan et al. Poly(lactide-co-glycolide) microparticles for the development of single-dose controlled-release vaccines. *Adv. Drug Deliv. Rev.* 32:225-246 (1998); Hedley, M. L., Curley, J. & Urban, R. Microspheres containing plasmid-encoded antigens elicit cytotoxic T-cell responses. *Nat. Med.* 4:365-368 (1998); O'Hagan et al. Induction of potent immune responses by cationic microparticles with adsorbed human immunodeficiency virus DNA vaccines. *J. Virol.* 75:9037-9043 (2001); each of which is incorporated herein by reference). Despite these advantages, even low molecular weight PLGA systems need two weeks to fully release their encapsulated payloads after dendritic cell uptake in vitro (Walter et al. Hydrophilic poly(DL-lactide-co-glycolide) microspheres for the delivery of DNA to human-derived macrophages and dendritic cells. *J. Control. Release* 76:149-168 (2001); incorporated herein by reference). This is an excessively long period of time given new results which suggest that most dendritic cells die 7 days after external stimulus and migration to the lymph nodes. Furthermore, PLGA microparticles can produce an extremely low pH microclimate (pH<2 after 3 days in an aqueous environment) (Fu, K., Pack, D. W., Klibanov, A. M. & Langer, R. Visual evidence of acidic environment within degrading poly(lactic-co-glycolic acid) (PLGA) microspheres. *Pharm. Res.* 17:100-106 (2000); incorporated herein by reference) which reduces the activity of plasmid DNA released from these particles (Walter, E., Moelling, K., Pavlovic, J. & Merkle, H. P. Microencapsulation of DNA using poly(DL-lactide-co-glycolide): stability issues and release characteristics. *J. Control. Release* 61:361-374 (1999); incorporated herein by reference). PLGA also lacks the ability to facilitate phagosomal escape of the microparticles, and trigger intracellular release. As a result, PLGA microparticles remain confined in phagolysosomal vesicles, resulting in low gene expression (Walter, E., Thiele, L. & Merkle, H. P. Gene delivery systems to phagocytic antigen-presenting cells. *STP Pharma Sci.* 11:45-56 (2001); incorporated herein by reference).

There exists a continuing need for non-viral immunogenic and non-immunogenic drug delivery systems that allow for the rapid release of their payloads intracellularly, especially in the context of gene therapy with the delivery of fragile biomolecules such as DNA.

SUMMARY OF THE INVENTION

The present invention provides a novel drug delivery system that allows for the release of an agent to be delivered in response to an acidic pH, such as that found in a phagosome, endosome, or lysosome. The delivery system includes pH triggering agents such as poly(beta-amino esters) to facilitate the dissolution or disruption of particles and thereby release their payload. The invention also provides methods of making and using these drug delivery devices. The drug delivery devices are typically polymeric particles comprising an agent to be delivered and a pH triggering agent that leads to dissolution or disruption of the particle when it is exposed to an acidic environment. The drug delivery system also includes films used to coat biomedical devices. These drug delivery systems are particularly useful in delivering pharmaceutical agents, such as small molecules, proteins, peptides, and nucleic acids, intracellularly. In one particular embodiment, the system is used to immunize a subject using a genetic vaccine.

In certain embodiments, the drug delivery devices are microparticles wherein the agent to be delivered is encapsulated in a polymeric matrix comprising a pH triggering agent and at least one polymer. The microparticles typically range in size from 100 nm to 10 microns in diameter. Particles in the size range from 1-10 microns are phagocytosed by antigen presenting cells so they are particularly useful in vaccination. Particles that are even small, for example, approximately 100-600 nm, have been found to be taken up by any type of cells, and therefore, may be useful in delivering agents such as DNA into a cell. The polymer of the microparticles is a synthetic polymer including but not limited to polyesters, polyanhydrides, polyamides, polyureas, polyethers, polyacrylates, polymethacrylates, polycarbonates, polycarbamates, poly(beta-amino esters), and co-polymers and blends thereof. These polymers are mixed with a pH triggering agent to make the particles pH triggerable, i.e., susceptible to dissolution or disruption upon exposure to acidic environments (e.g., pH<7) or exposure to an environment with a pH less than the $pK_a$ of the pH triggering agent. Typically, a pH triggering agent is a chemical compound with a $pK_a$ below pH 7.0. In certain embodiments, the pH triggering agent is a polymer with functional groups having a $pK_a$ below pH 7.0, for example, poly(beta-amino esters). In certain other embodiments, a characteristic of a pH triggering agent is that it is more soluble in aqueous medium below pH 7.0 than above pH 7.0. The weight percent of the pH triggering agent in the microparticles may range from 1% to 70%; preferably, the percentage of pH triggering agent is between 1% to 30%, more preferably around 15% or 25%. By the lowering the concentration of pH triggering agent in the microparticles, the release of the payload is generally improved and/or the cytotoxicity of the particles is decreased. As would be appreciated by one of skill in this art, the percentage of pH triggering agent in the particles is determined by various factors including the agent being delivered, the release kinetics desired, the target, and the pH triggering agent being used in the particles.

The pH-triggerable particles of the invention may be made by the spray drying technique, the phase inversion technique, the double emulsion technique, or a modified version of one of these techniques. The techniques may be modified to achieve particles with a certain characteristic, e.g., porosity, stickiness, etc. Other methods of preparing particles may also be used to prepare or modify the inventive particles, for example, the particles may be coated with a pH triggering agent or a targeting agent. The particles may be mixed with pharmaceutically acceptable excipients to form pharmaceutical compositions. The particles may also be used to prepare tablets, capsules, patches, suspensions, or other drug delivery devices for administration to a subject.

The particles and pharmaceutical compositions thereof may be administered to a subject using any type of administration method known in the field of medicine. Typically the particles are administered parenterally or orally. The subject may be any type of animal including mammals such as humans, dogs, cats, and domesticated animals. A pharmaceutically effective amount of the particles is administered to the subject to achieve a desired biological effect. For example, in treating cancer, the particles may contain a chemotherapeutic agent and a sufficient amount of the particles may be delivered to cause a shrinkage in the tumor or an inhibition in the growth of the tumor. In vaccinating a subject, the particle may contain a peptide or protein of an organism to be vaccinated against or a nucleic acid that encodes such a peptide or protein. An effective quantity of the particles is then administered to the subject in order to immunize the subject from subsequent infection. In certain embodiments, the particles may be administered to the subject multiple times.

Particularly useful pH triggering agents in the invention are poly(β-amino esters) and salts, derivatives, co-polymers, and blends thereof. Preferred poly(β-amino esters) are biodegradable and biocompatible; however, in certain embodiments where an immune response is desired (e.g., vaccination), the polymer may be immunostimulatory. Typically, the polymers have one or more tertiary amines in the backbone of the polymer. Preferred polymers have one or two tertiary amines per repeating backbone unit. The polymers may also be co-polymers in which one of the components is a poly(β-amino ester). Poly(β-amino esters) may be prepared by condensing bis(secondary amines) or primary amines with bis(acrylate esters). A poly(beta-amino ester) is represented by the formulae below:

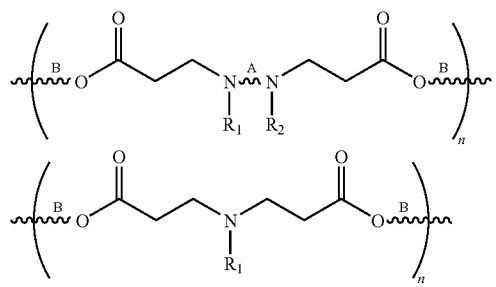

wherein A and B are linkers which may be any substituted or unsubstituted, cyclic or acyclic, branched or unbranched chain of carbon atoms or heteroatoms. The molecular weights of the polymers may range from 1000 g/mol to 20,000 g/mol, preferably from 5000 g/mol to 15,000 g/mol. Specifically preferred polymers that function as pH triggering agents in the inventive particles are insoluble in aqueous solutions at physiologic pH (pH 7.2-7.4) and are soluble in aqueous solutions below physiologic pH (pH<7.2). Preferred polymers are useful in the preparation of pH triggerable particles when mixed with another synthetic polymer.

The inventive drug delivery system includes pH triggerable particles, pharmaceutical compositions including the inventive particles, methods of making these particles, methods of administering these particles, and useful pH trigger agents such as poly(beta-amino esters). The inventive system is particularly useful in administering agents intracellularly. In certain embodiments, the system is used for genetic vaccination to treat or prevent diseases such as infections and cancer.

DEFINITIONS

The following are chemical terms used in the specification and claims:

The term acyl as used herein refers to a group having the general formula —C(=O)R, where R is alkyl, alkenyl, alkynyl, aryl, carbocylic, heterocyclic, or aromatic heterocyclic. An example of an acyl group is acetyl.

The term alkyl as used herein refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-10 carbon atoms. In another embodiment, the alkyl group employed contains 1-8 carbon atoms. In still other embodiments, the alkyl group contains 1-6 carbon atoms. In yet another embodiments, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents.

The term alkoxy as used herein refers to a saturated (i.e., alkyl-O—) or unsaturated (i.e., alkenyl-O— and alkynyl-O—) group attached to the parent molecular moiety through an oxygen atom. In certain embodiments, the alkyl group contains 1-20 aliphatic carbon atoms. In certain other embodiments, the akyl, akenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples include, but are not limited to, methoxy, ethoxy, propoxy, isopropoxy, n-butoxy, tert-butoxy, i-butoxy, sec-butoxy, neopentoxy, n-hexoxy, and the like.

The term alkenyl denotes a monovalent group derived from a hydrocarbon moiety having at least one carbon-carbon double bond by the removal of a single hydrogen atom. In certain embodiments, the alkenyl group employed in the invention contains 1-20 carbon atoms. In some embodiments, the alkenyl group employed in the invention contains 1-10 carbon atoms. In another embodiment, the alkenyl group employed contains 1-8 carbon atoms. In still other embodiments, the alkenyl group contains 1-6 carbon atoms. In yet another embodiments, the alkenyl group contains 1-4 carbons. Alkenyl groups include, for example, ethenyl, propenyl, butenyl, 1-methyl-2-buten-1-yl, and the like.

The term alkynyl as used herein refers to a monovalent group derived form a hydrocarbon having at least one carbon-carbon triple bond by the removal of a single hydrogen atom. In certain embodiments, the alkynyl group employed in the invention contains 1-20 carbon atoms. In some embodiments, the alkynyl group employed in the invention contains 1-10 carbon atoms. In another embodiment, the alkynyl group employed contains 1-8 carbon atoms. In still other embodiments, the alkynyl group contains 1-6 carbon atoms. Representative alkynyl groups include, but are not limited to, ethynyl, 2-propynyl (propargyl), 1-propynyl, and the like.

The term alkylamino, dialkylamino, and trialkylamino as used herein refers to one, two, or three, respectively, alkyl groups, as previously defined, attached to the parent molecular moiety through a nitrogen atom. The term alkylamino refers to a group having the structure —NHR' wherein R' is an alkyl group, as previously defined; and the term dialkylamino refers to a group having the structure —NR'R'', wherein R' and R'' are each independently selected from the group consisting of alkyl groups. The term trialkylamino refers to a group having the structure —NR'R''R''', wherein R', R'', and R''' are each independently selected from the group consisting of alkyl groups. In certain embodiments, the alkyl group contain 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contain 1-6 aliphatic carbon atoms. In yet other embodiments, the alkyl group contain 1-4 aliphatic carbon atoms. Additionally, R', R'', and/or R''' taken together may optionally be —$CH_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylanino, and propylamino.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of thioalkoxyl moieties include, but are not limited to, methylthio, ethylthio, propylthio, isopropylthio, n-butylthio, and the like.

The term aryl as used herein refers to an unsaturated cyclic moiety comprising at least one aromatic ring. Aryl groups may contain 5 to 15 carbon atoms, preferably from 5 to 12, and may include 5- to 7-membered rings. In certain embodiments, aryl group refers to a mono- or bicyclic carbocyclic ring system having one or two aromatic rings including, but not limited to, phenyl, naphthyl, tetrahydronaphthyl, indanyl, indenyl, and the like. Aryl groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. In addition, substituted aryl groups include tetrafluorophenyl and pentafluorophenyl.

The term carboxylic acid as used herein refers to a group of formula —$CO_2H$.

The terms halo and halogen as used herein refer to an atom selected from fluorine, chlorine, bromine, and iodine.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl) amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl) piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4-(2-nitrophenyl) piperazine, 4-(2-nitrophenyl)piperazine, 4-(2-phenylethyl) piperazine, 4-(2-pyridyl)piperazine, 4-(2-pyrimidinyl) piperazine, 4-(2,3-dimethylphenyl)piperazine, 4-(2,4-difluorophenyl) piperazine, 4-(2,4-dimethoxyphenyl) piperazine, 4-(2,4-dimethylphenyl)piperazine, 4-(2,5-dimethylphenyl)piperazine, 4-(2,6-dimethylphenyl) piperazine, 4-(3-chlorophenyl)piperazine, 4-(3-methylphenyl)piperazine, 4-(3-trifluoromethylphenyl) piperazine, 4-(3,4-dichlorophenyl)piperazine, 4-3,4-dimethoxyphenyl)piperazine, 4-(3,4-dimethylphenyl) piperazine, 4-(3,4-methylenedioxyphenyl)piperazine, 4-(3,4,5-trimethoxyphenyl)piperazine, 4-(3,5-dichlorophenyl) piperazine, 4-(3,5-dimethoxyphenyl)piperazine, 4-(4-(phenylmethoxy)phenyl)piperazine, 4-(4-(3,1- dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term carbamoyl, as used herein, refers to an amide group of the formula —$CONH_2$.

The term carbonyldioxyl, as used herein, refers to a carbonate group of the formula —O—CO—OR.

The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The term thiohydroxyl or thiol, as used herein, refers to a group of the formula —SH.

The term ureido, as used herein, refers to a urea group of the formula —NH—CO—$NH_2$.

The following are more general terms used throughout the present application:

"Adjuvant": The term adjuvant refers to any compound which is a nonspecific modulator of the immune response. In certain preferred embodiments, the adjuvant stimulates the immune response. Any adjuvant may be used in accordance with the present invention. A large number of adjuvant compounds are known; a useful compendium of many such compounds is prepared by the National Institutes of Health and can be found on the world wide web (see Allison *Dev. Biol. Stand.* 92:3-11, 1998; Unkeless et al. *Annu. Rev. Immunol.* 6:251-281, 1998; and Phillips et al. *Vaccine* 10:151-158, 1992, each of which is incorporated herein by reference). Adjuvants may include lipids, oils, proteins, polynucleotides, DNAs, DNA-protein hybrids, DNA-RNA hybrids, lipoproteins, aptamers, and antibodies.

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a domesticated animal. An animal may be a transgenic animal. In certain preferred embodiments, the animal is a human.

"Approximately" and "about": The terms approximately and about, when in reference to a number, are taken to include numbers that fall within a range 2.5% in either direction (greater than or less than) of the number. In certain embodiments, the numbers are within a range 5% in either direction of the number.

"Associated with": When two entities are "associated with" one another as described herein, they are linked by a direct or indirect covalent or non-covalent interaction. Preferably, the association is covalent (e.g., amide, disulfide, or ester linkage). Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce unwanted inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of microparticles containing an antigen to be delivered to immunize an individual is the amount that results in an immune response sufficient to prevent infection with an organism having the administered antigen.

"Immunostimulatory": The term "immunostimulatory" as used herein describes the ability of a polymer, pH triggering agent, adjuvant, agent to be delivered, particle, microparticle, etc. to induce an immune response. The immune response generated by such an immunostimulatory substance may include the recruitment of cells (i.e., chemotaxis); the upregulation of cell surface markers such as MHC class II, CD83, CD86, and CD40; the down-regulation of cell surface markers such a F480; the activation of immune cells; the proliferation of immune cells; the production of cytokines; the production of a Th1 or Th2 response; a foreign body reaction; the production of a fever in a subject; and/or other immune signs and symptoms of an immune response in a subject. In certain embodiments of the present invention, the generation of an immune response is particularly useful, for example, in vaccinating a subject using a traditional vaccine or using a genetic vaccine. In other embodiments, the immunostimulatory aspect of a substance is minimized, for example, in the delivery of a therapeutic agent such as an anesthetic or antibiotic.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

BRIEF DESCRIPTION OF THE DRAWING

FIG. 15. DNA binding polymers as determined by agarose gel electrophoresis. The data was were tabulated in the following manner: 1) fully shifted DNA is represented by (+), 2) partially shifted DNA is represented by (+/−), 3) unbound DNA is represented by (−).

DETAILED DESCRIPTION OF CERTAIN PREFERRED EMBODIMENTS OF THE INVENTION

Figure 1:
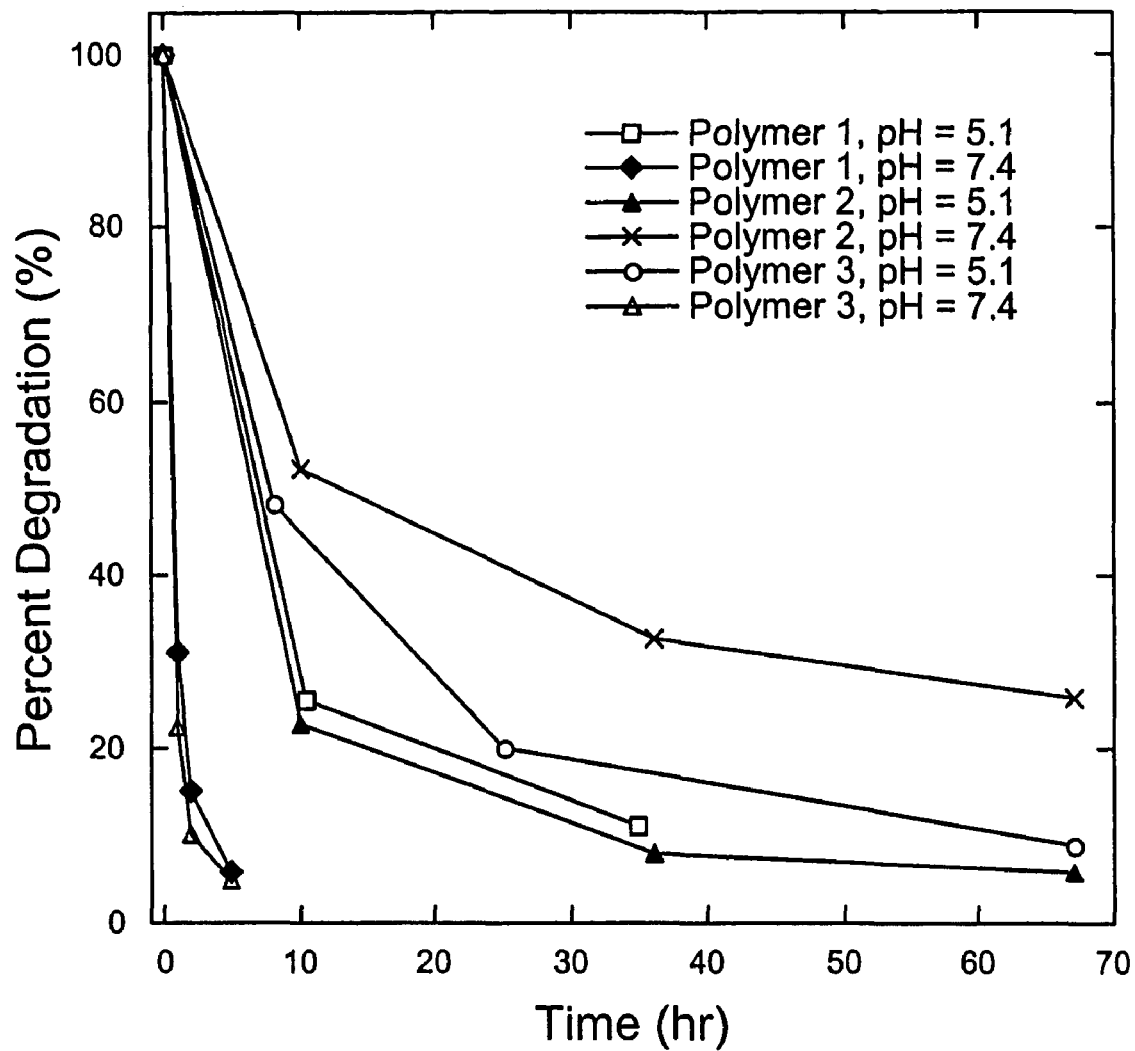
FIG. 1 shows the time profile for the degradation of polymers 1-3 at 37° C. at pH 5.1 and pH 7.4. Degradation is expressed as percent degradation over time based on GPC data.

The present invention provides polymeric encapsulation and drug delivery systems based on the use of pH triggering agents, such as β-amino ester polymers. The systems may be used in the pharmaceutical/drug delivery arts to delivery polynucleotides, proteins, small molecules, peptides, antigen, drugs, biomolecules, prophylactic agents, imaging agents, etc. to a subject.

pH-Triggerable Microparticles

The present invention provides a drug delivery system including microparticles that comprise a pH-triggering agent to allow for release of the active agent or payload in response to a change in pH. The present invention also provides a pharmaceutical composition with the inventive microparticles as well as methods of preparing and administering the pH-triggerable microparticles and pharmaceutical compositions. Agents administered using the pH-triggerable particles may be administered to any animal to be treated, imaged, diagnosed, or prophylaxed. In certain embodiments, the matrix of the inventive microparticles are preferably substantially biocompatible and preferably causes minimal inflammatory reaction, and the degradation products are preferably easily eliminated by the body (i.e., the components of the matrix are biodegradable). As would be appreciated by one of skill in this art, the particles themselves being foreign bodies may be immunostimulatory to a certain degree.

In certain other embodiments such as vaccinating an individual, the matrix and the particles are designed to actually stimulate a desired immune response and thereby facilitate immunization of the animal. In addition, adjuvants or immunostimulatory polymers may be added to the particles to stimulate an immune response, which may include the recruitment of immune cells such as macrophages, monocytes, neutrophils, eosinophils, basophils, etc., and the release of costimulatory factors such as cytokines or complement. In certain embodiments, particles used in the vaccination of a subject upregulate the cell surface markers on immune cells indicating the activation of these cells. The cell surface markers found to be upregulated by immunostimulatory polymers and particle made therefrom include MHC Class II molecules, CD86, CD40, and CD83. In certain embodiments, other cell surface markers such as F480 may be downregulated.

Agent

The agents capable of being delivered by the system of the present invention may be therapeutic, diagnostic, or prophylactic agents. Any chemical compound to be administered to an individual may be delivered using pH-triggerable microparticles. The agent may be a small molecule, organometallic compound, nucleic acid, protein, peptide, metal, biomolecule, an isotopically labeled chemical compound, drug, vaccine, immunological agent, etc.

In a preferred embodiment, the agents are organic compounds with pharmaceutical activity. In another embodiment of the invention, the agent is a clinically used drug that has been approved by the FDA. In a particularly preferred embodiment, the drug is an antibiotic, anti-viral agent, anesthetic, steroidal agent, anti-inflammatory agent, anti-neoplastic agent, antigen, vaccine, adjuvant, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

The agents delivered may also be a mixture of pharmaceutically active agents. For example, two or more antibiotics may be combined in the same microparticle, or two or more anti-neoplastic agents may be combined in the same microparticle. To give but another example, an antibiotic may be combined with an inhibitor of the enzyme commonly produced by bacteria to inactivate the antibiotic (e.g., penicillin and clavulanic acid). Therefore, the agents are synergistic. In another embodiment, an antigen may be combined with an adjuvant to increase the immune reaction generated by the antigen to be delivered. Also, a pharmaceutical composition of the inventive pH triggerable particles may include different particles, each of which contains a different agent or combinations of agents to be delivered.

Diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials. Radiolabelled biomolecules or metabolites may also be delivered using the inventive particles.

Prophylactic agents include vaccines. Vaccines may comprise isolated proteins or peptides, inactivated organisms and viruses, dead organisms and virus, genetically altered organisms or viruses, and cell extracts. Vaccines may also include polynucleotides which encode antigenic proteins or peptides. In certain embodiments, the vaccines are cancer vaccines comprising antigens from cancer cells. Prophylactic agents may be combined with interleukins, interferon, cytokines, CpGs, and adjuvants such as cholera toxin, alum, Freund's adjuvant, etc. Prophylactic agents include antigens of such bacterial organisms as *Streptococccus pnuemoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chiamydial psittaci, Chiamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof. More than one antigen may be combined in a particular microparticle, or a pharmaceutical composition may include microparticles each containing different antigens or combinations of antigens. Adjuvants may also be combined with an antigen in the microparticles. Adjuvants may also be included in pharmaceutical compositions of the pH triggered microparticles of the present invention.

As would be appreciated by one of skill in this art, the variety and combinations of agents that can be delivered using the pH triggered microparticles are almost limitless. The pH triggered microparticles find particular usefulness in delivering agents to an acidic environment or into cells.

Polynucleotide

The polynucleotides may be complexed or encapsulated in the inventive pH triggerable microparticles. The polynucleotides may be any nucleic acid including but not limited to RNA and DNA. The polynucleotides may be of any size or sequence, and they may be single- or double-stranded. In certain preferred embodiments, the polynucleotide is greater than 100 base pairs long. In certain other preferred embodiments, the polynucleotide is greater than 1000 base pairs long and may be greater than 10,000 base pairs long. The polynucleotide is preferably purified and substantially pure. Preferably, the polynucleotide is greater than 50% pure, more preferably greater than 75% pure, and most preferably greater than 95% pure. The polynucleotide may be provided by any means known in the art. In certain preferred embodiments, the polynucleotide has been engineered using recombinant techniques (for a more detailed description of these techniques, please see Ausubel et al. *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In a preferred embodiment, the polynucleotide is synthesized using standard solid phase chemistry.

The polynucleotide may be modified by chemical or biological means. In certain preferred embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art (e.g., solid phase synthesis, automated DNA or RNA synthesizer); however, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, a natural chromosome, etc.

The polynucleotide may be of any sequence. In certain preferred embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In other particularly preferred embodiments, the polynucleotide is not intended to encode a protein. For example, the polynucleotide may be used to fix an error in the genome of the cell being transfected.

The polynucleotide may also be provided as an antisense agent or RNA interference (RNAi) (Fire et al. *Nature* 391: 806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1):31-44, 1999; Crooke "Evaluating the mechanism of action of antiproliferative antisense drugs" *Antisense Nucleic Acid Drug Dev.* 10(2):123-126, discussion 127, 2000; Methods in Enzymology volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J. Mol. Med.* 75(4):267-282, 1997; incorporated herein by reference).

In a particularly preferred embodiment, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, CpG sequences, and adjuvants such as cholera toxin, alum, Freund's adjuvant, etc. A large number of adjuvant compounds are known; a useful compendium of many such compounds is prepared by the National Institutes of Health (see Allison *Dev. Biol. Stand.* 92:3-11, 1998; Unkeless et al. *Annu. Rev. Immunol.* 6:251-281, 1998; and Phillips et al. *Vaccine* 10:151-158, 1992, each of which is incorporated herein by reference).

The antigenic protein or peptides encoded by the polynucleotide may be derived from such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

When the particle carries a polynucleotide, the particle may also carry a chelator such as EDTA to prevent or reduce the degradation of the polynucleotide. The particle may also contain other inhibitors of enzymes that degrade polynucleotides. The particles may contain other agents including salts (e.g., NaCl), buffering agents, sugars (e.g., lactose), polymers, proteins, or other pharmaceutically acceptable excipients.

pH Triggering Agent

The pH triggering agents useful in the present invention are any chemical compounds that lead to the destruction, degradation, or dissolution of a microparticle containing the pH triggering agent in response to a change in pH, for example, a decrease in pH. In certain embodiments, the pH triggering agent may degrade in response to an acidic pH (e.g., acid hydrolysis of ortho-esters). In other embodiments, the pH triggering agent may dissolve at an acidic pH. The pH triggering agents useful in the present invention may include any chemical compound with a $pK_a$ between 3 and 7. Preferably the $pK_a$ of the triggering agent is between 5 and 6.5. In certain embodiments, the pH triggering agent is insoluble or substantially insoluble at physiologic pH (i.e., 7.4), but water soluble at acidic pH (i.e., pH<7, preferably, pH<6.5). Without being bound by any particular theory, the pH sensitivity of the microparticles containing a pH triggering agent stems from the fact that the pH triggering agent within the matrix of the microparticles becomes protonated when exposed to a low pH environment. This change in state of protonation causes the pH triggering agent to become more soluble in the surrounding environment, and/or the change in protonation state disrupts the integrity of the matrix of the microparticle causing it to fall apart. When the triggering agent dissolves or the microparticle is disrupted, the agent contained within the microparticle is released. The pH triggered microparticles are particularly useful in delivering agents to acidic environments such as the phagosomes, lysosomes, or endosomes of cells.

The pH triggering agent may be a small molecule or a polymer. In certain preferred embodiments, the pH triggering agent is a polymer with a $pK_a$ between 5 and 6.5. In certain embodiments, the pH triggering agent has nitrogen-containing functional groups such as amino, alkylamino, dialkylamino, arylamino, diarylamino, imidazolyl, thiazolyl, oxazolyl, pyridinyl, piperidinyl, etc. Certain preferred polymers include polyacrylates, polymethacrylates, poly(beta-amino esters), polyamides, polyesters, polycarbonates, and proteins. Preferably the polymer is biocompatible and biodegradable. In other embodiments, the pH triggering agent is a polymer that is soluble in an acidic aqueous solution. In other embodiments, the pH triggering agent is a cationic protein at physiological pH (pH 7.4). pH triggering agents may also be lipids or phospholipids.

The pH triggering agents may comprise 1-80% of the total weight of the microparticle. In certain embodiments, the weight:weight percent of the pH triggering agent is less than or equal to 40%, more preferable less than or equal to 25%, and most preferably, ranging from 1-5%. In other embodiments, the weight:weight percent of the pH triggering agent ranges from approximately 10% to approximately 30%, preferably from approximately 15% to approximately 25%, and most preferably approximately 15%. As would be appreciated by one of skill in this art, the percent of pH triggering agent will depend on the other components of the particle and the pH triggering agent being used. Decreasing the concentration of the pH triggering agent in the microparticles may lead to less cytotoxicity and/or greater release of the agent to be delivered.

The pH triggering agent is preferably part of the matrix of the microparticle. The pH triggering agent may be associated with the components of the matrix through covalent or non-covalent interactions. In certain embodiments, the pH triggering agent will be dispersed throughout the matrix of the particle. In other embodiments, the pH triggering agent may only be found in a shell of the microparticle and will not be dispersed throughout the particle. For example, the pH triggering agent may only be found on the inside of the particle.

Poly(β-amino esters) containing tertiary amines in their backbones and salts thereof are particularly useful as pH triggering agents used in the inventive particles. The molecular weights of the polymers may range from 5,000 g/mol to over 100,000 g/mol, more preferably from 4,000 g/mol to 50,000 g/mol. In a particularly preferred embodiment, the polymers are relatively non-cytotoxic. In another particularly preferred embodiment, the polymers are biocompatible and biodegradable. In other embodiments, the polymers are immunostimulatory. In a particularly preferred embodiment, the polymers used in pH triggerable particles have $pK_a$s in the range of 5.5 to 7.5, more preferably between 6.0 and 7.0. In another particularly preferred embodiment, the polymer may be designed to have a desired $pK_a$ between 3.0 and 7.0, more preferably between 5.0 and 7.0. The inventive polymers are particularly attractive for drug delivery for several reasons: 1) they contain amino groups for interacting with DNA and other negatively charged agents, for buffering the pH, for causing endosomolysis, etc.; 2) they contain degradable polyester linkages; 3) they can be synthesized from commercially available starting materials; and 4) they are pH responsive and future generations could be engineered with a desired $pK_a$. For example, in delivering nucleic acids, the polymer may complex the nucleic acid as the microparticle dissolves or disrupts thereby protecting the fragile nucleic acid from degradation by cellular enzymes.

The polymers useful as pH triggering agents can generally be defined by the formula (I):

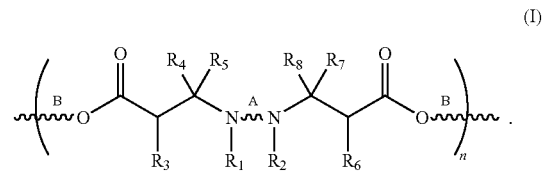

(I)

The linkers A and B are each a chain of atoms covalently linking the amino groups and ester groups, respectively. These linkers may contain carbon atoms or heteroatoms (e.g., nitrogen, oxygen, sulfur, etc.). Typically, these linkers are 1 to 30 atoms long, more preferably 1-15 atoms long. The linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted. The groups $R_1$, $R_2$, $R_3$, $R_4$, $R_5$, $R_6$, $R_7$, and $R_8$ may be any chemical groups including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, and ureido groups. In the inventive polymers, n is an integer ranging from 5 to 10,000, more preferably from 10 to 500.

In a particularly preferred embodiment, the bis(secondary amine) is a cyclic structure, and the polymer is generally represented by the formula II:

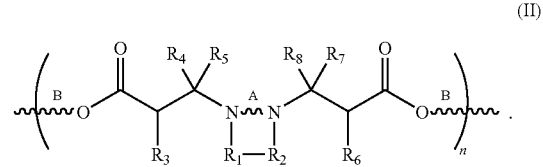

(II)

In this embodiment, $R_1$ and $R_2$ are directly linked together as shown in formula II. Examples of polymers in this embodiment include, but are not limited to formulas III and IV:

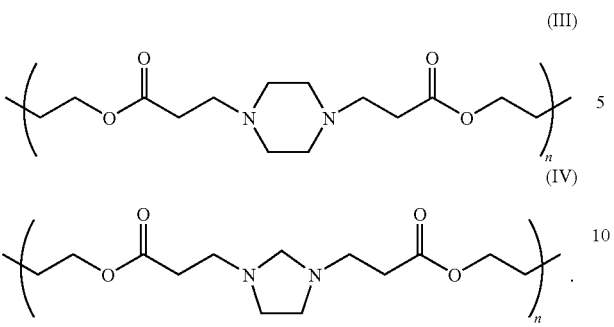

(III)

(IV)

As described above in the preceding paragraph, any chemical group that satisfies the valency of each atom may be substituted for any hydrogen atom.

In another particularly preferred embodiment, the groups $R_1$ and/or $R_2$ are covalently bonded to linker A to form one or two cyclic structures. The polymers of the present embodiment are generally represented by the formula V in which both $R_1$ and $R_2$ are bonded to linker A to form two cyclic structures:

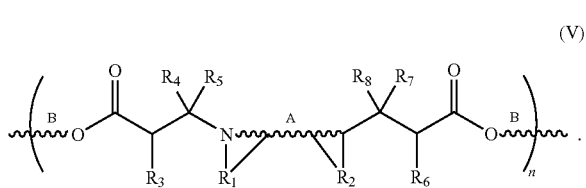

(V)

The cyclic structures may be 3-, 4-, 5-, 6-, 7-, or 8-membered rings or larger. The rings may contain heteroatoms and be unsaturated. Examples of polymers of formula V include formulas VI, VII, and VIII:

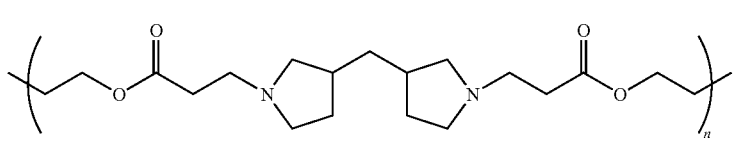

(VI)

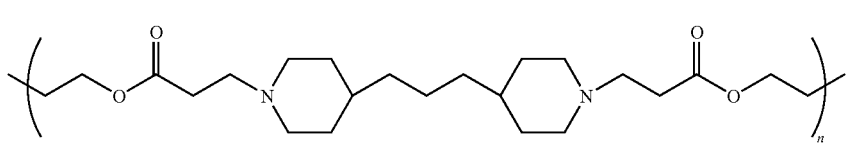

(VII)

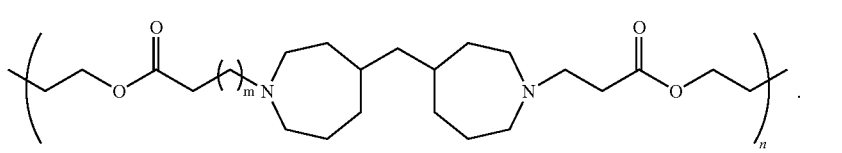

(VIII)

As described above, any chemical group that satisfies the valency of each atom in the molecule may be substituted for any hydrogen atom.

In another embodiment, the polymers useful in the present invention can generally be defined by the formula (IX):

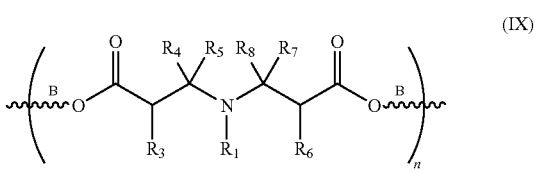

(IX)

The linker B is a chain of atoms covalently linking the ester groups. The linker may contain carbon atoms or heteroatoms (e.g., nitrogen, oxygen, sulfur, etc.). Typically, the linker is 1 to 30 atoms long, preferably 1-15 atoms long, and more preferably 2-10 atoms long. In certain embodiments, the linker B is a substituted or unsubstituted, linear or branched alkyl chain, preferably with 3-10 carbon atoms, more preferably with 3, 4, 5, 6, or 7 carbon atoms. In other embodiments, the linker B is a substituted or unsubstituted, linear or branched heteroaliphatic chain, preferably with 3-10 atoms, more preferably with 3, 4, 5, 6, or 7 atoms. In certain embodiments, the linker B is comprises of repeating units of oxygen and carbon atoms. The linker may be substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, acyl, acetyl, and ureido groups. As would be appreciated by one of skill in this art, each of these groups may in turn be substituted. Each of R1, R3, R4, R5, R6, R7, and R8 may be independently any chemical group including, but not limited to, hydrogen atom, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, acyl, acetyl, and ureido groups. In certain embodiments, R1 includes hydroxyl groups. In other embodiments, R1 includes amino, alkylamino, or dialkylamino groups. In the polymer, n is an integer ranging from 5 to 10,000, more preferably from 10 to 500.

In certain embodiments, the polymers useful in the present invention are generally defined as follows:

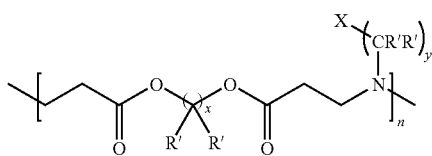

wherein

X is selected from the group consisting of $C_1$-$C_6$ lower alkyl, $C_1$-$C_6$ lower alkoxy, halogen, OR and $NR_2$; more preferably, methyl, OH, or $NH_2$;

R is selected from the group consisting of hydrogen, alkyl, alkenyl, alkynyl, cyclic, heterocyclic, aryl, and heteroaryl;

each R' is independently selected from the group consisting of hydrogen, $C_1$-$C_6$ lower alkyl, $C_1$-$C_6$ lower alkoxy, hydroxy, amino, alkylamino, dialkylamino, cyano, thiol, heteroaryl, aryl, phenyl, heterocyclic, carbocyclic, and halogen; preferably, R' is hydrogen, methyl, ethyl, propyl, isopropyl, butyl, methoxy, ethoxy, propoxy, isopropoxy, hydroxyl, amino, fluoro, chloro, or bromo; more preferably, R' is fluoro, hydrogen, or methyl;

n is an integer between 3 and 10,000;

x is an integer between 1 and 10; preferably, x is an integer between 2 and 6;

y is an integer between 1 and 10; preferably, x is an integer between 2 and 6; and derivatives and salts thereof.

In certain embodiments, the polymers useful in the present invention are generally defined as follows:

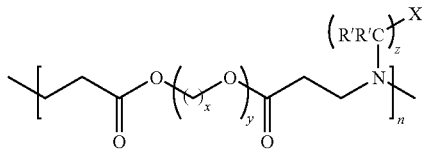

wherein

X is selected from the group consisting of $C_1$-$C_6$ lower alkyl, $C_1$-$C_6$ lower alkoxy, halogen, OR and $NR_2$; more preferably, methyl, OH, or $NH_2$;

R is selected from the group consisting of hydrogen, alkyl, alkenyl, alkynyl, cyclic, heterocyclic, aryl, and heteroaryl;

each R' is independently selected from the group consisting of hydrogen, $C_1$-$C_6$ lower alkyl, $C_1$-$C_6$ lower alkoxy, hydroxy, amino, alkylamino, dialkylamino, cyano, thiol, heteroaryl, aryl, phenyl, heterocyclic, carbocyclic, and halogen; preferably, R' is hydrogen, methyl, ethyl, propyl, isopropyl, butyl, methoxy, ethoxy, propoxy, isopropoxy, hydroxyl, amino, fluoro, chloro, or bromo; more preferably, R' is fluoro, hydrogen, or methyl;

n is an integer between 3 and 10,000;

x is an integer between 1 and 10; preferably, x is an integer between 2 and 6;

y is an integer between 1 and 10; preferably, y is an integer between 2 and 6;

z is an integer between 1 and 10; preferably, z is an integer between 2 and 6; and derivatives and salts thereof.

In another embodiment, the bis(acrylate ester) unit in the inventive polymer is chosen from the following group of bis(acrylate ester) units (A'-G'):

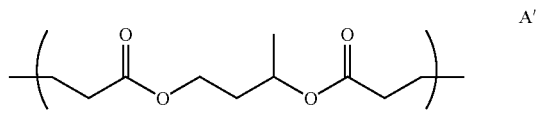

A'

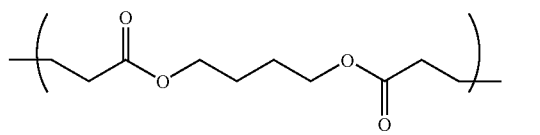

B'

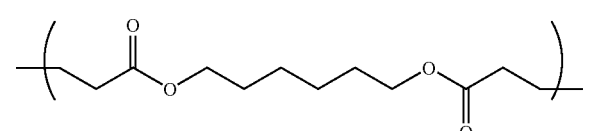

C'

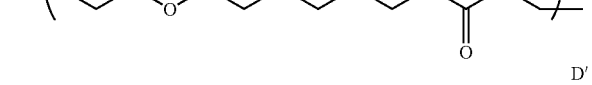

D'

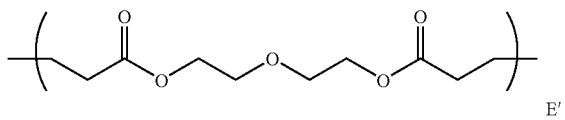

E'

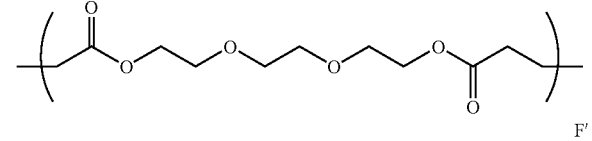

F'

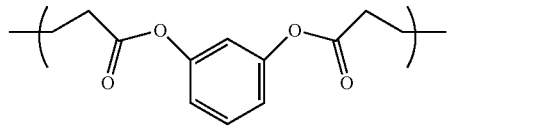

G'

In certain embodiments, the polymer comprises the bis(acrylate ester) G'.

In another embodiment, the bis(acrylate ester) unit in the polymer is chosen from the following group of bis(arcrylate ester) units (A-PP):

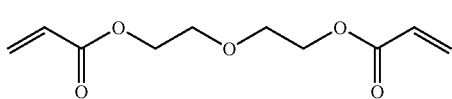

A

-continued
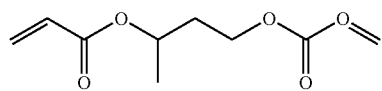
B
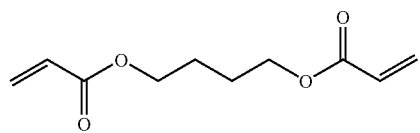
C
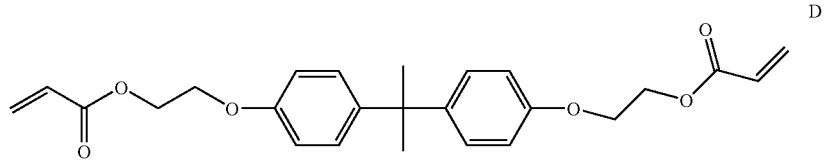
D
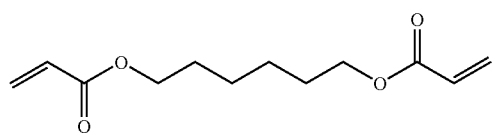
E
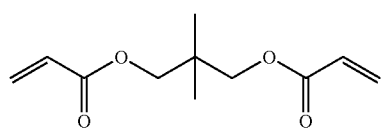
F
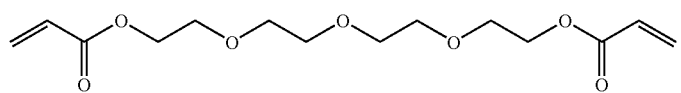
J
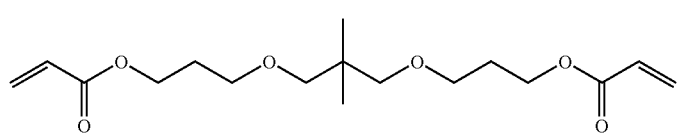
K
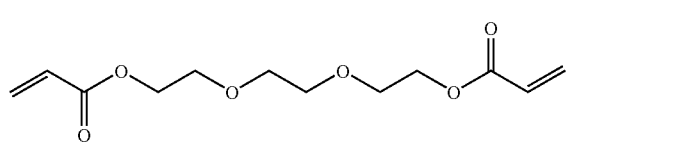
L
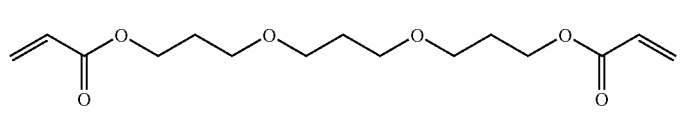
M
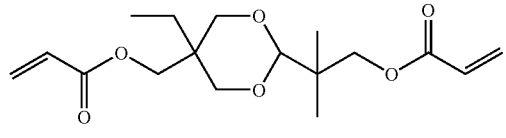
O
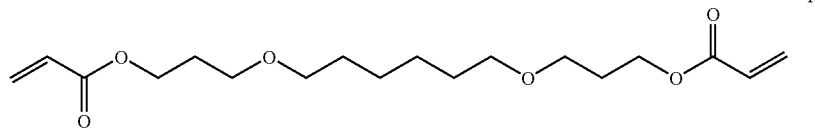
P
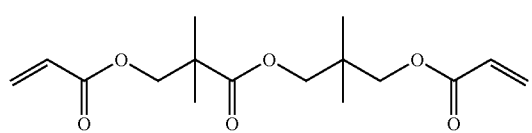
Q -continued
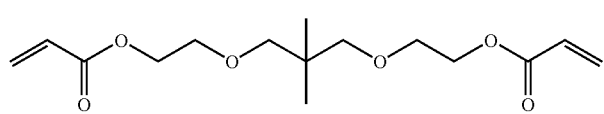
R
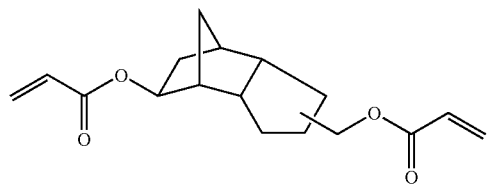
S
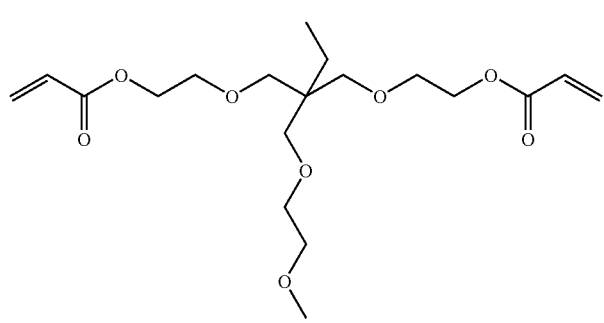
T
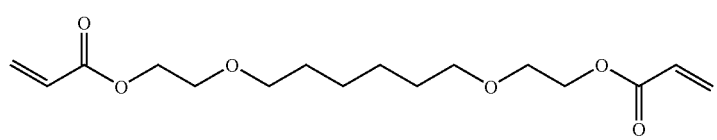
U
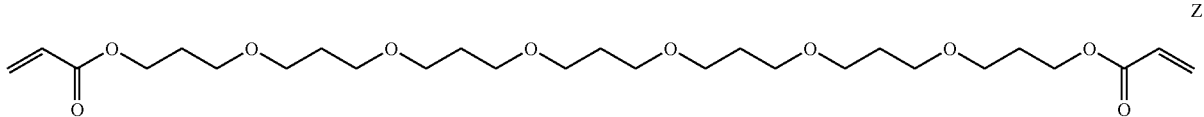
Z
AA
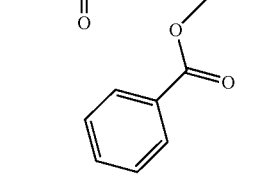
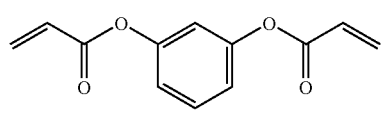
BB
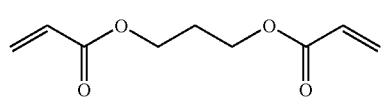
II
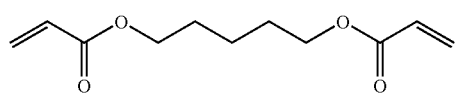
JJ
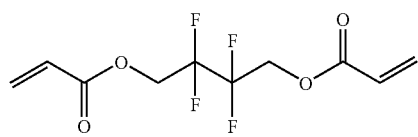
KK

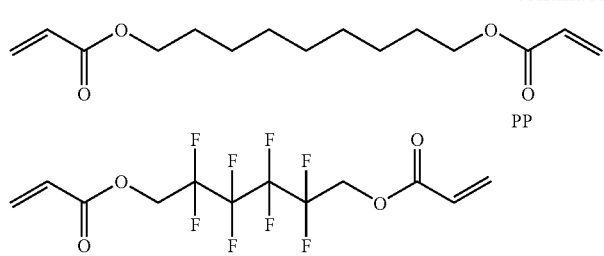

Particularly preferred bis(acrylate esters) in this group include E, F, M, U, JJ, KK, LL, C, and D.

In another embodiment, the amine in the polymer is chosen from the following group of amines (1'-20'):

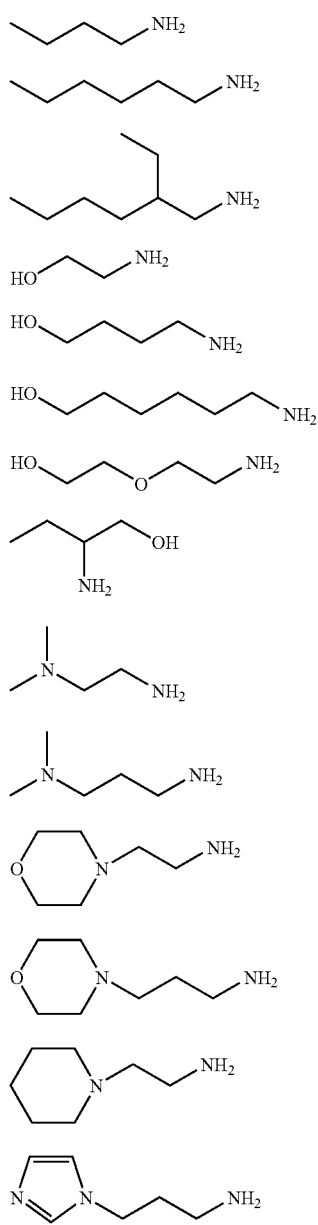

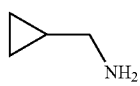

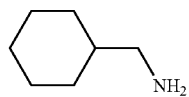

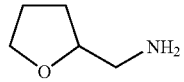

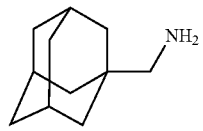

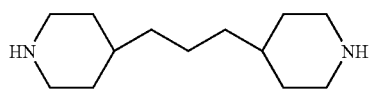

In certain embodiments, the polymer comprises the amine 5'. In other embodiments, the polymer comprises amine 14'.

In another embodiment, the amine in the polymer is chosen from the following group of amines (1-94):

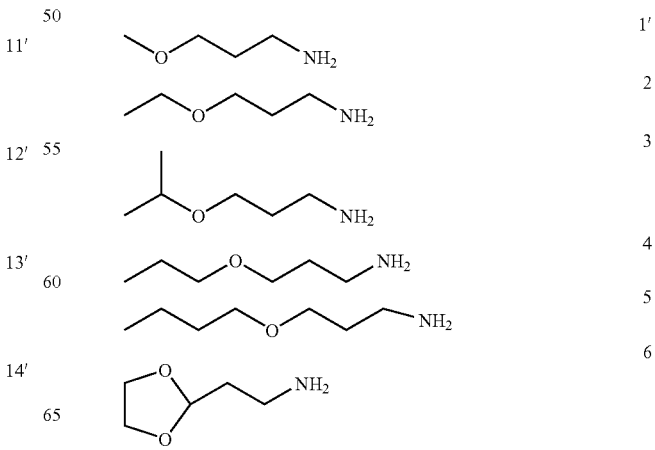

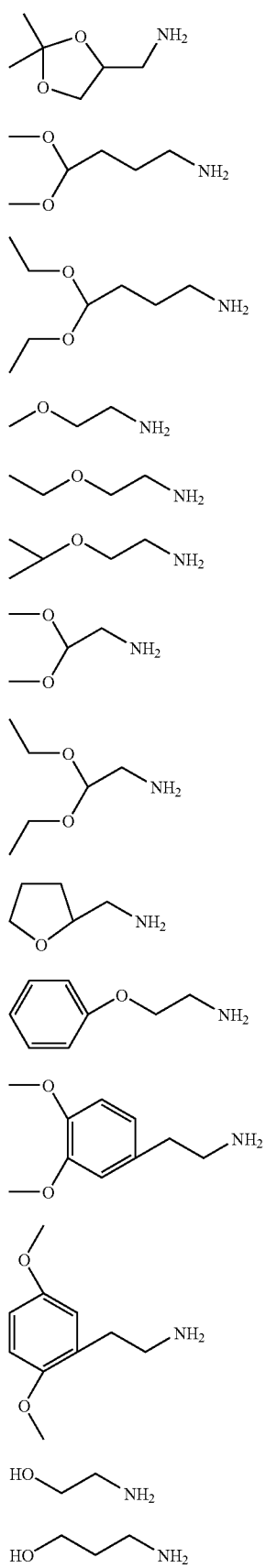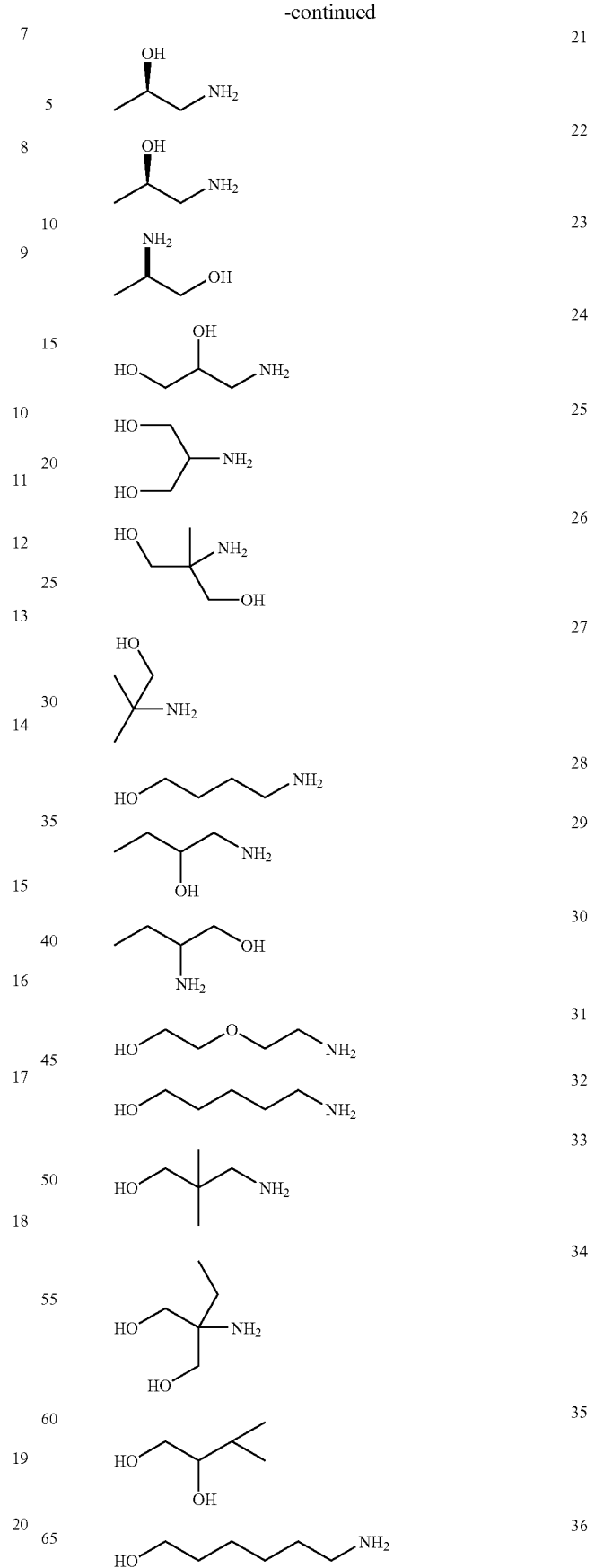

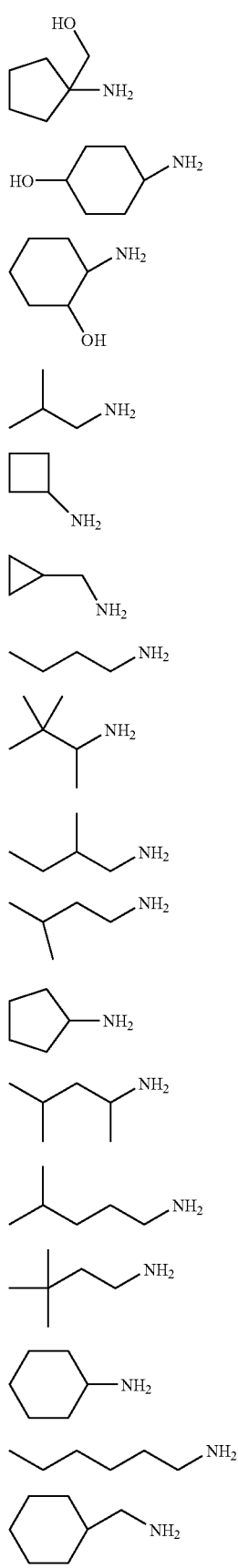
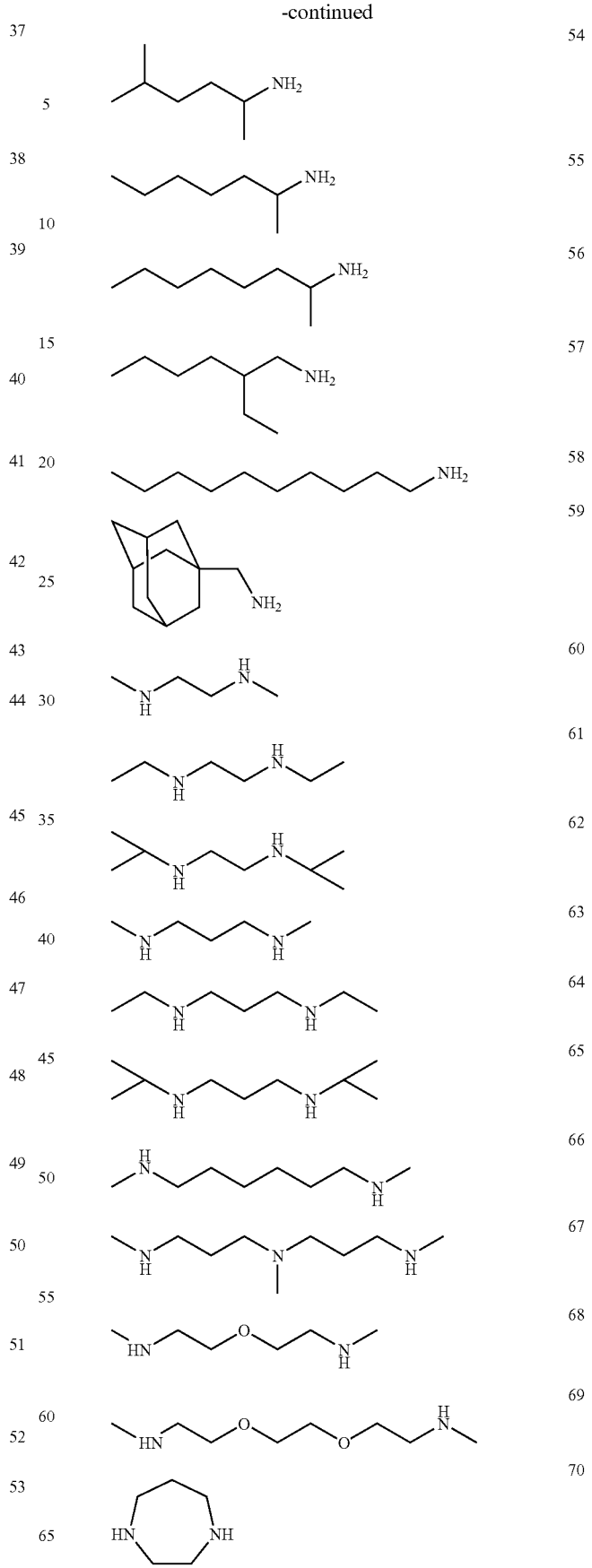

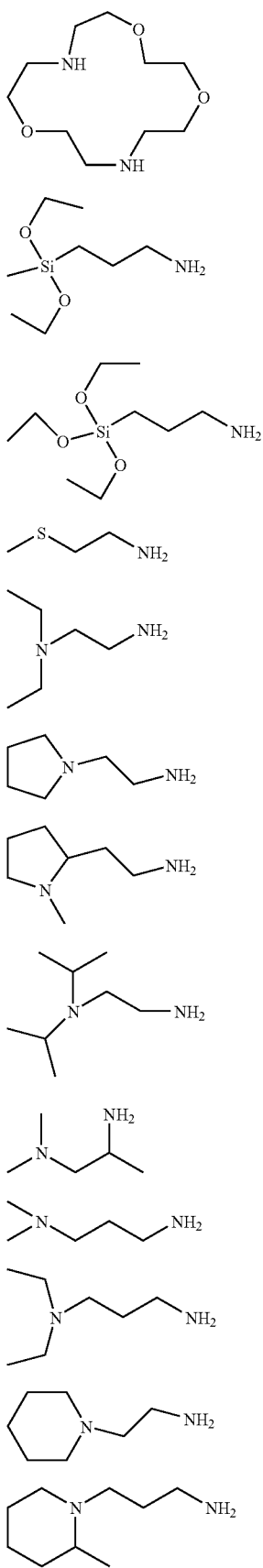
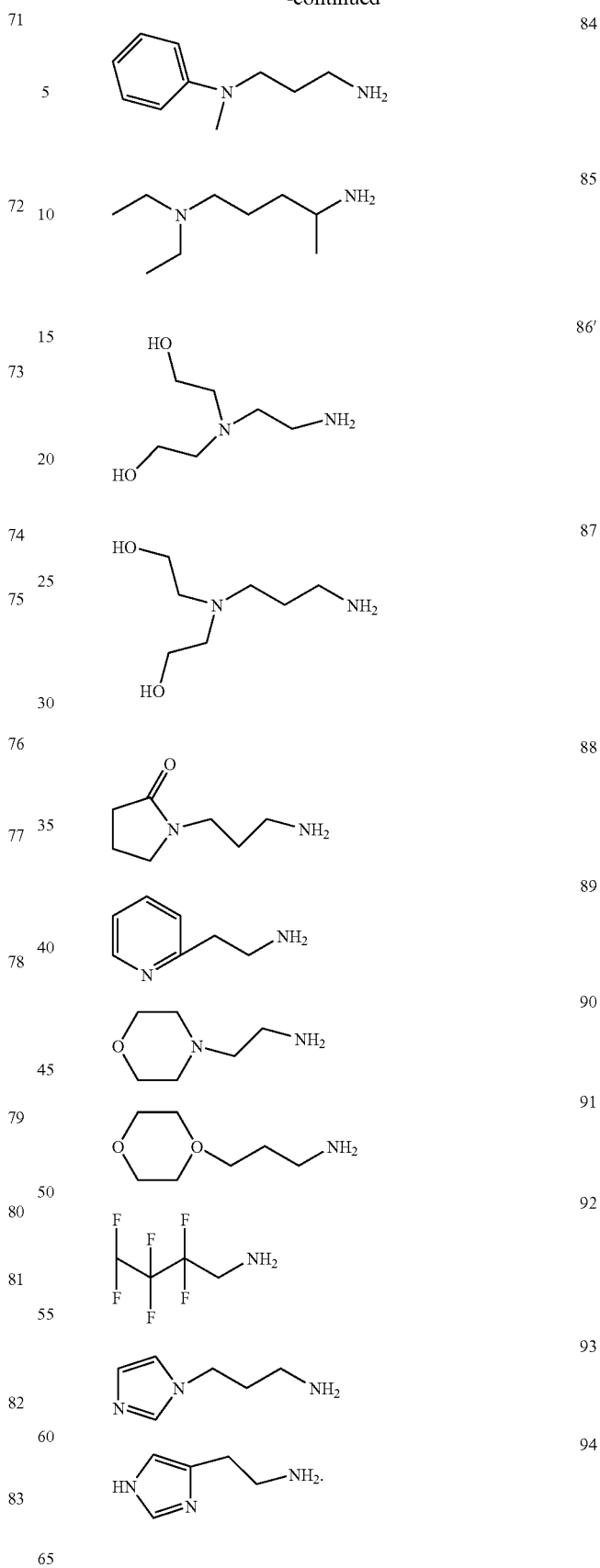
In certain embodiments, the polymers include amines 6, 17, 20, 28, 32, 36, 60, 61, 86, 89, or 94.

Particular examples of the polymers useful as pH triggering agents include:
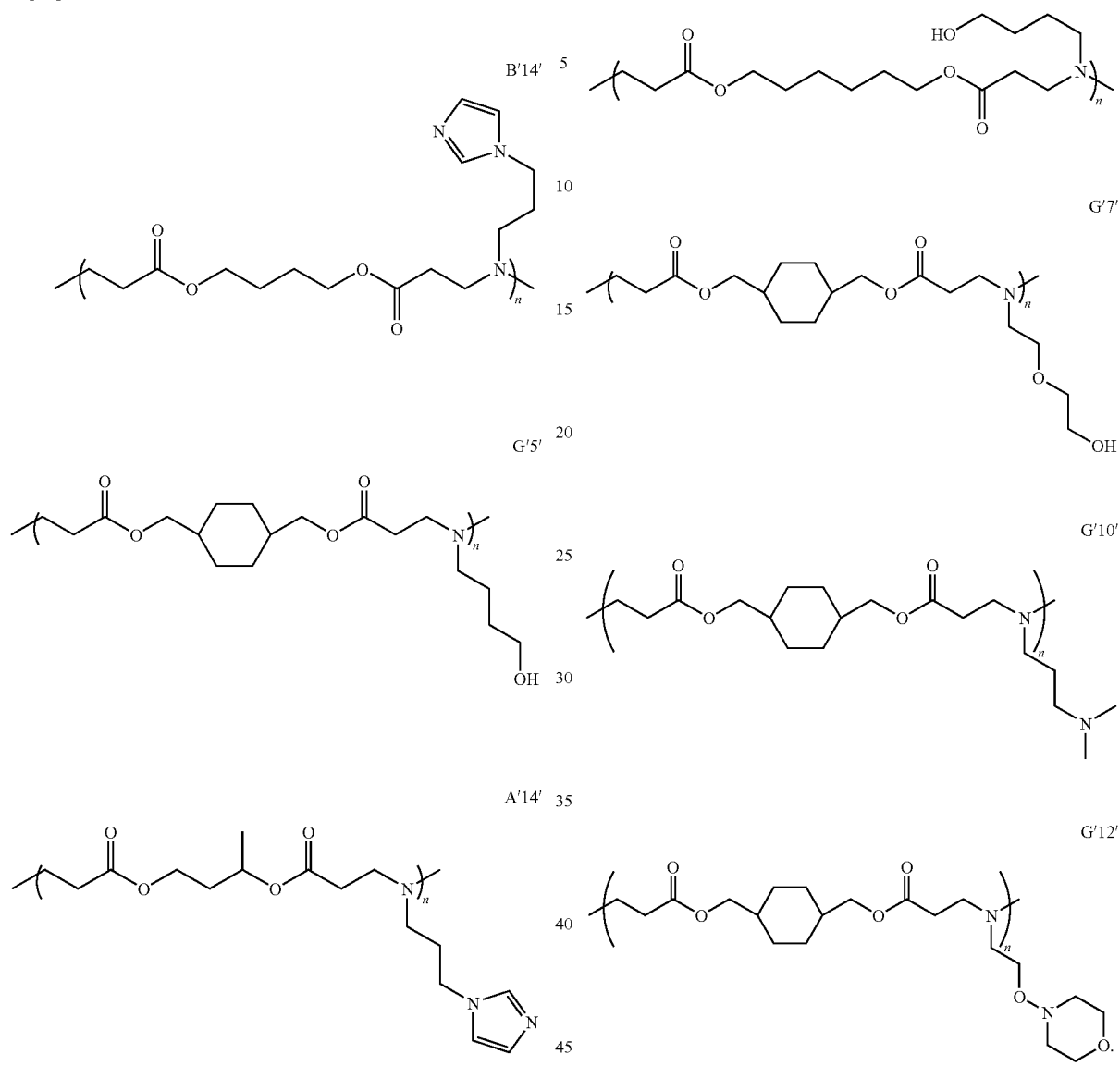
Other particularly useful poly(beta-amino ester)s include:
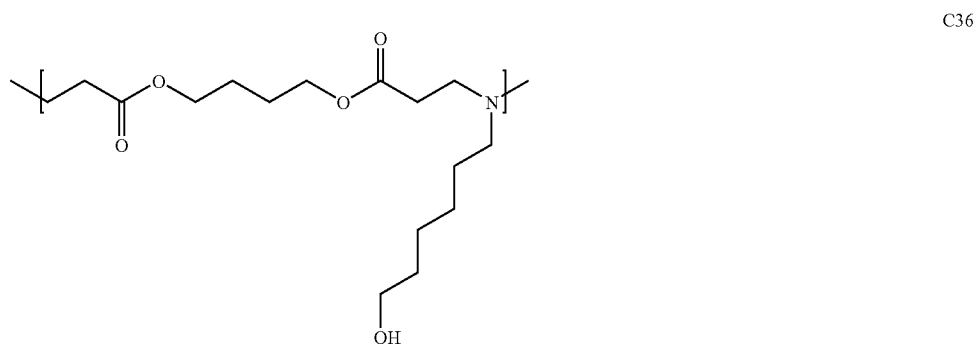

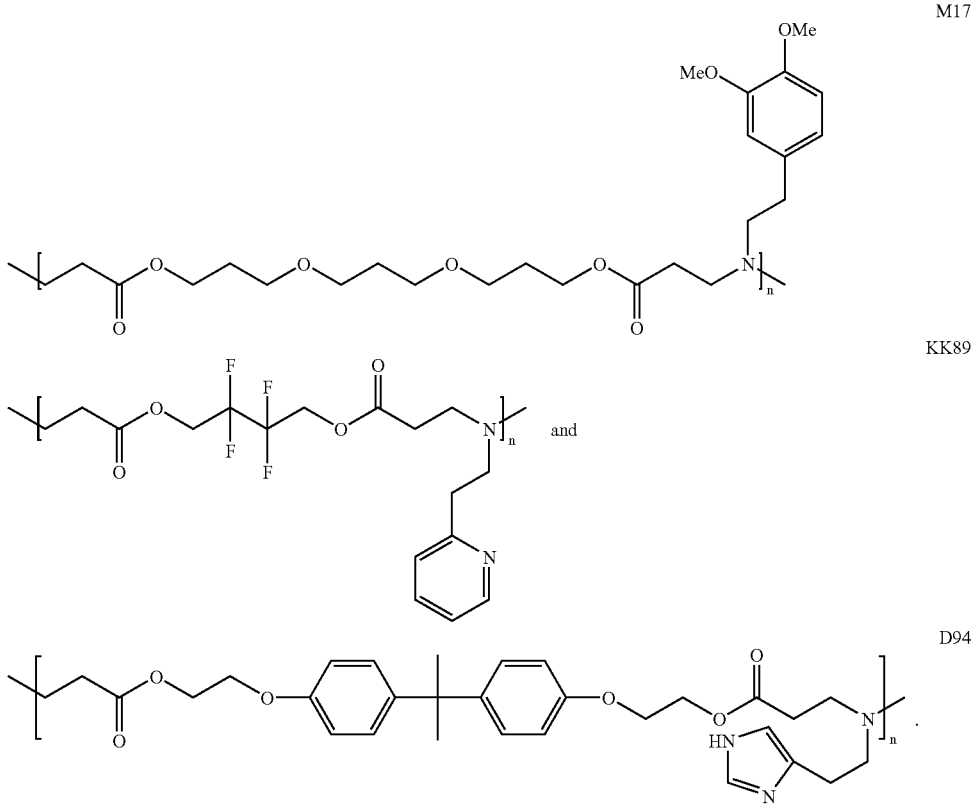

In a particularly preferred embodiment, one or both of the linkers A and B are polyethylene polymers. In another particularly preferred embodiment, one or both of the linkers A and B are polyethylene glycol polymers. Other biocompatible, biodegradable polymers may be used as one or both of the linkers A and B.

In certain preferred embodiments, the polymers of the present invention are amine-terminated. In other embodiments, the polymers of the present invention are acrylate-terminated.

In certain embodiments, the average molecular weight of the polymers of the present invention range from 1,000 g/mol to 50,000 g/mol, preferably from 2,000 g/mol to 40,000 g/mol, more preferably from 5,000 g/mol to 20,000 g/mol, and even more preferably from 10,000 g/mol to 17,000 g/mol. Since the polymers of the present invention are prepared by a step polymerization, a broad, statistical distribution of chain lengths is typically obtained. In certain embodiments, the distribution of molecular weights in a polymer sample is narrowed by purification and isolation steps known in the art. In other embodiments, the polymer mixture may be a blend of polymers of different molecular weights.

In another particularly preferred embodiment, the pH triggering polymer is a co-polymer wherein one of the repeating units is a poly(β-amino ester) of the present invention. Other repeating units to be used in the co-polymer include, but are not limited to, polyethylene, poly(glycolide-co-lactide) (PLGA), polyglycolic acid, polymethacrylate, etc.

Microparticle Matrix

The agent is encapsulated in a matrix to form the inventive microparticles. Any material known in the art to be useful in preparing microparticles may be used in preparing pH-triggerable microparticles. The pH-triggering agent is typically incorporated into the matrix of the microparticle. The matrix may include a synthetic polymer, or a blend or mixture of polymers. In certain embodiments, the pH triggering agent and the polymer of the matrix may be the same polymer, or in other embodiments, the matrix may comprise a co-polymer of a pH triggering polymer such as a poly(beta-amino ester). Polymers useful in the present invention include polyesters, polyanhydrides, polyethers, polyamides, polyacrylates, polymethacrylates, polycarbamates, polycarbonates, polystyrenes, polyureas, and polyamines. Preferably the polymer is biodegradable and/or biocompatible.

The size of the microparticles will depend on the use of the particles. For example, an application requiring the microparticles to be phagocytosed by cells such as antigen presenting cells (APCs) may use particles ranging from 1-10 microns in diameter, more preferably 2-6 microns in diameter. In certain preferred embodiments, the diameter of the microparticles ranges from 50 nanometers to 50 microns. In other preferred embodiments, the microparticles are less than 10 micrometers, and more preferably less than 5 micrometers. In certain embodiments, the microparticles range in size from 2-5 microns in diameter. The size of the microparticles and distribution of sizes may be selected by one of ordinary skill in the art based on the agent being delivered, the target tissue, route of administration, method of uptake by the cells, etc. The specific ratios of the components of the particles may range widely depending on factors including size of particle, porosity of particle, agent to be delivered, desired agent release profile, target tissue, etc. One of ordinary skill in the art may test a variety of ratios and specific components to determine the composition correct for the desired purpose.

Methods of Preparing Microparticles

The inventive microparticles may be prepared using any method known in this art. These include, but are not limited to, spray drying, single and double emulsion solvent evaporation, solvent extraction, phase separation, simple and complex coacervation, and other methods known to those of ordinary skill in the art. Particularly preferred methods of preparing the particles are the double emulsion process and spray drying. The conditions used in preparing the microparticles may be altered to yield particles of a desired size or property (e.g., hydrophobicity, hydrophilicity, external morphology, "stickiness", shape, etc.). The method of preparing the particle and the conditions (e.g., freezing the primary emulsion, solvent, temperature, concentration, air flow rate, etc.) used may also depend on the agent being encapsulated and/or the composition of the polymer matrix.

In one embodiment, the particles are prepared by the double emulsion technique which comprises first preparing a first water-in-oil emulsion by combining the agent to be delivered in an aqueous phase with a larger organic phase including the pH triggering agent and polymer. The first emulsion is essentially small aqueous bubbles in a greater organic phase. In certain embodiments, methylene chloride or chloroform is used as the organic solvent in the double emulsion technique. Optionally, the emulsion may be frozen at −10 to −20° C. to freeze the aqueous bubbles before formation of the second emulsion. This additional freezing step has been found to prevent the degradation of such fragile molecules as nucleic acids. After the first emulsion is formed, it is then poured into a larger aqueous phase to create bubbles within bubbles, i.e., the second water-in-oil-in-water emulsion. The organic solvent from this emulsion is then evaporated to yield the desired particles.

In other embodiments, the particles are prepared by a modified double emulsion technique. The agent to be delivered (e.g. DNA) is dissolved or suspended in an aqueous solution. This aqueous solution may contain additives such as buffering agents, salts, chelators, polymers, or other pharmaceutically acceptable excipients. The solution is them emulsified with an organic solution containing the encapsulating polymer and a triggering agent such as a poly(beta-amino ester). A probe sonicator may be used to form the emulsion. The resulting emulsion is then added to an aqueous solution. This aqueous solution may contain salts, buffering agents, polymers, or other pharmaceutically acceptable excipients. The resulting water-oil-water mixture may then be added to a second aqueous solution. The resulting particles are then washed and collected. The particles may then be lyophilized to form a powder. The above procedure may be performed at approximately 4° C. to reduce the aggregation of particles. In addition, the difference between osmolarities of the internal and external phase is minimized to provide for maximal loading and uniform particles. Preferably, the osmolarities are within 20% of each other. In certain other embodiments, the osmolarities are within approximately 10%, 5%, 3%, 2%, or 1% of each other.

Other methods developed for making microparticles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al. *Reactive Polymers* 6:275-283, 1987; Mathiowitz et al. *J. Appl. Polymer Sci.* 35:755-774, 1988; each of which is incorporated herein by reference).

If the particles prepared by any of the above methods have a size range outside of the desired range, the particles can be sized, for example, using a sieve.

Targeting Agents

The inventive particles may be modified to include targeting agents since it is often desirable to target a particular cell, collection of cells, tissue, or organ system. A variety of targeting agents that direct pharmaceutical compositions to particular cells are known in the art (see, for example, Cotten et al. *Methods Enzym.* 217:618, 1993; incorporated herein by reference). The targeting agents may be included throughout the particle or may be only on the surface. The targeting agent may be a protein, peptide, carbohydrate, glycoprotein, lipid, small molecule, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen boding, van der Waals, or other interactions) the formed particles using standard chemical techniques.

Pharmaceutical Compositions

Once the pH triggerable particles have been prepared, they may be combined with one or more pharmaceutical excipients to form a pharmaceutical composition that is suitable to administer to animals including humans. As would be appreciated by one of skill in this art, the excipients may be chosen based on the route of administration as described below, the agent being delivered, time course of delivery of the agent, etc.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, polynucleotide/polymer complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In a particularly preferred embodiment, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the microparticles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulations, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

Administration

The pH triggerable particles and pharmaceutical compositions containing the inventive particles may be administered to an animal via any route known in the art. These include, but are not limited to, oral, sublingual, nasal, intradermal, subcutaneous, intramuscular, rectal, vaginal, intravenous, intraarterial, and inhalational administration. In certain embodiments, the particles or pharmaceutical compositions are delivered to a mucosal surface. As would be appreciated by one of skill in this art, the route of administration and the effective dosage to achieve the desired biological effect is determined by the agent being administered, the target organ, the preparation being administered, time course of administration, disease being treated, etc.

The inventive particles are also useful in the transfection of cells making them useful in gene therapy. The particles with polynucleotides to be delivered are contacted with cells under suitable conditions to have the polynucleotide delivered intracellularly. Conditions useful in transfection may include adding calcium phosphate, adding a lipid, adding a lipohilic polymer, sonication, etc. The cells may be contacted in vitro or in vivo. Any type of cells may be transfected using the pH triggerable particles. In certain embodiments, the particles are administered inhalationally to delivery a polynucleotide to the lung epithelium of a patient. This method is useful in the treatment of hereditary diseases such as cystic fibrosis.

Films

The drug delivery system also includes films or coatings used to deliver pharmaceutical agents. For example, these films comprising the agent to be delivered, a polymer matrix, and a pH triggering agent may be used to coat biomedical devices, such as orthopaedic implants, stents, catheter, cardiac valves, and other biomedical devices. The components of the film may comprise a homogenous matrix in certain embodiments. In other embodiments, the film is comprised of various discrete layers of the components; for example, a layer of pH trigger agent may be sandwiched between layers of polymeric matrix embedded with the pharmaceutical agent to be delivered. Once the film is exposed to an acidic environment the film will degrade and release any agent within the polymeric matrix. In certain embodiments, the film may decompose into particles which release the agent to be delivered. For certain pH triggering agents used in the delivery of nucleic acids, the pH triggering agent may bind and thereby protect the nucleic acid from degradation by enzymes in the intracellular milieu. Various coating methods known in the art may be used to prepare the inventive films.

These and other aspects of the present invention will be further appreciated upon consideration of the following Examples, which are intended to illustrate certain particular embodiments of the invention but are not intended to limit its scope, as defined by the claims.

EXAMPLES

Example 1

Degradable Poly(β-Amino Esters): Synthesis, Characterization, and Self-Assembly with Plasmid DNA Experimental Section General Considerations. All manipulations involving live cells or sterile materials were performed in a laminar flow using standard sterile technique. $^1$H NMR (300.100 MHz) and $^{13}$C NMR (75.467 MHz) spectra were recorded on a Varian Mercury spectrometer. All chemical shift values are given in ppm and are referenced with respect to residual proton or carbon signal from solvent. Organic phase gel permeation chromatography (GPC) was performed using a Hewlett Packard 1100 Series isocratic pump, a Rheodyne Model 7125 injector with a 100-µL injection loop, and two PL-Gel mixed-D columns in series (5 µm, 300×7.5 mm, Polymer Laboratories, Amherst, Mass.). THF/0.1 M piperidine was used as the eluent at a flow rate of 1.0 mL/min. Data was collected using an Optilab DSP interferometric refractometer (Wyatt Technology, Santa Barbara, Calif.) and processed using the TriSEC GPC software package (Viscotek Corporation, Houston, Tex.). The molecular weights and polydispersities of the polymers are reported relative to monodispersed polystyrene standards. Aqueous phase GPC was performed by American Polymer Standards (Mentor, Ohio) using Ultrahydrogel L and 120 A columns in series (Waters Corporation, Milford, Mass.). Water (1% acetic acid, 0.3 M NaCl) was used as the eluent at a flow rate of 1.0 mL/min. Data was collected using a Knauer differential refractometer and processed using an IBM/PC GPC-PRO 3.13 software package (Viscotek Corporation, Houston, Tex.). The molecular weights and polydispersities of the polymers are reported relative to poly(2-vinylpyridine) standards. For cytotoxicity assays, absorbance was measured using a Dynatech Laboratories MR5000 microplate reader at 560 nm. Materials. N,N'-dimethylethylenediamine, piperazine, and 4,4'-trimethylenedipiperidine were purchased from Aldrich Chemical Company (Milwaukee, Wis.). 1,4-butanediol diacrylate was purchased from Alfa Aesar Organics (Ward Hill, Mass.). (3-[4,5-dimethylthiazol-2-yl]-2,5-diphenyltetrazolium bromide (MTT) was purchased from Sigma Chemical Company (St. Louis, Mo.). Plasmid DNA (pCMV-Luc) was produced in *E. coli* (DH5a, a kind gift from Zycos, Inc., Cambridge, Mass.), isolated with a Qiagen kit, and purified by ethanol precipitation. NIH 3T3 cells were purchased from American Type Culture Collection (Manassas, Va.) and grown at 37° C., 5% $CO_2$ in Dulbecco's modified Eagle's medium, 90%; fetal bovine serum, 10%; penicillin, 100 units/mL; streptomycin, 100 µg/mL. All other materials and solvents were used as received without further purification.

General Polymerization Procedure. In a typical experiment, 1,4-butanediol diacrylate (0.750 g, 0.714 mL, 3.78 mmol) and diamine (3.78 mmol) were weighed into two separate vials and dissolved in THF (5 mL). The solution containing the diamine was added to the diacrylate solution via pipette. A Teflon-coated stirbar was added, the vial was sealed with a Teflon-lined screw-cap, and the reaction was heated at 50° C. After 48 hours, the reaction was cooled to room temperature and dripped slowly into vigorously stirring diethyl ether or hexanes. Polymer was collected and dried under vacuum prior to analysis.

Synthesis of Polymer 1. Polymer 1 was prepared according to the general procedure outlined above. $^1$H NMR δ ($CDCl_3$, 300 MHz) 4.11 (br t, 4H), 2.75 (br t, J=7.05 Hz, 4H), 2.53 (br s, 4H), 2.50 (br t, (obsc), J=7.20 Hz, 4H), 2.28 (br s, 6H), 1.71, (br m, 4H). $^{13}$C NMR δ ($CDCl_3$, 75.47 MHz) 172.55, 64.14, 55.31, 53.39, 42.47, 32.54, 25.53.

Synthesis of Polymer 2. Polymer 2 was prepared according to the general procedure outlined above. $^1$H NMR δ ($CDCl_3$, 300 MHz) 4.11 (br t, 4H), 2.74 (br t, J=7.35, 4H), 2.56 (br m, 12H), 1.71 (br t, 4H). $^{13}$C NMR δ ($CDCl_3$, 75.47 MHz) 172.24, 64.19, 53.55, 52.75, 32.27, 25.52.

Synthesis of Polymer 3. Polymer 3 was prepared according to the general procedure outlined above. $^1$H NMR δ ($CDCl_3$, 300 MHz) 4.11 (br t, 4H), 3.00 (br m, 4H), 2.79 (br m, 4H), 2.65 (br m, 4H), 2.11 (br m, 4H), 1.70 (br m, 8H), 1.25 (br m, 12H). $^{13}$C NMR δ ($CDCl_3$, 75.47 MHz) 172.37, 64.13, 53.89 (br), 36.74, 35.58, 32.11 (br), 25.45, 24.05.

Polymer Degradation Studies. The hydrochloride salts of polymers 1-3 were dissolved in acetate buffer (1 M, pH=5.1) or HEPES buffer (1 M, pH=7.4) at a concentration of 5 mg/mL (the use of millimolar concentrations of buffer resulted in substantial reduction of pH during degradation due to the production of acidic degradation products). Samples were incubated at 37° C. on a mechanical rotator, and aliquots (1 mL) were removed at appropriate time intervals. Aliquots were frozen immediately in liquid nitrogen and lyophilized. Polymer was extracted from dried buffer salts using THF/0.1 M piperidine (1 mL), and samples were analyzed directly by GPC.

Formation of DNA/Polymer Complexes and Agarose Gel Retardation Assays.

DNA/polymer complexes were formed by adding 50 µL of a plasmid DNA solution (pCMV Luc, 2 µg/50 µL in water) to a gently vortexing solution of the hydrochloride salt of polymers 1-3 (50 µL in 25 mM MES, pH=6.0, concentrations adjusted to yield desired DNA/polymer weight ratios). The samples were incubated at room temperature for 30 minutes, after which 20 µL was run on a 1% agarose gel (HEPES, 20 mM, pH=7.2, 65V, 30 min). Samples were loaded on the gel with a loading buffer consisting of 10% Ficoll 400 (Amersham Pharmacia Biotech, Uppsala, Sweden) in HEPES (25 mM, pH=7.2). Bromphenol blue was not included as a visual indicator in the loading buffer, since this charged dye appeared to interfere with the complexation of polymer and DNA. DNA bands were visualized under UV illumination by ethidium bromide staining.

Quasi-Elastic Laser Light Scattering (QELS) and Measurement of ζ-potentials. QELS experiments and ζ-potential measurements were made using a ZetaPALS dynamic light scattering detector (Brookhaven Instruments Corporation, Holtsville, N.Y., 15 mW laser, incident beam=676 nm). DNA/polymer complexes were formed as described above for agarose gel retardation assays. Samples were diluted with 900 μL of HEPES (20 mM, pH=7.0), added to a gently vortexing sample of DNA/polymer complex (total volume=1 mL, pH=7.0). Average particle sizes and ζ-potentials were determined at 25° C. Correlation functions were collected at a scattering angle of 90°, and particle sizes were calculated using the MAS option of BIC's particle sizing software (ver. 2.30) using the viscosity and refractive index of pure water at 25° C. Particle sizes are expressed as effective diameters assuming a lognormal distribution. Average electrophoretic mobilities were measured at 25° C. using BIC PALS zeta potential analysis software and zeta potentials were calculated using the Smoluchowsky model for aqueous suspensions. Three measurements were made on each sample, and the results are reported as average diameters and zeta potentials.

Cytotoxicity Assays. Immortalized NIH 3T3 cells were grown in 96-well plates at an initial seeding density of 10,000 cells/well in 200 μL growth medium (90% Dulbecco's modified Eagle's medium, 10% fetal bovine serum, penicillin 100 units/mL, streptomycin 100 μg/mL). Cells were grown for 24 hours, after which the growth medium was removed and replaced with 180 μL of serum-free medium. Appropriate amounts of polymer were added in 20 μL aliquots. Samples were incubated at 37° C. for 5 hours, and the metabolic activity of each well was determined using a MTT/thiazolyl blue assay: to each well was added 25 μL of a 5 mg/mL solution of MTT stock solution in sterile PBS buffer. The samples were incubated at 37° C. for 2 hours, and 100 μL of extraction buffer (20% w/v SDS in DMF/water (1:1), pH=4.7) was added to each well. Samples were incubated at 37° C. for 24 hours. Optical absorbance was measured at 560 nm with a microplate reader and expressed as a percent relative to control cells.

Results and Discussion

Polymer Synthesis and Characterization

The synthesis of linear poly(amido amines) containing tertiary amines in their backbones was reported by Ferruti et al. in 1970 via the addition of bifunctional amines to bisacrylamides (Anderson *Nature* 392 (Suppl.):25-30, 1996; Friedman *Nature Med.* 2:144-147, 1996; Crystal *Science* 270:404-410, 1995; Mulligan *Science* 260:926-932, 1993; each of which is incorporated herein by reference). Linear poly(amido amines) were initially investigated as heparin and ion complexing biomaterials (Ferruti et al. *Advances in Polymer Science* 58:55-92, 1984; Ferruti et al. *Biomaterials* 15:1235-1241, 1994; Ferruti et al. *Macromol. Chem. Phys.* 200:1644-1654, 1999; Ferruti et al. *Biomaterials* 15:1235-1241, 1994; each of which is incorporated herein by reference). Dendritic poly(amido amines) (PAMAMs) have seen increasing use in gene transfer applications due to their ability to complex DNA (Kukowska-Latallo et al. *Proc. Natl. Acad. Sci. USA* 93:4897-4902, 1996; Tang et al. *Bioconjugate Chem.* 7:703-714, 1996; Haensler et al. *Bioconjugate Chem.* 4:372-379, 1993; each of which is incorporated herein by reference), and a recent report describes the application of a family of linear poly(amido amines) to cell transfection and cytotoxicity studies (Hill et al. *Biochim. Biophys. Acta* 1427:161-174, 1999; incorporated herein by reference). In contrast, analogous poly (ester amines) formed from the Michael-type addition of bifunctional amines to diacrylate esters have received less attention (Danusso et al. *Polymer* 11:88-113, 1970; Ferruti et al. *Polymer* 26:1336, 1985; Ferruti et al. *Advances in Polymer Science* 58:55-92, 1984; Ferruti et al. *Biomaterials* 15:1235-1241, 1994; Ferruti et al. *Macromol. Chem. Phys.* 200:1644-1654, 1999; Ferruti et al. *Biomaterials* 15:1235-1241, 1994; Kargina et al. *Vysokomol. Soedin. Seriya A* 28:1139-1144, 1986; Rao et al. *J. Bioactive and Compatible Polymers* 14:54-63, 1999; each of which is incorporated herein by reference).

The poly(amino ester) approach presents a particularly attractive basis for the development of new polymeric transfection vectors for several reasons: 1) the polymers contain the requisite amines and readily degradable linkages, 2) multiple analogs could potentially be synthesized directly from commercially available starting materials, and 3) if the resulting polymers were useful as DNA condensing agents, future generations of polymer could easily be engineered to possess amine $pK_a$ values spanning the range of physiologically relevant pH. This last point was particularly intriguing, because the buffering capacity of polyamines has recently been implicated as a factor influencing the escape of DNA from cell endosomes following endocytosis (Boussif et al. *Proc. Natl. Acad. Sci. USA* 92:7297-7301, 1995; Haensler et al. *Bioconjugate Chem.* 4:372-379, 1993; Behr *Chimia* 51:34-36, 1997; Demeneix et al., in *Artificial Self-Assembling Systems for Gene Delivery* (Felgner et al., Eds.), American Chemical Society, Washington, D.C., 1996, pp. 146-151; Kabanov et al., in *Self-Assembling Complexes for Gene Delivery: From Laboratory to Clinical Trial*, John Wiley and Sons, New York, 1998; each of which is incorporated herein by reference). While the complexation of DNA with a cationic polymer is required to compact and protect DNA during early events in the transfection process, DNA and polymer must ultimately decomplex in the nucleus to allow efficient transcription (Luo et al. *Nat. Biotechnol.* 18:33-37, 2000; incorporated herein by reference). In view of this requirement, degradable polycations could play an important role in "vector unpackaging" events in the nucleus (Luo et al. Nat. *Biotechnol.* 18:33-37, 2000; Schaffer et al. *Biotechnol. Bioeng.* 67:598-606, 2000; Kabanov *Pharm. Sci. Technol. Today* 2:365-372, 1999; each of which is incorporated herein by reference). Finally, we hypothesized that polymers of this general structure, and the β-amino acid derivatives into which they would presumably degrade, would be significantly less toxic than poly(lysine) and PEI. As outlined above, degradable polycations (Putnam et al. *Macromolecules* 32:3658-3662, 1999; Lim et al. *J. Am. Chem. Soc.* 121:5633-5639, 1999; Lim et al. *J. Am. Chem. Soc.* 122:6524-6525, 2000; each of which is incorporated herein by reference) and linear polymers containing relatively hindered amines located close to the polymer backbone (Gonzalez et al. *Bioconjugate Chem.* 10:1068-1074, 1999; incorporated herein by reference) are less toxic than poly (lysine) and PEI.

The synthesis of polymers 1-3 via the addition of the bis (secondary amines), N,N'-dimethylethylenediamine, piperazine, and 4,4'-trimethylenedipiperidine, to 1,4-butanediol diacrylate was investigated (Danusso et al. *Polymer* 11:88-113, 1970; Kargina et al. *Vysokomol. Soedin. Seriya A* 28:1139-1144, 1986; each of which is incorporated herein by reference). The polymerization of these monomers proceeded in THF and CH$_2$Cl$_2$ at 50° C. to yield the corresponding polymers in up to 86% yields (Table 1). Polymers were purified through repeated precipitation into diethyl ether or hexane. Polymer 1 was isolated as a clear viscous liquid; polymers 2 and 3 were obtained as white solids after drying under high vacuum. Alternatively, polymers 1-3 could be isolated as solid hydrochloride salts upon addition of diethyl ether/HCl to a solution of polymer in THF or CH$_2$Cl$_2$. All three polymers were soluble in organic solvents such as THF, CH$_2$Cl$_2$, CHCl$_3$, and MeOH and were also soluble in water at reduced pH. Polymer 1 and the hydrochloride salts of polymers 1-3 were freely soluble in water.

TABLE 1

Representative Molecular Weight Data for Polymers 1-3.

| Polymer | Solvent | $M_n{}^c$ | PDI | Yield, % |
|---|---|---|---|---|
| 1$^a$ | THF | — | — | —$^d$ |
| 1$^a$ | CH$_2$Cl$_2$ | — | — | 82% |
| 2$^a$ | THF | 10000 | 1.77 | 64% |
| 2$^a$ | CH$_2$Cl$_2$ | 17500 | 2.15 | 75% |
| 3$^a$ | THF | 24400 | 1.55 | 58% |
| 3$^a$ | CH$_2$Cl$_2$ | 30800 | 2.02 | 70% |
| 1$^b$ | THF | 5800 | 2.83 | 55% |

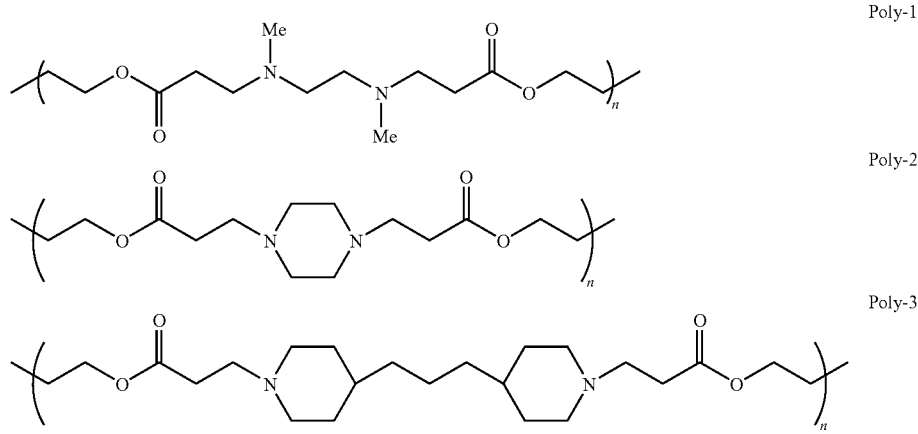

Poly-1

Poly-2

Poly-3

The molecular weights of polymers 1-3 and their corresponding hydrochloride salts were determined by both organic and aqueous phase gel permeation chromatography (GPC). Polymer molecular weights (M$_n$) ranged from up to 5,800 for polymer 1 to up to 32,000 for polymer 3, relative to polystyrene standards. Molecular weight distributions for these polymers were monomodal with polydispersity indices (PDIs) ranging from 1.55 to 2.55. Representative molecular weight data are presented in Table 1. While the synthesis of linear poly(amido amines) is generally performed using alcohols or water as solvents (Danusso et al. *Polymer* 11:88-113, 1970; Ferruti et al. *Polymer* 26:1336, 1985; Ferruti et al. *Advances in Polymer Science* 58:55-92, 1984; Ferruti et al. *Biomaterials* 15:1235-1241, 1994; Ferruti et al. *Macromol. Chem. Phys.* 200:1644-1654, 1999; Ferruti et al. *Biomaterials* 15:1235-1241, 1994; each of which is incorporated herein by reference), anhydrous THF and CH$_2$Cl$_2$ were employed in the synthesis of poly(β-amino esters) to minimize hydrolysis reactions during the synthesis. The yields and molecular weights of polymers synthesized employing CH$_2$Cl$_2$ as solvent were generally higher than those of polymers synthesized in THF (Table 1) (Polymer 1 could not by synthesized in CH$_2$Cl$_2$. The color of the reaction solution progressed from colorless to an intense pink color almost immediately after the introduction of a solution of N,N'-dimethylethylenediamine in CH$_2$Cl$_2$ to a solution of 1,4-butanediol diacrylate in CH$_2$Cl$_2$ (see Experimental Section above). The color progressed to light orange over the course of the reaction, and an orange polymer was isolated after precipitation into hexane. The isolated polymer was insoluble in CH$_2$Cl$_2$, THF, and water at reduced pH and was not structurally characterized. This problem was not encountered for the analogous reaction in THF.).

TABLE 1-continued

Representative Molecular Weight Data for Polymers 1-3.

| Polymer | Solvent | $M_n{}^c$ | PDI | Yield, % |
|---|---|---|---|---|
| 2$^b$ | CH$_2$Cl$_2$ | 16500 | 2.37 | 80%$^e$ |
| 3$^b$ | CH$_2$Cl$_2$ | 31200 | 2.55 | 86%$^e$ |

$^a$Conditions: [diamine] = [1,4-butanediol diacrylate] = 0.38 M, 50° C., 48 h.
$^b$Conditions: [diamine] = [1,4-butanediol diacrylate] = 1.08 M, 50° C., 48 h.
$^c$GPC analysis was performed in THF/0.1M piperidine and molecular weights are reported versus polystyrene standards.
$^d$No polymer was isolated under these conditions.
$^e$The reaction solution became very viscous and eventually solidified under these conditions.

The structures of polymers 1-3 were confirmed by $^1$H and $^{13}$C NMR spectroscopy. These data indicate that the polymers were formed through the conjugate addition of the secondary amines to the acrylate moieties of 1,4-butanediol diacrylate and not through the formation of amide linkages under our reaction conditions. Additionally, the newly formed tertiary amines in the polymer backbones do not participate in subsequent addition reactions with diacrylate monomer, which would lead to branching or polymer crosslinking. This fortunate result appears to be unique to polymers of this type produced from bis(secondary amine) monomers. The synthesis of analogous polymers employing difunctional primary amines as monomers (such as 1,4-diaminobutane) may lead to polymer branching and the formation of insoluble crosslinked polymer networks if conditions are not explicitly controlled.

In view of the juxtaposition of amines and esters within the backbones of polymers 1-3, we were initially concerned that hydrolysis might occur too rapidly for the polymers to be of practical use. For example, poly(4-hydroxy-L-proline ester) and poly[α-(4-aminobutyl)-L-glycolic acid] degrade quite rapidly near neutral pH, having half lives of roughly 2 hr (Lim et al. *J. Am. Chem. Soc.* 121:5633-5639, 1999; incorporated herein by reference) and 30 min (Lim et al. *J. Am. Chem. Soc.* 122:6524-6525, 2000; incorporated herein by reference), respectively (Such rapid degradation times did not preclude the application of these polymers to gene delivery (See references, Lim et al. *J. Am. Chem. Soc.* 121:5633-5639, 1999; Lim et al. *J. Am. Chem. Soc.* 122:6524-6525, 2000; each of which is incorporated herein by reference). However, extremely rapid degradation rates generally introduce additional concerns surrounding the manipulation, storage, and application of degradable polymers.). Analysis of polymers 1 and 2 by aqueous GPC using 1% acetic acid/water as eluent, however, revealed that degradation was sufficiently slow in acidic media. For example, the GPC traces of polymers 1 and 2 sampled under these conditions over a period of 4-5 hours revealed no changes in molecular weights or polydispersities (Polymer 3 could not be analyzed by aqueous GPC.). We were also concerned that significant backbone hydrolysis might occur during the isolation of the hydrochloride salts of polymers 1-3. To prevent hydrolysis during the protonation and isolation of these polymers, anhydrous solvents were employed and reactions were performed under an argon atmosphere. Analysis of the polymers before and after protonation revealed no observable hydrolysis. For example, the GPC trace of a sample of polymer 3 after precipitation from $CH_2Cl_2$ with 1.0 M diethyl ether/HCl ($M_n$=15,300; PDI=1.90) was virtually identical to the molecular weight of the polymer prior to protonation ($M_n$=15,700; PDI=1.92) and no lower molecular weight species were evident (Comparative GPC data were collected employing THF/0.1M piperidine as eluent (see Experimental Section above). The HCl salts of the polymers were insoluble in THF, but were soluble in THF/0.1 M piperidine concomitant with the production of a fine white precipitate which was filtered prior to injection.). Solid samples of polymers 1-3 could be stored for several months without detectable decreases in molecular weight.

Polymers 1-3 were specifically designed to degrade via hydrolysis of the ester bonds in the polymer backbones. However, an additional concern surrounding the overall stability and biocompatibility of these polymers is the potential for unwanted degradation to occur through retro-Michael reaction under physiological conditions. Because these polymers were synthesized via the Michael-type reaction of a secondary amine to an acrylate ester, it is possible that the polymers could undergo retro-Michael reaction to regenerate free acrylate groups, particularly under acidic conditions. Acrylate esters are potential DNA-alkylating agents and are therefore suspected carcinogens (for recent examples, see: Schweikl et al. *Mutat. Res.* 438:P71-P78, 1999; Yang et al. *Carcinogenesis* 19:P1117-P1125, 1998; each of which is incorporated herein by reference). Because these polymers are expected to encounter the reduced pH environment within the endosomal vesicles of cells (pH=5.0-5.5) during transfection, we addressed the potential for the degradation of these polymers to occur through a retro-Michael pathway.

Under extremely acidic (pH<3) or basic (pH>12) conditions, polymers 1-3 degraded rapidly and exclusively to 1,4-butanediol and the anticipated bis(β-amino acid) byproducts 4a-6a as determined by $^1H$ NMR spectroscopy. No spectroscopic evidence for retro-Michael addition under these conditions was found. It is worth noting that bis(β-amino acid) degradation products 4a-6a would be less likely to undergo a retro-Michael reaction, as acrylic acids are generally less activated Michael addition partners (Perlmutter, P., in *Conjugate Addition Reactions in Organic Synthesis*, Pergamon Press, New York, 1992; incorporated herein by reference). Further degradation of compounds 4a-6a under these conditions was not observed.

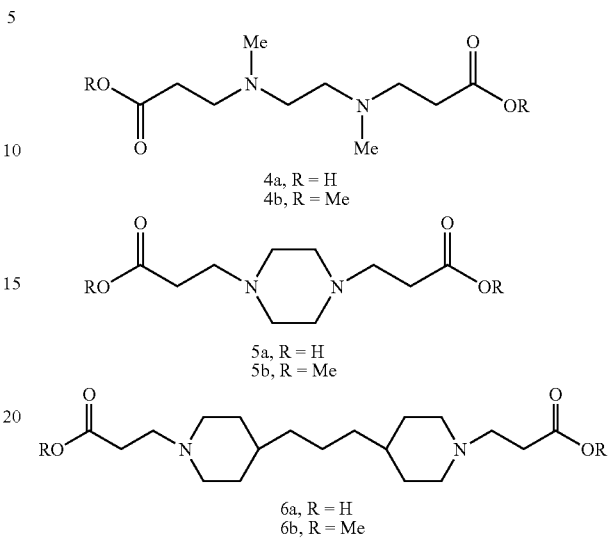

4a, R = H
4b, R = Me

5a, R = H
5b, R = Me

6a, R = H
6b, R = Me

The kinetics of polymer degradation were investigated under the range of conditions likely to be encountered by these polymers during transfection. Degradation was monitored at 37° C. at buffered pH values of 5.1 and 7.4 in order to approximate the pH of the environments within endosomal vesicles and the cytoplasm, respectively. The hydrochloride salts of polymers 1-3 were added to the appropriate buffer, incubated at 37° C., and aliquots were removed at appropriate times. Aliquots were frozen immediately, lyophilized, and polymer was extracted into THF/0.1 M piperidine for analysis by GPC. FIG. 1 shows the degradation profiles of polymers 1-3 as a function of time. The polymers degraded more slowly at pH 5.1 than at pH 7.4. Polymers 1-3 displayed similar degradation profiles at pH 5.1, each polymer having a half-life of approximately 7-8 hours. In contrast, polymers 1 and 3 were completely degraded in less than 5 hours at pH 7.4. These results are consistent with the pH-degradation profiles of other amine-containing polyesters, such as poly(4-hydroxy-L-proline ester), in which pendant amine functionalities are hypothesized to act as intramolecular nucleophilic catalysts and contribute to more rapid degradation at higher pH (Lim et al. *J. Am. Chem. Soc.* 121:5633-5639, 1999; Lim et al. *J. Am. Chem. Soc.* 122:6524-6525, 2000; each of which is incorporated herein by reference). While the possibility of intramolecular assistance cannot be ruled out, it is less likely for polymers 1-3 because the tertiary amines in these polymers should be less nucleophilic. The degradation of polymer 2 occurred more slowly at pH 7.4 than at pH 5.1 (FIG. 1). This anomalous behavior is most likely due to the incomplete solubility of polymer 2 at pH 7.4 and the resulting heterogeneous nature of the degradation milieu (Polymers 2 and 3 are not completely soluble in water at pH 7.4. While polymer 3 dissolved relatively rapidly during the degradation experiment, solid particles of polymer 2 were visible for several days.

Cytotoxicity Assays

Poly(lysine) and PEI have been widely studied as DNA condensing agents and transfection vectors (Luo et al. *Nat. Biotechnol.* 18:33-37, 2000; Behr *Acc. Chem. Res.* 26:274-278, 1993; Zauner et al. *Adv. Drug Del. Rev.* 30:97-113, 1998; Kabanov et al. *Bioconjugate Chem.* 6:7-20, 1995; Boussif et al. *Proc. Natl. Acad. Sci. USA* 92:7297-7301, 1995; Behr *Chimia* 51:34-36, 1997; Demeneix et al., in *Artificial Self-Assembling Systems for Gene Delivery* (Felgner et al., Eds.), American Chemical Society, Washington, D.C., 1996, pp. 146-151; Kabanov et al., in *Self-Assembling Complexes for Gene Delivery: From Laboratory to Clinical Trial*, John Wiley and Sons, New York, 1998; each of which is incorporated herein by reference) and are the standards to which new polymeric vectors are often compared (Putnam et al. *Macromolecules* 32:3658-3662, 1999; Lim et al. *J. Am. Chem. Soc.* 121:5633-5639, 1999; Lim et al. *J. Am. Chem. Soc.* 122:6524-6525, 2000; Gonzalez et al. *Bioconjugate Chem.* 10:1068-1074, 1999; each of which is incorporated herein by reference). Unfortunately, as outlined above, these polymers are also associated with significant levels of cytotoxicity and high levels of gene expression are usually realized only at a substantial cost to cell viability. To determine the toxicity profile of polymers 1-3, a MTT/thiazolyl blue dye reduction assay using the NIH 3T3 cell line and the hydrochloride salts of polymers 1-3 was conducted as an initial indicators. The 3T3 cell line is commonly employed as a first level screening population for new transfection vectors, and the MTT assay is generally used as an initial indicator of cytotoxicity, as it determines the influences of added substances on cell growth and metabolism (Hansen et al. *Immunol. Methods* 119:203-210, 1989; incorporated herein by reference).

Figure 2:
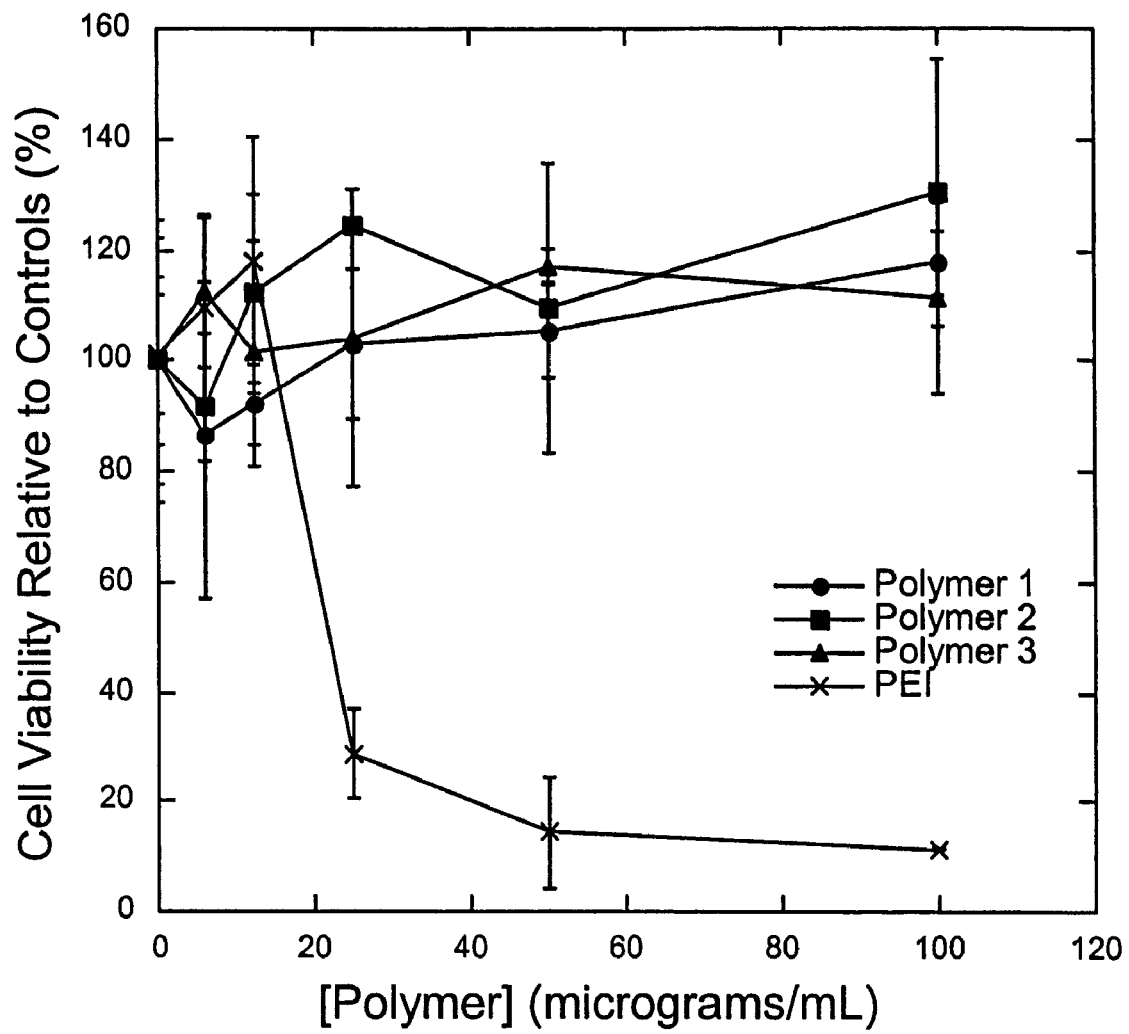
FIG. 2 shows cytotoxicity profiles of polymers 1-3 and PEI. Viability of NIH 3T3 cells is expressed as a function of polymer concentration. The molecular weights of polymers 1, 2, and 3 were 5800, 11300, and 22500, respectively. The molecular weight of the PEI employed was 25000.

Cells were incubated with polymer 1 ($M_n$=5 800), polymer 2 ($M_n$=11 300), and polymer 3 ($M_n$=22 500) as described in the Experimental Section. As shown in FIG. 2, cells incubated with these polymers remained 100% viable relative to controls at concentrations of polymer up to 100 μg/mL. These results compare impressively to data obtained for cell populations treated with PEI ($M_n$≈25 000), included as a positive control for our assay as well as to facilitate comparison to this well-known transfection agent. Fewer than 30% of cells treated with PEI remained viable at a polymer concentration of 25 μg/mL, and cell viability was as low as 10% at higher concentrations of PEI under otherwise identical conditions. An analogous MTT assay was performed using independently synthesized bis(β-amino acid)s 4a-6a to screen the cytotoxicity of the hydrolytic degradation products of these polymers. (Bis(β-amino acid)s 4a-6a should either be biologically inert or possess mild or acute toxicities which are lower than traditional polycationic transfection vectors. In either case, the degradation of these materials should facilitate rapid metabolic clearance.). Compounds 4a-6a and 1,4-butanediol did not perturb cell growth or metabolism in this initial screening assay (data not shown). A more direct structure/function-based comparison between polymers 1-3 and PEI cannot be made due to differences in polymer structure and molecular weight, both of which contribute to polycation toxicity. Nonetheless, the excellent cytotoxicity profiles of polymers 1-3 alone suggested that they were interesting candidates for further study as DNA condensing agents.

Self Assembly of Polymers 1-3 with Plasmid DNA

The tendency of cationic polyamines to interact electrostatically with the polyanionic backbone of DNA in aqueous solution is well known. Provided that the polymers are sufficiently protonated at physiological pH, and that the amines are sterically accessible, such interactions can result in a self-assembly process in which the positively and negatively charged polymers form well-defined conjugates (Kabanov et al., in *Self-Assembling Complexes for Gene Delivery: From Laboratory to Clinical Trial*, John Wiley and Sons, New York, 1998; each of which is incorporated herein by reference). The majority of polyamines investigated as DNA-complexing agents and transfection vectors have incorporated amines at the terminal ends of short, conformationally flexible side chains (e.g., poly(lysine) and methacrylate/methacrylamide polymers) (Zauner et al. *Adv. Drug Del. Rev.* 30:97-113, 1998; Kabanov et al. *Bioconjugate Chem.* 6:7-20, 1995; van de Wetering et al. *Bioconjugate Chem.* 10:589-597, 1999; each of which is incorporated herein by reference), or accessible amines on the surfaces of spherical or globular polyamines (e.g., PEI and PAMAM dendrimers) (Boussif et al. *Proc. Natl. Acad. Sci. USA* 92:7297-7301, 1995; Kukowska-Latallo et al. *Proc. Natl. Acad. Sci. USA* 93:4897-4902, 1996; Tang et al. *Bioconjugate Chem.* 7:703-714, 1996; Haensler et al. *Bioconjugate Chem.* 4:372-379, 1993; each of which is incorporated herein by reference). Because polymers 1-3 contain tertiary amines, and those tertiary amines are located in a sterically crowded environment (flanked on two sides by the polymer backbones), we were initially concerned that the protonated amines might not be sufficiently able to interact intimately with DNA.

The ability of polymers 1-3 to complex plasmid DNA was demonstrated through an agarose gel shift assay. Agarose gel electrophoresis separates macromolecules on the basis of both charge and size. Therefore, the immobilization of DNA on an agarose gel in the presence of increasing concentrations of a polycation has been widely used as an assay to determine the point at which complete DNA charge neutralization is achieved (Putnam et al. *Macromolecules* 32:3658-3662, 1999; Lim et al. *J. Am. Chem. Soc.* 121:5633-5639, 1999; Lim et al. *J. Am. Chem. Soc.* 122:6524-6525, 2000; Gonzalez et al. *Bioconjugate Chem.* 10:1068-1074, 1999; each of which is incorporated herein by reference). As mentioned above, the hydrochloride salts of polymers 1-3 are soluble in water. However, polymers 2 and 3 are not completely soluble at pH 7.2 over the full range of desired polymer concentrations. Therefore, DNA/polymer complexes were prepared in MES buffer (25 mM, pH=6.0). DNA/polymer complexes were prepared by adding an aqueous solution of DNA to vortexing solutions of polymer in MES at desired DNA/polymer concentrations (see Experimental Section). The resulting DNA/polymer complexes remained soluble upon dilution in the electrophoresis running buffer (20 mM HEPES, pH=7.2) and data were obtained at physiological pH. As a representative example, FIG. 3 depicts the migration of plasmid DNA (pCMV-Luc) on an agarose gel in the presence of increasing concentrations of polymer 1.

Figure 3:
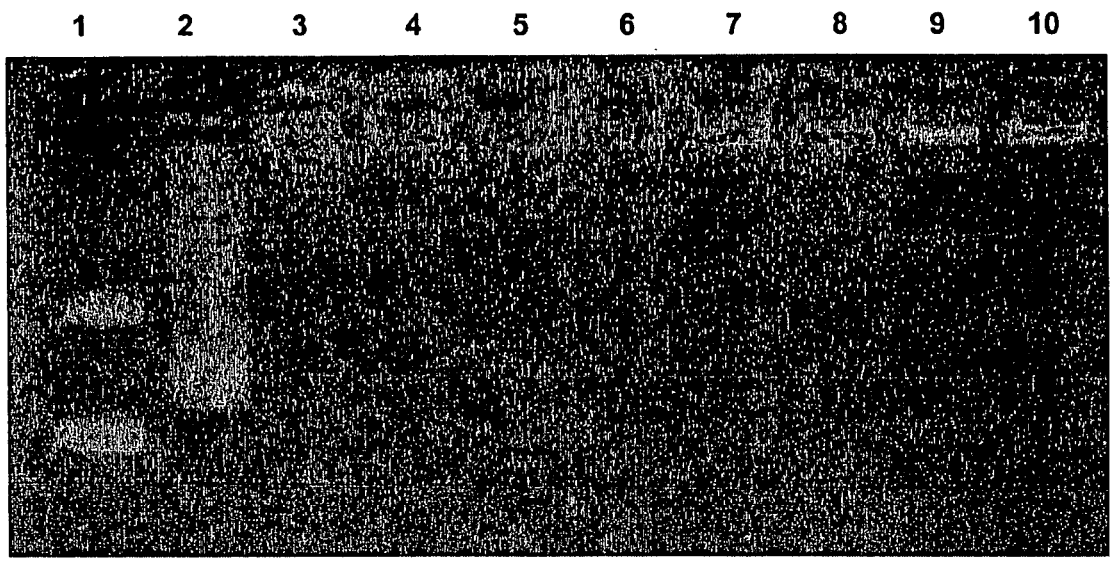
FIG. 3 shows the retardation of pCMV-Luc DNA by polymer 1 in agarose gel electrophoresis. Each lane corresponds to a different DNA/polymer weight ratio. The ratios are as follows: 1) 1:0 (DNA only); 2) 1:0.5; 3) 1:1; 4) 1:2; 5) 1:3; 6) 1:4; 7) 1:5; 8) 1:6; 9) 1:7; and 10) 1:8.

As shown in FIG. 3, retardation of DNA migration begins at DNA/1 ratios as low as 1:0.5 (w/w) and migration is completely retarded at DNA/polymer ratios above 1:1.0 (w/w) (DNA/polymer weight ratios rather than DNA/polymer charge ratios are reported here. Although both conventions are used in the literature, we find weight ratios to be more practical and universal, since the overall charge on a polyamine is subject to environmental variations in pH and temperature. While DNA/polymer charge ratios are descriptive for polymers such as poly(lysine), they are less meaningful for polymers such as PEI and 1-3 which incorporate less basic amines.). Polymers 2 and 3 completely inhibit the migration of plasmid DNA at DNA/polymer ratios (w/w) above 1:10 and 1:1.5, respectively (data not shown). These results vary markedly from gel retardation experiments conducted using model "monomers." Since the true monomers and the degradation products of polymers 1-3 do not adequately represent the repeat units of the polymers, we used bis(methyl ester)s 4b-6b to examine the extent to which the polyvalency and cooperative binding of polycations 1-3 is necessary to achieve DNA immobilization. "Monomers" 4b-6b did not inhibit the migration of DNA at DNA/"monomer" ratios (w/w) of up to 1:30 (data not shown).

The reasons for the less-efficient complexation employing polymer 2 in the above gel electrophoresis assays most likely results from differences in the $pK_a$ values of the amines in these polymers. The direct measurement of the $pK_a$ values of polymers 1-3 is complicated by their degradability. However, we predict the range of $pK_a$ values of the amines in polymers 1 and 2 to extend from approximately 4.5 and 8.0 for polymer 1, to 3.0 and 7.0 for polymer 2, based on comparisons to structurally related poly(β-amino amides) (The $pK_a$ values of structurally-related poly(β-amino amides) containing piperazine and dimethylethylene diamine units in their backbones have been reported. Barbucci et al. *Polymer* 21:81-85, 1980; Barbucci et al. *Polymer* 19:1329-1334, 1978; Barbucci et al. *Macromolecules* 14:1203-1209, 1981; each of which is incorporated herein by reference). As a result, polymer 2 should be protonated to a lesser extent than polymer 1 at physiological or near-neutral pH, and would therefore be a less effective DNA condensing agent. The range of $pK_a$ values for polymer 3 should be higher than the range for polymers 1 and 2 due to the increased distance between the nitrogen atoms. Accordingly, polymer 3 forms complexes with DNA at substantially reduced concentrations relative to polymer 2.

Agarose gel retardation assays are useful in determining the extent to which polycations interact with DNA. To be useful transfection agents, however, polycations must also be able to self-assemble plasmid DNA into polymer/DNA complexes small enough to enter a cell through endocytosis. For most cell types, this size requirement is on the order of 200 nm or less (Zauner et al. *Adv. Drug Del. Rev.* 30:97-113, 1998; incorporated herein by reference), although larger particles can also be accommodated (Demeneix et al., in *Artificial Self-Assembling Systems for Gene Delivery* (Felgner et al., Eds.), American Chemical Society, Washington, D.C., 1996, pp. 146-151; Kabanov et al., in *Self-Assembling Complexes for Gene Delivery: From Laboratory to Clinical Trial*, John Wiley and Sons, New York, 1998; each of which is incorporated herein by reference). The ability of polymers 1-3 to compact plasmid DNA into nanometer-sized structures was determined by quasi-elastic laser light scattering (QELS), and the relative surface charges of the resulting complexes were quantified through ζ-potential measurements. DNA/polymer particles used for particle sizing and ζ-potential measurements were formed as described above for agarose gel electrophoresis assays and diluted in 20 mM HEPES buffer (pH=7.0) for analysis, as described in the Experimental Section.

Polymer 1 formed complexes with diameters ranging from 90-150 nm at DNA/polymer ratios above 1:2 (w/w), and polymer 2 condensed DNA into particles on the order of 60-125 nm at DNA/polymer ratios above 1:10. These results are consistent with the data obtained from agarose gel electrophoresis experiments above. However, the particles in these experiments aggregated over a period of hours to yield larger complexes with diameters in the range of 1-2 microns. The tendency of these particles to aggregate can be rationalized by the low ζ-potentials of the DNA/polymer particles observed under these conditions. For example, complexes formed from polymer 1 at DNA/polymer ratios above 1:10 had average ζ-potentials of +4.51 (±0.50) mV. The ζ-potentials of complexes formed from polymer 2 at DNA/polymer ratios above 1:20 were lower, reaching a limiting value of ±1.04 (±57) mV. These differences correlate with the estimated $pK_a$ values for these polymers, as the surfaces of particles formed from polymer 1 would be expected to slightly more protonated than particles formed from polymer 2 at pH=7.0.

Figure 4:
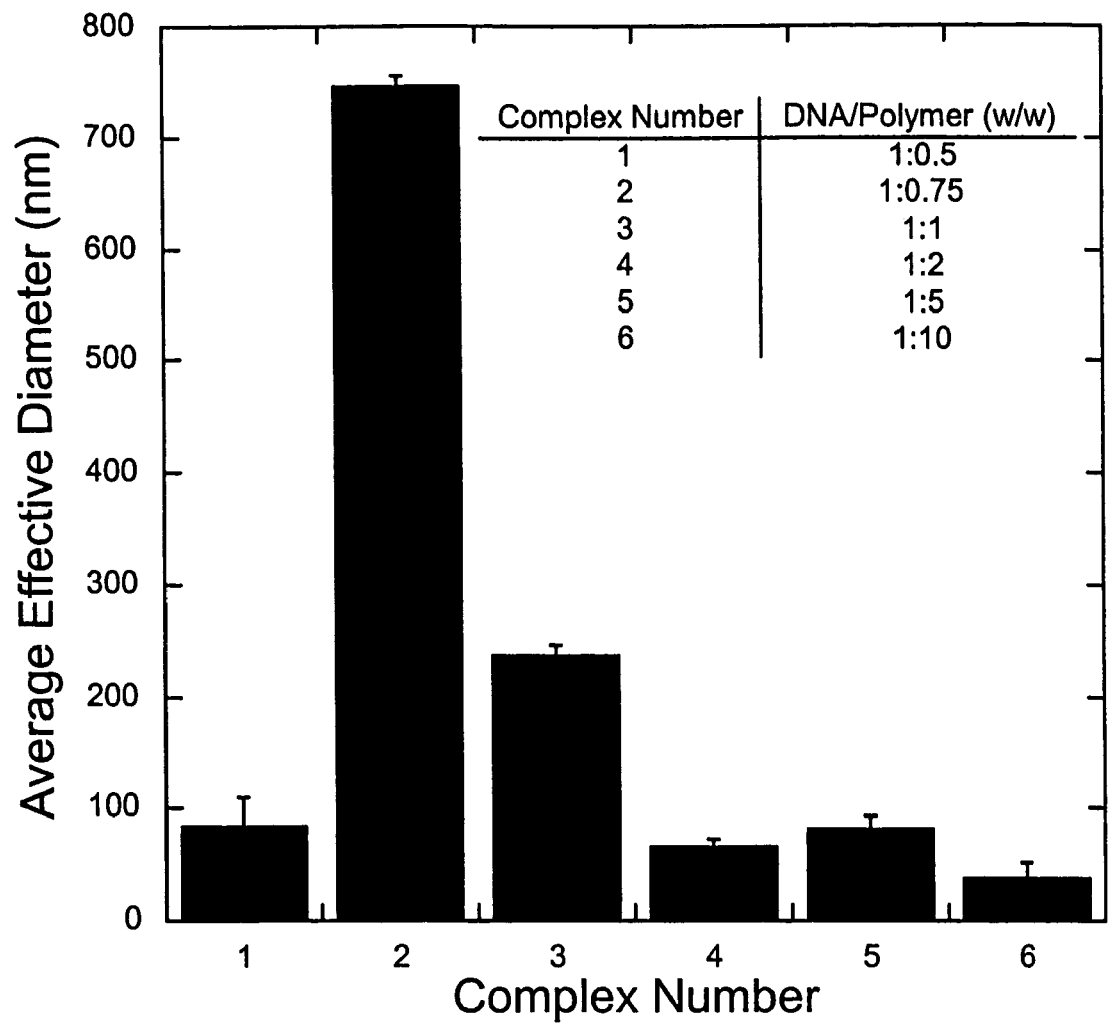
FIG. 4 shows the average effective diameters of DNA/polymer complexes formed from pCMV-Luc plasmid and polymer 3 ($M_n$=31,000) as a function of polymer concentration.

Polymer 3 formed complexes with diameters in the range of 50-150 nm at DNA/polymer ratios above 1:2. As a representative example, FIG. 4 shows the average effective diameters of particles formed with polymer 3 as a function of polymer concentration. The diameters of the particles varied within the above range from experiment to experiment under otherwise identical conditions, possibly due to subtle differences during the stirring or addition of DNA solutions during complex formation (The order of addition of polymer and DNA solutions had considerable impact on the nature of the resulting DNA/polymer complexes. In order to form small particles, for example, it was necessary to add the DNA solution to a vortexing solution of polymer. For cases in which polymer solutions were added to DNA, only large micron-sized aggregates were observed. Thus, it is possible that subtle differences in stirring or rate of addition could be responsible for variation in particle size). The ζ-potentials for complexes formed from polymer 3 were on the order of ±10 to ±15 mV at DNA/polymer ratios above 1:1, and the complexes did not aggregate extensively over an 18 hour period (pH=7, 25° C.) The positive ζ-potentials of these complexes may be significant beyond the context of particle stability, as net positive charges on particle surfaces may play a role in triggering endocytosis (Kabanov et al. *Bioconjugate Chem.* 6:7-20, 1995; Lim et al. *J. Am. Chem. Soc.* 122:6524-6525, 2000; Behr *Chimia* 51:34-36, 1997; Demeneix et al., in *Artificial Self-Assembling Systems for Gene Delivery* (Felgner et al, Eds.), American Chemical Society, Washington, D.C., 1996, pp. 146-151; Kabanov et al., in *Self-Assembling Complexes for Gene Delivery: From Laboratory to Clinical Trial*, John Wiley and Sons, New York, 1998; each of which is incorporated herein by reference).

Particles formed from polymer 3 were also relatively stable at 37° C. For example, a sample of DNA/3 (DNA/3=1:5, average diameter=83 nm) was incubated at 37° C. for 4 hours. After 4 hours, a bimodal distribution was observed consisting of a fraction averaging 78 nm (>98% by number, 70% by volume) and a fraction of larger aggregates with average diameters of approximately 2.6 microns. These results suggest that the degradation of complexes formed from polymer 3 occurred more slowly than the degradation of polymer in solution, or that partial degradation did not significantly affect the stability of the particles. The apparently increased stability of DNA/polymer complexes formed from degradable polycations relative to the degradation of the polymers in solution has also been observed for DNA/polymer complexes formed from poly(4-hydroxy-L-proline ester) (Lim et al. *J. Am. Chem. Soc.* 121:5633-5639, 1999; incorporated herein by reference).

Figure 5:
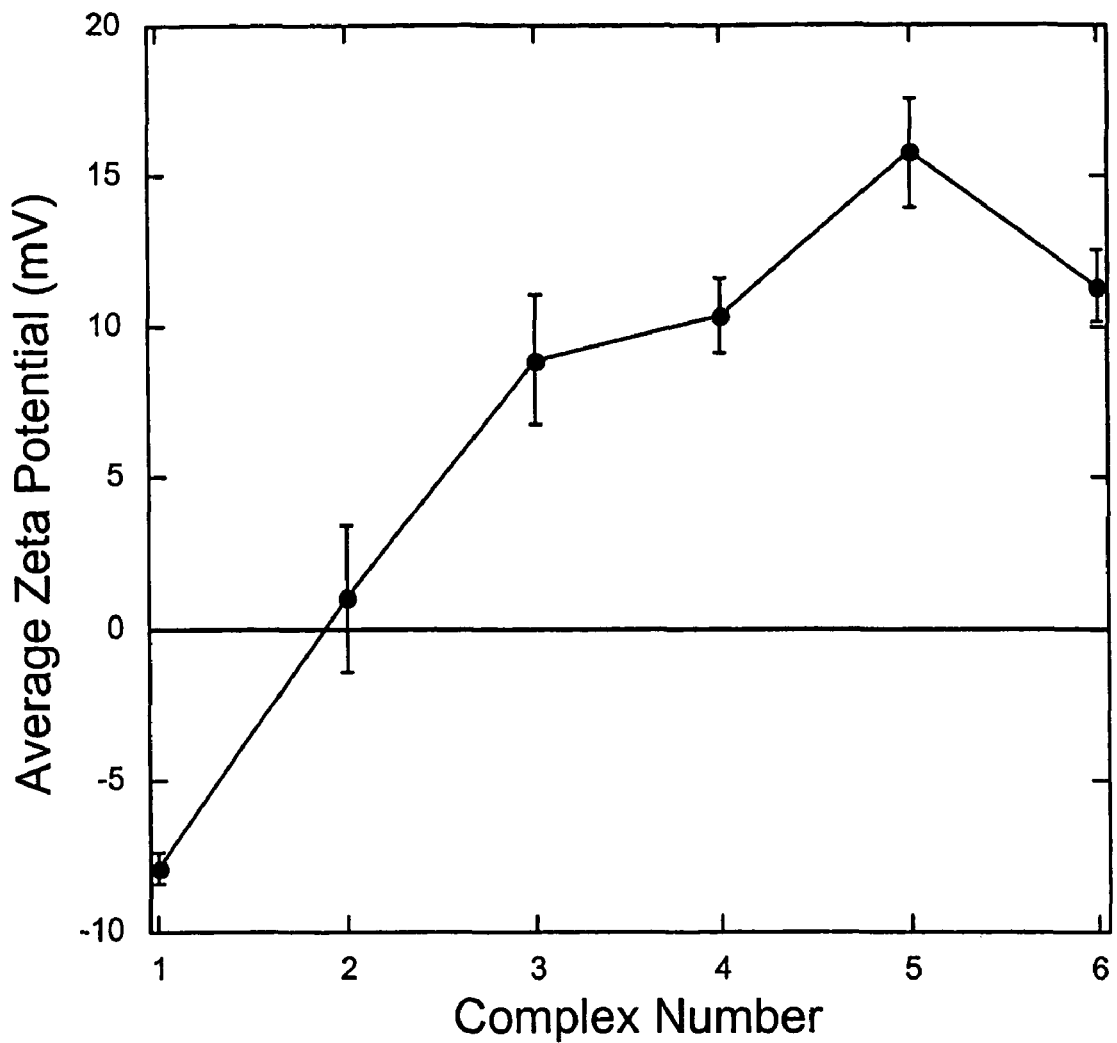
FIG. 5 shows average ζ-potentials of DNA/polymer complexes formed from pCMV-Luc plasmid and polymer 3 ($M_n$=31,000) as a function of polymer concentration. The numbers for each complex correspond to the complex numbers in FIG. 4.

The particle size and ζ-potential data in FIGS. 4 and 5 are consistent with models of DNA condensation observed with other polycations (Kabanov et al. *Bioconjugate Chem.* 6:7-20, 1995; Putnam et al. *Macromolecules* 32:3658-3662, 1999; Lim et al. *J. Am. Chem. Soc.* 121:5633-5639, 1999; Lim et al. *J. Am. Chem. Soc.* 122:6524-6525, 2000; Gonzalez et al. *Bioconjugate Chem.* 10:1068-1074, 1999; each of which is incorporated herein by reference). DNA is compacted into small negatively charged particles at very low polymer concentrations and particle sizes increase with increasing polymer concentration (Accurate light scattering data could not be obtained for DNA alone or for DNA/polymer associated species at DNA/polymer ratios lower than 1:0.5, since flexible, uncondensed DNA does not scatter light as extensively as compacted DNA (Kabanov et al., in *Self-Assembling Complexes for Gene Delivery: From Laboratory to Clinical Trial*, John Wiley and Sons, New York, 1998; incorporated herein by reference).). Complexes reach a maximum diameter as charge neutrality is achieved and aggregation occurs. Particle sizes decrease sharply at DNA/polymer concentrations above charge neutrality up to ratios at which additional polymer does not contribute to a reduction in particle diameter. This model is confirmed by ζ-potential measurements made on complexes formed from these polymers. As shown in FIG. 5, the ζ-potentials of polymer/DNA particles formed from polymer 3 were negative at low polymer concentrations and charge neutrality was achieved near DNA/polymer ratios of 1:0.75, resulting in extensive aggregation. The ζ-potentials of the particles approached a limiting value ranging from ±10 to ±15 mV at DNA/polymer ratios above 1:2.

The average diameters of the complexes described above fall within the general size requirements for cellular endocytosis. We have initiated transfection experiments employing the NIH 3T3 cell line and the luciferase reporter gene (pCMV-Luc). Thus far, polymers 1 and 2 have shown no transfection activity in initial screening assays. By contrast, polymer 3 has demonstrated transfection efficiencies exceeding those of PEI under certain conditions. Transfection experiments were performed according to the following general protocol: Cells were grown in 6-well plates at an initial seeding density of 100,000 cells/well in 2 mL of growth medium. Cells were grown for 24 hours after which the growth medium was removed and replaced with 2 mL of serum-free medium. DNA/polymer complexes were formed as described in the Experimental Section (2 µg DNA, DNA/3=1:2 (w/w), 100 µL in MES (pH=6.0)] and added to each well. DNA/PEI complexes were formed at a weight ratio of 1:0.75, a ratio generally found in our laboratory to be optimal for PEI transfections. Transfections were carried out in serum-free medium for 4 hours, after which medium was replaced with growth medium for 20 additional hours. Relative transfection efficiencies were determined using luciferase (Promega) and cell protein assay (Pierce) kits. Results are expressed as relative light units (RLU) per mg of total cell protein: for complexes of polymer 3, $1.07 (\pm 0.43) \times 10^6$ RLU/mg; for PEI complexes, $8.07 (\pm 0.16) \times 10^5$ RLU/mg). No luciferase expression was detected for control experiments employing naked DNA or performed in the absence of DNA. These transfection data are the results of initial screening experiments. These data suggest that polymers of this general structure hold promise as synthetic vectors for gene delivery and are interesting candidates for further study. The relative efficacy of polymer 3 relative to PEI is interesting, as our initial screening experiments were performed in the absence of chloroquine and polymer 3 does not currently incorporate an obvious means of facilitating endosomal escape. It should be noted, however, that the $pK_a$ values of the amines in these polymers can be "tuned" to fall more directly within the range of physiologically relevant pH using this modular synthetic approach. Therefore, it will be possible to further engineer the "proton sponge" character (Behr *Chimia* 51:34-36, 1997; Demeneix et al., in *Artificial Self-Assembling Systems for Gene Delivery* (Felgner et al., Eds.), American Chemical Society, Washington, D.C., 1996, pp. 146-151; Kabanov et al., in *Self-Assembling Complexes for Gene Delivery: From Laboratory to Clinical Trial*, John Wiley and Sons, New York, 1998; each of which is incorporated herein by reference) of these polymers, and thus enhance their transfection efficacies, directly through the incorporation of or copolymerization with different diamine monomers.

Summary

A general strategy for the preparation of new degradable polymeric DNA transfection vectors is reported. Poly(β-amino esters) 1-3 were synthesized via the conjugate addition of N,N'-dimethylethylenediamine, piperazine, and 4,4'-trimethylenedipiperidine to 1,4-butanediol diacrylate. The amines in the bis(secondary amine) monomers actively participate in bond-forming processes during polymerization, obviating the need for amine protection/deprotection processes which characterize the synthesis of other poly(amino esters). Accordingly, this approach enables the generation of a variety of structurally diverse polyesters containing tertiary amines in their backbones in a single step from commercially available staring materials. Polymers 1-3 degraded hydrolytically in acidic and alkaline media to yield 1,4-butanediol and β-amino acids 4a-6a and the degradation kinetics were investigated at pH 5.1 and 7.4. The polymers degraded more rapidly at pH 7.4 than at pH 5.1, consistent with the pH/degradation profiles reported for other poly(amino esters). An initial screening assay designed to determine the effects of polymers 1-3 on cell growth and metabolism suggested that these polymers and their hydrolytic degradation products were non-cytotoxic relative to PEI, a non-degradable cationic polymer conventionally employed as a transfection vector.

Polymers 1-3 interacted electrostatically with plasmid DNA at physiological pH, initiating self-assembly processes that resulted in nanometer-scale DNA/polymer complexes. Agarose gel electrophoresis, quasi-elastic dynamic light scattering (QELS), and zeta potential measurements were used to determine the extent of the interactions between the oppositely charged polyelectrolytes. All three polymers were found to condense DNA into soluble DNA/polymer particles on the order of 50-200 nm. Particles formed from polymers 1 and 2 aggregated extensively, while particles formed from polymer 3 exhibited positive ζ-potentials (e.g., +10 to +15 mV) and did not aggregate for up to 18 hours. The nanometer-sized dimensions and reduced cytotoxicities of these DNA/polymer complexes suggest that polymers 1-3 may be useful as degradable polymeric gene transfection vectors. A thorough understanding of structure/activity relationships existing for this class of polymer will expedite the design of safer polymer-based alternatives to viral transfection vectors for gene therapy.

Example 2

Rapid, pH-Triggered Release from Biodegradable Poly(β-Amino Ester) Microspheres within the Ranger of Intracellular pH Experimental Section Fabrication of microspheres. The optimized procedure for the fabrication of microspheres was conducted in the following general manner: An aqueous solution of rhodamine-conjugated dextran (200 µL of a 10 µg/µL solution, $M_n \approx 70$ kD) was suspended in a solution of poly-1 in $CH_2Cl_2$ (200 mg of poly-1 in 4 mL $CH_2Cl_2$, $M_n \approx 10$ kD), and the mixture was sonicated for 10 seconds to form a primary emulsion. The cloudy pink emulsion was added directly to a rapidly homogenized (5,000 rpm) solution of poly(vinyl alcohol) [50 mL, 1% PVA (w/w)] to form the secondary emulsion. The secondary emulsion was homogenized for 30 seconds before adding it to a second aqueous PVA solution [100 mL, 0.5% PVA (w/w)]. Direct analysis of the microsphere suspension using a Coulter microparticle analyzer revealed a mean particle size of approximately 5 micrometers. The secondary emulsion was stirred for 2.5 hours at room temperature, transferred to a cold room (4° C.), and stirred for an additional 30 minutes. Microspheres were isolated at 4° C. via centrifugation, resuspended in cold water, and centrifuged again to remove excess PVA. The spheres were resuspended in water (15 mL) and lyophilized to yield a pink, fluffy powder. Characterization of the lyophilized microspheres was performed by optical, fluorescence, and scanning electron microscopies as described. Zeta potential was determined using a Brookhaven Instruments ZetaPALS analyzer.

Discussion

Microparticles formed from biodegradable polymers are attractive for use as delivery devices, and a variety of polymer-based microspheres have been employed for the sustained release of therapeutic compounds (Anderson *Nature* 392 (Suppl.):25-30, 1996; Friedman *Nature Med.* 2:144-147, 1996; Crystal *Science* 270:404-410, 1995; Mulligan *Science* 260:926-932, 1993; Luo et al. *Nat. Biotechnol.* 18:33-37, 2000; Behr *Acc. Chem. Res.* 26:274-278, 1993; each of which is incorporated herein by reference). However, for small-molecule-, protein-, and DNA-based therapeutics that require intracellular administration and trafficking to the cytoplasm, there is an increasing demand for new materials that facilitate triggered release in response to environmental stimuli such as pH (Zauner et al. *Adv. Drug Del. Rev.* 30:97-113, 1998; incorporated herein by reference). Following endocytosis, the pH within cellular endosomal compartments is lowered, and foreign material is degraded upon fusion with lysosomal vesicles (Kabanov et al. *Bioconjugate Chem.* 6:7-20, 1995; incorporated herein by reference). New materials that release molecular payloads upon changes in pH within the intracellular range and facilitate escape from hostile intracellular environments could have a fundamental and broad-reaching impact on the administration of hydrolytically- and/or enzymatically-labile drugs (Zauner et al. *Adv. Drug Del. Rev.* 30:97-113, 1998; Kabanov et al. *Bioconjugate Chem.* 6:7-20, 1995; each of which is incorporated herein by reference). Herein, the fabrication of pH-responsive polymer microspheres that release encapsulated contents quantitatively and essentially instantaneously upon changes in pH within the intracellular range is reported.

The synthesis of poly(β-amino ester) 1 has been described above in Example 1 (Miller *Angew. Chem. Int. Ed.* 37:1768-1785, 1998; Hope et al. *Molecular Membrane Technology* 15:1-14, 1998; Deshmukh et al. *New J. Chem.* 21:113-124, 1997; each of which is incorporated herein by reference). Poly-1 is hydrolytically degradable, was non-cytotoxic in initial screening assays, and is currently under investigation as a synthetic vector for DNA delivery in gene therapy applications. The solubility of the polymer in aqueous media is directly influenced by solution pH. Specifically, the solid, unprotonated polymer is insoluble in aqueous media in the pH range 7.0 to 7.4, and the transition between solubility and insolubility occurs at a pH around 6.5. Based on the differences between extracellular and endosomal pH (7.4 and 5.0-6.5, respectively), we hypothesized that microspheres formed from poly-1 might be useful for the encapsulation and triggered release of compounds within the range of intracellular pH.

The encapsulation of therapeutic compounds within polymer microspheres is often achieved employing a double emulsion process (O'Donnell et al. *Adv. Drug Delivery Rev.* 28:25-42, 1997; incorporated herein by reference). The double emulsion process is well established for the fabrication of microspheres from hydrophobic polymers such as poly(lactic-co-glycolic acid) (PLGA), a biodegradable polymer conventionally employed in the development of drug delivery devices (Anderson et al. *Adv. Drug Delivery Rev.* 28:5-24, 1997; Okada *Adv. Drug Delivery Rev.* 28:43-70, 1997; each of which is incorporated herein by reference). Preliminary experiments demonstrated the feasibility of the double emulsion process for the encapsulation of water-soluble compounds using poly-1. Rhodamine-conjugated dextran was chosen as a model for subsequent encapsulation and release studies for several reasons: 1) rhodamine is fluorescent, allowing loading and release profiles to be determined by fluorescence spectroscopy, 2) loaded microspheres could be imaged directly by fluorescence microscopy, and 3) the fluorescence intensity of rhodamine is relatively unaffected by pH within the physiological range (Haugland, *Handbook of Fluorescent Probes and Research Chemicals*, 6th ed., Molecular Probes, Inc., 1996, p. 29; incorporated herein by reference).

Microspheres encapsulating labeled dextran were fabricated from poly-1 and compared to controls formed from PLGA. The size distributions of microspheres formed from poly-1 correlated well with the distributions of PLGA microspheres within the range of 5-30 μm. Average particle sizes could be controlled by variations in experimental parameters such as homogenization rates and aqueous/organic solvent ratios (O'Donnell et al. *Adv. Drug Delivery Rev.* 28:25-42, 1997; incorporated herein by reference). In contrast to PLGA microspheres, however, spheres formed from poly-1 aggregated extensively during centrifugation and washing steps (see Experimental Section above). Microspheres resuspended at pH 7.4 consisted primarily of large aggregates, and scanning electron microscopy (SEM) images revealed clusters of spheres that appeared to be physically joined or "welded" (data not shown).

Figure 6:
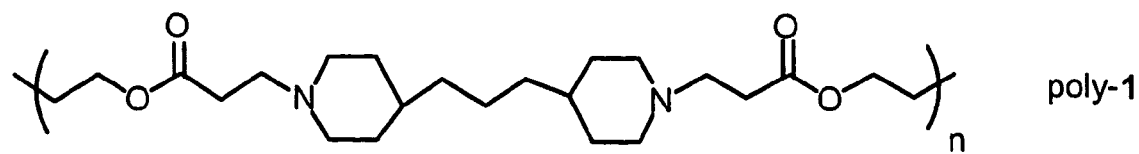
FIG. 6 is an SEM image of rhodamine/dextran-loaded microspheres fabricated from polymer 1.
Figure 6:
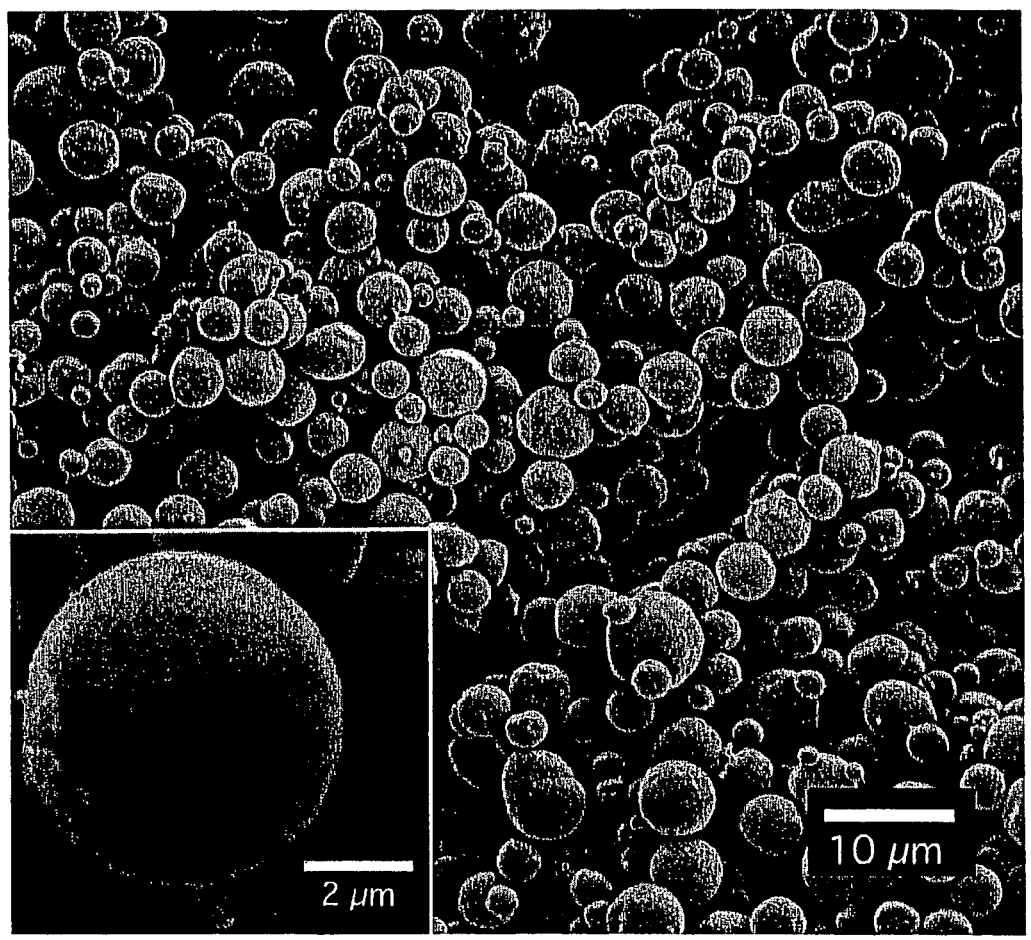

It was found that aggregation could be eliminated if centrifugation and washing were conducted at reduced temperatures (4° C.), presumably due to the hardening of the polymer spheres at this lower temperature. SEM images of dextran-loaded poly-1 microspheres prepared in the 8-10 μm range revealed significant fracturing and the formation of large holes on their surfaces. Microspheres targeted in the range of 4-6 μm, however, were essentially free of cracks, holes, and other defects (FIG. 6). Microspheres formulated for subsequent release experiments were fabricated in the smaller (<6 μm) range. Encapsulation efficiencies for loaded poly-1 microspheres, determined by dissolving the spheres at pH 5.1 and measuring fluorescence intensity, were as high as 53%.

Figure 8A:
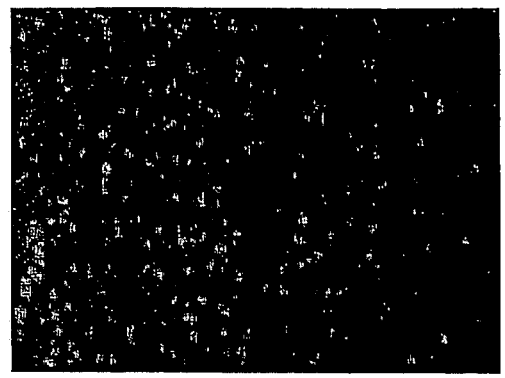
FIG. 8a shows a representative fluorescence microscopy image of rhodamine/dextran-loaded polymer 1 microspheres suspended in HEPES buffer (pH 7.4).

Suspensions of dried poly-1 microspheres at pH=7.4 consisted primarily of single, isolated microspheres as determined by optical and fluorescence microscopy (FIG. 8a). The zeta potential (ζ) of microparticle suspensions of poly-1 microspheres at pH 7 was ±3.75 (±0.62) mV, suggesting that the surfaces of the microspheres carry an overall positive charge at physiological pH. This could be relevant to the targeting of these microspheres for cellular uptake, because net positive charges on particle surfaces may play a role in triggering endocytosis (Zauner et al. *Adv. Drug Delivery Rev.* 30:97-113, 1998; incorporated herein by reference).

Figure 40:
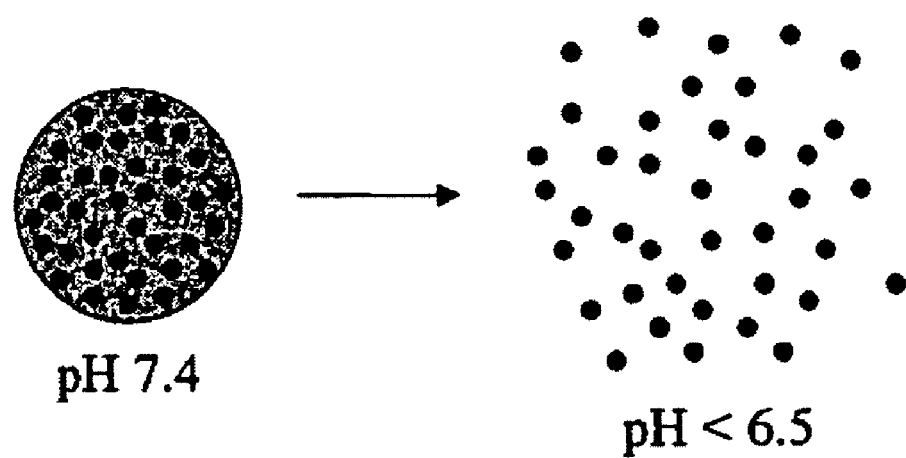
FIG. 40 shows an illustration of a microsphere dissolving when the pH of the suspending medium was lowered to less than 6.5.

Poly-1 microspheres suspended at pH 7.4 remained stable toward aggregation and degradation for several weeks (by visual inspection), but the microspheres dissolved instantly when the pH of the suspending medium was lowered between 5.1 and 6.5, as shown in FIG. 40.

Figure 7:
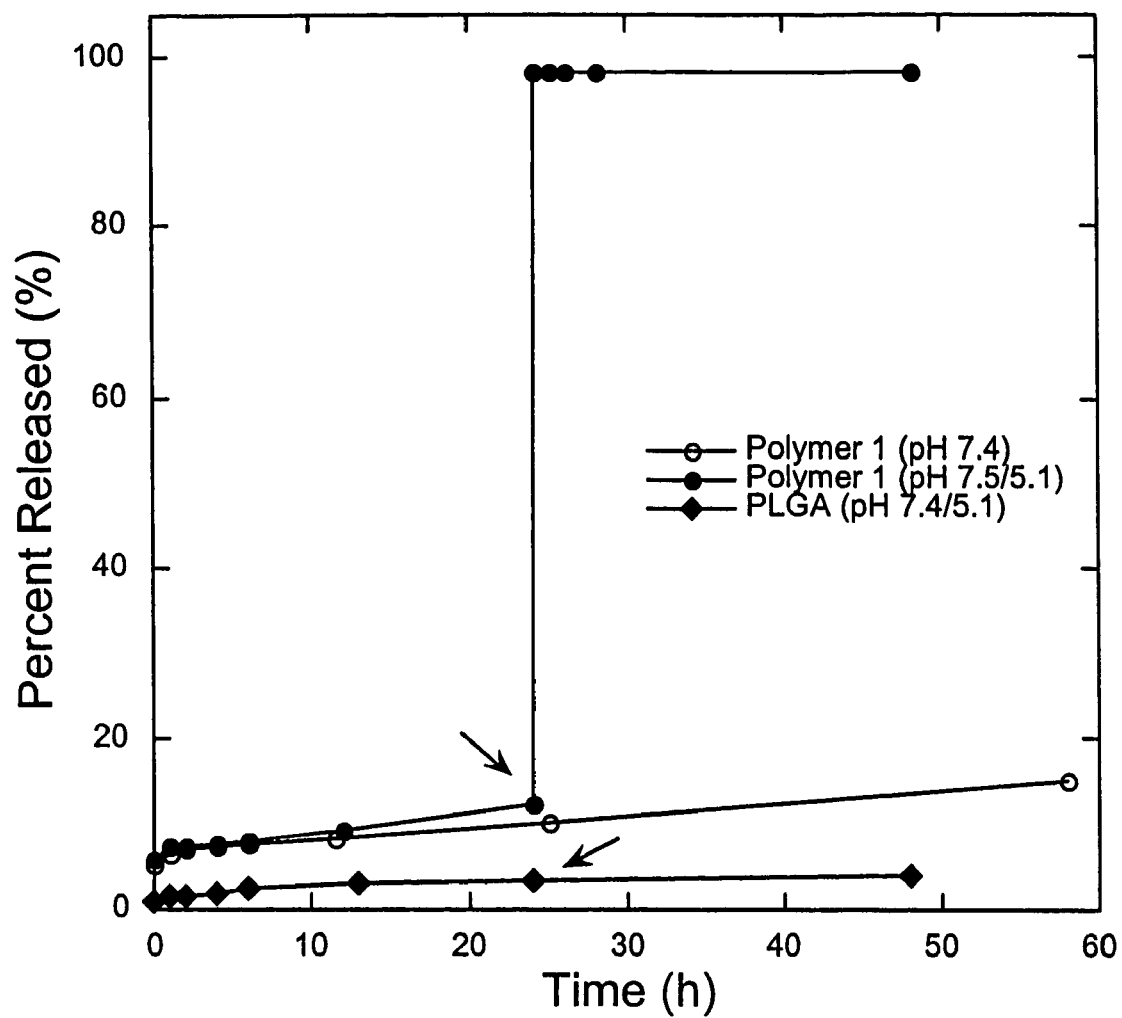
FIG. 7 shows the release profiles of rhodamine/dextran from polymer 1 and PLGA microspheres at various pH values. The arrows indicate the points at which HEPES buffer (pH 7.4) was exchanged with acetate buffer (pH 5.1).

The release of labeled dextran from poly-1 microspheres was determined quantitatively by fluorescence microscopy (FIG. 7). The release profile at pH 7.4 was characterized by a small initial burst in fluorescence (7-8%) which reached a limiting value of about 15% after 48 hours. This experiment demonstrated that the degradation of poly-1 was relatively slow under these conditions and that greater than 90% of encapsulated material could be retained in the polymer matrix for suitably long periods of time at physiological pH.

Figure 8B:
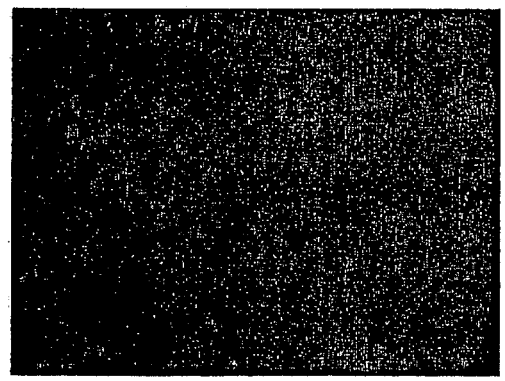
FIG. 8b shows a sample of loaded polymer 1 microspheres at pH 7.4 after addition of acetate buffer (pH 5.1). The direction of diffusion of acid is from the top right to the bottom left of the image (elapsed time 5 seconds).

To examine the application of poly-1 microspheres to the triggered release of encapsulated drugs in the endosomal pH range, we conducted a similar experiment in which the pH of the suspension medium was changed from 7.4 to 5.1 during the course of the experiment. As shown in FIG. 7, the microspheres dissolved rapidly when the suspension buffer was exchanged with acetate buffer (0.1 M, pH=5.1), resulting in essentially instantaneous and quantitative release of the labeled dextran remaining in the polymer matrices. In sharp contrast, the release from dextran-loaded PLGA microspheres did not increase for up to 24 hours after the pH of the suspending medium was lowered (FIG. 7). FIG. 8 shows fluorescence microscopy images of: (a) a sample of dextran-loaded microspheres at pH 7.4; and (b) a sample to which a drop of acetate buffer was added at the upper right edge of the microscope coverslip. The rapid release of rhodamine-conjugated dextran was visualized as streaking extending from the dissolving microspheres in the direction of the diffusion of added acid and an overall increase in background fluorescence (elapsed time≈5 seconds).

When targeting therapeutic compounds for intracellular delivery via endocytosis or phagocytosis, it is not only important to consider a means by which the drug can be released from its carrier, but also a means by which the drug can escape endosomal compartments prior to being routed to lysosomal vesicles (Luo et al. *Nat. Biotechnol.* 18:33-37, 2000; Zauner et al. *Adv. Drug Delivery Rev.* 30:97-113, 1998; each of which is incorporated herein by reference). One strategy for facilitating endosomal escape is the incorporation of weak bases, or "proton sponges," which are believed to buffer the acidic environment within an endosome and disrupt endosomal membranes by increasing the internal osmotic pressure within the vesicle (Demeneix et al., in *Artificial Self-Assembling Systems for Gene Delivery* (Felgner et al, Eds.), American Chemical Society, Washington, D.C., 1996, pp. 146-151; incorporated herein by reference). Poly-1 microspheres are capable of releasing encapsulated material in the endosomal pH range via a mechanism (dissolution) that involves the protonation of amines in the polymer matrix. Thus, in addition to the rapid release of drug, poly-1 microspheres may also provide a membrane-disrupting means of endosomal escape, enhancing efficacy by prolonging the lifetimes of hydrolytically unstable drugs contained in the polymer matrix.

Microspheres fabricated from poly-1 could represent an important addition to the arsenal of pH-responsive materials applied for intracellular drug delivery, such as pH-responsive polymer/liposome formulations (Gerasimov et al. *Adv. Drug Delivery Rev.* 38:317-338, 1999; Linhart et al. *Langmuir* 16:122-127, 2000; Linhardt et al. *Macromolecules* 32:4457-4459, 1999; each of which is incorporated herein by reference). In contrast to many liposomal formulations, polymer microspheres are physically robust and can be stored dried for extended periods without deformation, decomposition, or degradation (Okada *Adv. Drug Delivery Rev.* 28:43-70, 1997; incorporated herein by reference)—an important consideration for the formulation and packaging of new therapeutic delivery systems. The microspheres investigated in this current study fall within the size range of particles commonly used to target delivery to macrophages (Hanes et al. *Adv. Drug Delivery Rev.* 28:97-119, 1997; incorporated herein by reference). The rapid pH-release profiles for the poly-1 microspheres described above may therefore be useful in the design of new DNA-based vaccines which currently employ PLGA as an encapsulating material (Singh et al. *Proc. Natl. Acad. Sci. USA* 97:811-816, 2000; Ando et al. *J. Pharm. Sci.* 88:126-130, 1999; Hedley et al. *Nat. Med.* 4:365-368, 1998; each of which is incorporated herein by reference).

Example 3

Accelerated Discovery of Synthetic Transfection Vectors: Parallel Synthesis and Screening of a Degradable Polymer Library Introduction The safe and efficient delivery of therapeutic DNA to cells represents a fundamental obstacle to the clinical success of gene therapy (Luo et al. *Nat. Biotechnol.* 18:33-37, 2000; Anderson *Nature* 392 Suppl.:25-30, 1996; each of which is incorporated herein by reference). The challenges facing synthetic delivery vectors are particularly clear, as both cationic polymers and liposomes are less effective at mediating gene transfer than viral vectors. The incorporation of new design criteria has led to recent advances toward functional delivery systems (Lim et al. *J. Am. Chem. Soc.* 123:2460-2461, 2001; Lim et al. *J. Am. Chem. Soc.* 122:6524-6525, 2000; Hwang et al. *Bioconjugate Chem.* 12:280-290, 2001; Putnam et al. *Proc. Natl. Acad. Sci. USA* 98:1200-1205, 2001; Benns et al. *Bioconjugate Chem.* 11:637-645, 2000; Midoux et al. *Bioconjugate Chem.* 10:406-411, 1999; each of which is incorporated herein by reference). However, the paradigm for the development of polymeric gene delivery vectors remains the incorporation of these design elements into materials as part of an iterative, linear process—an effective, albeit slow, approach to the discovery of new vectors. Herein, we report a parallel approach suitable for the synthesis of large libraries of degradable cationic polymers and oligomers and the discovery of new synthetic vector families through rapid cell-based screening assays (for a report on the parallel synthesis and screening of degradable polymers for tissue engineering, see: Brocchini et al. *J. Am. Chem. Soc.* 119:4553-4554, 1997; incorporated herein by reference).

Experimental Section

General Considerations. All manipulations involving live cells or sterile materials were performed in a laminar flow hood using standard sterile technique. Gel permeation chromatography (GPC) was performed using a Hewlett Packard 1100 Series isocratic pump, a Rheodyne Model 7125 injector with a 100-µL injection loop, and two PL-Gel mixed-D columns in series (5 µm, 300×7.5 mm, Polymer Laboratories, Amherst, Mass.). THF/0.1M piperidine was used as the eluent at a flow rate of 1.0 mL/min. Data was collected using an Optilab DSP interferometric refractometer (Wyatt Technology, Santa Barbara, Calif.) and processed using the TriSEC GPC software package (Viscotek Corporation, Houston, Tex.). The molecular weights and polydispersities of the polymers are reported relative to monodisperse polystyrene standards.

Materials. Primary amine and secondary amine monomers 1-20 were purchased from Aldrich Chemical Company (Milwaukee, Wis.), Lancaster (Lancashire, UK), Alfa Aesar Organics (Ward Hill, Mass.), and Fluka (Milwaukee, Wis.). Diacrylate monomers A-G were purchased from Polysciences, Inc. (Warrington, Pa.), Alfa Aesar, and Scientific Polymer Products, Inc. (Ontario, N.Y.). All monomers were purchased in the highest purity available (from 97% to 99+%) and were used as received without additional purification. Plasmid DNA containing the firefly luciferase reporter gene (pCMV-Luc) was purchased from Elim Biopharmaceuticals, Inc. (San Francisco, Calif.) and used without further purification. (3-[4,5-dimethylthiazol-2-yl]-2,5-diphenyltetrazolium bromide (MTT) was purchased from Sigma Chemical Company (St. Louis, Mo.). Monkey kidney fibroblasts (COS-7 cells) used in transfection assays were purchased from American Type Culture Collection (Manassas, Va.) and grown at 37° C., 5% CO$_2$ in Dulbecco's modified Eagle's medium, 90%; fetal bovine serum, 10%; penicillin, 100 units/mL; streptomycin, 100 μg/mL. Luciferase detection kits used in high-throughput transfection assays were purchased from Tropix (Bedford, Mass.). All other materials and solvents were used as received without additional purification.

Synthesis of Polymer Library. All 140 polymerization reactions were conducted simultaneously as an array of individually labeled vials according to the following general protocol. Individual exceptions are noted where appropriate. Amine monomers 1-20 (2.52 mmol) were charged into appropriately labeled vials (as shown below): liquid monomers were measured and transferred quantitatively using microliter pipettes; solid monomers were weighed directly into each vial. Anhydrous CH$_2$Cl$_2$ (1 mL) was added to each vial. One equivalent of liquid diacrylates A-F (2.52 mmol) was added to each appropriate reaction vial using a microliter pipette, and the vial was capped tightly with a Teflon-lined cap. One equivalent of semi-solid diacrylate G was added to the appropriate vials as a solution in CH$_2$Cl$_2$ (2.52 mmol, 1 mL of a 2.52M solution in CH$_2$Cl$_2$) and the vials were tightly capped. An additional aliquot of CH$_2$Cl$_2$ (2 mL) was added to the reaction vials containing 19 and 20 to aid in the solubility of these monomers. The tightly capped vials were arrayed in two plastic test tube racks and secured to an orbital shaker in a 45° C. oven. (CAUTION: The heating of capped vials represents a possible explosion hazard. Oven temperature was monitored periodically for one week prior to the experiment to ensure reliable thermal stability. Temperatures were found to vary within +/−1° C. during this time period. Several test vials were monitored prior to conducting the larger experiment). The reaction vials were shaken vigorously at 45° C. for 5 days and allowed to cool to room temperature. Vials were placed in a large dessicator and placed under aspirator vacuum for 1 day and high vacuum for an additional 5 days to ensure complete removal of solvent. The samples obtained were analyzed by GPC (55% of total library, see Table 2) and used directly in all subsequent screening experiments.

TABLE 2

GPC survey of 55% of the screening library showing molecular weights (M$_w$) and polydispersities (shown in parentheses).

| | A | B | C | D | E | F | G |
|---|---|---|---|---|---|---|---|
| 1 | 5900 (1.93) | 4725 (1.89) | | | 5220 (1.95) | 1690 (1.74) | |
| 2 | 6920 (1.87) | 6050 (1.78) | | | 5640 (1.85) | | |
| 3 | 6690 (1.79) | 6050 (1.78) | | | | | 2060 (1.76) |
| 4 | 7810 (2.49) | 5720 (2.20) | 9720 (2.49) | 7960 (4.08) | 7940 (3.25) | | |
| 5 | 10800 (2.75) | 5000 (2.50) | 15300 (3.17) | 17200 (6.91) | 15300 (3.92) | Insol. | 9170 (2.50) |
| 6 | 21000 (3.70) | 10200 (3.4) | | 18000 (6.06) | | | |
| 7 | 14300 (3.25) | 11880 (3.3) | 20200 (3.44) | 10300 (4.26) | 15500 (4.89) | | 22500 (3.92) |
| 8 | 2310 (1.62) | 11520 (3.60) | | 2230 (1.73) | | | |
| 9 | 1010 (1.33) | 2505 (1.67) | 1240 (1.16) | | | Insol. | |
| 10 | | <1000 | Insol. | | | | |
| 11 | 6800 (1.91) | Insol. | 9440 (1.79) | 5550 (2.23) | 6830 (1.93) | 1990 (1.43) | 6420 (1.75) |
| 12 | 9310 (2.06) | 9100 (2.53) | 11900 (2.18) | 5810 (1.77) | | | 12300 (1.85) |
| 13 | 2990 (1.64) | 3180 (2.12) | 3680 (1.64) | 2550 (1.82) | 3230 (1.82) | | 3580 (1.64) |
| 14 | 1350 (1.35) | 3180 (2.12) | 2110 (1.69) | 1400 (1.4) | 1752 (1.46) | | 2025 (1.62) |
| 15 | | 1550 (1.51) | | | | | |
| 16 | | 16380 (2.60) | | | | | |
| 17 | | 8520 (2.13) | | 7290 (1.94) | | | |
| 18 | | <1000 | | | | | |
| 19 | 12400 (2.28) | 18445 (2.17) | 39700 (1.90) | 17400 (1.93) | 14800 (1.98) | | 13900 (1.86) |
| 20 | 16900 (2.40) | 46060 (3.29) | 49600 (2.25) | 30700 (2.72) | 18700 (2.72) | | 17100 (2.22) |

Determination of Water Solubility. The solubilities of all samples sample were determined simultaneously at a concentration of 2 mg/mL in the following general manner. Each polymer sample (5 mg) was weighed into a 12 mL scintillation vial and 2.5 mL of acetate buffer (25 mM, pH=5.0) was added to each sample using an a pipettor. Samples were shaken vigorously at room temperature for 1 hour. Each sample was observed visually to determine solubility.

Agarose Gel Electrophoresis Assay. The agarose gel electrophoresis assay used to determine the ability of polymers to form complexes with DNA was performed in the following manner. Using the solutions prepared in the above solubility assay (2 mg/mL in acetate buffer, 25 mM, pH=5.0), stock solutions of the 70 water-soluble polymers were arrayed into a 96-well cell culture plate. DNA/polymer complexes were formed at a ratio of 1:5 (w/w) by transferring 10 μL of each polymer solution from the stock plate to a new plate using a multichannel pipettor. Each polymer was further diluted with 90 µL of acetate buffer (25 mM, pH=5.0, total volume=100 µL) and the plate was shaken for 30 seconds on a mechanical shaker. An aqueous solution of plasmid DNA (100 µL of a 0.04 µg/µL solution) was added to each well in the plate and the solutions were vigorously mixed using a multichannel pipettor and a mechanical shaker. DNA/polymer complexes were formed at a ratio of 1:20 (w/w) in the same manner with the following exceptions: 40 µL of polymer stock solution was transferred to a new plate and diluted with 60 µL of acetate buffer (total volume=100 µL) prior to adding the aqueous DNA solution (100 µL). DNA/polymer complexes were incubated at room temperature for 30 minutes, after which samples of each solution (15 µL) were loaded into a 1% agarose gel (HEPES, 20 mM, pH=7.2, 500 ng/mL ethidium bromide) using a multichannel pipettor. NOTE: Samples were loaded on the gel with a loading buffer consisting of 10% Ficoll 400 (Amersham Pharmacia Biotech, Uppsala, Sweden) in HEPES (25 mM, pH=7.2). Bromphenol blue was not included as a visual indicator in the loading buffer, since this charged dye appeared to interfere with the complexation of polymer and DNA. Samples were loaded according to the pattern shown in FIG. 9, such that samples corresponding to DNA/polymer ratios of 1:5 and 1:20 were assayed in adjacent positions on the gel. The gel was run at 90V for 30 minutes and DNA bands were visualized by ethidium bromide staining.

General Protocol for Cell Transfection Assays. Transfection assays were performed in triplicate in the following general manner. COS-7 cells were grown in 96-well plates at an initial seeding density of 15,000 cells/well in 200 µL of phenol red-free growth medium (90% Dulbecco's modified Eagle's medium, 10% fetal bovine serum, penicillin 100 units/mL, streptomycin 100 µg/mL). Cells were grown for 24 hours in an incubator, after which the growth medium was removed and replaced with 200 µL of Optimem medium (Invitrogen Corp., Carlsbad, Calif.) supplemented with HEPES (total concentration=25 mM). Polymer/DNA complexes prepared from the 56 water-soluble/DNA-complexing polymers previously identified were prepared as described above at a ratio of 1:20 (w/w)) using a commercially available plasmid containing the firefly luciferase reporter gene (pCMV-Luc). An appropriate volume of each sample was added to the cells using a multichannel pipettor (e.g., 15 µL yielded 300 ng DNA/well; 30 µL yielded 600 ng DNA/well). Controls employing poly(ethylene imine) (PEI) and polylysine, prepared at DNA/polymer ratios of 1:1, were prepared in a similar manner and included with DNA and no-DNA controls. Controls employing Lipofectamine 2000 (Invitrogen Corp.) were performed at several concentrations (0.1, 0.2, 0.4, and 0.6 µL) as described in the technical manual for this product (http://lifetechnologies.com). Cells were incubated for 4 hours, after which the serum-free growth medium was removed and replaced with 100 µL of phenol-red-free growth medium. Cells were incubated for an additional period of time (typically varied between 36 to 60 hours) and luciferase expression was determined using a commercially available assay kit (Tropix, Inc., Bedford, Mass.). Luminescence was quantified in white, solid-bottom polypropylene 96-well plates using a 96-well bioluminescence plate reader. Luminescence was expressed in relative light units and was not normalized to total cell protein in this assay.

Results and Discussion

Poly(β-amino ester)s are hydrolytically degradable, condense plasmid DNA at physiological pH, and are readily synthesized via the conjugate addition of primary or secondary amines to diacrylates (Eq. 1 and 2) (Lynn et al. *J Am. Chem. Soc.* 122:10761-10768, 2000; incorporated herein by reference). An initial screen of model polymers identified these materials as potential gene carriers and demonstrated that structural variations could have a significant impact on DNA binding and transfection efficacies (Lynn et al. *J. Am. Chem. Soc.* 122:10761-10768, 2000; incorporated herein by reference). We reasoned that this approach provided an attractive framework for the elaboration of large libraries of structurally-unique polymers for several reasons: 1) diamine and diacrylate monomers are inexpensive, commercially available starting materials, 2) polymerization can be accomplished directly in a single synthetic step, and 3) purification steps are generally unnecessary as no byproducts are generated during polymerization.

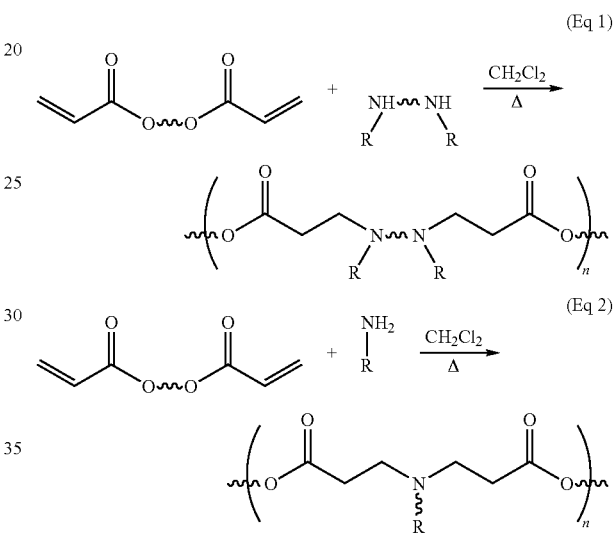

The paucity of commercially available bis(secondary amines) limits the degree of structural diversity that can be achieved using the above synthetic approach. However, the pool of useful, commercially available monomers is significantly expanded when primary amines are considered as potential library building blocks. Because the conjugate addition of amines to acrylate groups is generally tolerant of functionalities such as alcohols, ethers, and tertiary amines (Ferruti et al. *Adv. Polym. Sci.* 58:55-92, 1984; incorporated herein by reference), we believed that the incorporation of functionalized primary amine monomers into our synthetic strategy would serve to broaden structural diversity. Diacrylate monomers A-G and amine monomers 1-20 were selected for the synthesis of an initial screening library.

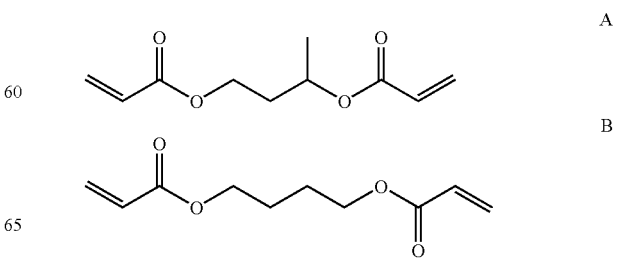

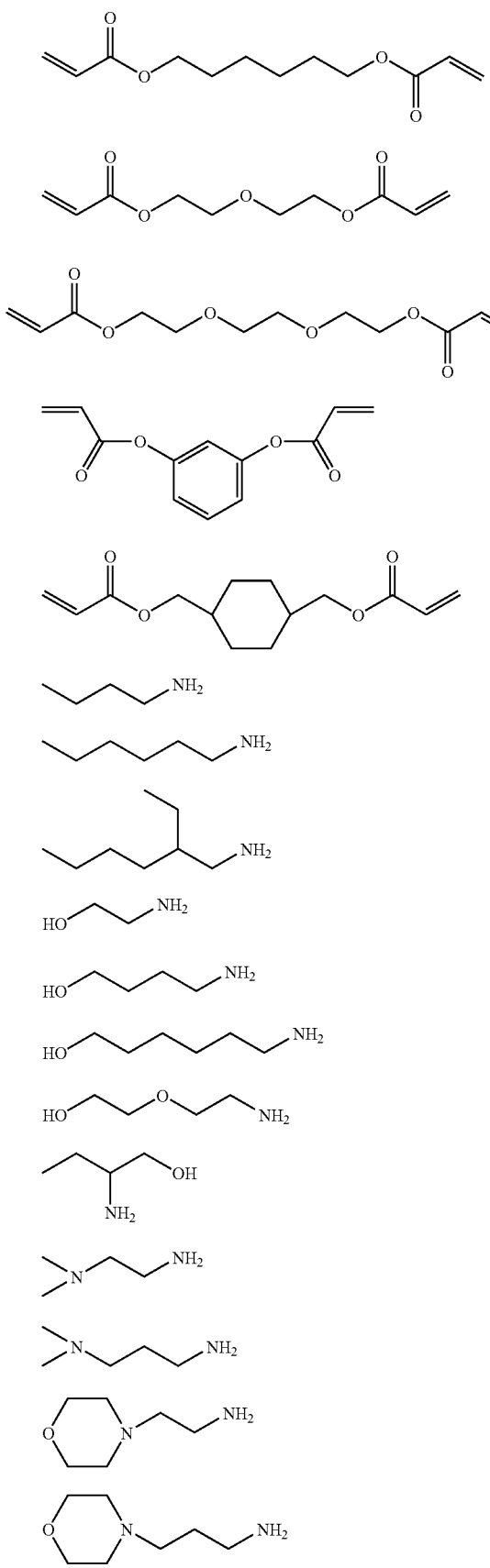
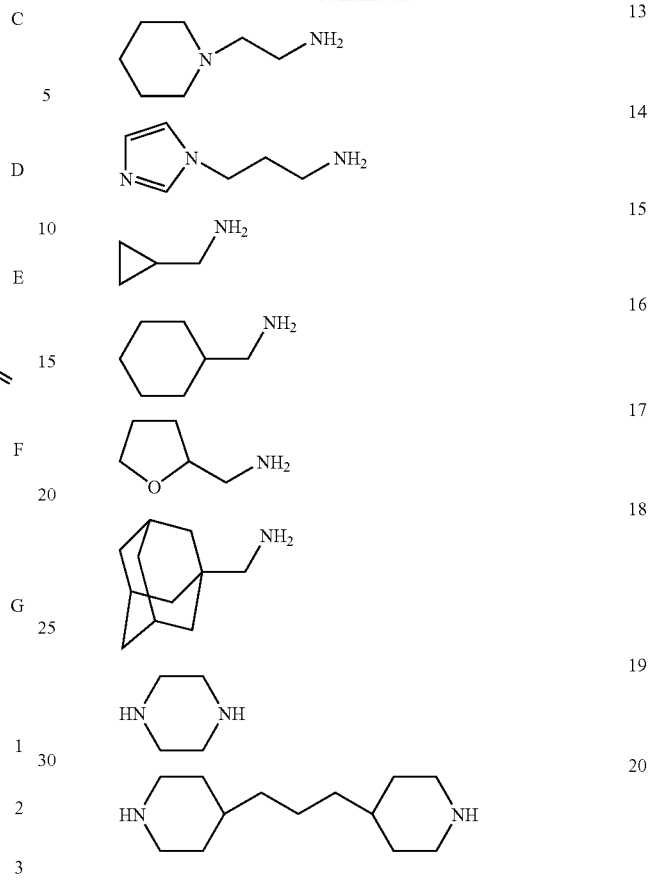

The size of the library constructed from this set of monomers (7 diacrylates×20 amines=140 structurally-unique polymers) was chosen to be large enough to incorporate sufficient diversity, yet small enough to be practical without the need for automation in our initial studies. It was unclear at the outset whether a polymer such as G16 (formed from hydrophobic and sterically bulky monomers G and 16) would be water-soluble at physiological pH or be able to condense DNA sufficiently. However, monomers of this type were deliberately incorporated to fully explore diversity space, and in anticipation that this library may ultimately be useful as a screening population for the discovery of materials for applications other than gene delivery (For a report on the parallel synthesis and screening of degradable polymers for tissue engineering, see: Brocchini et al. *J. Am. Chem. Soc.* 119: 4553-4554, 1997, incorporated herein by reference; Lynn et al. *Angew. Chem. Int. Ed.* 40:1707-1710, 2001; incorporated herein by reference).

Polymerization reactions were conducted simultaneously as an array of individually labeled vials. Reactions were performed in methylene chloride at 45° C. for 5 days, and polymers were isolated by removal of solvent to yield 600-800 mg of each material. Reactions performed on this scale provided amounts of each material sufficient for routine analysis by GPC and all subsequent DNA-binding, toxicity, and transfection assays. A survey of 55% of the library by GPC indicated molecular weights ranging from 2000 to 50 000 (relative to polystyrene standards). As high molecular weights are not required for DNA-complexation and transfection (as shown below) (Kabanov et al., in *Self-Assembling Complexes for Gene Delivery: From Laboratory to Clinical Trial*, John Wiley and Sons, New York, 1998; incorporated herein by reference), this library provided a collection of polymers and oligomers suitable for subsequent screening assays.

Figure 9:
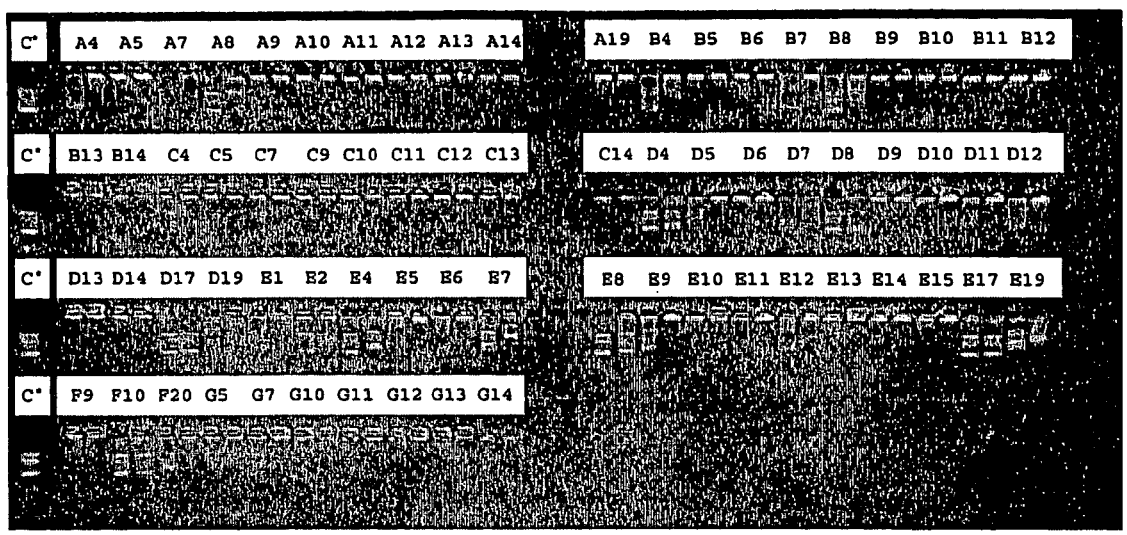
FIG. 9 demonstrates the gel electrophoresis assay used to identify DNA-complexing polymers. Lane annotations correspond to the 70 water-soluble members of the screening library. For each polymer, assays were performed at DNA/polymer ratios of 1:5 (left well) and 1:20 (right well). Lanes marked C* contain DNA alone (no polymer) and were used as a control.

Of the 140 members of the screening library, 70 samples were sufficiently water-soluble (2 mg/mL, 25 mM acetate buffer, pH=5.0) to be included in an electrophoretic DNA-binding assay (FIG. 9). To perform this assay as rapidly and efficiently as possible, samples were mixed with plasmid DNA at ratios of 1:5 and 1:20 (DNA/polymer, w/w) in 96-well plates and loaded into an agarose gel slab capable of assaying up to 500 samples using a multi-channel pipettor. All 70 water-soluble polymer samples were assayed simultaneously at two different DNA/polymer ratios in less than 30 minutes. As shown in FIG. 9, 56 of the 70 water-soluble polymer samples interacted sufficiently with DNA to retard migration through the gel matrix (e.g., A4 or A5), employing the 1:20 DNA/polymer ratio as an exclusionary criterion. Fourteen polymers were discarded from further consideration (e.g., A7 and A8), as these polymers did not complex DNA sufficiently.

Figure 10:
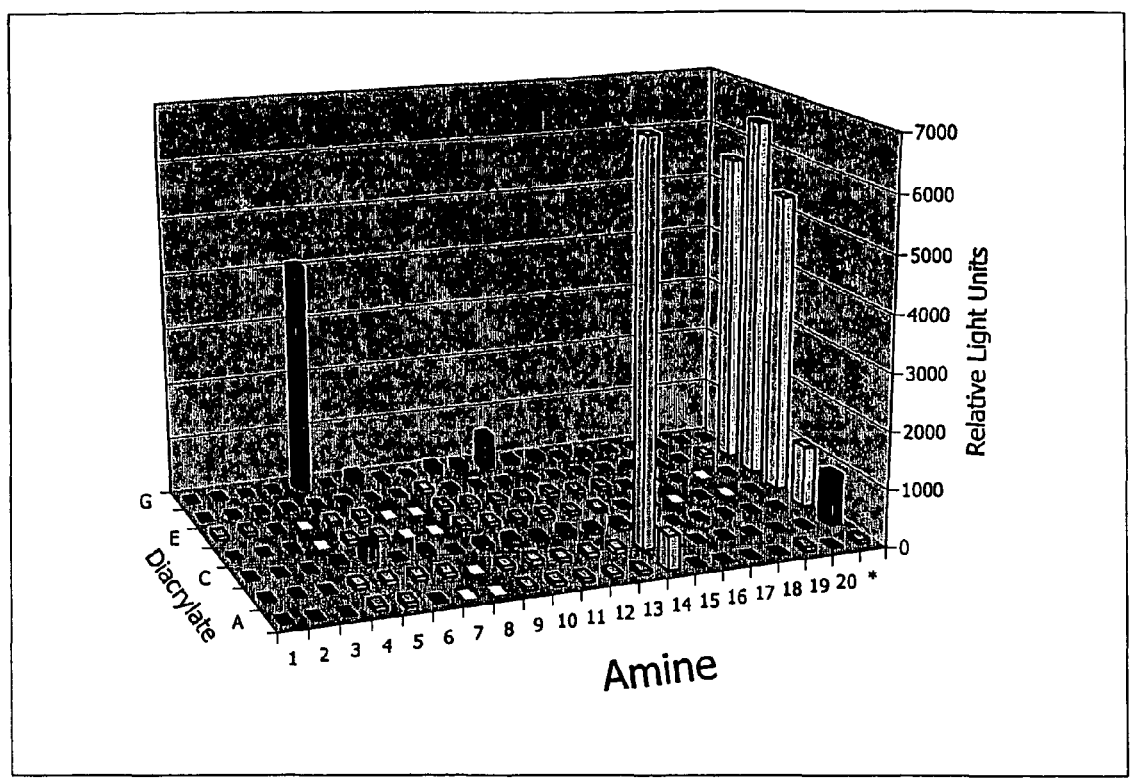
FIG. 10 shows transfection data as a function of structure for an assay employing pCMV-Luc (600 ng/well, DNA/polymer=1:20). Light units are arbitrary and not normalized to total cell protein; experiments were performed in triplicate (error bars not shown). Black squares represent water-insoluble polymers, white squares represent water-soluble polymers that did not complex DNA in FIG. 9. The right column (marked "*") displays values for the following control experiments: no polymer (green), PEI (red), and Lipofectamine (light blue).

The DNA-complexing materials identified in the above assay were further investigated in transfection assays employing plasmid DNA and the COS-7 cell line. All assays were performed simultaneously with the firefly luciferase reporter gene (pCMV-Luc) and levels of expressed protein were determined using a commercially available assay kit and a 96-well luminescence plate reader. FIG. 10 displays data generated from an assay employing pCMV-Luc (600 ng/well) at DNA/poly ratios of 1:20 (w/w). The majority of the polymers screened did not mediate transfection above a level typical of "naked" DNA (no polymer) controls under these conditions. However, several wells expressed higher levels of protein and the corresponding polymers were identified as "hits" in this assay. Polymers B14 ($M_w$=3180) and G5 ($M_w$=9170), for example, yielded transfection levels 4-8 times higher than control experiments employing poly(ethylene imine) (PEI), a polymer conventionally employed as a synthetic transfection vector (Boussif et al. *Proc. Natl. Acad. Sci. USA* 92:7297-7301, 1995; incorporated herein by reference), and transfection levels within or exceeding the range of expressed protein using Lipofectamine 2000 (available from Invitrogen Corp. (Carlsbad, Calif.)), a leading commercially available lipid-based transfection vector system. Polymers A14, C5, G7, G10, and G12 were also identified as positive "hits" in the above experiment, but levels of gene expression were lower than B14 and G5.

Structural differences among synthetic polymers typically preclude a general set of optimal transfection conditions. For example, polymers C5, C14, and G14 were toxic at the higher concentrations employed above (Determined by the absence of cells in wells containing these polymers as observed upon visual inspection. These polymers were less toxic and mediated transfection at lower concentration.), but mediated transfection at lower DNA and polymer concentrations (data not shown). The assay system described above can easily be modified to evaluate polymers as a function of DNA concentration, DNA/polymer ratio, cell seeding densities, or incubation times. Additional investigation will be required to more fully evaluate the potential of this screening library, and experiments to this end are currently underway.

The assays above were performed in the absence of chloroquine, a weak base commonly added to enhance in vitro transfection (Putnam et al. *Proc. Natl. Acad. Sci. USA* 98:1200-1205, 2001; Benns et al. *Bioconjugate Chem.* 11:637-645, 2000; Midoux et al. *Bioconjugate Chem.* 10:406-411, 1999; Kabanov et al., in *Self-Assembling Complexes for Gene Delivery: From Laboratory to Clinical Trial*, John Wiley and Sons, New York, 1998; each of which is incorporated herein by reference), and the results therefore reflect the intrinsic abilities of those materials to mediate transfection. The polymers containing monomer 14 are structurally similar to other histidine containing "proton sponge" polymers (Putnam et al. *Proc. Natl. Acad. Sci. USA* 98:1200-1205, 2001; Benns et al. *Bioconjugate Chem.* 11:637-645, 2000; Midoux et al. *Bioconjugate Chem.* 10:406-411, 1999; each of which is incorporated herein by reference), and could enhance transfection by buffering acidic intracellular compartments and mediating endosomal escape (Putnam et al. *Proc. Natl. Acad. Sci. USA* 98:1200-1205, 2001; Benns et al. *Bioconjugate Chem.* 11:637-645, 2000; Midoux et al. *Bioconjugate Chem.* 10:406-411, 1999; Boussif et al. *Proc. Natl. Acad. Sci. USA* 92:7297-7301, 1995; each of which is incorporated herein by reference). The efficacy of polymers containing monomer 5 is surprising in this context, as these materials do not incorporate an obvious means of facilitating endosomal escape. While the efficacy of these latter polymers is not yet understood, their discovery helps validate our parallel approach and highlights the value of incorporating structural diversity, as these polymers may not have been discovered on an ad hoc basis, Polymers incorporating hydrophilic diacrylates D and E have not produced "hits" under any conditions thus far, providing a possible basis for the development of more focused libraries useful for the elucidation of structure/activity relationships.

We have generated a library of 140 degradable polymers and oligomers useful for the discovery of new DNA-complexing materials and gene delivery vectors. Several of these materials are capable of condensing DNA into structures small enough to be internalized by cells and release the DNA in a transcriptionally active form. The total time currently required for library design, synthesis, and initial screening assays is approximately two weeks. However, the incorporation of robotics and additional monomers could significantly accelerate the pace at which new DNA-complexing materials and competent transfection vectors are identified.

Example 4

Semi-Automated Synthesis and Screening of a Large Library of Degradable Cationic Polymers for Gene Delivery One of the major barriers to the success of gene therapy in the clinic is the lack of safe and efficient methods of delivering nucleic acids. Currently, the majority of clinical trials use modified viruses as delivery vehicles, which, while effective at transferring DNA to cells, suffer from potentially serious toxicity and production problems (Somia et al. *Nat Rev Genet.* 1:91 (2000); incorporated herein by reference). In contrast, non-viral systems offer a number of potential advantages, including ease of production, stability, low immunogenicity and toxicity, and reduced vector size limitations (Ledley *Human Gene Therapy* 6:1129 (1995); incorporated herein by reference). Despite these advantages, however, existing non-viral delivery systems are far less efficient than viral vectors (Luo et al. *Nature Biotechnology* 18:33 (2000); incorporated herein by reference).

Figure 11:
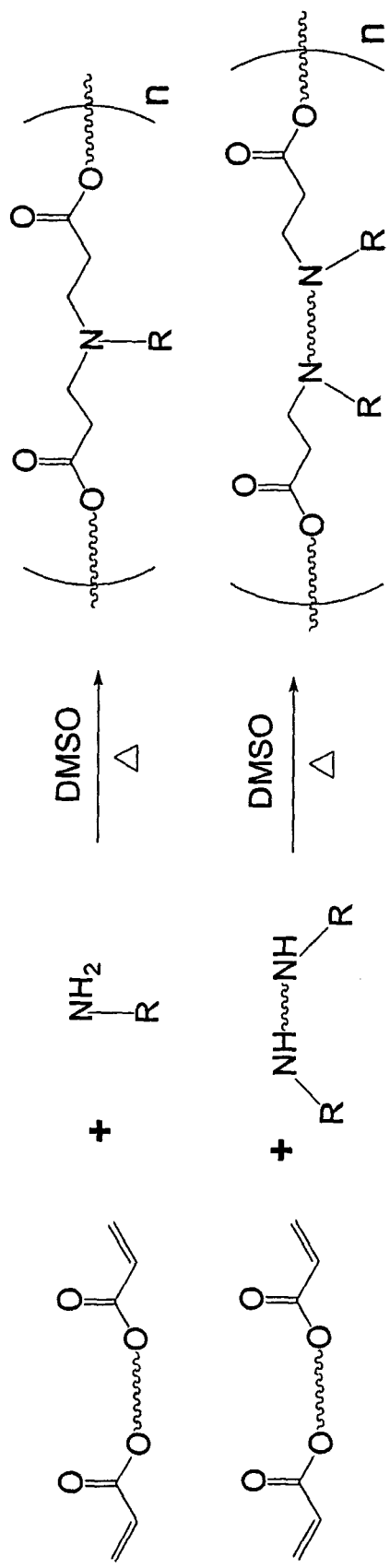
FIG. 11 shows a synthesis of poly(beta-amino ester)s. Poly (beta-amino ester)s may be synthesized by the conjugate addition of primary amines (equation 1) or bis(secondary amines) (equation 2) to diacrylates.

One promising group of non-viral delivery compounds are cationic polymers, which spontaneously bind and condense DNA. A wide variety of cationic polymers that transfect in vitro have been characterized, both natural, such as protein (Fominaya et al. *Journal of Biological Chemistry* 271:10560 (1996); incorporated by reference) and peptide systems (Schwartz et al. *Curr Opin Mol Ther.* 2:162 (2000); incorporated herein by reference), and synthetic polymers such as poly(ethylene imine) (Boussif et al. *Proceedings of the National Academy of Sciences of the United States of America* 92:7297 (1995); incorporated herein by reference) and dendrimers (Kabanov et al. *Self-assembling complexes for gene delivery: from laboratory to clinical trial*, Wiley, Chichester; New York, 1998; incorporated herein by reference). Recent advances in polymeric gene delivery have in part focused on making the polymers more biodegradable to decrease toxicity. Typically, these polymers contain both chargeable amino groups, to allow for ionic interactions with the negatively charged phosphate backbone of nucleic acids, and a biodegradable linkage such as a hydrolyzable ester linkage. Several examples of these include poly(alpha-(4-aminobutyl)-L-glycolic acid) (Lim et al. *Journal of the American Chemical Society* 122:6524 (2000); incorporated herein by reference), network poly(amino ester) (Lim et al. *Bioconjugate Chemistry* 13:952 (2002); incorporated herein by reference), and poly(beta-amino ester)s (Lynn et al. *Journal of the American Chemical Society* 122:10761 (2000); Lynn et al. *Journal of the American Chemical Society* 123: 8155 (2001); each of which is incorporated herein by reference). Poly(beta-amino ester)s are particularly interesting because they show low cytotoxicity and are easily synthesized via the conjugate addition of a primary amine or bis (secondary amine) to a diacrylate (FIG. 11) (Lynn et al. *Journal of the American Chemical Society* 122:10761 (2000); Lynn et al. *Journal of the American Chemical Society* 123: 8155 (2001); each of which is incorporated herein by reference).

Traditional development of new biomedical polymers has been an iterative process. Polymers were typically designed one at a time and then individually tested for their properties. More recently, attention has focused on the development of parallel, combinatorial approaches that facilitate the generation of structurally-diverse libraries of polymeric biomaterials (Brocchini *Advanced Drug Delivery Reviews* 53:123 (2001); incorporated herein by reference). This combinatorial approach has also been applied to the discovery of gene delivery polymers. For example, Murphy et al. generated a targeted combinatorial library of 67 peptoids via solid-phase synthesis and screened them to identify new gene delivery agents (Murphy et al. *Proceedings of the National Academy of Sciences of the United States of America* 95:1517 (1998); incorporated herein by reference).

In this Example is described new tools for high-throughput, parallel combinatorial synthesis and cell-based screening of a large library of 2350 structurally diverse, poly(beta-amino ester)s. This approach allows for the screening of polymers in cell-based assays without the polymers ever leaving the solution phase following synthesis. This approach combined with the use of robotic fluid handling systems allows for the generation and testing of thousands of synthetic polymers in cell-based assays in a relatively short amount of time. Using this approach, 46 new polymers that perform as well or better than conventional non-viral delivery systems such as poly(ethylene imine) have been identified.

Results and Discussion

High-throughput polymer synthesis. The primary factors limiting the throughput and automation of poly(beta-amino esters) synthesis and testing was the viscosity of monomer and polymer solutions, and the difficulty with manipulating the solid polymer products. While automation of liquid handling is straightforward using conventional robotics, the manipulation of solids and viscous liquids on a small scale is not. Therefore, a system was developed in which polymers could be synthesized and screened in cell-based assays without leaving the solution phase. Since this would require the presence of residual solvent in the cell assays, the relatively non-toxic solvent, dimethyl sulfoxide (DMSO) was chosen. DMSO is a commonly used solvent in cell culture and is routinely used in storing frozen stocks of cells. DMSO is miscible with water and is generally well tolerated in living systems.

Figure 12:
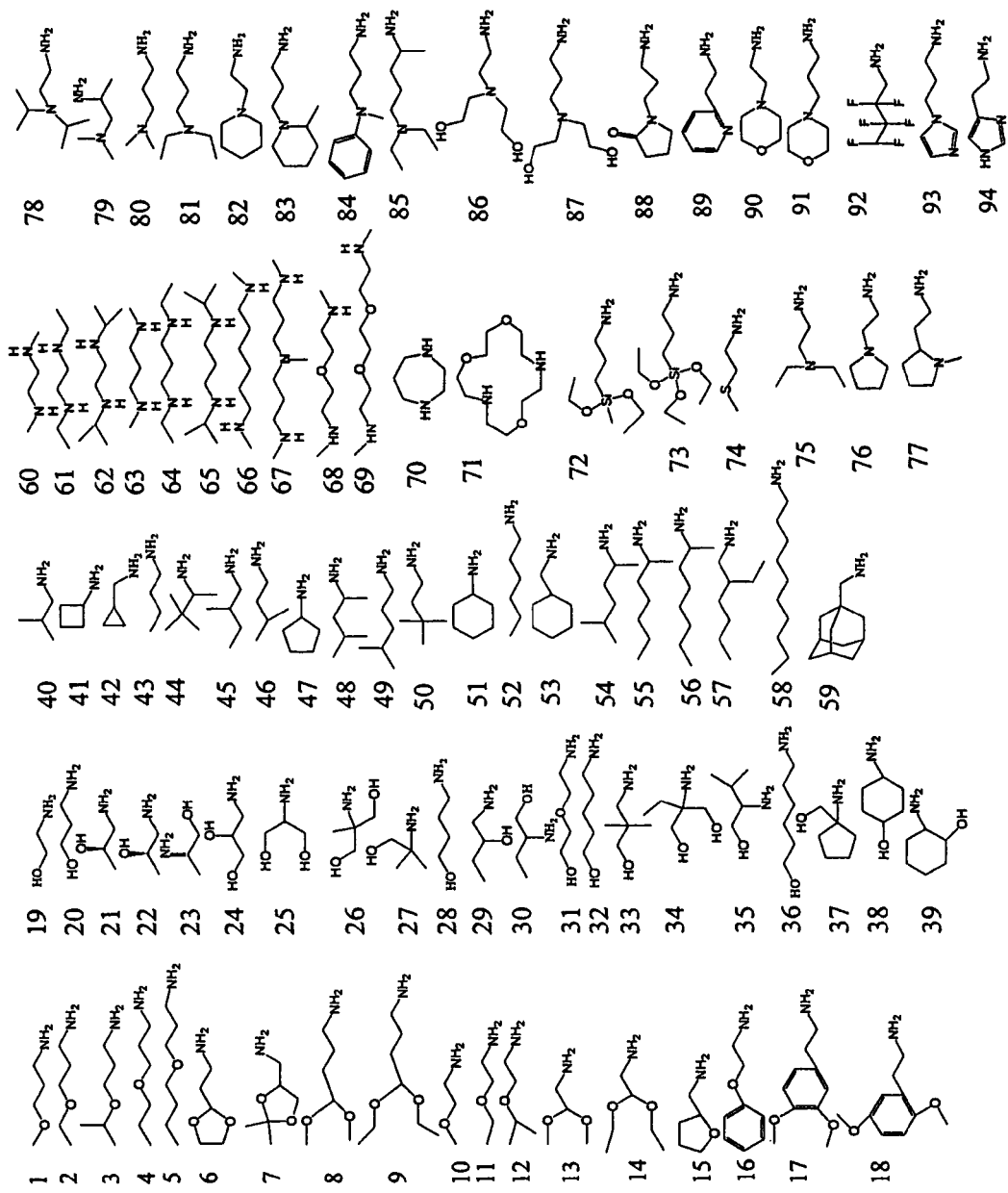
FIG. 12 shows a variety of amine (A) and diacrylate (B) monomers used in the synthesis of the polymer library.

The first step in preparing for high-throughput synthesis was to identify conditions that would allow for the production of polymer yet possess a manageable viscosity. Small scale, pilot experiments showed that polymerization could be performed effectively at 1.6 M in DMSO at 56° C. for 5 days. Based on these experiments, a general strategy was developed for polymer synthesis and testing. All monomers (FIG. 12) were diluted to 1.6 M in DMSO, and then using both a fluid-handling robot and a 12 channel micropipettor, we added 150 microliters of each amine and diacrylate monomer into a polypropylene deep well plate and then sealed it with aluminum foil. The plates were placed on an orbital shaker and incubated at 56° C. for 5 days. To compensate for the increased viscosity of polymeric solutions, 1 ml of DMSO was added to each well of the plate, and the plates were then stored at 4° C. until further use. These methods allow for 2350 reactions in a single day. Furthermore, the production and storage of polymers in a 96-well format allowed for an easy transition into 96-well format cell-based testing of polymer transfection efficiency.

High-throughput polymer testing. Once synthesized, all polymers were tested for their ability to deliver the Luciferase expressing plasmid, pCMV-luc, into the monkey kidney fibroblast cell line COS-7. Due to the large size of the polymer library, a high-throughput method for cell based screening of transfection efficiency was developed. Since polymers were stored in 96 well plates, all polymer dilutions, DNA complexation, and cell transfections were performed in parallel by directly transferring polymers from plate to plate using a liquid handling robot. All polymers were synthesized using the same concentration of amine monomer, thus comparison between polymers at a fixed amine monomer:DNA phosphate ratio (N:P ratio) was straightforward. While the amine monomers contain either one, two, or three amines per monomer, initial broad-based screens for transfection efficiency were greatly simplified by maintaining a constant monomer concentration in all wells of a single plate, and therefore a constant volume of polymer solution per reaction (see methods below).

Figure 13:
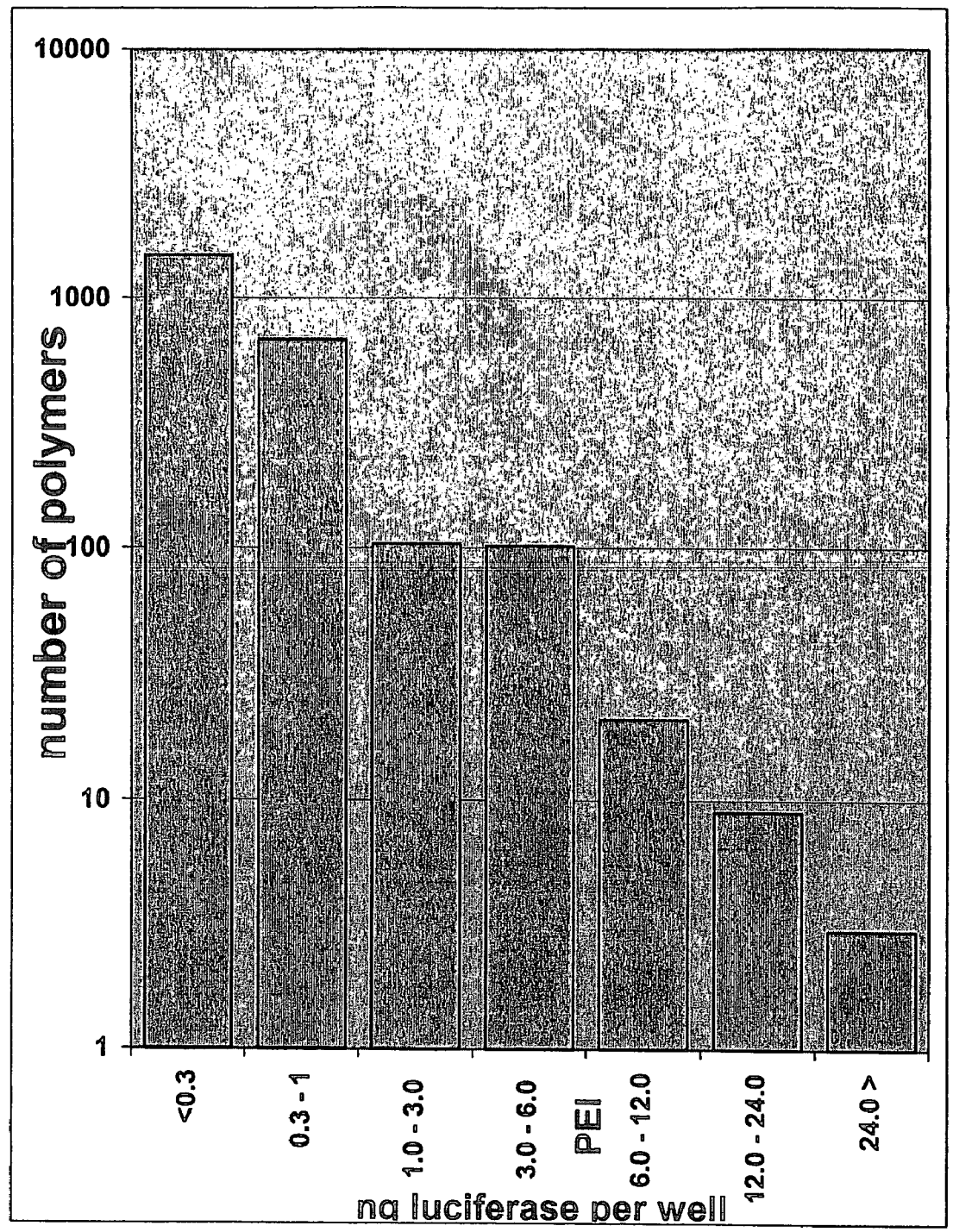
FIG. 13 is a histogram of polymer transfection efficiencies. In the first screen all 2350 polymers were tested for their ability to deliver pCMV-luc DNA at N:P ratios of 40:1, 20:1, and 10:1 to COS-7 cells. Transfection efficiency is presented in ng Luciferase per well. For reference, PEI transfection efficiency is shown. COS-7 cells readily take up naked DNA, and in our conditions produce 0.15±0.05 ng per well, and the lipid reagent, Lipofectamine 2000, produces 13.5±1.9 ng per well.

The efficiency of in vitro transfection using cationic polymers such as poly(ethylene imine) is very sensitive to the ratio of polymer to DNA present during complex formation (Gebhart et al. *Journal of Controlled Release* 73:401 (2001); incorporated herein by reference). N:P rations of 10:1, 20:1, and 40:1 were selected for our initial screens based on previous experience with these types of polymers. Using our high-throughput system, we screened all 2350 polymers at these three ratios. Transfection values at the best condition for each polymer were tabulated into a histogram (FIG. 13). These results were compared to three controls: naked DNA (no transfection agent), poly(ethylene imine) (PEI), and Lipofectamine 2000. The low, residual levels of DMSO present in the transfection solutions did not affect transfection efficiency of either naked DNA or PEI. Thirty-three of the 2350 polymers were found to be as good or better than PEI in this unoptimized system.

Figure 14:
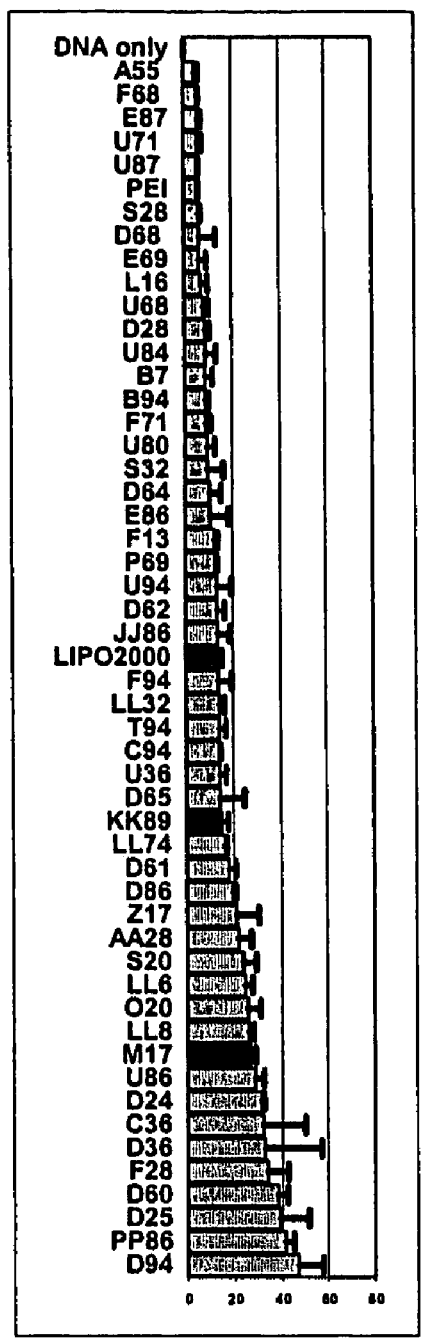
FIG. 14. Optimized transfection efficiency of the top 50 polymers relative to PEI and lipofectamine 2000. Polymers were tested as described in methods. In the first broad screen N:P ratios of 40:1, 20:1, and 10:1 with an n of 1 were tested. The top 93 were rescreened at six different N:P ratios=(optimal N:P form the first screen)×1.75, 1.5, 1.25, 1.0, 0.75, and 0.5, in triplicate. Control reactions are labeled in Red, and polymers that did not bind DNA in a gel electrophoresis assay are shown in black.

Since cationic polymer transfections tend to be sensitive to polymer:DNA ratio, we decided to optimize transfection conditions with the best polymers from our preliminary screen. Using the results above as a rough guide, the transfection condition for the best 93 polymers were optimized by testing them at N:P ratios above and below the optimal transfection conditions identified in the broad based screen. In order to develop a high-throughput optimization system, these were tested using an N:P ratio multiplier system to simplify simultaneous testing and plate-to-plate transfer. Starting with the best N:P ratio identified in the preliminary screen, the polymers were retested at six N:P ratios equal to the best ratio times 0.5, 0.75, 1.0, 1.25, 1.5, and 1.75, in triplicate. For example, if the optimal ratio identified in the screen for a given polymer was 20:1, then that polymer was rescreened in triplicate at N:P ratios of 10:1, 15:1, 20:1, 25:1, 30:1, and 35:1. The average transfection efficiencies with standard deviation from the best condition for the best 50 polymers are shown in FIG. 14, along with control data. In this experiment, 46 polymers were identified that transfect as good or better than PEI. All 93 of these polymers were also tested for their ability to bind DNA using agarose gel electrophoresis (FIG. 15). Interestingly, while almost all of the polymers bind DNA as expected, two polymers that transfect at high levels do not: M17 and KK89 (FIG. 14).

Figure 16:
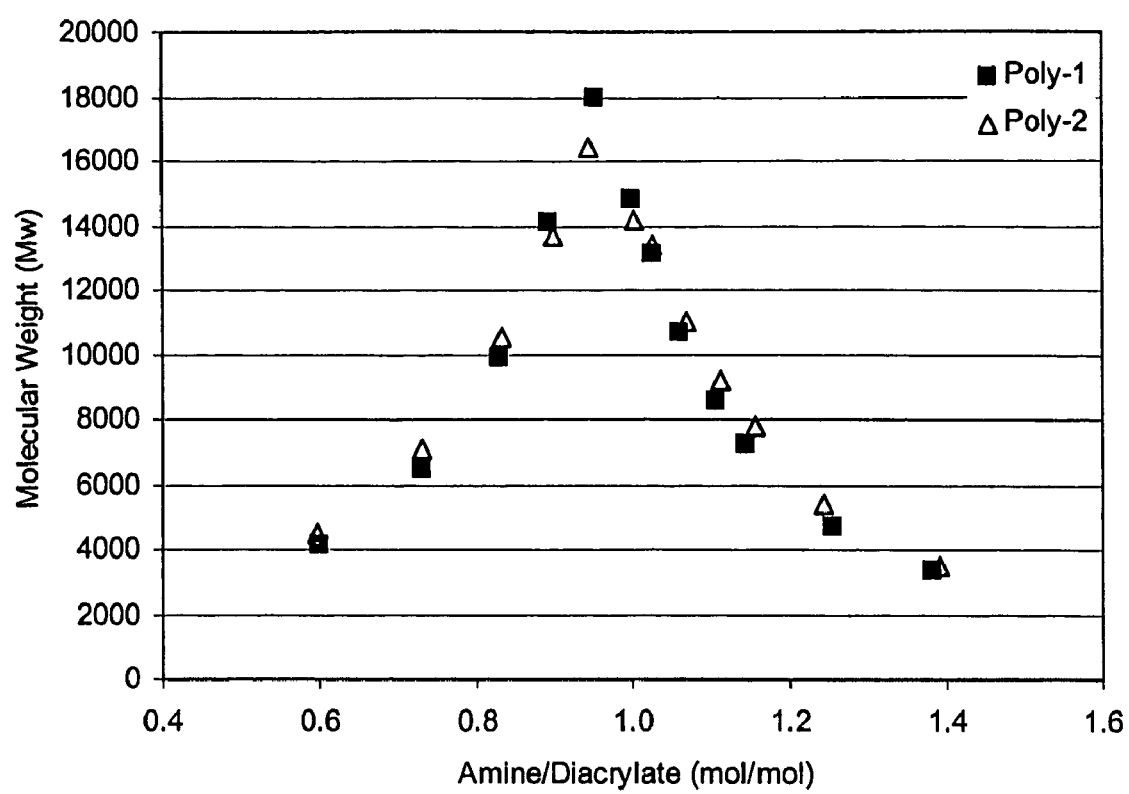
FIG. 16 shows how the polymer molecular weight and the chain end-group is affected by varying the amine/diacrylate ratio in the reaction mixture. Molecular weights ($M_w$) (relative to polystyrene standards) were determined by organic phase GPC. Polymers synthesized with amine/diacrylate ratios of >1 have amine end-groups, and polymers synthesized with amine/diacrylate ratios of <1 have acrylate end-groups.

To further examine the transfection properties of these polymers, ten high transfecting polymers were tested for their ability to deliver the green fluorescent protein plasmid, pCMV-eGFP. Unlike pCMV-luc, pCMV-eGFP provides information concerning what percentage of cells is transfected. High levels of transfection were observed for all 10 polymers, and two of the best are shown in FIG. 16.

The "hits" identified in the above assays reveal a surprisingly diverse and unexpected collection of polymers. Particularly surprising is the large collection of hydrophobic, D-monomer-based polymers. In fact, the diacrylate monomers used to make the best performing 50 polymers are almost always hydrophobic. Further analysis reveals two more common features of the effective polymers: 1) twelve of the 26 polymers that are better than the best conventional reagent, Lipofectamine 2000, have mono- an di-alcohol side groups, and 2) linear, bis(secondary amines) are also prevalent in the hit structures. Also surprising was the identification of two polymers that transfect at high levels but do not appear to bind DNA (KK89 and M17). Both are also insoluble at pH 5 and pH 7. Their ability to facilitate DNA uptake may be due to permeabilization of the cellular membrane.

Also important for the function of gene delivery polymers is length (Remy et al. *Advanced Drug Delivery Reviews* 30:85 (1998); Schaffer et al. *Biotechnol Bioeng* 67:598 (2000); each of which is incorporated herein by reference). Using these results as a framework, a range of polymer lengths for each hit polymer may be prepared by carefully varying relative monomer concentrations. Evidence shows that (1) like PEI, poly (beta-amino ester) length is important in the gene delivery proficiency of these polymers, and (2) that the hits identified here can be resynthesized using conventional methods and still deliver DNA effectively.

Experimental Protocols

Polymer synthesis. Monomers were purchased from Aldrich (Milwaukee, Wis.), TCI (Portland, Oreg.), Pfaltz & Bauer (Waterbury, Conn.), Matrix Scientific (Columbia, S.C.), Acros-Fisher (Pittsburgh, Pa.), Scientific Polymer (Ontario, N.Y.), Polysciences (Warrington, Pa.), and Dajac monomer-polymer (Feasterville, Pa.). These were dissolved in DMSO (Aldrich) to a final concentration of 1.6 M. All possible pair wise combinations amine and diacrylate monomers were added in 150 µl aliquots to each well of 2 ml 96 well polypropylene masterblock deep well plates (Griener America, Longwood, Fla.). The plates were sealed with aluminum foil, and incubated at 56° C. while rotating on an orbital shaker. After 5 days, 1 ml of DMSO was added to each well, and the plates were resealed and stored frozen at 4° C. until ready to be used. Transfection experiments. 14,000 cos-7 cells (ATCC, Manassas, Va.) were seeded into each well of a solid white or clear 96 well plate (Corning-Costar, Kennebunk, Me.) and allowed to attached overnight in growth medium, composed of: 500 ml phenol red minus DMEM, 50 ml heat inactivated FBS, 5 ml penicillin/streptomycin (Invitrogen, Carlsbad, Calif.). Each well of a master block 96-well plate was filled with 1 ml of 25 mM sodium acetate pH 5. To this, 40 µl, 20 µl, or 10 µl of the polymer/DMSO solution was added. 25 µl of the diluted polymer was added to 25 µl of 60 µg/ml pCMV-luc DNA (Promega, Madison, Wis.) or pEGFP-N1 (Invitrogen) in a half volume 96 well plate. These were incubated for 10 minutes, and then 30 µl of the polymer-DNA solution was added to 200 µl of Optimem with sodium bicarbonate (Invitrogen) in 96 well polystyrene plates. The medium was removed from the cells using a 12-channel wand (V & P Scientific, San Diego, Calif.) after which 150 µl of the optimum-polymer-DNA solution was immediately added. Complexes were incubated with the cells for 1 hour and then removed using the 12-channel wand and replaced with 105 µl of growth medium. Cells were allowed to grow for three days at 37° C., 5% $CO_2$ and then analyzed for luminescence (pCMV-luc) or fluorescence (pEGFP-N1). Control experiments were performed by as described above, but using poly (ethylene imine) MW 25,000 (Aldrich) replacing synthesized polymer, and at polymer:DNA weight ratios of 0.5:1, 0.75:1, 1:1, 1.25:1, 1.5:1, and 2:1. Lipofectamine 2000 (Invitrogen) transfections were performed as described by the vendor, except that complexes were removed after 1 hour.

Luminescence was analyzed using bright-glo assay kits (Promega). Briefly, 100 µl of bright-glo solution was added to each well of the microtiter plate containing media and cells. Luminescence was measured using a Mithras Luminometer (Berthold, Oak Ridge, Tenn.). In some cases, a neutral density filter (Chroma, Brattleboro, Vt.) was used to prevent saturation of the luminometer. A standard curve for Luciferase was generated by titration of Luciferase enzyme (Promega) into growth media in white microtiter plates. eGFP expression was examined using a Zeiss Aciovert 200 inverted microscope.

Agarose gel electrophoresis DNA-binding assays were done at a N:P ratio of 40:1, as previously described (Lynn et al. *Journal of the American Chemical Society* 123:8155 (2001); incorporated herein by reference). All liquid handling was performed using an EDR384S/96S robot (Labcyte, Union City, Calif.) or a 12 channel micropippettor (Thermo Labsystems, Vantaa, Finland) in a laminar flow hood.

Example 5

Synthesis of Poly(Beta-Amino Esters) Optimized for Highly Effective Gene Delivery The effect of molecular weight, polymer/DNA ratio, and chain end-group on the transfection properties of two unique poly(β-amino ester) structures was determined. These factors can have a dramatic effect on gene delivery function. Using high throughput screening methods, poly(β-amino esters) that transfect better than PEI and Lipofectamine 2000 (two of the best commercially available transfection reagents) have been discovered.

Materials and Methods

Polymer Synthesis. Poly-1 and Poly-2 polymers were synthesized by adding 1,4-butanediol diacrylate (99+%) and 1,6-hexanediol diacrylate (99%), respectively, to 1-amino butanol (98%). These monomers were purchased from Alfa Aesar (Ward Hill, Mass.). Twelve versions each of Poly-1 and Poly-2 were generated by varying the amine/diacrylate stoichiometric ratio. To synthesize each of the 24 unique polymers, 400 mg of 1-amino butanol was weighed into an 8 mL sample vial with Teflon-lined screw cap. Next, the appropriate amount of diacrylate was added to the vial to yield a stoichiometric ratio between 1.4 and 0.6. A small Teflon-coated stir bar was then put in each vial. The vials were capped tightly and placed on a multi-position magnetic stir-plate residing in an oven maintained at 100° C. After a reaction time of 5 hr, the vials were removed from the oven and stored at 4° C. All polymers were analyzed by GPC.

Gel Permeation Chromatography (GPC). GPC was performed using a Hewlett Packard 1100 Series isocratic pump, a Rheodyne Model 7125 injector with a 100-μL injection loop, and a Phenogel MXL column (5μ mixed, 300×7.5 mm, Phenomenex, Torrance, Calif.). 70% THF/30% DMSO (v/v)+0.1 M piperidine was used as the eluent at a flow rate of 1.0 mL/min. Data was collected using an Optilab DSP interferometric refractometer (Wyatt Technology, Santa Barbara, Calif.) and processed using the TriSEC GPC software package (Viscotek Corporation, Houston, Tex.). The molecular weights and polydispersities of the polymers were determined relative to monodisperse polystyrene standards.

Luciferase Transfection Assays. COS-7 cells (ATCC, Manassas, Va.) were seeded (14,000 cells/well) into each well of an opaque white 96-well plate (Corning-Costar, Kennebunk, Me.) and allowed to attach overnight in growth medium. Growth medium was composed of 90% phenol red-free DMEM, 10% fetal bovine serum, 100 units/mL penicillin, 100 μg/mL streptomycin (Invitrogen, Carlsbad, Calif.). To facilitate handling, polymers stock solutions (100 mg/mL) were prepared in DMSO solvent. A small residual amount of DMSO in the transfection mixture does not affect transfection efficiency and does not result in any observable cytotoxicity. Working dilutions of each polymer were prepared (at concentrations necessary to yield the different polymer/DNA weight ratios) in 25 mM sodium acetate buffer (pH 5). 25 μl of the diluted polymer was added to 25 μl of 60 μg/ml pCMV-Luc DNA (Elim Biopharmaceuticals, South San Francisco, Calif.) in a well of a 96-well plate. The mixtures were incubated for 10 minutes to allow for complex formation, and then 30 μl of the each of the polymer-DNA solutions were added to 200 μl of Opti-MEM with sodium bicarbonate (Invitrogen) in 96-well polystyrene plates. The growth medium was removed from the cells using a 12-channel aspirating wand (V&P Scientific, San Diego, Calif.) after which 150 μl of the Opti-MEM-polymer-DNA solution was immediately added. Complexes were incubated with the cells for 1 hr and then removed using the 12-channel wand and replaced with 105 μl of growth medium. Cells were allowed to grow for three days at 37° C., 5% $CO_2$ and were then analyzed for luciferase expression. Control experiments were also performed with PEI (MW=25,000, Sigma-Aldrich) and Lipofectamine 2000 (Invitrogen). PEI transfections were performed as described above, but using polymer:DNA weight ratios of 1:1. Lipofectamine 2000 transfections were performed as described by the vendor, except that complexes were removed after 1 hour.

Luciferase expression was analyzed using Bright-Glo assay kits (Promega). Briefly, 100 μl of Bright-Glo solution was added to each well of the 96-well plate containing media and cells. Luminescence was measured using a Mithras Luminometer (Berthold, Oak Ridge, Tenn.). A 1% neutral density filter (Chroma, Brattleboro, Vt.) was used to prevent saturation of the luminometer. A standard curve for Luciferase was generated by titration of Luciferase enzyme (Promega) into growth media in an opaque white 96-well plate.

Measurement of Cytotoxicity. Cytotoxicity assays were performed in the same manner as the luciferase transfection experiments with the following exception. Instead of assaying for luciferase expression after 3 days, cells were assayed for metabolic activity using the MTT Cell Proliferation Assay kit (ATCC) after 1 day. 10 μL of MTT Reagent was added to each well. After 2 hr incubation at 37° C., 100 μL of Detergent Reagent was added to each well. The plate was then left in the dark at room temperature for 4 hr. Optical absorbance was measured at 570 nm using a SpectaMax 190 microplate reader (Molecular Devices, Sunnyvale, Calif.) and converted to % viability relative to control (untreated) cells.

Cellular Uptake Experiments. Uptake experiments were done as previously described, with the exception that a 12-well plate format was used instead of a 6-well plate format (Akinc, A., et al., *Parallel synthesis and biophysical characterization of a degradable polymer library of gene delivery*. J. Am. Chem. Soc., 2003; incorporated herein by reference). COS-7 cells were seeded at a concentration of $1.5 \times 10^5$ cells/well and grown for 24 hours prior to performing the uptake experiments. Preparation of polymer/DNA complexes was done in the same manner as in the luciferase transfection experiments, the only differences being an increase in scale (2.5 μg DNA per well of 12-well plate as opposed to 600 ng DNA per well of 96-well plate) and the use of Cy5-labeled plasmid instead of pCMV-Luc (Akinc, A. and R. Langer, *Measuring the pH environment of DNA delivered using non-viral vectors: Implications for lysosomal trafficking*. Biotechnol. Bioeng., 2002. 78(5): p. 503-8; incorporated herein by reference). As in the transfection experiments, complexes were incubated with cells for 1 hr to allow for cellular uptake by endocytosis. The relative level of cellular uptake was quantified using a flow cytometer to measure the fluorescence of cells loaded with Cy5-labeled plasmid.

GFP Transfections. GFP transfections were carried in COS-7 (green monkey kidney), NIH 3T3 (murine fibroblast), HepG2 (human hepatocarcinoma), and CHO (Chinese Hamster Ovary) cell lines. All cell lines were obtained from ATCC (Manassas, Va.) and maintained in DMEM containing 10% fetal bovine serum, 100 units/mL penicillin, 100 μg/mL streptomycin at 37° C. in 5% $CO_2$ atmosphere. Cells were seeded on 6-well plates and grown to roughly 80-90% confluence prior to performing the transfection experiments. Polymer/DNA complexes were prepared as described above using the pEGFP-N1 plasmid (Clontech, Palo Alto, Calif.) (5 μg/well). Complexes were diluted in 1 mL Opti-MEM and added to the wells for 1 hr. The complexes were then removed and fresh growth media was added to the wells. After 2 days, cells were harvested and analyzed for GFP expression by flow cytometry. Propidium iodide staining was used to exclude dead cells from the analysis.

Flow Cytometry. Flow cytometry was performed with a FACSCalibur (Becton Dickinson) equipped with an argon ion laser capable of exciting GFP (488 nm excitation) and a red diode laser capable of exciting Cy5 (635 nm excitation). The emission of GFP was filtered using a 530 nm band pass filter and the emission of Cy5 was filtered using a 650 long pass filter. The cells were appropriately gated by forward and side scatter and 30,000 events per sample were collected.

Results and Discussion

Polymer Synthesis. As previously described (Lynn, D. M. and R. Langer, *Degradable poly(β-amino esters): synthesis, characterization, and self-assembly with plasmid DNA*. J. Am. Chem. Soc., 2000. 122(44): p. 10761-10768; incorporated herein by reference), the synthesis of poly(β-amino esters) proceeds via the conjugate addition of amines to acrylate groups. Because the reaction is a step polymerization, a broad, statistical distribution of chain lengths is obtained, with average molecular weight and chain end-groups controlled by monomer stoichiometry (Flory, P., in *Principles of Polymer Chemistry*. 1953, Cornell University Press: Ithaca, N.Y. p. 40-46, 318-323; Odian, G., *Step Polymerizaton, in Principles of Polymerization*. 1991, John Wiley & Sons, Inc.: New York. p. 73-89; each of which is incorporated herein by reference). Molecular weight increases as the ratio of monomers nears stoichiometric equivalence, and an excess of amine or diacrylate monomer results in amine- or acrylate-terminated chains, respectively. For this class of polymers, precise control of stoichiometry is essential for controlling polymer molecular weight. While monomer stoichiometry is the most important factor affecting chain length, consideration should also be given to competing side reactions that can impact the molecular weight and structure of polymer products. In particular, intramolecular cyclization reactions, where an amine on one end of the growing polymer chain reacts with an acrylate on the other end, can limit obtained molecular weights (Odian, G., *Step Polymerizaton, in Principles of Polymerization*. 1991, John Wiley & Sons, Inc.: New York. p. 73-89; incorporated herein by reference). These cyclic chains may also have properties that differ from those of their linear counterparts.

In this work, we have modified the previously reported polymerization procedure in order to better control monomer stoichiometry and to minimize cyclization reactions. First, the scale of synthesis was increased from roughly 0.5 g to 1 g to allow for control of stoichiometry within 1%. Further improvement in accuracy is limited by the purity (98-99%) of the commercially available monomers used. Second, all monomers were weighed into vials instead of being dispensed volumetrically. Discrepancies between actual and reported monomer densities were found to be non-negligible in some cases, leading to inaccuracies in dispensed mass. Third, polymerizations were performed in the absence of solvent to maximize monomer concentration, thus favoring the intermolecular addition reaction over the intramolecular cyclization reaction. Eliminating the solvent also provides the added benefits of increasing the reaction rate and obviating the solvent removal step. Finally, since the previously employed methylene chloride solvent was not used, the reaction temperature could be increased from 45° C. to 100° C. Increasing temperature resulted in an increased reaction rate and a decrease in the viscosity of the reacting mixture, helping to offset the higher viscosity of the solvent-free system. The combined effect of increased monomer concentration and reaction temperature resulted in a decrease in reaction time from roughly 5 days to 5 hours.

We synthesized polymers Poly-1 and Poly-2 by adding 1,4-butanediol diacrylate and 1,6-hexanediol diacrylate, respectively, to 1-amino butanol. Twelve unique versions of each polymer were synthesized by varying amine/diacrylate mole ratios between 0.6 and 1.4.

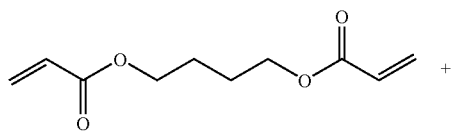

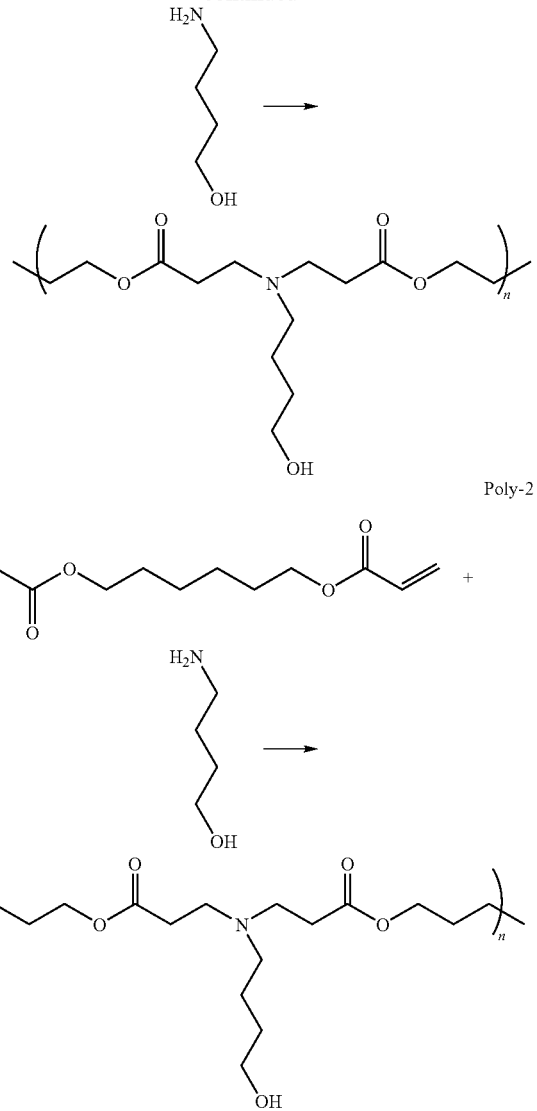

For both sets of polymers (Poly-1 and Poly-2), 7 of the 12 had amine/diacrylate ratios>1, resulting in amine-terminated polymers, and 5 of the 12 had amine/diacrylate ratios<1, resulting in acrylate-terminated polymers. After 5 hr reaction at 100° C., polymers were obtained as clear, slightly yellowish, viscous liquids. The polymers had observable differences in viscosity, corresponding to differences in molecular weight. Polymers were analyzed by organic phase gel permeation chromatography (GPC) employing 70% THF/30% DMSO (v/v)+0.1 M piperidine eluent. Polymer molecular weights ($M_w$) ranged from 3350 (Poly-1, amine/diacrylate=1.38) to 18,000 (Poly-1, amine/diacrylate=0.95), relative to polystyrene standards (FIG. 16). Molecular weight distributions were monomodal with polydispersity indices (PDIs) ranging from 1.55 to 2.20.

Figure 17:
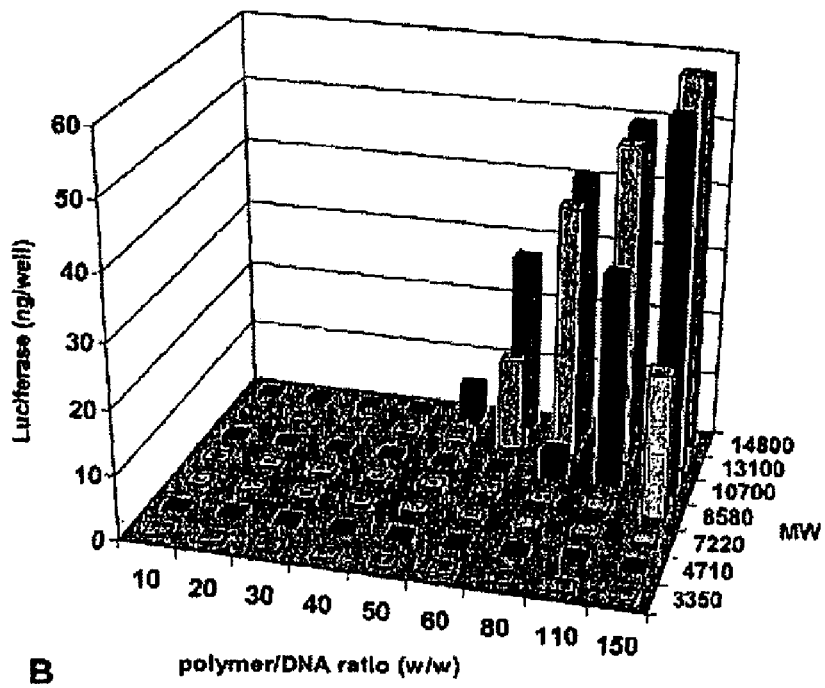
FIG. 17 shows luciferase transfection results for Poly-1 as a function of polymer molecular weight, polymer/DNA ratio (w/w), and polymer end-group. (A) amine-terminated chains; (B) acrylate-terminated chains. (n=4, error bars are not shown.)
Figure 17:
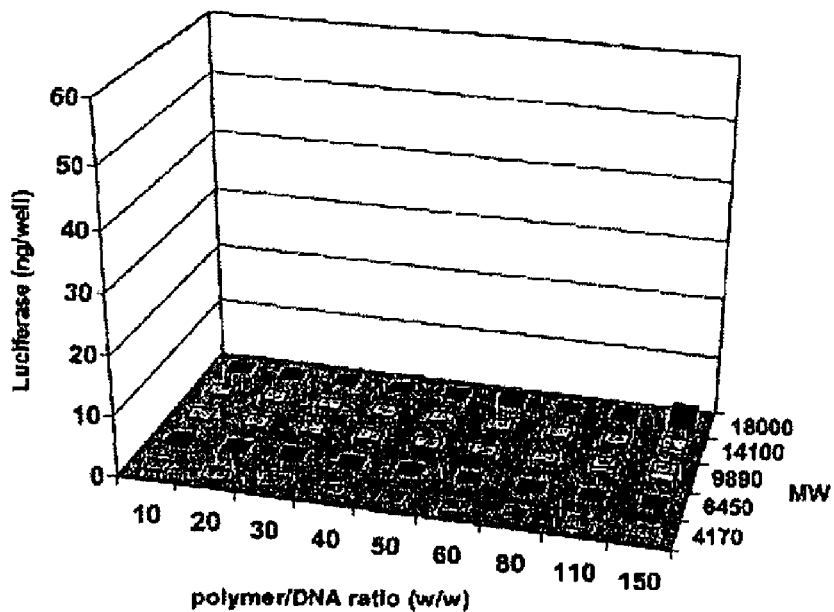
Figure 18:
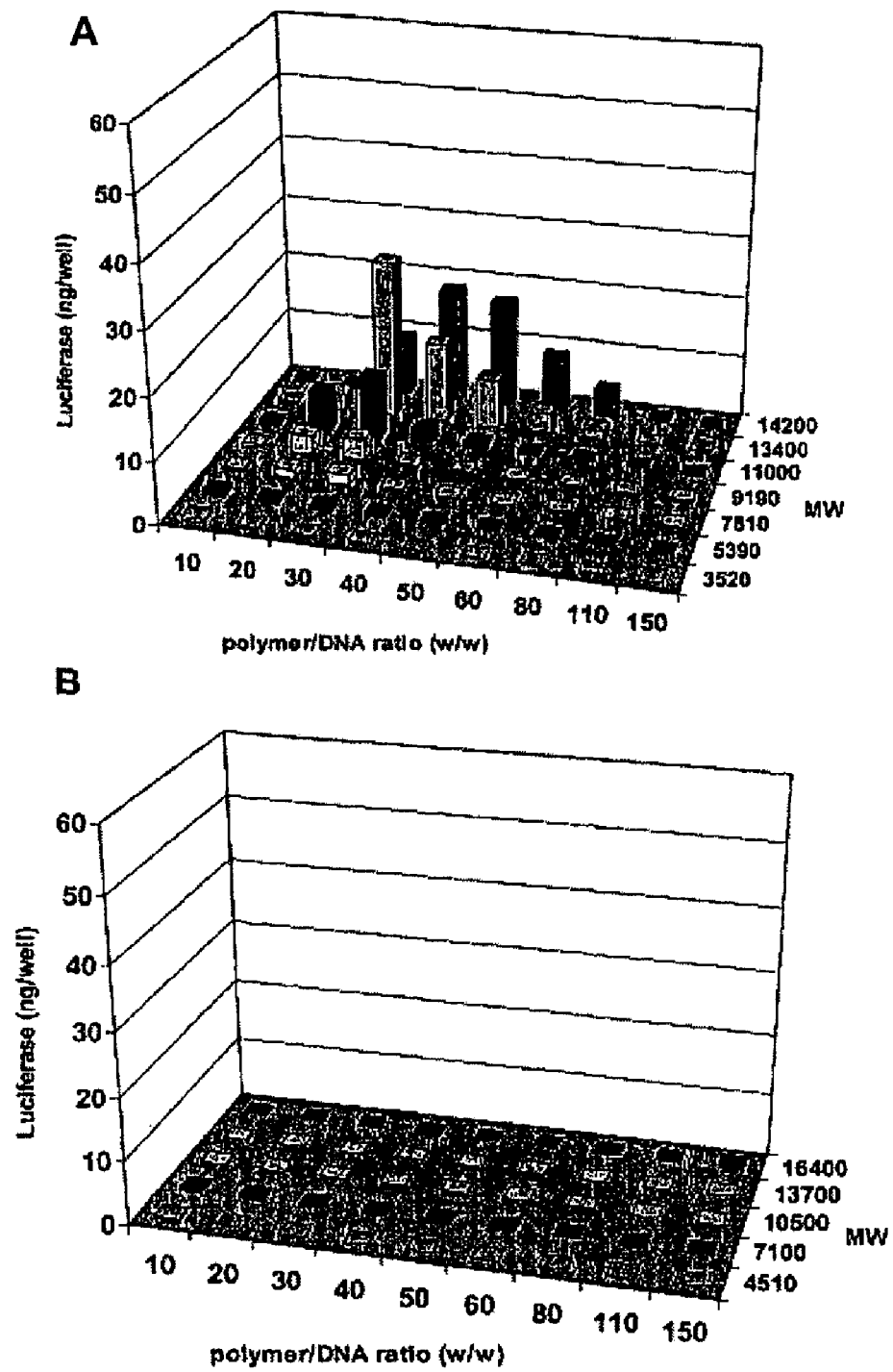
FIG. 18 shows luciferase transfection results for Poly-2 as a function of polymer molecular weight, polymer/DNA ratio (w/w), and polymer end-group. (A) amine-terminated chains; (B) acrylate-terminated chains. (n=4, error bars not shown).

Luciferase Transfection Results. Transfection experiments were performed with all 24 synthesized polymers (12 each of Poly-1 and Poly-2) at 9 different polymer/DNA ratios to determine the impact of molecular weight, polymer/DNA ratio, and chain end-group on transfection efficiency (FIGS. 17 and 18). As a model system, we used the COS-7 cell line and a plasmid coding for the firefly luciferase reporter gene (pCMV-Luc) (600 ng/well). To facilitate performance of the nearly 1000 transfections (data obtained in quadruplicate), experiments were done in 96-well plate format. Reporter protein expression levels were determined using a commercially available luciferase assay kit and a 96-well luminescence plate reader.

The data displayed in FIGS. 17 and 18 demonstrate that polymer molecular weight, polymer/DNA ratio, and chain end-group impact the transfection properties of both Poly-1 and Poly-2 polymers. One striking, and somewhat unexpected, result was that none of the acrylate-terminated polymers mediated appreciable levels of transfection under any of the evaluated conditions. This result may be more broadly applicable for poly(β-amino esters), as we have yet to synthesize a polymer, using an excess of diacrylate monomer, that mediates appreciable reporter gene expression at any of the polymer/DNA ratios we have employed. These findings suggest that perhaps only amine-terminated poly(β-amino esters) are suitable for use as gene delivery vehicles. In contrast, there were distinct regions of transfection activity in the MW-polymer/DNA space for amine-terminated versions of both Poly-1 and Poly-2 (FIGS. 17-A and 18-A). Maximal reporter gene expression levels of 60 ng luc/well and 26 ng luc/well were achieved using Poly-1 ($M_w$=13,100) and Poly-2 ($M_w$=13,400), respectively. These results compare quite favorably with PEI (polymer/DNA=1:1 w/w), which mediated an expression level of 6 ng luc/well (data not shown) under the same conditions.

While the highest levels of transfection occurred using the higher molecular weight versions of both polymer structures, the optimal polymer/DNA ratios for these polymers were markedly different (polymer/DNA=150 for Poly-1, polymer/DNA=30 for Poly-2). The transfection results we have obtained for Poly-1 and Poly-2 highlight the importance of optimizing polymer molecular weight and polymer/DNA ratio, and the importance of controlling chain end-groups. Further, the fact that two such similar polymer structures, differing by only two carbons in the repeat unit, have such different optimal transfection parameters emphasizes the need to perform these optimizations for each unique polymer structure. To improve our understanding of the obtained transfection results, we chose to study two important delivery characteristics that directly impact transgene expression, cytotoxicity and the ability to enter cells via endocytosis (Wiethoff, C. M. and C. R. Middaugh, *Barriers to nonviral gene delivery*. Journal of Pharmaceutical Sciences, 2003. 92(2): p. 203-217; incorporated herein by reference).

Figure 19:
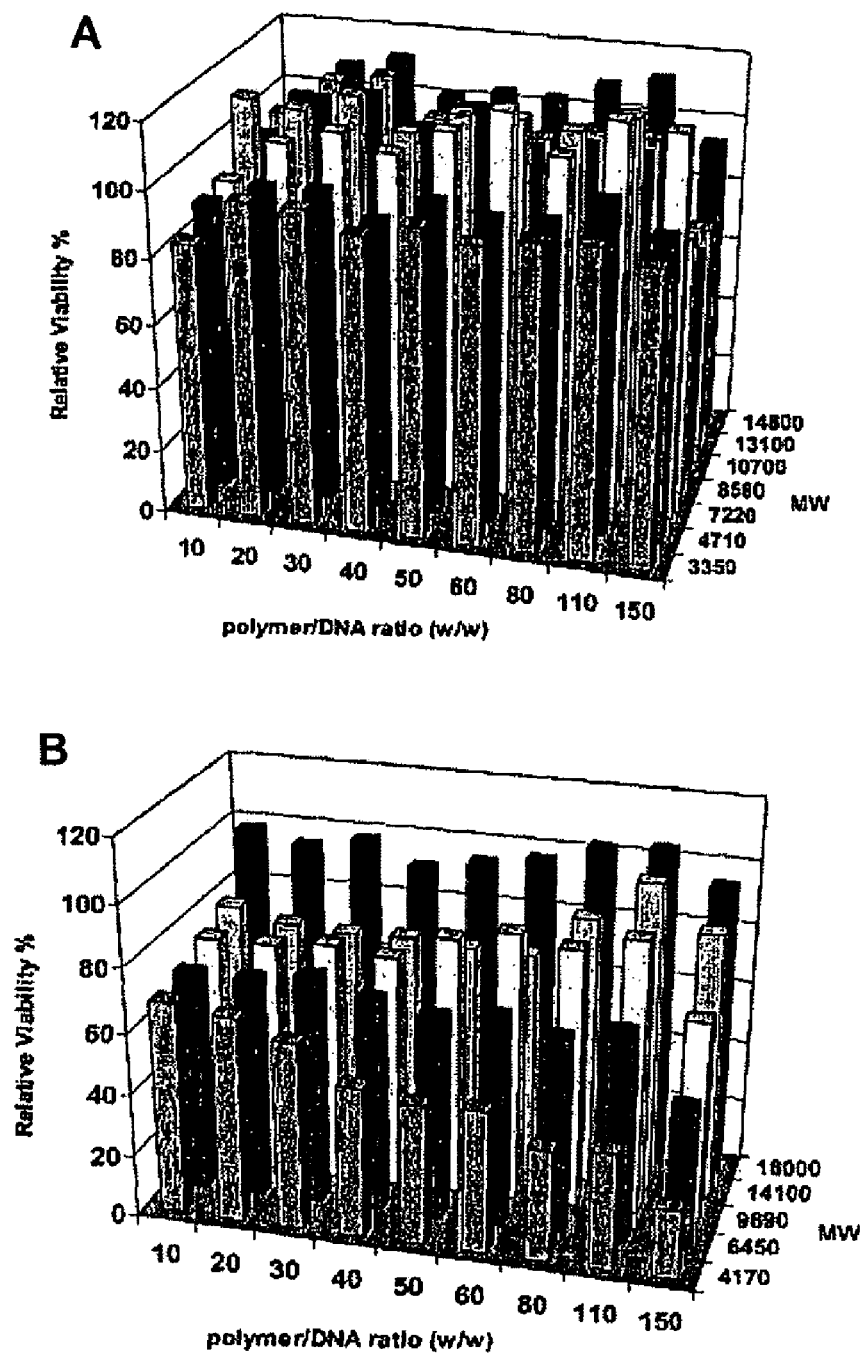
FIG. 19 shows the cytotoxicity of poly-1/DNA complexes as a function of polymer molecular weight, polymer/DNA ratio (w/w), and polymer end-group. (A) amine-terminated chains; (B) acrylate-terminated chains. (n=4, error bars are not shown.)
Figure 20:
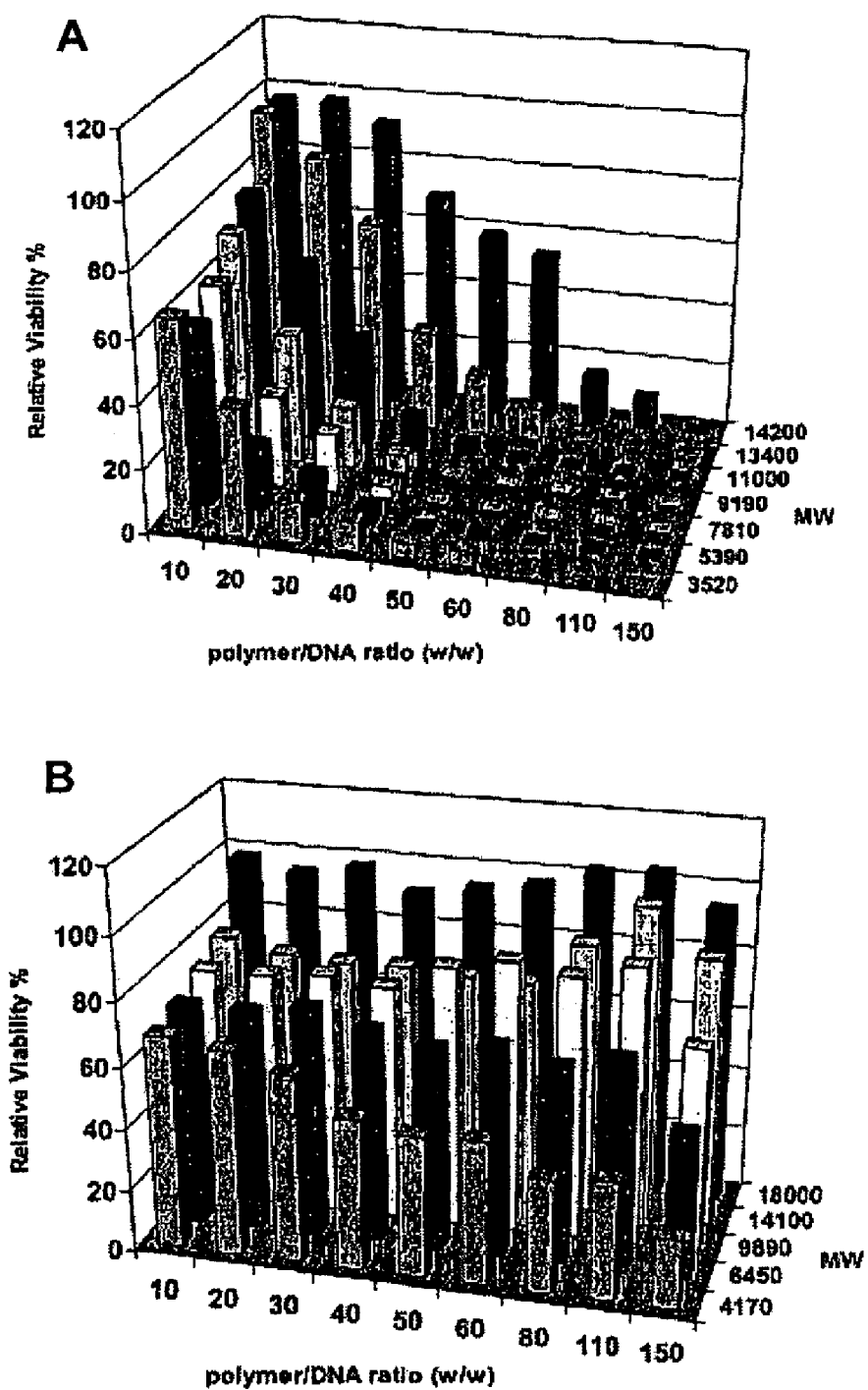
FIG. 20 shows the cytotoxicity of poly-2/DNA complexes as a function of polymer molecular weight, polymer/DNA ratio (w/w), and polymer end-group. (A) amine-terminated chains; (B) acrylate-terminated chains. (n=4, error bars are not shown.)

Cytotoxicity. We evaluated the cytotoxicities of the various polymer/DNA complexes using a standard MTT/thiazolyl blue dye reduction assay. The experiments were performed exactly as the transfection experiments described above, except that instead of assaying for reporter gene expression on day 3, the MTT assay was performed after day 1 (see Materials and Methods). We initially hypothesized that the lack of transfection activity observed for acrylate-terminated polymers may have been due to the cytotoxicity of the acrylate end-groups. FIGS. 19-B and 20-B do indicate that high concentrations of acrylate are cytotoxic, as viability is seen to decrease with increasing polymer/DNA ratio and decreasing polymer $M_w$ (lower $M_w$ corresponds to a higher concentration of end-groups). However, cytotoxicity of acrylates does not sufficiently explain the lack of transfection activity at lower polymer/DNA ratios or higher molecular weights. Data shown in FIG. 19-A demonstrates that cytotoxicity is not a limiting factor for Poly-1 vectors, since cells remain viable even at the highest polymer/DNA ratios. On the other hand, the data displayed in FIG. 20-A suggests that cytotoxicity is a major factor limiting the transfection efficiency of Poly-2 vectors, especially for the lower molecular weight polymers. This result may explain why transfection activity is non-existent or decreasing for Poly-2 vectors at polymer/DNA>30 (see FIG. 18-A).

Figure 21:
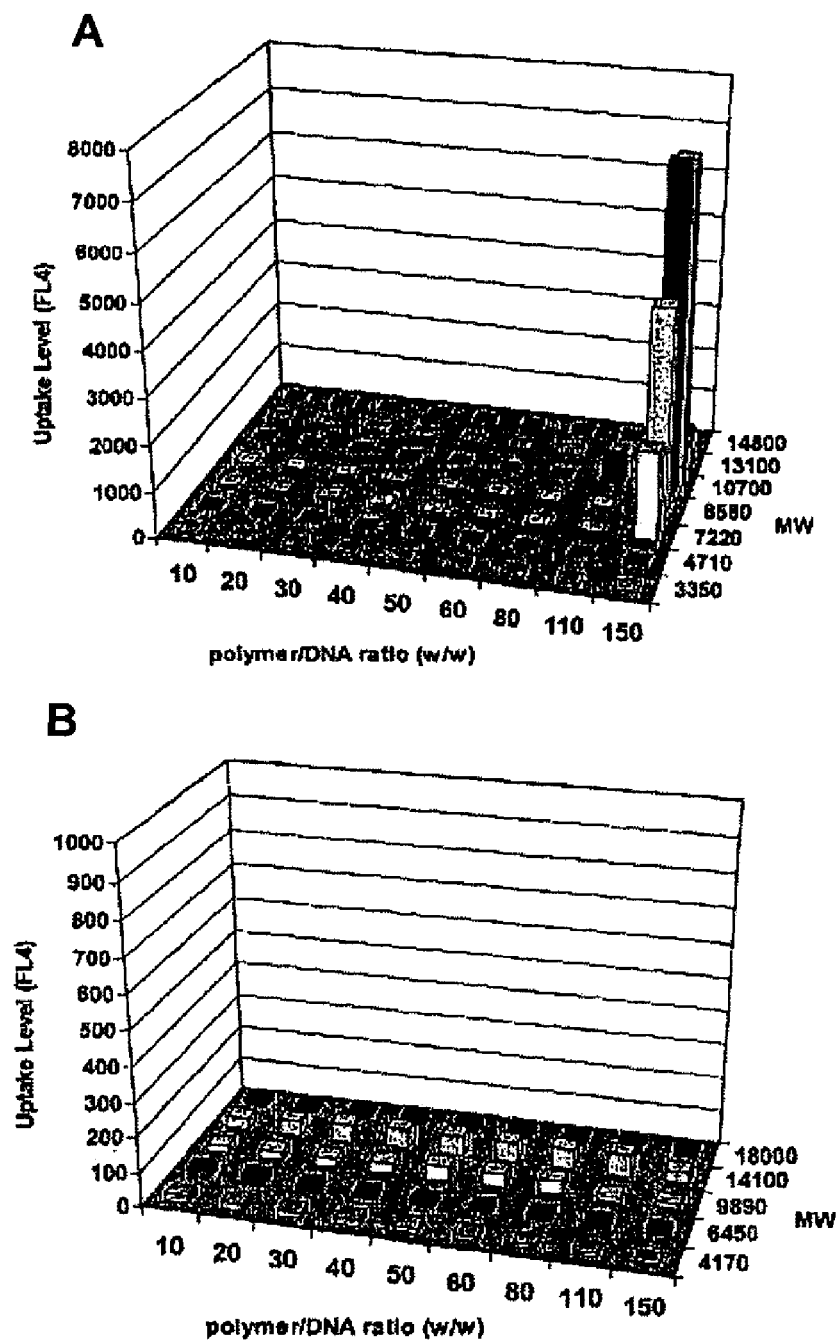
FIG. 21 shows the relative cellular uptake level of poly-1/DNA complexes as a function of polymer molecular weight, polymer/DNA ratio (w/w), and polymer end-group. (A) amine-terminated chains; (B) acrylate-terminated chains. (n=4, error bars are not shown.)
Figure 22:
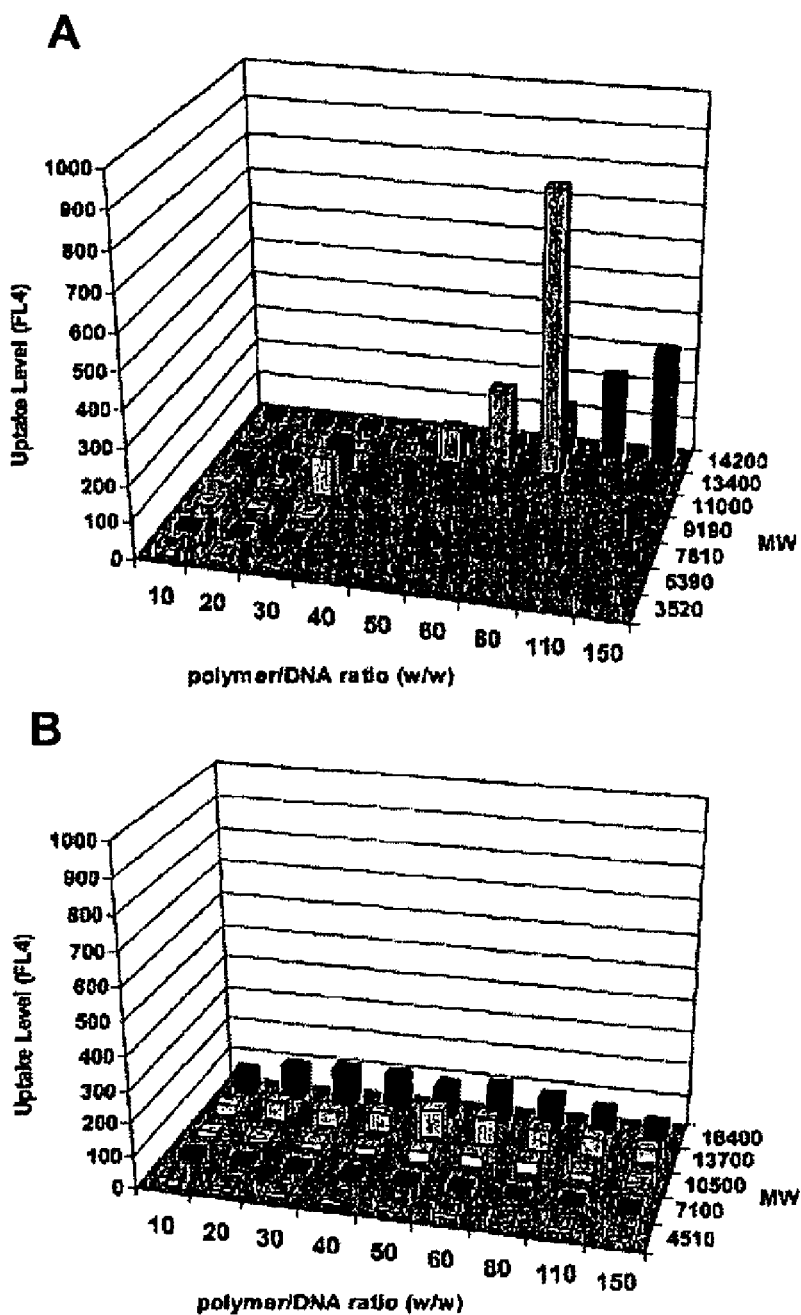
FIG. 22 shows the relative cellular uptake level of poly-2/DNA complexes as a function of polymer molecular weight, polymer/DNA ratio (w/w), and polymer end-group. (A) amine-terminated chains (blank squares represent conditions where cytotoxicity of the complexes prevented a reliable measurement of cellular uptake); (B) acrylate-terminated chains. (n=4, error bars not shown.)

Cellular Uptake. The ability of polymer/DNA complexes to be taken up by cells was evaluated using a previously described flow cytometry-based technique to measure the fluorescence of vector-delivered DNA (Akinc, A., et al., *Parallel synthesis and biophysical characterization of a degradable polymer library of gene delivery*. J. Am. Chem. Soc., 2003; incorporated herein by reference). Briefly, polymer/DNA complexes were prepared using plasmid DNA covalently labeled with the fluorescent dye Cy5. To allow for comparison of the cellular uptake data with the gene expression data outlined above, complexes were formed at the same polymer/DNA ratios and in the same manner as in the transfection experiments. Labeled complexes were incubated with COS-7 cells for 1 hr at 37° C. to allow for uptake. The relative level of particle uptake was then quantified by measuring the fluorescence of cells loaded with Cy5-labeled DNA. The results of these uptake experiments are summarized in FIGS. 21 and 22. Data shown in FIGS. 21-B and 22-B suggest that the lack of transfection activity for the acrylate-terminated polymers is not due to cytotoxicity, as initially thought, but rather to an inability to enter the cell. Similarly, Poly-1 complexes are severely uptake-limited at all but the highest polymer/DNA ratios (FIG. 21-A). While this data doesn't correlate exactly with the transfection results obtained for Poly-1, it is consistent with the fact that transfection activity is not observed until very high polymer/DNA ratios are employed. Poly-2 complexes show no appreciable cellular uptake at polymer/DNA ratios<30 and increasing levels of uptake as polymer/DNA ratios increase beyond 30 (FIG. 22-A). This result, combined with the above cytotoxicity results, helps to explain the transfection activity of Poly-2 complexes. At polymer/DNA ratios less than 30, complexes do not effectively enter the cell, but as polymer/DNA ratios increase much beyond 30, cytotoxicity begins to limit transfection efficiency, resulting in optimal transfection activity near polymer/DNA=30.

Where endocytosis is the main route of cellular entry, the effective formation of nanometer-scale polymer/DNA complexes is one requirement for achieving high levels of cellular uptake (De Smedt, S. C., J. Demeester, and W. E. Hennink, *Cationic polymer based gene delivery systems*. Pharmaceutical Research, 2000. 17(2): p. 113-126; Prabha, S., et al., *Size-dependency of nanoparticle-mediated gene transfection: studies with fractionated nanoparticles*. International Journal of Pharmaceutics, 2002. 244(1-2): p. 105-115; each of which is incorporated herein by reference). The poor uptake levels observed for many of the polymer/DNA complexes may have been attributable to the unsuccessful formation of stable, nanoscale complexes. Unfortunately, the poor neutral pH solubility of the polymers prevented making dynamic light scattering measurements of complex size using the transfection medium (Opti-MEM reduced serum media, pH 7.2) as the diluent. The obtained readings were attributable to polymer precipitates, which were in some cases visible as turbidity in solutions of polymer in Opti-MEM. However, we were able to measure the effective diameters of complexes using 25 mM sodium acetate (pH 5) as the sample diluent. While this data cannot shed light on the size or stability of complexes in the transfection medium, it can indicate whether complexes were successfully formed prior to addition to the transfection medium. Specifically, we found that the lower molecular weight versions ($M_w$<10,700) of Poly-1 were unable to form nanoscale complexes, even in acetate buffer. In all other cases we found that nanometer-sized polymer/DNA complexes were formed. While these results may explain the poor uptake levels associated with low molecular weight versions of Poly-1, they do not satisfactorily explain the low uptake activity of the acrylate-terminated polymers or the dependence of polymer/DNA ratio on cellular uptake. Although particle size and stability are important factors impacting cellular uptake, it is likely that other, yet unidentified, factors must also be considered in order to provide a more complete explanation of the obtained cellular uptake results.

Figure 23:
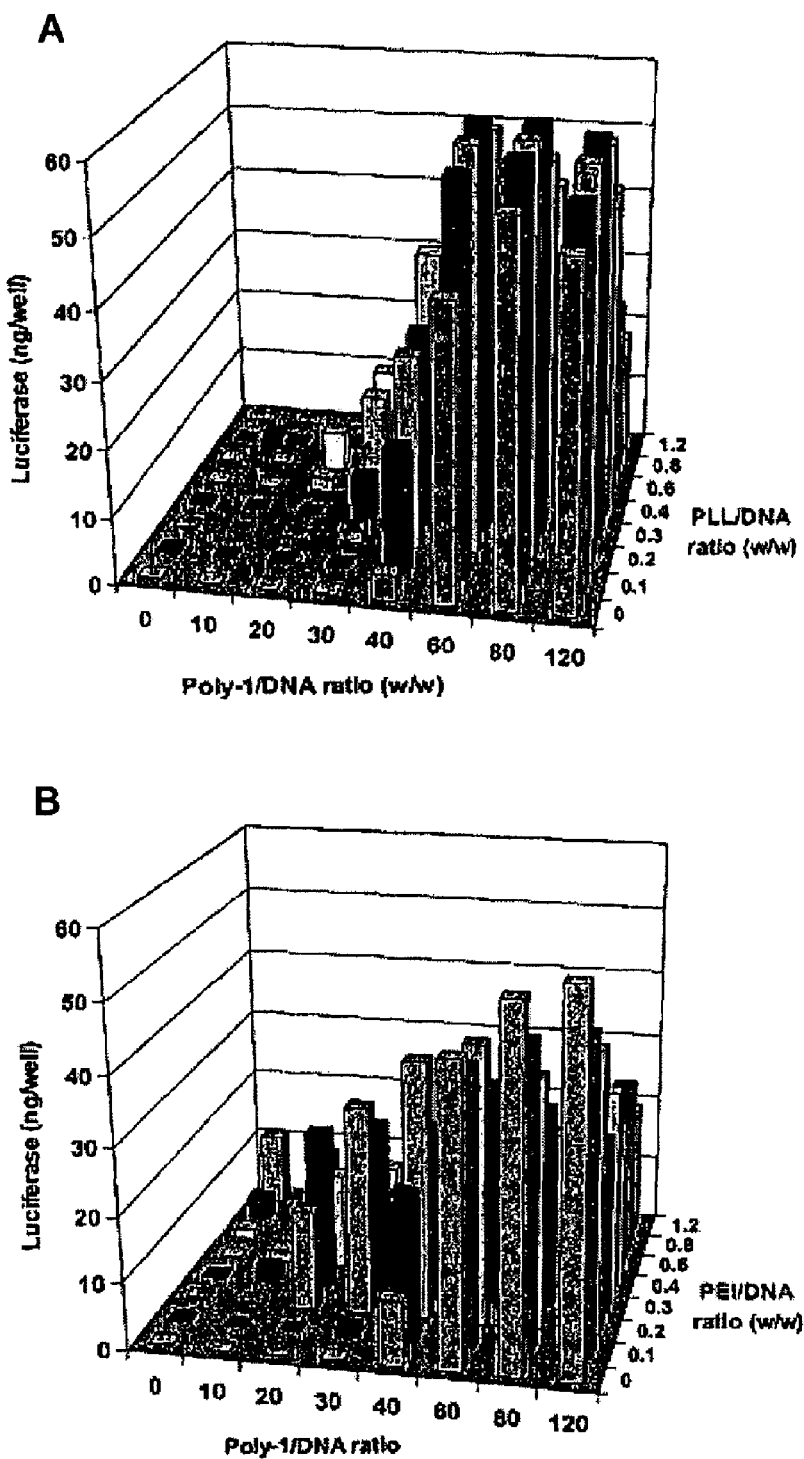
FIG. 23 shows the enhancement of transfection activity of poly-1 (amine-terminated chains, $M_w$=13,100) based delivery vectors through the use of co-complexing agents. (A) polylysine (PLL); (B) polyethyleneimine (PEI). (n=4, error bars are not shown).
Figure 24:
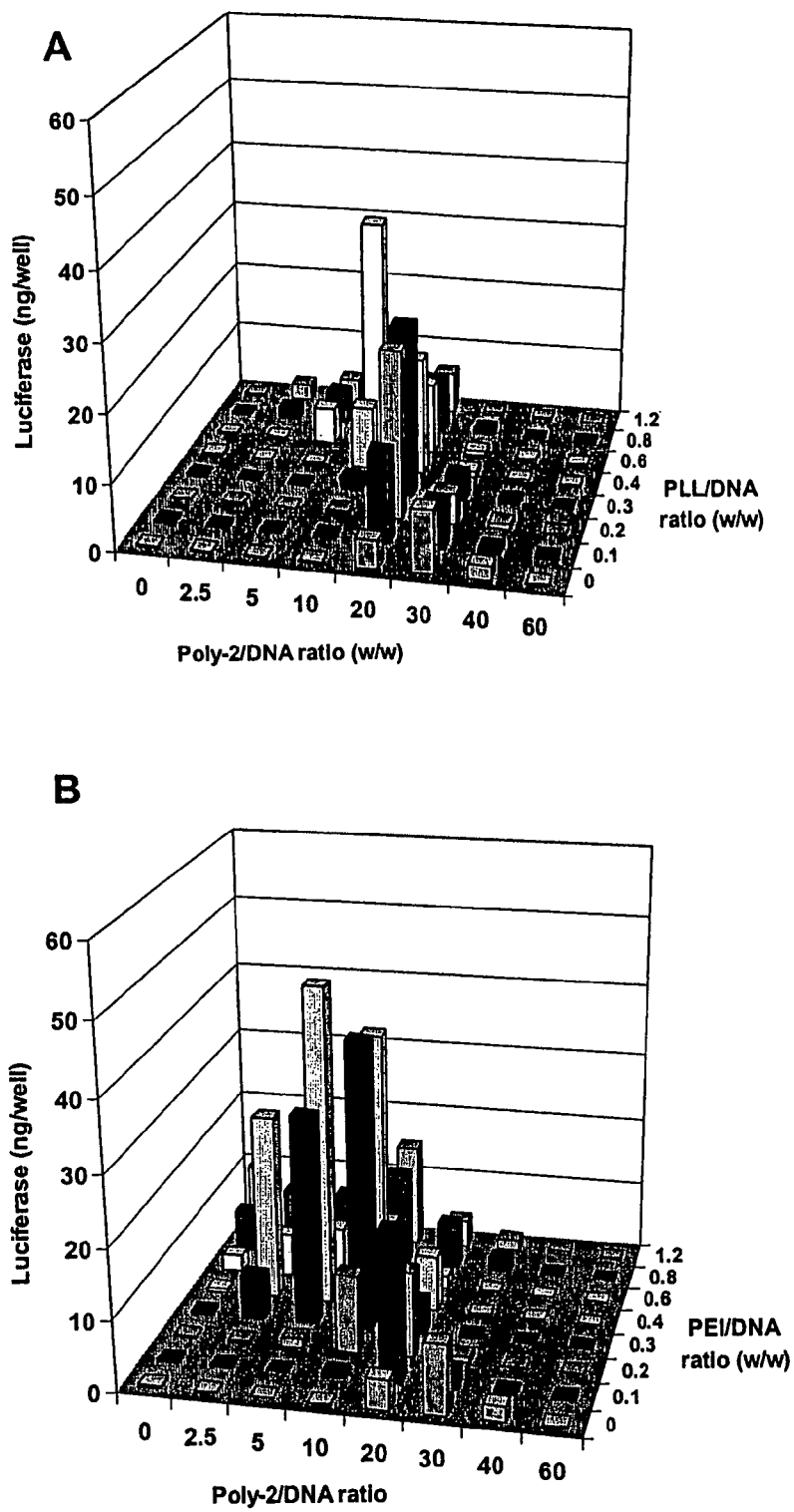
FIG. 24 shows the enhancement of transfection activity of poly-2 (amine-terminated chains, MW=13,400) based delivery vectors through the use of co-complexing agents. (A) poly-lysine (PLL); (B) polyethyleneimine (PEI). (n=4, error bars are not shown.)

Enhancement of Transfection Using a Co-Complexing Agent. Both Poly-1 and Poly-2 require relatively high polymer/DNA weight ratios to achieve high levels of gene transfer. One explanation may be that, compared to other polymers often used to compact DNA (e.g., polylysine (PLL) and PEI), these polymers have relatively low nitrogen densities. Poly-1 has a molecular weight per nitrogen atom (MW/N) of 301, and Poly-2 has a MW/N of 329. By comparison, for PLL and PEI, these figures are roughly 65 and 43, respectively. It might be possible to reduce the amount of Poly-1 or Poly-2 necessary to achieve high levels of transfection by incorporating a small amount of co-complexing agent. This approach could be especially beneficial for Poly-2 vectors, since cytotoxicity appears to be an important limitation for these vectors. To test this hypothesis, PLL and PEI were used as model co-complexing agents. We focused our attention on the most promising member in each of the Poly-1 (amine-terminated, $M_w$=13,100) and Poly-2 (amine-terminated, $M_w$=13,400) sets of polymers. The data displayed in FIGS. 23 and 24 indicate that a significant reduction in polymer could be achieved, while maintaining high levels of transfection efficiency, through the use of PLL or PEI as co-complexing agents. In some cases, significant enhancement of transfection activity was realized. As expected, this co-complexation approach was particularly beneficial for Poly-2 vectors. This work, and prior work (Wagner et al., *Influenza virus hemagglutinin HA-2 N-terminal fusogenic peptides augment gene transfer by transferrin-polylysine-DNA complexes: toward a synthetic virus-like gene-transfer vehicle*. Proc. Natl. Acad. Sci. U.S.A., 1992. 89(17): p. 7934-8; Fritz et al., *Gene transfer into mammalian cells using histone-condensed plasmid DNA*. Hum Gene Ther, 1996. 7(12): p. 1395-404; Pack, D. W., D. Putnam, and R. Langer, *Design of imidazole-containing endosomolytic biopolymers for gene delivery*. Biotechnol. Bioeng., 2000. 67(2): p. 217-23; Lim, Y. B., et al., *Self-Assembled Ternary Complex of Cationic Dendrimer, Cucurbituril, and DNA: Noncovalent Strategy in Developing a Gene Delivery Carrier*. Bioconjug Chem, 2002. 13(6): p. 1181-5; each of which is incorporated herein by reference), demonstrates that the blending of polymers with complementary gene transfer characteristics can in some cases produce more effective gene delivery reagents.

GFP Transfections

To further evaluate the transfection properties of the Poly-1/PLL and Poly-2/PLL blended reagents, we performed transfection experiments using a reporter plasmid coding for green fluorescent protein (pCMV-EGFP). Though the luciferase and GFP transfection assay systems both measure transfection activity, they provide different types of information. The luciferase system quantifies the total amount of exogenous luciferase protein produced by all the cells in a given well, providing a measure of cumulative transfection activity. In contrast, the GFP system can be used to quantify the percentage of cells that have been transfected, providing a cell-by-cell measure of transfection activity. Both systems are useful and offer complementary information regarding the transfection properties of a given gene delivery system.

Figure 25:
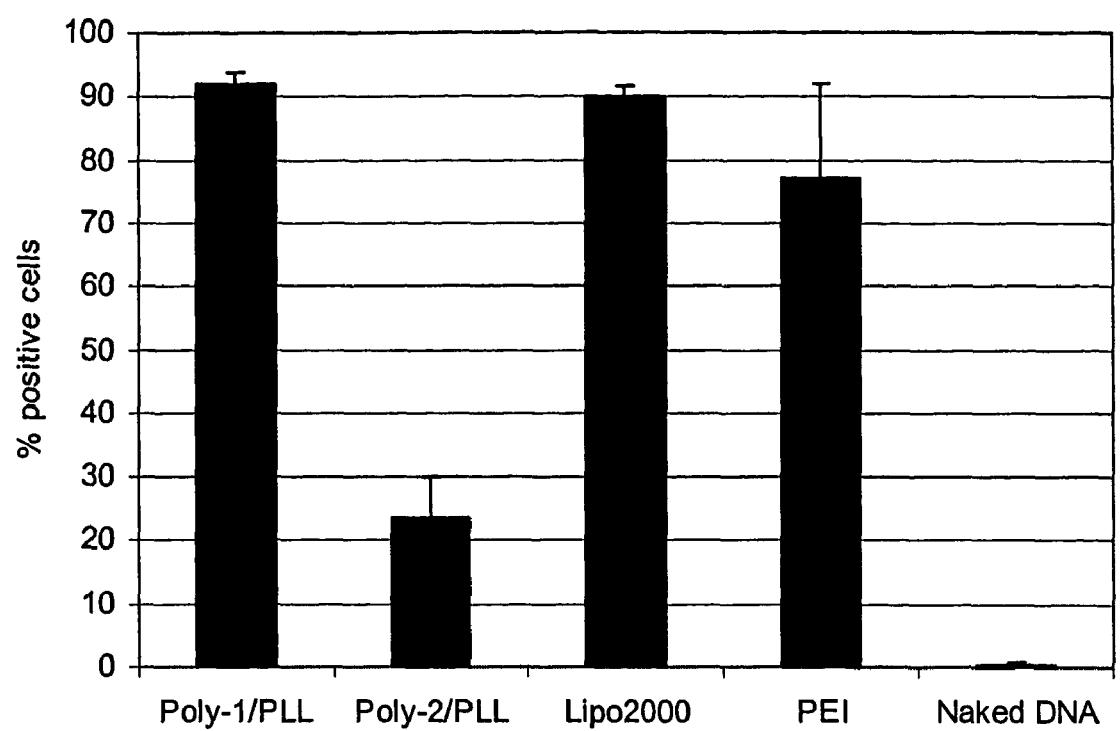
FIG. 25 is a comparison of GFP gene transfer into COS-7 cells using Poly-1/PLL (Poly-1:PLL:DNA=60:0.1:1 (w/w/w)), Poly-2/PLL (Poly-2:PLL:DNA=15:0.4:1 (w/w/w)), Lipofectamine 2000 (μL reagent: μg DNA=1:1), PEI (PEI:DNA 1:1 (w/w), N/P~8), and naked DNA. Cells were seeded on 6-well plates and grown to new confluence. Cells were the incubated with complexes (5 μg DNA/well) for 1 hour, after which time complexes were removed and fresh growth media was added. Two days later GFP expression was assayed by flow cytometry. (n=3, error bars indicate one standard deviation.)
Figure 26:
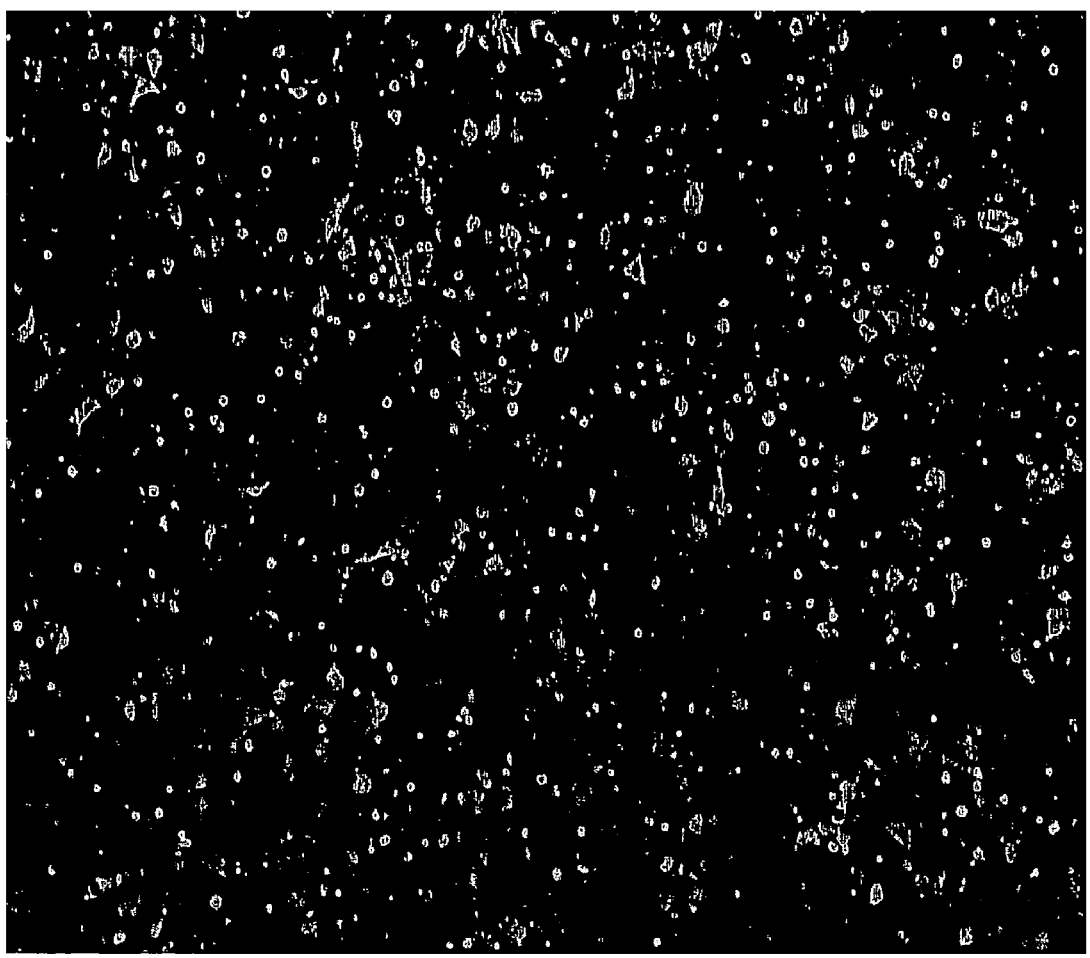
FIG. 26 shows GFP expression in COS-7 cells transfected using Poly-1/PLL.

GFP transfections were performed in a similar manner as the luciferase experiments, but were scaled up to 6-well plate format (5 µg plasmid/well). COS-7 cells were transfected using Poly-1/PLL (Poly-1:PLL:DNA=60:0.1:1 w/w/w) and Poly-2/PLL (Poly-2:PLL:DNA=15:0.4:1 w/w/w). Lipofectamine 2000 (µL reagent: µg DNA=1:1), PEI (PEI: DNA=1:1 w/w, N/P~8), and naked DNA were used as controls in the experiment. After 1 hr incubation with cells, vectors were removed and fresh growth media was added. Two days later GFP expression was assayed using a flow cytometer. Nearly all cells transfected with Poly-1/PLL were positive for GFP expression (FIGS. 25 and 26). Experiments indicated that Poly-2/PLL vectors were less effective, resulting in roughly 25% positive cells. Positive controls Lipofectamine 2000 and PEI were also able to mediate effective transfection of COS-7 cells under the conditions employed. Although Lipofectamine 2000 and PEI transfections resulted in nearly the same percentage of GFP-positive cells as Poly-1/PLL, the fluorescence level of GFP-positive cells was higher for Poly-1/PLL (mean fluorescence=6033) than that of both Lipofectamine 2000 (mean fluorescence=5453) and PEI (mean fluorescence=2882). Multiplying the percentage of positive cells by the mean fluorescence level of positive cells provides a measure of aggregate expression for the sample and should, in theory, better correlate with the results of luciferase gene expression experiments. Quantifying total GFP expression in this manner indicates that the highest expression level is achieved by Poly-1/PLL, followed by Lipofectamine 2000 and PEI. This result is in general agreement with the luciferase expression results.

Figure 27:
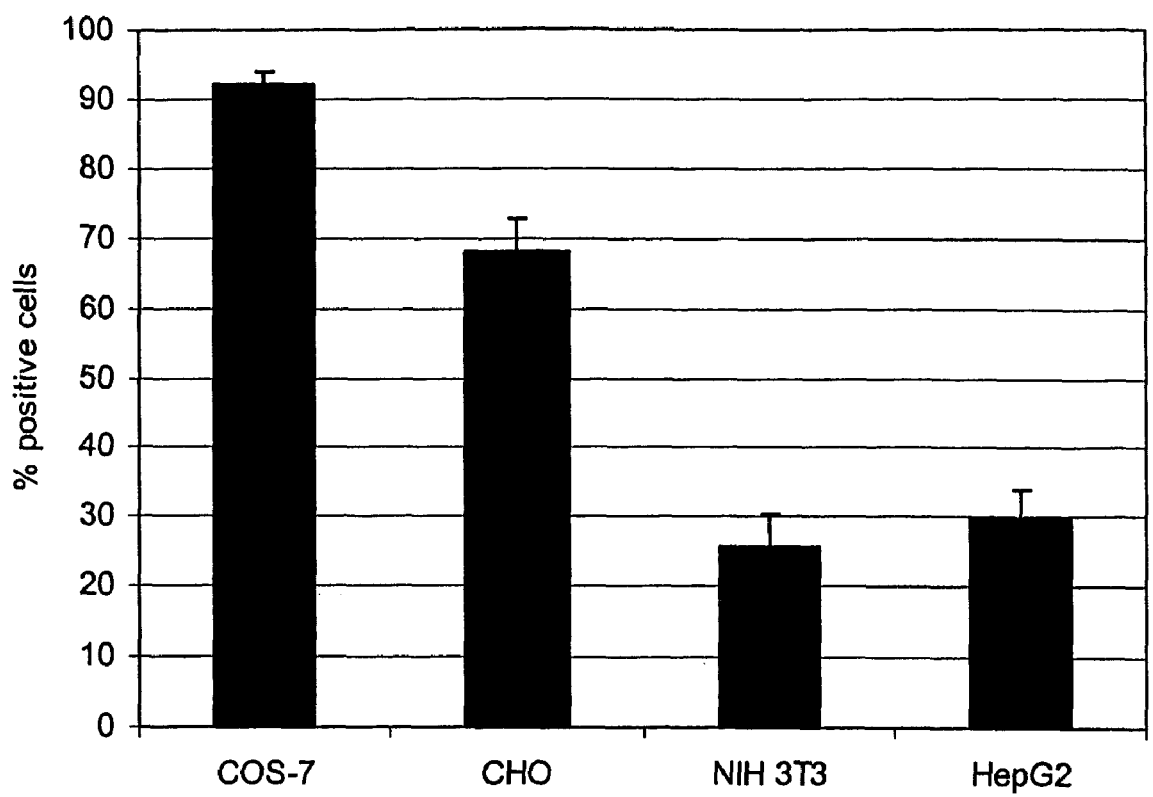
FIG. 27 shows GFP gene transfer into four different cell lines using Poly-1/PLL (Poly-1:PLL:DNA=60:0.1:1 (w/w/w). Cells were seeded on 6-well plates and grown to near confluence. Cells were then incubated with complexes (5 μg DNA/well) for 1 hour, after which time complexes were removed and fresh growth media was added. Two days later GFP expression was assayed by flow cytometry. (n=5, error bars indicate one standard deviation.)

Experiments have shown that Poly-1/PLL (Poly-1:PLL: DNA=60:0.1:1 w/w/w) is a highly effective vector for transfecting COS-7 cells. The ability of this vector to mediate transfection in three other commonly used cell lines (CHO, NIH 3T3, and HepG2) was also investigated. It is very likely that each of these cell lines have optimal transfection conditions that differ from those used to transfect COS-7 cells; however, as a preliminary evaluation of the ability to transfect multiple cell lines, transfections were performed in the same manner and under the same conditions as the COS-7 transfections. Results indicate that Poly-1/PLL (Poly-1:PLL: DNA=60:0.1:1 w/w/w) is able to successfully transfect CHO, NIH 3T3, and HepG2 cells, though not as effectively as COS-7 cells (FIG. 27). This is not too surprising since the vector used was optimized by screening for gene transfer in COS-7 cells. Optimization of vector composition and transfection conditions specific for each cell type would be expected to result in even higher transfection levels.

Summary

In this work, the role of polymer molecular weight, polymer chain end-group, and polymer/DNA ratio on a number of important gene transfer properties has been investigated. All three factors were found to have a significant impact on gene transfer, highlighting the benefit of carefully controlling and optimizing these parameters. In addition, the incorporation of a small amount of PLL, used to aid complexation, further enhances gene transfer. Through these approaches degradable poly(beta-amino esters)-based vectors that rival some of the best available non-viral vectors for in vitro gene transfer.

Example 6

Further Studies of Selected Poly(Beta-Amino Esters)

To further characterize and synthesize some of the poly (beta-amino esters) identified in previous screens, a twentyone polymers were re-synthesized at various ratios of amine monomer to acrylate monomer. The resulting polymers were characterized by gel permeation chromatography to determine the molecular weight and polydispersitie of each polymer. Each of the polymer was then tested for its ability to transfect cells.

Polymer Synthesis. The polymers were synthesized as described in Example 5. Several versions of each polymer were created by varying the amin/diacrylated stoichiometric ratio. For example, C36-1 corresponds to the stoichiometric ratio of 1.4, and C36-12 to 0.6, with all the intermediates given in the table below:

| Version of C36 | Amine:Acrylate Stoichiometric Ratio |
|---|---|
| C36-1 | 1.4 |
| C36-2 | 1.3 |
| C36-3 | 1.2 |
| C36-4 | 1.1 |
| C36-5 | 1.05 |
| C36-6 | 1.025 |
| C36-7 | 1.0 |
| C36-8 | 0.975 |
| C36-9 | 0.950 |
| C36-10 | 0.9 |
| C36-11 | 0.8 |
| C36-12 | 0.6 |

The polymers were typically prepared in glass vials with no solvent at 100° C. for 5 hours. In some syntheses, the polymerization at 100° C. yielded highly cross-linked polymers when certain monomers such as amine 94 were used; therefore, the polymerization reactions were repeated at 50° C. with 2 mL of DMSO added to avoid cross-linking.

The resulting polymers were analyzed by GPC as described in Example 5. The molecular weights and polydispersities of each of the polymers is shown in the table below:

| Polymer | $M_w$ | $M_n$ | Polydispersity |
|---|---|---|---|
| F28-1 | 5540 | 2210 | 2.50678733 |
| F28-2 | 6150 | 2460 | 2.5 |
| F28-3 | 8310 | 2920 | 2.845890411 |
| F28-4 | 11600 | 3660 | 3.169398907 |
| F28-5 | 16800 | 4360 | 3.853211009 |
| F28-6 | 16100 | 4850 | 3.319587629 |
| F28-7 | 18000 | 5040 | 3.571428571 |
| F28-8 | 18200 | 5710 | 3.187390543 |
| F28-9 | 22300 | 7880 | 2.829949239 |
| F28-10 | 23700 | 8780 | 2.699316629 |
| F28-11 | 12100 | 5660 | 2.137809187 |
| F28-12 | 4850 | 2920 | 1.660958904 |
| C36-1 | 7080 | 3270 | 2.165137615 |
| C36-2 | 5100 | 2640 | 1.931818182 |
| C36-3 | 21200 | 8090 | 2.620519159 |
| C36-4 | 20500 | 6710 | 3.05514158 |
| C36-5 | 112200 | 33200 | 3.379518072 |
| C36-6 | 21700 | 6890 | 3.149492017 |
| C36-7 | 36800 | 15700 | 2.343949045 |
| C36-8 | 35700 | 12600 | 2.833333333 |
| C36-9 | 35200 | 15100 | 2.331125828 |
| C36-10 | 22500 | 9890 | 2.275025278 |
| C36-11 | 26000 | 6060 | 4.290429043 |
| D60-1 | 1890 | 1400 | 1.35 |
| D60-2 | 2050 | 1520 | 1.348684211 |
| D60-3 | 2670 | 1720 | 1.552325581 |
| D60-4 | 3930 | 2210 | 1.778280543 |
| D60-5 | 5130 | 2710 | 1.89298893 |
| D60-6 | 5260 | 2800 | 1.878571429 |
| D60-7 | 1130 | 1090 | 1.036697248 |
| D60-8 | 1840 | 1510 | 1.218543046 |
| D60-9 | 6680 | 3440 | 1.941860465 |
| D60-10 | 8710 | 4410 | 1.975056689 |
| D60-11 | 9680 | 4410 | 2.195011338 |
| D60-12 | 7450 | 3470 | 2.146974063 |
| D61-1 | 1710 | 1410 | 1.212765957 |
| D61-2 | 2600 | 1790 | 1.452513966 |
| D61-3 | 3680 | 2280 | 1.614035088 |
| D61-4 | 4630 | 2550 | 1.815686275 |
| D61-5 | NA | NA | NA |
| D61-6 | NA | NA | NA |
| D61-7 | 6110 | 3250 | 1.88 |
| D61-8 | 6410 | 3190 | 2.009404389 |
| D61-9 | 6790 | 3440 | 1.973837209 |
| D61-10 | 8900 | 4350 | 2.045977011 |
| D61-11 | 10700 | 4600 | 2.326086957 |
| D61-12 | 6760 | 2900 | 2.331034483 |
| F32-1 | 10300 | 3260 | 3.159509202 |
| F32-2 | 11100 | 3490 | 3.180515759 |
| F32-3 | 16600 | 4820 | 3.443983402 |
| F32-4 | 17300 | 5390 | 3.209647495 |
| F32-5 | 18600 | 5830 | 3.190394511 |
| F32-6 | 26200 | 8290 | 3.160434258 |
| C32-1 | 6670 | 2810 | 2.37366548 |
| C32-2 | 18100 | 5680 | 3.186619718 |
| C32-3 | 19300 | 6060 | 3.184818482 |
| C32-4 | 25600 | 9100 | 2.813186813 |
| C32-5 | 25000 | 7860 | 3.180661578 |
| C32-6 | 25700 | 8440 | 3.045023697 |
| C86-1 | 14200 | 2900 | 4.896551724 |
| C86-2 | 21000 | 2900 | 7.24137931 |
| C86-3 | 27500 | 4590 | 5.991285403 |
| U94-1 | 10700 | 3530 | 3.031161473 |
| U94-2 | NA | NA | NA |
| U94-3 | NA | NA | NA |
| F32-1 | 10300 | 3260 | 3.159509202 |
| F32-2 | 11100 | 3490 | 3.180515759 |
| F32-3 | 16600 | 4820 | 3.443983402 |
| F32-4 | 17300 | 5390 | 3.209647495 |
| F32-5 | 25000 | 7860 | 3.180661578 |
| F32-6 | 26200 | 8290 | 3.160434258 |
| C32-1 | 6670 | 2810 | 2.37366548 |
| C32-2 | 18100 | 5680 | 3.186619718 |
| C32-3 | 19300 | 6060 | 3.184818482 |
| C32-4 | 25600 | 9100 | 2.813186813 |
| C32-5 | 25000 | 7860 | 3.180661578 |
| C32-6 | 25700 | 8440 | 3.045023697 |
| U86-1 | Unusual | NA | NA |
| U86-2 | Unusual | NA | NA |
| U86-3 | Unusual | NA | NA |
| U86-4 | Unusual | NA | NA |
| U85-5 | Unusual | NA | NA |
| JJ32-1 | 9730 | 4010 | 2.426433915 |
| JJ32-2 | 12100 | 4580 | 2.641921397 |
| JJ32-3 | 19400 | 6510 | 2.980030722 |
| JJ32-4 | 27900 | 10000 | 2.79 |
| JJ32-5 | 32600 | 9720 | 3.353909465 |
| JJ32-6 | 28900 | 9870 | 2.928064843 |
| JJ36-1 | 7540 | 3550 | 2.123943662 |
| JJ36-2 | 143500 | 59600 | 2.407718121 |
| JJ36-3 | 20100 | 7310 | 2.749658003 |
| JJ36-4 | 30200 | 10200 | 2.960784314 |
| JJ36-5 | 33900 | 10600 | 3.198113208 |
| JJ36-6 | 36100 | 12500 | 2.888 |
| JJ28-1 | 7550 | 3240 | 2.330246914 |
| JJ28-2 | 9490 | 3460 | 2.742774566 |
| JJ28-3 | 16800 | 5420 | 3.099630996 |
| JJ28-4 | 23300 | 8090 | 2.880098888 |
| JJ28-5 | 25500 | 7700 | 3.311688312 |
| JJ28-6 | 32100 | 10900 | 2.944954128 |
| U28-1 | 7190 | 2580 | 2.786821705 |
| U28-2 | 10700 | 3990 | 2.681704261 |
| U28-3 | 15600 | 7300 | 2.136963601 |
| U28-4 | 20400 | 9880 | 2.064777328 |
| U28-5 | 20500 | 9670 | 2.119958635 |
| U28-6 | 24200 | 13000 | 1.861538462 |
| E28-1 | 5900 | 3280 | 1.798780488 |
| E28-2 | 7950 | 3550 | 2.23943662 |

| Polymer | $M_w$ | $M_n$ | Polydispersity |
|---|---|---|---|
| E28-3 | 14300 | 6300 | 2.26984127 |
| E28-4 | 6990 | 3320 | 2.105421687 |
| E28-5 | 17400 | 8180 | 2.127139364 |
| E28-6 | 19300 | 9030 | 2.137320044 |
| LL6-1 | 2380 | 1570 | 1.515923567 |
| LL6-2 | 3350 | 2070 | 1.618357488 |
| LL6-3 | 4110 | 2340 | 1.756410256 |
| LL6-4 | 5750 | 3010 | 1.910299003 |
| LL6-5 | 7810 | 5050 | 1.546534653 |
| LL6-6 | 6950 | 4190 | 1.658711217 |
| LL8-1 | 3160 | 1910 | 1.654450262 |
| LL8-2 | 3630 | 2560 | 1.41796875 |
| LL8-3 | 5300 | 3520 | 1.505681818 |
| LL8-4 | 6000 | 3320 | 1.807228916 |
| LL8-5 | 8160 | 4730 | 1.725158562 |
| LL8-6 | 7190 | 4650 | 1.546236559 |
| U36-1 | 7290 | 3370 | 2.163204748 |
| U36-2 | 11100 | 5000 | 2.22 |
| U36-3 | 12600 | 5470 | 2.303473492 |
| U36-4 | 21500 | 8550 | 2.514619883 |
| U36-5 | 24700 | 9430 | 2.619300106 |
| U36-6 | 31700 | 10700 | 2.962616822 |
| E36-1 | 6030 | 3130 | 1.926517572 |
| E36-2 | 8510 | 4040 | 2.106435644 |
| E36-3 | 12800 | 5730 | 2.233856894 |
| E36-4 | 18200 | 7620 | 2.388451444 |
| E36-5 | 20100 | 8050 | 2.49689441 |
| E36-6 | 32900 | 10900 | 3.018348624 |
| U32-1 | 9830 | 3790 | 2.593667546 |
| U32-2 | 12000 | 4460 | 2.69058296 |
| U32-3 | 18200 | 6780 | 2.684365782 |
| U32-4 | 25200 | 11100 | 2.27027027 |
| U32-5 | 26500 | 9360 | 2.831196581 |
| U32-6 | 26200 | 10600 | 2.471698113 |
| E32-1 | 7070 | 3310 | 2.135951662 |
| E32-2 | 9920 | 4180 | 2.373205742 |
| E32-3 | 14700 | 6080 | 2.417763158 |
| E32-4 | 23500 | 9160 | 2.565502183 |
| E32-5 | 28800 | 10000 | 2.88 |
| E32-6 | 26900 | 10300 | 2.611650485 |
| C94-1 | 6760 | 3110 | 2.173633441 |
| C94-2 | 10800 | 4190 | 2.577565632 |
| C94-3 | 18000 | 5330 | 3.377110694 |
| C94-4 | 38900 | 6660 | 5.840840841 |
| C94-5 | Didn't dissolve | NA | NA |
| C94-6 | Didn't dissolve | NA | NA |
| D94-1 | 6030 | 2980 | 2.023489933 |
| D94-2 | 6620 | 3370 | 1.964391691 |
| D94-3 | 9680 | 3950 | 2.450632911 |
| D94-4 | 11500 | 4510 | 2.549889135 |
| D94-5 | 13700 | 4940 | 2.773279352 |
| D94-6 | 18800 | 5650 | 3.327433628 |
| F94-1 | 5570 | 2740 | 2.032846715 |
| F94-2 | 7670 | 3180 | 2.411949686 |
| F94-3 | 12600 | 4230 | 2.978723404 |
| F94-4 | 20300 | 5160 | 3.934108527 |
| F94-5 | 21500 | 5390 | 3.988868275 |
| F94-6 | 27300 | 6310 | 4.326465927 |
| JJ94-1 | 7750 | 3360 | 2.306547619 |
| JJ94-2 | 12700 | 4590 | 2.766884532 |
| JJ94-3 | 30500 | 7280 | 4.18956044 |
| JJ94-4 | Didn't dissolve | NA | NA |
| JJ94-5 | Didn't dissolve | NA | NA |
| JJ94-6 | Didn't dissolve | NA | NA |
| F86-1 | 3940 | 2630 | 1.498098859 |
| F86-2 | 5300 | 3190 | 1.661442006 |
| F86-3 | 7790 | 4040 | 1.928217822 |
| F86-4 | 11000 | 5410 | 2.033271719 |
| F86-5 | 10600 | 5650 | 1.876106195 |
| F86-6 | 13300 | 6440 | 2.065217391 |
| D86-1 | 4610 | 2830 | 1.628975265 |
| D86-2 | 5570 | 3290 | 1.693009119 |
| D86-3 | 7120 | 3770 | 1.888594164 |
| D86-4 | 8310 | 4440 | 1.871621622 |
| D86-5 | 8950 | 4710 | 1.900212314 |
| D86-6 | 10400 | 5010 | 2.075848303 |
| U86-1 | 5940 | 3500 | 1.697142857 |
| U86-2 | 7780 | 4430 | 1.756207675 |
| U86-3 | 11900 | 6540 | 1.819571865 |
| U86-4 | 15100 | 7630 | 1.979030144 |
| U86-5 | 16300 | 8950 | 1.82122905 |
| U86-6 | 18100 | 9810 | 1.845056065 |
| E86-1 | 4880 | 3140 | 1.554140127 |
| E86-2 | 6300 | 3790 | 1.662269129 |
| E86-3 | 9780 | 5140 | 1.902723735 |
| E86-4 | 12500 | 6350 | 1.968503937 |
| E86-5 | 13400 | 6820 | 1.964809384 |
| E86-6 | 15500 | 7280 | 2.129120879 |
| JJ86-1 | 5460 | 3370 | 1.620178042 |
| JJ86-2 | 6880 | 4080 | 1.68627451 |
| JJ86-3 | 11900 | 6180 | 1.925566343 |
| JJ86-4 | 14200 | 7000 | 2.028571429 |
| JJ86-5 | 20500 | 9090 | 2.255225523 |
| JJ86-6 | 16300 | 7770 | 2.097812098 |
| C86-1 | 4870 | 3030 | 1.607260726 |
| C86-2 | 5720 | 3460 | 1.653179191 |
| C86-3 | 9970 | 5060 | 1.970355731 |
| C86-4 | 14200 | 7000 | 2.028571429 |
| C86-5 | 17700 | 8500 | 2.082352941 |
| C86-6 | 17800 | 8500 | 2.094117647 |
| C80-1 | 2450 | 1790 | 1.368715084 |
| C80-2 | 3770 | 2370 | 1.5907173 |
| C80-3 | 6080 | 3370 | 1.804154303 |
| C80-4 | 7960 | 4310 | 1.846867749 |
| C80-5 | 9030 | 4660 | 1.93776824 |
| C80-6 | 12600 | 6050 | 2.082644628 |
| E80-1 | 2840 | 2010 | 1.412935323 |
| E80-2 | 3720 | 2420 | 1.537190083 |
| E80-3 | 6080 | 3650 | 1.665753425 |
| E80-4 | 7210 | 4240 | 1.700471698 |
| E80-5 | 7640 | 4290 | 1.780885781 |
| E80-6 | 9000 | 5310 | 1.694915254 |
| JJ80-1 | 3410 | 2180 | 1.564220183 |
| JJ80-2 | 4590 | 2890 | 1.588235294 |
| JJ80-3 | 8430 | 4750 | 1.774736842 |
| JJ80-4 | 11300 | 6560 | 1.722560976 |
| JJ80-5 | 13200 | 7160 | 1.843575419 |
| JJ80-6 | 11600 | 6540 | 1.773700306 |
| U80-1 | 4300 | 2680 | 1.604477612 |
| U80-2 | 5130 | 3020 | 1.698675497 |
| U80-3 | 8320 | 4700 | 1.770212766 |
| U80-4 | 9130 | 4880 | 1.870901639 |
| U80-5 | 11300 | 5750 | 1.965217391 |
| U80-6 | 11200 | 5920 | 1.891891892 |

Luciferase Transfection Assay. As described in Example 5, COS-7 cells were transfected with pCMV-Luc DNA using each of the polymers at polymer-to-DNA ratios ranging from 10:1 to 100:1 (weight:weight). Luciferase expression was analysed using Bright-Glo assay kits (Promega). Luminescence was measured for each transfection, and the luminescence was used to calculate nanograms of Luciferase enzyme as described in Example 5. Experiments were done in quadruplicate, and the values shown in the tables below are the averaged values from the four experiments. These data are shown below for each polymer synthesized.

| C36-1 | C36-2 | C36-3 | C36-4 | C36-5 | C36-6 | Ratio |
|---|---|---|---|---|---|---|
| 0.168527 | 0.345149 | 0.627992 | 0.152258 | 0.068355 | 0.094073 | 10 |
| 3.58467 | 0.12639 | 21.27867 | 2.145388 | 0.163042 | 0.184298 | 20 |
| 4.295966 | 0.927605 | 18.84046 | 4.750661 | 0.287989 | 1.063834 | 30 |
| 7.150343 | 1.137242 | 17.04771 | 7.529555 | 0.080757 | 0.332789 | 40 |
| 3.74705 | 1.180274 | 6.875879 | 9.710764 | 0.582186 | 1.963895 | 60 |
| 0.705683 | 0.212297 | 0.560245 | 7.221382 | 5.003849 | 5.813189 | 100 |

| C36-7 | C36-8 | C36-9 | C36-10 | C36-11 | C-36-12 | Ratio |
|---|---|---|---|---|---|---|
| 0.164373 | 0.085336 | 0.116502 | 0.042173 | 0.062905 | 0.18877 | 10 |
| 0.134132 | 0.096043 | 0.091152 | 0.032851 | 0.032115 | 0.383965 | 20 |
| 0.020768 | 0.021203 | 0.0665 | 0.021953 | 0.017807 | 0.288102 | 30 |
| 0.05027 | 0.060731 | 0.017768 | 0.011885 | 0.008923 | 0.128469 | 40 |
| 0.031233 | 0.048807 | 0.025626 | 0.012516 | 0.002606 | 0.213173 | 60 |
| 0.116587 | 0.129504 | 0.332497 | 0.123413 | 0.058442 | 0.250708 | 100 |

| C86-1 | C86-2 | C86-3 | Ratio |
|---|---|---|---|
| 0.157713 | 0.475708 | 1.093272 | 10 |
| 0.242481 | 0.616621 | 1.439904 | 20 |
| 0.396888 | 0.992601 | 1.758045 | 30 |
| 0.300173 | 1.276707 | 1.901677 | 40 |

| D60-1 | D60-2 | D60-3 | D60-4 | D60-5 | D60-6 | Ratio |
|---|---|---|---|---|---|---|
| 0.604984 | 0.443875 | 0.363271 | 0.260475 | 0.498462 | 0.466087 | 10 |
| 0.115174 | 0.174976 | 0.250613 | 0.40783 | 0.587186 | 0.89381 | 20 |
| 0.138372 | 0.45915 | 0.81101 | 0.773161 | 1.264634 | 1.438474 | 30 |
| 0.135287 | 0.506303 | 2.344053 | 1.695591 | 2.302305 | 2.959638 | 40 |
| 0.203804 | 0.679718 | 3.908348 | 2.216808 | 3.129304 | 4.335511 | 60 |
| 0.233546 | 0.640246 | 0.251146 | 3.112999 | 7.65786 | 6.759895 | 100 |

| D60-7 | D60-8 | D60-9 | D60-10 | D60-11 | D60-12 | Ratio |
|---|---|---|---|---|---|---|
| 0.299777 | 0.333863 | 0.434027 | 0.46862 | 0.387458 | 0.211083 | 10 |
| 0.237477 | 0.266398 | 1.211246 | 1.385232 | 1.034892 | 0.215027 | 20 |
| 0.339709 | 0.665539 | 2.958346 | 5.607664 | 3.514454 | 0.485295 | 30 |
| 0.499842 | 1.216181 | 4.406196 | 6.736276 | 5.121445 | 0.444359 | 40 |
| 1.297394 | 1.009228 | 5.951785 | 9.565956 | 7.193687 | 0.35831 | 60 |
| 5.399266 | 0.135852 | 5.725666 | 10.45568 | 5.414051 | 0.245279 | 100 |

| D61-1 | D61-2 | D61-3 | D61-4 | D61-5 | D61-6 | Ratio |
|---|---|---|---|---|---|---|
| 0.329886 | 0.29803 | 0.190101 | 0.142813 | 0.114565 | 0.227593 | 10 |
| 0.299409 | 0.710035 | 0.295508 | 0.288845 | 0.247909 | 0.32839 | 20 |
| 0.155568 | 0.680763 | 0.618022 | 0.651633 | 0.402721 | 1.831437 | 30 |
| 0.085824 | 0.620294 | 3.722971 | 4.572264 | 3.010274 | 11.69027 | 40 |
| 0.188357 | 0.187979 | 3.970054 | 7.147033 | 10.85674 | 9.238981 | 60 |
| 0.019321 | 0.001369 | 0.034958 | 0.033062 | 0.202601 | 0.131544 | 100 |

| D61-7 | D61-8 | D61-9 | D61-10 | D61-11 | D61-12 | Ratio |
|---|---|---|---|---|---|---|
| 0.153122 | 0.180646 | 0.1073 | 0.244713 | 0.231561 | 0.18571 | 10 |
| 0.203312 | 0.217288 | 0.191108 | 0.185759 | 0.270723 | 0.119897 | 20 |
| 0.539455 | 0.239807 | 0.140418 | 0.174014 | 0.320869 | 0.094186 | 30 |
| 1.679507 | 1.020126 | 0.584908 | 0.229946 | 0.474142 | 0.154025 | 40 |
| 12.69543 | 5.9829 | 7.008946 | 1.308281 | 0.301803 | 0.067526 | 60 |
| 1.271189 | 2.402989 | 3.186707 | 5.576734 | 1.343239 | 0.115366 | 100 |

| U94-1 | U94-2 | U94-3 | Ratio |
|---|---|---|---|
| 0.233894 | 0.127165 | 0.804911 | 10 |
| 0.179855 | 1.35532 | 13.53974 | 20 |
| 0.275078 | 16.26098 | 20.65427 | 30 |
| 1.161574 | 19.93922 | 13.08098 | 40 |
| 1.961067 | 18.39299 | 9.319949 | 60 |
| 13.0485 | 7.591092 | 1.647718 | 100 |

| C32-1 | C32-2 | C32-3 | C32-4 | C32-5 | C32-6 | Ratio |
|---|---|---|---|---|---|---|
| 0.137436 | 0.544141 | 0.138034 | 0.112832 | 0.087552 | 0.131699 | 10 |
| 0.159782 | 28.93062 | 14.3276 | 0.316178 | 0.125792 | 0.242881 | 20 |
| 0.166661 | 53.90695 | 24.83791 | 0.67551 | 0.193545 | 0.181321 | 30 |
| 0.392402 | 90.62006 | 49.11244 | 2.271509 | 0.563168 | 0.632798 | 40 |
| 6.034825 | 73.59378 | 46.31 | 2.490156 | 0.111248 | 0.273411 | 60 |
| 38.17463 | 60.21433 | 51.86994 | 16.43407 | 2.01284 | 2.619288 | 100 |

| F32-1 | F32-2 | F32-3 | F32-4 | F32-5 | F32-6 | Ratio |
|---|---|---|---|---|---|---|
| 0.746563 | 2.446604 | 1.288067 | 0.210478 | 0.202798 | 0.112283 | 10 |
| 20.84138 | 20.94165 | 11.46963 | 1.780569 | 10.90572 | 0.100889 | 20 |
| 23.8042 | 23.7095 | 13.34488 | 5.01115 | 9.510119 | 0.255589 | 30 |
| 17.47681 | 17.35353 | 14.74619 | 8.361793 | 6.436393 | 0.599084 | 40 |
| 10.54807 | 11.78762 | 13.58168 | 7.499322 | 4.865577 | 0.322946 | 60 |
| 0.072034 | 0.090408 | 0.332458 | 2.300951 | 2.434663 | 1.644695 | 100 |

| F28-1 | F28-2 | F28-3 | F28-4 | F28-5 | F28-6 | Ratio |
|---|---|---|---|---|---|---|
| 0.245612 | 0.247492 | 0.140455 | 0.203674 | 0.09426 | 0.131075 | 10 |
| 0.464885 | 0.192584 | 0.217777 | 0.213391 | 0.171565 | 0.397716 | 20 |
| 0.290643 | 0.19239 | 0.396845 | 0.433955 | 0.361789 | 2.02073 | 30 |
| 0.325066 | 0.189405 | 1.048323 | 2.088649 | 3.888705 | 19.95507 | 40 |
| 0.108766 | 0.164709 | 13.95859 | 0.411927 | 7.851029 | 21.77709 | 60 |
| 0.163978 | 6.619239 | 6.832291 | 8.409421 | 6.682506 | 2.958283 | 100 |

| F28-7 | F28-8 | F28-9 | F28-10 | F28-11 | F28-12 | Ratio |
|---|---|---|---|---|---|---|
| 0.094505 | 0.043474 | 0.05224 | 0.050384 | 0.104016 | 0.149513 | 10 |
| 0.173987 | 0.098512 | 0.069287 | 0.057704 | 0.131067 | 0.028219 | 20 |
| 0.705917 | 0.254424 | 0.083005 | 0.04454 | 0.133842 | 0.001619 | 30 |
| 2.860034 | 0.928959 | 0.226468 | 0.076503 | 0.095093 | 0.003896 | 40 |
| 7.786755 | 1.932506 | 0.42898 | 0.028744 | 0.063298 | 0.001342 | 60 |
| 8.655579 | 12.729 | 1.396803 | 0.281853 | 0.115513 | 0.001145 | 100 |

| JJ28-1 | JJ28-2 | JJ28-3 | JJ28-4 | JJ28-5 | JJ28-6 | Ratio |
|---|---|---|---|---|---|---|
| 0.122351 | 0.056864 | 0.030798 | 0.041065 | 0.02373 | 0.051849 | 10 |
| 0.060598 | 0.059073 | 22.46575 | 2.229717 | 0.076134 | 0.053754 | 20 |
| 0.174243 | 0.211589 | 21.92396 | 4.089533 | 0.121043 | 0.115906 | 30 |
| 0.133603 | 36.42899 | 69.60415 | 19.16868 | 0.292215 | 0.337099 | 40 |
| 1.011778 | 64.69601 | 71.50927 | 47.49171 | 0.755335 | 0.654333 | 60 |
| 60.46546 | 56.7025 | 53.44758 | 39.13032 | 25.81403 | 3.936471 | 100 |

| JJ36-1 | JJ36-2 | JJ36-3 | JJ36-4 | JJ36-5 | JJ36-6 | Ratio |
| --- | --- | --- | --- | --- | --- | --- |
| 0.506359 | 1.634649 | 0.146132 | 0.053268 | 0.035023 | 0.033605 | 10 |
| 2.185596 | 4.332834 | 0.677853 | 0.017846 | 0.010687 | 0.004264 | 20 |
| 2.339652 | 5.039758 | 0.773873 | 0.024164 | 0.06932 | 0.009318 | 30 |
| 0.681878 | 1.871844 | 1.539743 | 0.087428 | 0.017886 | 0.009752 | 40 |
| 0.521703 | 1.592328 | 2.000554 | 0.201203 | 0.027165 | 0.004975 | 60 |
| 0.003277 | 0.067895 | 1.031285 | 0.284902 | 0.159879 | 0.008844 | 100 |

| JJ32-1 | JJ32-2 | JJ32-3 | JJ32-4 | JJ32-5 | JJ32-6 | Ratio |
| --- | --- | --- | --- | --- | --- | --- |
| 0.392821 | 1.158486 | 0.191533 | 0.127891 | 0.099083 | 0.076569 | 10 |
| 17.51289 | 21.24103 | 1.803172 | 0.065286 | 0.160362 | 0.108887 | 20 |
| 38.08705 | 43.77517 | 24.76927 | 0.09612 | 0.063692 | 0.044659 | 30 |
| 25.9567 | 34.88211 | 26.36994 | 0.201907 | 0.015214 | 0.026165 | 40 |
| 11.37519 | 17.48944 | 29.59326 | 0.175101 | 0.052321 | 0.098545 | 60 |
| 1.3311 | 1.288845 | 6.86144 | 0.70071 | 0.178921 | 0.70361 | 100 |

| LL6-1 | LL6-2 | LL6-3 | LL6-4 | LL6-5 | LL6-6 | Ratio |
| --- | --- | --- | --- | --- | --- | --- |
| 0.405305 | 0.583416 | 0.520853 | 0.50183 | 0.656802 | 1.060478 | 10 |
| 0.411758 | 0.747731 | 0.460075 | 0.287671 | 0.382454 | 1.099616 | 20 |
| 0.809416 | 0.377302 | 1.253481 | 1.099976 | 2.59164 | 1.138122 | 30 |
| 0.475903 | 0.854576 | 1.812577 | 2.018906 | 2.837056 | 0.69298 | 40 |
| 0.139647 | 0.29034 | 0.939013 | 1.992525 | 2.250511 | 3.059824 | 60 |
| 0.00154 | 0.002408 | 0.223682 | 2.932931 | 3.939451 | 6.879564 | 100 |

| LL8-1 | LL8-2 | LL8-3 | LL8-4 | LL8-5 | LL8-6 | Ratio |
| --- | --- | --- | --- | --- | --- | --- |
| 0.533009 | 1.180815 | 1.581011 | 2.254195 | 1.73015 | 1.76882 | 10 |
| 1.174539 | 1.228513 | 1.002632 | 2.369943 | 1.958308 | 2.928439 | 20 |
| 1.182611 | 1.620962 | 3.771897 | 3.988759 | 3.936124 | 0.000474 | 30 |
| 1.366191 | 1.875091 | 4.594308 | 4.253834 | 4.07168 | 0.000948 | 40 |
| 0.120086 | 0.866135 | 1.925861 | 4.423822 | 4.081074 | 5.083137 | 60 |
| 0.003316 | 0.029499 | 0.336777 | 4.077347 | 4.416413 | 4.241522 | 100 |

| U28-1 | U28-2 | U28-3 | U28-4 | U28-5 | U28-6 | Ratio |
| --- | --- | --- | --- | --- | --- | --- |
| 0.049477 | 0.044465 | 0.045254 | 0.034669 | 0.031628 | 0.025942 | 10 |
| 0.111915 | 0.050661 | 0.03988 | 0.015399 | 0.049004 | 0.020729 | 20 |
| 0.041895 | 0.050582 | 0.048212 | 0.064917 | 0.069067 | 0.02756 | 30 |
| 0.122271 | 0.078429 | 1.647405 | 0.488561 | 1.036216 | 0.058913 | 40 |
| 0.059982 | 0.051095 | 18.03734 | 5.718868 | 1.991446 | 0.176516 | 60 |
| 0.059585 | 44.91463 | 51.17075 | 34.01612 | 32.39362 | 3.488256 | 100 |

| E28-1 | E28-2 | E28-3 | E28-4 | E28-5 | E28-6 | Ratio |
|---|---|---|---|---|---|---|
| 0.109892 | 0.150078 | 0.630192 | 0.187585 | 0.311968 | 0.168724 | 10 |
| 0.088189 | 0.509429 | 0.589377 | 0.106743 | 0.70723 | 0.144608 | 20 |
| 1.672278 | 12.4166 | 21.41889 | 3.405963 | 8.337341 | 1.32881 | 30 |
| 5.658186 | 12.17055 | 13.3351 | 7.272109 | 17.92266 | 5.089686 | 40 |
| 6.016333 | 5.424512 | 5.549474 | 5.185252 | 15.62457 | 8.706483 | 60 |
| 1.146098 | 0.804227 | 0.592348 | 0.529551 | 1.752402 | 5.438448 | 100 |

| U36-1 | U36-2 | U36-3 | U36-4 | U36-5 | U36-6 | Ratio |
|---|---|---|---|---|---|---|
| 0.158334 | 0.388325 | 0.255439 | 0.139618 | 0.069735 | 0.054654 | 10 |
| 0.281155 | 2.119615 | 0.34803 | 0.196109 | 0.111805 | 0.067406 | 20 |
| 0.968904 | 2.501669 | 3.74982 | 0.370814 | 0.103744 | 0.077397 | 30 |
| 0.559332 | 1.595139 | 4.650123 | 0.65127 | 0.078343 | 0.029797 | 40 |
| 0.565322 | 0.540675 | 4.182981 | 1.59494 | 0.250723 | 0.029297 | 60 |
| 0.238507 | 0.008686 | 1.052448 | 2.269889 | 1.310025 | 0.23654 | 100 |

| E36-1 | E36-2 | E36-3 | E36-4 | E36-5 | E36-6 | Ratio |
|---|---|---|---|---|---|---|
| 0.130066 | 2.940734 | 0.350723 | 0.077836 | 0.051293 | 0.018123 | 10 |
| 0.496911 | 1.866482 | 2.236257 | 0.135236 | 0.063655 | 0.020018 | 20 |
| 1.044698 | 0.617286 | 4.27308 | 0.882725 | 0.187495 | 0.01532 | 30 |
| 0.342085 | 0.025849 | 1.935655 | 1.170393 | 0.23494 | 0.004896 | 40 |
| 0.112427 | 0.211108 | 1.068847 | 1.362371 | 0.628612 | 0.070175 | 60 |
| 0.002566 | 0.003672 | 0.131476 | 1.367514 | 1.194649 | 0.11883 | 100 |

| U32-1 | U32-2 | U32-3 | U32-4 | U32-5 | U32-6 | Ratio |
|---|---|---|---|---|---|---|
| 0.202681 | 0.107654 | 0.035536 | 0.037195 | 0.041027 | 0.047701 | 10 |
| 0.106511 | 0.084192 | 0.067327 | 0.012951 | 0.028982 | 0.012003 | 20 |
| 1.497135 | 2.867785 | 1.828273 | 0.056586 | 0.033682 | 0.010305 | 30 |
| 4.411592 | 13.8534 | 0.272404 | 0.056588 | 0.029377 | 0.021045 | 40 |
| 17.28347 | 38.37457 | 3.026925 | 0.017452 | 0.015556 | 0.060968 | 60 |
| 11.81885 | 13.6584 | 15.23297 | 0.673546 | 0.121004 | 0.15261 | 100 |

| E32-1 | E32-2 | E32-3 | E32-4 | E32-5 | E32-6 | Ratio |
|---|---|---|---|---|---|---|
| 0.481414 | 0.898699 | 0.149685 | 0.093788 | 0.086886 | 0.046001 | 10 |
| 5.170892 | 6.057429 | 1.52106 | 0.054373 | 0.099557 | 0.01378 | 20 |
| 0.965091 | 2.279423 | 4.380769 | 0.112159 | 0.027166 | 0.038894 | 30 |
| 0.848062 | 1.086906 | 3.971834 | 0.13767 | 0.068236 | 0.090555 | 40 |
| 0.225141 | 0.688091 | 2.653561 | 0.570809 | 0.080796 | 0.01603 | 60 |
| 0.046762 | 0.176583 | 0.897883 | 1.365759 | 0.845009 | 0.111133 | 100 |

| C94-1 | C94-2 | C94-3 | C94-4 | Ratio |
|---|---|---|---|---|
| 0.289113 | 0.086166 | 0.151651 | 0.203119 | 10 |
| 0.133487 | 0.045908 | 0.067867 | 7.650297 | 20 |
| 0.293536 | 0.086328 | 0.853319 | 10.31612 | 30 |
| 0.198737 | 0.170611 | 1.955433 | 9.745005 | 40 |
| 0.312808 | 0.908991 | 3.536115 | 3.580573 | 60 |
| 0.32801 | 0.853063 | 2.414853 | 1.731594 | 100 |

| D94-1 | D94-2 | D94-3 | D94-4 | D94-5 | D94-6 | Ratio |
|---|---|---|---|---|---|---|
| 0.223798 | 0.091225 | 9.083876 | 0.272732 | 0.46751 | 5.545365 | 10 |
| 9.682036 | 15.16589 | 24.65534 | 25.45656 | 27.30727 | 25.52283 | 20 |
| 14.53736 | 22.28715 | 29.68042 | 38.12112 | 42.28773 | 33.35092 | 30 |
| 9.804481 | 14.97104 | 18.63768 | 28.87773 | 35.67401 | 28.4263 | 40 |
| 6.36291 | 11.60176 | 16.02556 | 27.2195 | 29.006 | 16.62105 | 60 |
| 2.681942 | 2.585502 | 3.03267 | 9.218975 | 12.48001 | 9.63693 | 100 |

Example 7

Novel pH-Sensitive Microparticles

Formulations designed to release DNA more rapidly in response to a specific intracellular stimulus such as pH facilitate the intracellular targeting of DNA, leading to higher levels of gene expression and an increase in vaccine potency. Recently, we described the synthesis of a degradable, pH sensitive poly-β amino ester (Lynn, D. M. & Langer, R. Degradable poly(beta-amino esters): Synthesis, characterization, and self-assembly with plasmid DNA. *J. Am. Chem. Soc.* 122, 10761-10768 (2000); incorporated herein by reference) and its application to microparticles capable of releasing fluorescently labeled payloads instantaneously upon pH changes in the physiological range (Lynn et al. pH-responsive polymer microspheres: Rapid release of encapsulated material within the range of intracellular pH. *Angew. Chem.-Int. Edit.* 40, 1707-1710 (2001); incorporated herein by reference). In this Example, we report the encapsulation of plasmid DNA within hybrid PLGA/poly-β amino ester microparticles and demonstrate a resulting enhancement in intracellular delivery and immunogenicity. These new hybrid microparticles can overcome a weakly immunogenic antigen to induce a protective immune rejection of lethal tumor dosage in vivo while conventional PLGA microparticle and naked DNA formulations fail to inhibit tumor progression.

Results

Hybrid Polymeric Microparticles have Properties well Suited for Genetic Vaccine Delivery.

Plasmid DNA was encapsulated into polymeric microparticles as described in Materials and Methods. Reducing the amount of Poly-1 to 25%, with respect to PLGA, resulted in microspheres which demonstrated toxicity similar to that of microparticles made exclusively with PLGA. Scanning Electron Microscopy (SEM) analysis of microsphere preparations indicates a smooth, spherical surface on all microsphere preparations (FIGS. 1C & D), and all formulations had average volume % diameters between 1 and 10 micrometers (Table 1) allowing for a passive, APC targeting mechanism by phagocytosis.

Plasmid DNA loading, as determined by detection of dsDNA in aqueous extracts of dissolved microparticles, was higher for formulations incorporating Poly-1, but was typically greater than 50% for all formulations (see Table below).

| Formulation (% by weight) | Volume % Mean Diameter (μm) ± σ | Encapsulation Efficiency | % Supercoiled Content | Mean Zeta Potential (mV) ± σ |
|---|---|---|---|---|
| 100% PLGA | 4.35 ± 2.34 | ~69% | ~45% | −3.76 ± 0.40 |
| 15% Poly-1/ 85% PLGA | 6.01 ± 2.06 | ~68% | ~72% | −0.86 ± 0.62 |
| 25% Poly-1/ 75% PLGA | 5.53 ± 2.31 | ~78% | ~64% | 0.46 ± 0.38 |
| 25% Poly-1/ 75% PLGA No DNA | 5.12 ± 2.20 | — | — | 0.41 ± 0.36 |

Properties of PLGA and Poly-1 microsphere formulations. All values shown were recorded after lyophilization. All tests were preformed (as described in Materials and Methods) after resuspension of dry, lyophilized microsphere preparations. Values provided are representative of several microsphere productions.

Figure 28:
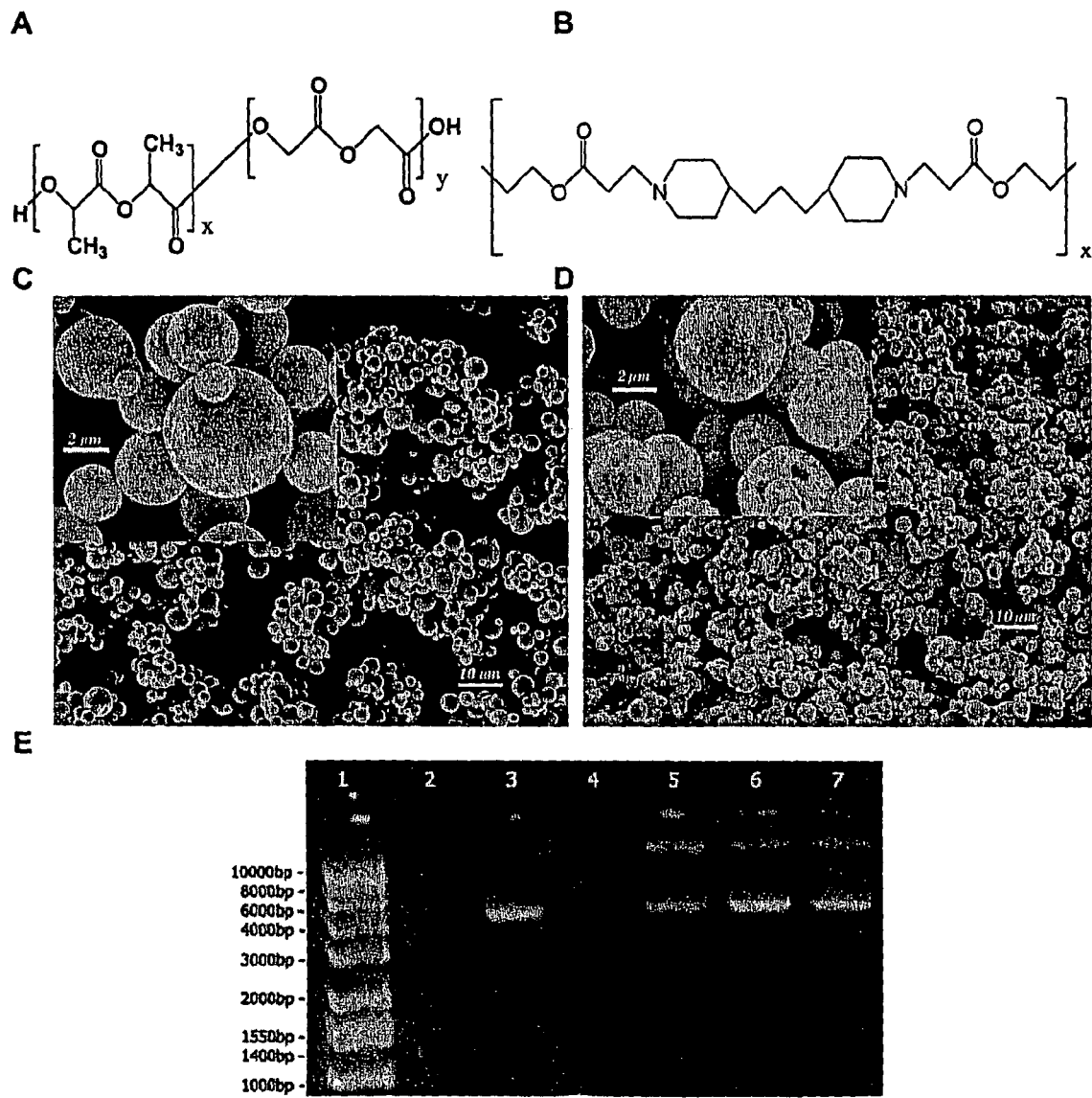
FIG. 28 shows the characteristics of DNA microspheres prepared by the double emulsion technique using 502H PLGA and Poly-1. Molecular formulas of A. PLGA and B. Poly-1. Scanning electron micrographs of DNA microspheres prepared with C. 100% PLGA and D. 15% Poly-1/85% PLGA demonstrate smooth, intact surfaces. Magnifications are 1000× (body) and 5000× (inset). E. 1% agarose electrophoresis demonstrating DNA extracted from microspheres prepared by double emulsion. Lane 1: Ladder, Lanes 2 and 4: empty, Lane 3: unprocessed control (88% supercoiled), lanes 5-7: aqueous extract from PLGA, 15% poly-1/85% PLGA, and 25% poly-1/75% PLGA microparticles respectively after lyophilization.

Microspheres incorporating Poly-1 (FIG. 28E; Lanes 6 and 7) also exhibited higher supercoiled plasmid content than formulations prepared with PLGA alone (Lane 5) as shown by agarose gel electrophoresis. Zeta potential analysis of microspheres indicate a negative surface charge on PLGA micoparticles similar to those previously reported (Sahoo, S. K., Panyam, J., Prabha, S. & Labhasetwar, V. Residual polyvinyl alcohol associated with poly(D,L-lactide-co-glycolide) nanoparticles affects their physical properties and cellular uptake. *J. Control. Release* 82, 105-114 (2002); incorporated herein by reference). In contrast, 15% and 25% Poly-1 preparations showed neutral and slightly positive zeta potentials respectively.

Antigen Presenting Cells Efficiently Phagocytose Poly-1 Containing Formulations and Exhibit Intracellular Distributions of Released Payload Typical of Phagosomal Escape.

To examine the effects of Poly-1 on antigen presenting cell phagocytosis, human peripheral dendritic blood mononuclear derived dendritic cells (PBMC) and Jaws II dendritic cells were incubated with particle formulations, fluorescently stained, and visualized using microscopy. Rhodamine-conjugated dextran was encapsulated in several microparticle formulations to easily view the cell associated fluorescent microspheres.

Figure 29:
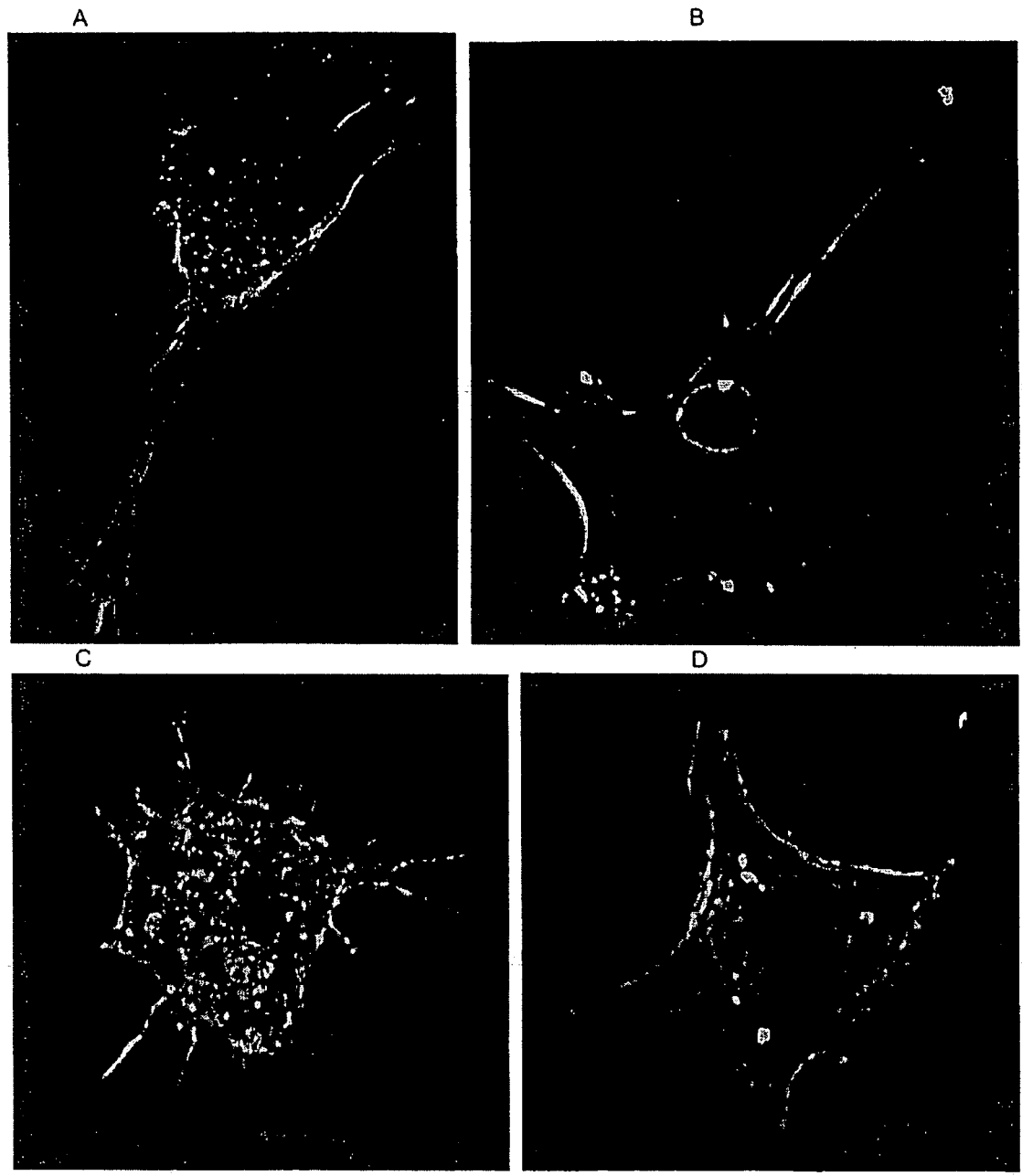
FIG. 29 shows the efficient phagocytosis of microparticle formulations of PLGA and poly-1 in vitro by dendritic cells (A and B). Jaws II dendritic cells (C and D) were incubated with rhodamine conjugated dextran encapsulated microparticles (red) for 5 hours, and then fixed with Hoechst dye for nucleus (blue), and Phalloidin-Alexa Fluor 488 for actin (green). 3D fluorescent microscopy images indicate multiple sites of uptake in each cell for both PLGA microsphere formulations (A & C) and 25% poly-1/75% PLGA microsphere formulations (B & D). Intracellular rhodamine signals were always seen as bright, localized spheres in 100% PLGA treated dendritic cells (A & C). In 25% poly-1 microsphere treated cells, rhodamine distributions were sometimes seen as dim and dispersed, as though in the cytoplasm (B & D).

Imaging of antigen presenting cells incubated with PLGA and 25% Poly-1 particle formulations revealed efficient uptake of all microparticle formulations. Even with microparticle concentrations as low as 1 μg/ml in the incubation media, both human PBMCs and Jaws II dendritic cells demonstrated uptake of fluorescent microparticles after 4-5 hours. In general, the intracellular distribution of the fluorescently labeled dextran in PLGA microparticles remained restricted to phagosomal compartments, indicated by sharp, bright, and spherical rhodamine signals (FIGS. 29A & C and supplemental material). In contrast, a population of cells treated with 25% Poly-1 formulations demonstrated a dimmer, diffuse fluorescent signal, suggesting release from phagosomal compartments (FIGS. 29B & D).

Poly-1/PLGA blends induce higher levels of reporter gene expression in P388D1 macrophages than conventional PLGA microparticles. To compare the transfection efficiency of formulations composed of Poly-1 and PLGA, we used an established antigen presenting cell system that previously exhibited positive transfection using PLGA microparticles (Hedley, M. L., Curley, J. & Urban, R. Microspheres containing plasmid-encoded antigens elicit cytotoxic T-cell responses. *Nat. Med.* 4, 365-368 (1998); incorporated herein by reference). To cover a wide range of interaction conditions, several microparticle incubation concentrations were applied to the cells. Lipofectamine 2000/pCMV-Luc plasmid complexes were chosen as a positive control due to its ability to efficiently transfect many different types of cells in vitro.

Figure 30:
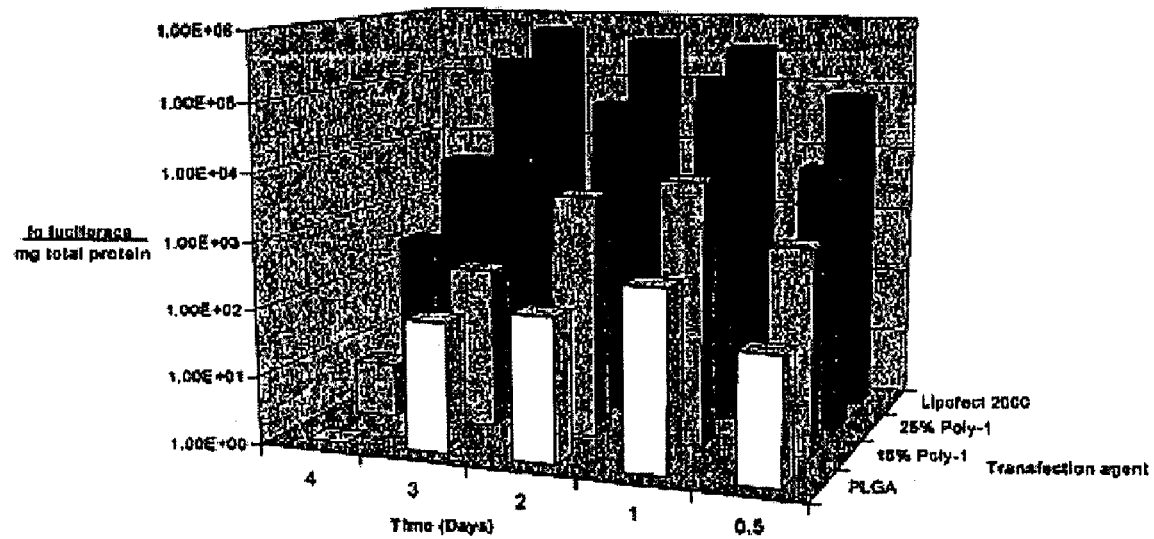
FIG. 30 shows the transfection of firefly luciferase into P388D1 macrophages using poly-1/PLGA pCMV-Luc plasmid microspheres. Results are displayed as femptograms of luciferase (determined by luminescence assay) per mg of total protein (determined by BCA colorimetric assay) on the Z-axis vs. time (Y-axis) and formulation (X-axis). The concentration of microspheres incubated with the cells was 100 (μg/ml). An optimal formulation of Lipofectamine 2000 (0:8:1 Lipofectamine:DNA) is displayed in blue as a positive control in each plot. 25% poly-1 formulations (red) consistently performed at par with the Lipofectamine positive controls while 15% poly-1 formulations (pink), although lower than 25% formulations, consistently performed at a higher level than PLGA microparticles (white) at luciferase transfection.

Microsphere formulations composed of 25% Poly-1 demonstrated reporter gene expression comparable to that of an optimal formulation of Lipofectamine 2000 (FIG. 30). However, Lipofectamine required 25 times more DNA than our microparticles to achieve the same level of transfection (300 ng/well vs. 12 ng/well). An optimal formulation of 25% Poly-1 microparticles generated about 3 orders of magnitude higher transfection efficiency than an optimal formulation of PLGA (FIG. 29C) and at some time points, 25% Poly-1 microparticles exhibited up to 5 orders of magnitude lower luciferase expression than formulations containing only PLGA. 15% Poly-1 microspheres were not as effective as 25% Poly-1 formulations, but still maintained a significant 1-3 orders of magnitude increase in transfection efficiency relative to PLGA microspheres at most time points (FIG. 30). Formulation groups were compared using ANOVA and t-test analysis for significance ($\alpha=0.95$).

Poly-1 containing microparticles activate dendritic cells as indicated by co-stimulatory surface expression analysis. Dendritic cells were analyzed for surface expression of activation markers after incubation with microparticle formulations using a flow cytometry based assay. MHC Class II up-regulation was selected because of its common use as an activation marker in dendritic cells. F4/80 surface expression was chosen due to its characteristic down-regulation upon dendritic cell maturation (McKnight, A. J. et al. Molecular cloning of F4/80, a murine macrophage-restricted cell surface glycoprotein with homology to the G-protein linked transmembrane 7 hormone receptor family. *J. Biol. Chem.* 271, 486-489 (1996); Caminschi, I. et al. Molecular cloning of F4/80-like-receptor, a seven-span membrane protein expressed differentially by dendritic cell and monocyte-macrophage subpopulations. *J. Immunol.* 167, 3570-3576 (2001); each of which is incorporated herein by reference). These two markers are both expressed on the surface of the constitutively immature dendritic cell line, Jaws II (MacKay, V. L. M., Emma E. in US Patent and Trademark Office 18 (ZymoGenetics, Inc, United States; 1997); incorporated herein by reference) and can be quantitated using fluorescently labeled antibodies specific to these markers. A cytokine cocktail (If-$\gamma$, TNF-$\alpha$, IL-4) treatment was used as a positive control for maturing the cells.

Figure 31:
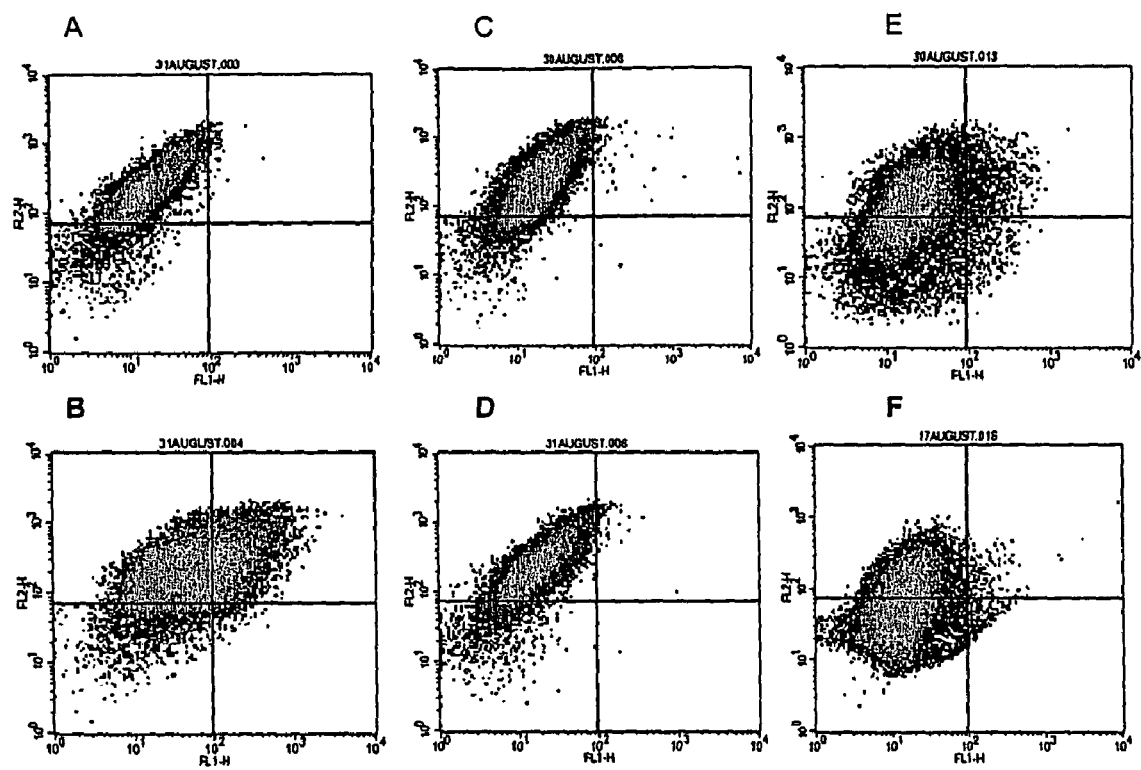
FIG. 31 shows the activation of antigen presenting cells by incubation with poly-1 microsphere formulations as indicated by cell surface expression of maturation markers. Expression of F4/80-R-Phycoetherin is shown on the y-axis log scale and expression of MHC-Class II-FITC on the x-axis log scale after incubation of Jaws II dendritic cells with microspheres for 1 day (A, C, E) and 3 days (B, D, F). Untreated controls exhibited an immature phenotype indicated by low levels of MHC-Class II and high levels of F4/80 (A). Cells incubated with a cocktail of cytokines indicated by low levels of MHC-Class II and high levels of F4/80 (B). PLGA microsphere treated (50 μg/ml) cells appear to have an immature phenotype after 1 and 3 days of incubation (C & D), while cells incubated with 25% Poly-1/75% PLGA (50 μg/ml) microsphere formulations are activated as indicated by down-regulation of F4-80 and up-regulation of MHC class II at both time points (E, F).

After both 1 and 3 days of incubation with conventional PLGA microparticle formulations, the activation marker expression profile failed to change and dendritic cells continued to exhibit an immature phenotype (FIGS. 31C & D). However, treatment of the dendritic cells with 25% Poly-1 formulations greatly decreased the amount of F4/80 and increased the amount of MHC Class II on the surface of the dendritic cells, indicating a mature phenotype (FIGS. 31E & F). The data shown in FIG. 4 is representative of 5 different assays performed identically. The same dendritic cell stimulatory effect was demonstrated with CD40, and CD86 up-regulation on the Jaws II dendritic cells and also CD83 up-regulation using human PBMCs in 25% Poly-1 microsphere incubations. No up-regulation of these activation markers was seen on untreated or PLGA microparticle formulation treated PBMCs.

Figure 32:
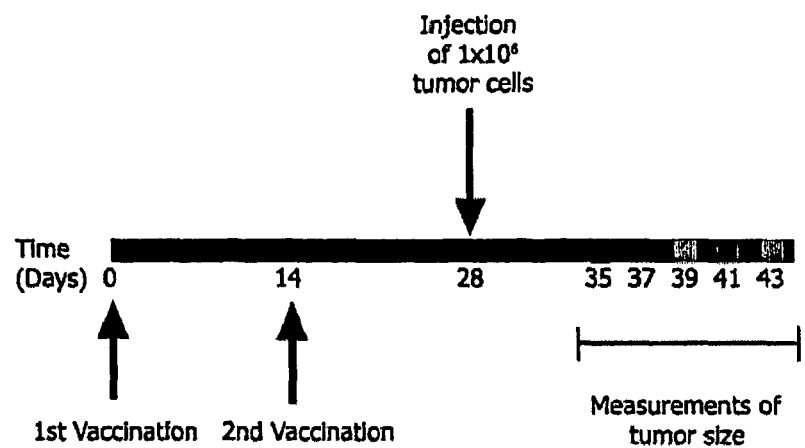
FIG. 32 shows anti-tumor response of B-6 mice after treatment with genetic vaccine formulations. A. Timeline showing the vaccination schedule along with tumor induction and measurement in mice. B. Mean tumor size as a function of vaccine formulation and time. Measurements, using a caliper in 2 dimensions, were taken 7 (blue), 9 (red), 11 (orange), 13 (green), and 15 (pink) days after sub-cutaneous injection of $3\times10^6$ DP-1 thymoma cells. Standard error bars are shown for comparison. Asterisks (*) indicates one mouse in which the DP-1 tumor had completely regressed.
Figure 32:
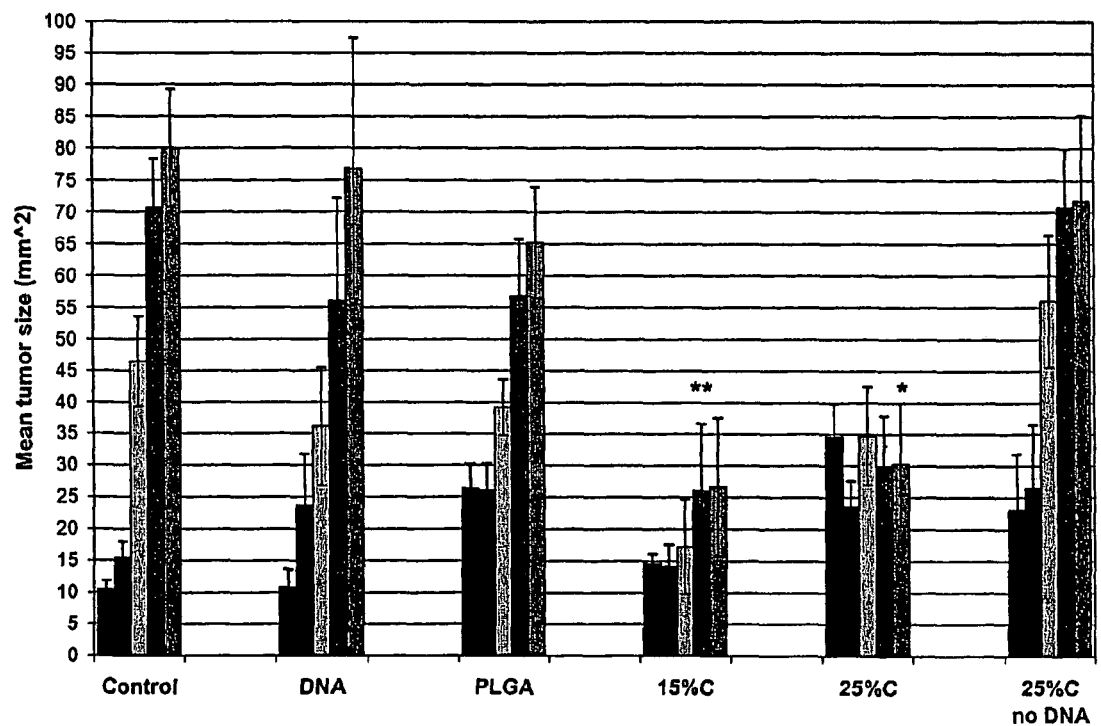

Vaccination with Poly-1 containing, DNA microspheres elicit anti-tumor responses in B6 mice using a weakly immunogenic antigen construct. B6 mice (5 per group) were vaccinated following the schedule represented in FIG. 32A and described in the Materials and Methods section. The plasmid delivered in all the vaccine formulations, pCMV-SYRGL, encodes a $K^b$ associated class I MHC peptide (SIYRYYGL) presented on the surface of DP-1 tumor cells (administered left flank) but not presented on the surface of EL-4 tumor cells (administered right flank) (Cho, B. K. et al. A proposed mechanism for the induction of cytotoxic T lymphocyte production by heat shock fusion proteins. *Immunity* 12, 263-272 (2000); Cho, B. K., Rao, V. P., Ge, Q., Eisen, H. N. & Chen, J. Z. Homeostasis-stimulated proliferation drives naive T cells to differentiate directly into memory T cells. *J. Exp. Med.* 192, 549-556 (2000); each of which is incorporated herein by reference). DP-1 tumors on the left flank grew at similar rates for control, naked DNA, PLGA/DNA microparticles, and blank 25% Poly-1 microparticle formulations. Conversely, formulations composed of 15 and 25% Poly-1 containing pCMV-SYRGL slowed the average rate of growth of DP-1 tumors over the course of the experiment (FIG. 32b). In addition, two of the five mice in the 15% and one of the five mice in the 25% Poly-1 formulations demonstrated tumors that decreased in size and completely disappeared on the days indicated (*). On the right flank, the non-specific EL4 tumors did not reduce in size over time in any group and vaccination with a plasmid which exclusively expresses $\beta$-galactosidase (no SYRGL antigen expression) did not inhibit growth of DP-1, antigen specific tumor cells.

Statistical analysis using comparative ANOVA showed that 15% Poly-1 were significantly different from the control after day 11 and formulations containing 25% Poly-1 were significantly different after day 13. No other group showed significantly reduced tumor size when compared to the control group at any time point. Mice did not exhibit irritation, redness, or swelling from the vaccinations in any experimental group and no other harmful side effects were noticed.

Discussion

DNA delivery to antigen presenting cells using non-viral methods could likely be the preferred choice of genetic vaccination in the future (Walter, E., Thiele, L. & Merkle, H. P. Gene delivery systems to phagocytic antigen-presenting cells. *STP Pharma Sci.* 11, 45-56 (2001); incorporated herein by reference) but these systems lack the gene transfer efficiency and immunogenicity offered by viral vaccine systems (Clark, K. R. & Johnson, P. R. Gene delivery of vaccines for infectious disease. *Curr Opin Mol Ther* 3, 375-384. (2001); incorporated herein by reference). Polymeric microparticles that physically encapsulate DNA offer several benefits to genetic vaccine formulations, including: 1) ease of manufacturability, 2) the ability to protect the encapsulated plasmid (Capan, Y., Woo, B. H., Gebrekidan, S., Ahmed, S. & DeLuca, P. P. Preparation and characterization of poly(D,L-lactide-co-glycolide) microspheres for controlled release of poly(L-lysine) complexed plasmid DNA. *Pharm. Res.* 16, 509-513 (1999); incorporated herein by reference), and 3) size based immunogenicity and targeting to antigen presenting cells (O'Hagan, D. T., Singh, M. & Gupta, R. K. Poly(lactide-co-glycolide) microparticles for the development of single-dose controlled-release vaccines. *Adv. Drug Deliv. Rev.* 32, 225-246 (1998); incorporated herein by reference). Furthermore, unlike viral delivery, microparticle systems possess the capacity to hold large payloads, allowing for multi-valent vaccines (vaccines with multiple antigen expression constructs) and co-encapsulation of immuno-modulating cytokines. Despite these advantages, current microparticle systems prepared from PLGA exhibit extremely low levels of gene expression in antigen presenting cells. In fact, in a recent study on dendritic cell gene expression using a PLGA microparticle carrier, it was necessary to use RT-PCR amplification to detect the low levels of expression (Denis-Mize, K. S. et al. Plasmid DNA adsorbed onto cationic microparticles mediates target gene expression and antigen presentation by dendritic cells. *Gene Ther.* 7, 2105-2112 (2000); incorporated herein by reference). Although such low amounts of antigen expression may be sufficient to induce immune responses, we believe that increasing levels of gene expression will lead to a corresponding increase in vaccine potency. We hypothesized that the incorporation of a degradable, pH sensitive polymer to conventional PLGA microparticle formulations would increase gene delivery capacity by facilitating the targeted, intracellular release of plasmid payload upon phagosomal acidification.

Incorporation of Poly-1 into the microsphere matrix did not alter the structure or loading of the particles significantly. It was possible to encapsulate relatively high quantities of supercoiled plasmid in our formulations using standard double emulsion techniques, despite previous indications that this is difficult (Singh, M. et al. Cationic microparticles are an effective delivery system for immune stimulatory CpG DNA. *Pharm. Res.* 18, 1476-1479 (2001); each of which is incorporated herein by reference), and loading of plasmid DNA was generally higher in formulations containing Poly-1. This is most likely due to the presence of an increasing amount of partially cationic polymer, which correlates to the increasingly positive zeta potentials seen upon addition of Poly-1 to the formulations.

Addition of Poly-1 to conventional PLGA microparticles may introduce intracellular delivery fnctionalities similar to those displayed by viruses during intracellular delivery of DNA. We demonstrated previously that microspheres fabricated from 100% Poly-1 have the ability to rapidly release contents when exposed to acidic endosomal pH (Lynn, D. M., Amiji, M. M. & Langer, R. pH-responsive polymer microspheres: Rapid release of encapsulated material within the range of intracellular pH. *Angew. Chem.-Int. Edit.* 40, 1707-1710 (2001); incorporated herein by reference). Although to a lower extent than seen in formulations prepared with 100% Poly-1, incorporation of smaller amounts of Poly-1 into PLGA microparticles should act to compromise particle integrity and facilitate intracellular delivery of plasmid DNA upon exposure to an acidic phagosomal environment. Release experiments using 25% Poly-1 formulations encapsulating fluorescently labeled compounds support this reasoning. Furthermore, small amounts of the cationic Poly-1 may bind electrostatically to DNA upon release, forming self-assembled nanoparticles which may further protect the DNA from the harsh intracellular environment. Poly-1 has been shown to spontaneously complex plasmid DNA (Lynn, D. M. & Langer, R. Degradable poly(beta-amino esters): Synthesis, characterization, and self-assembly with plasmid DNA. *J. Am. Chem. Soc.* 122, 10761-10768 (2000); incorporated herein by reference) and we have detected evidence of such nano-scale conjugates (~200 nm) in the supernatant of partially degraded/dissolved microparticles using dynamic light scattering techniques. Also, a population of dendritic cells treated with Poly-1/PLGA microparticles exhibit an internally dispersed rhodamine fluorescence (FIG. 29) suggesting that Poly-1 may facilitate release from phagosomal compartments. In a solid state, Poly-1 in the microparticle structure should remain mostly in an unprotonated state which would subsequently absorb protons during phagosomal acidification. It is possible Poly-1 may provide a means of phagosomal escape by osmotic membrane disruption using a proton sponge like mechanism (Demeneix, B.a.J.P.B. in Artificial Self-Assembling Systems for Gene Delivery. (ed. P. L. Felgner, Heller, M. J., Lehn, P., Behr, J. P., Szoka, F. C. Jr.) 146-151 Washington, D.C.; 1996); incorporated herein by reference). Although it is unclear as to the exact intracellular delivery mechanism, we observe a 3-5 orders of magnitude increase in reporter gene transfection upon addition of Poly-1 to the microparticle formulations, indicating a corresponding increase in targeted, intracellular delivery of plasmid DNA (FIG. 30).

In addition to sufficient gene expression, activation of antigen presenting cells during epitope presentation is crucial to vaccine potency. Costimulatory up-regulation following an activation signal is necessary for APC mediated T-cell stimulation (Banchereau, J. & Steinman, R. M. Dendritic cells and the control of immunity. *Nature* 392, 245-252 (1998); Coombes, B. K. & Mahony, J. B. Dendritic cell discoveries provide new insight into the cellular immunobiology of DNA vaccines. *Immunol Lett* 78, 103-111. (2001); each of which is incorporated herein by reference). For genetic vaccination, this activiation is particularly important as surface presentation of antigen by an immature/inactivated dendritic cell (i.e., in the absence of co-stimulatory signals) may actually induce tolerance to that antigen by clonal T-cell deletion or anergy (Steinman, R. M. et al. in Immune Mechanisms and Disease, Vol. 987 15-25 (2003); Steinman, R. M., Hawiger, D. & Nussenzweig, M. C. Tolerogenic dendritic cells. *Annu. Rev. Immunol.* 21, 685-711 (2003); each of which is incorporated herein by reference). We observed a phenotypical change indicative of maturation in the Jaws II murine dendritic cell line and with human PBMCs when incubated with Poly-1 containing formulations. Possible explanations for this immunogenicity include: 1) the increasingly positive surface charge of the Poly-1 containing formulations may be involved in inducing maturation, 2) the soluble Poly-1 or Poly-1/DNA complexes could mediate cell surface receptor activation similar to the way naked DNA activates through toll like receptors, or 3) large amounts of phagocytosed Poly-1 particles may induce cell to cell distress signaling leading to activation. Efforts are currently underway to elucidate the mechanism behind the inherent immunogenicity of this delivery system.

To examine the efficiency of Poly-1 containing microparticle vaccinations in generating protective immune responses to a weak antigen, we employed a SIYRYYGL (SYRGL) octapeptide antigen expression system which is normally used in an adoptive transfer model that exploits a specific T-cell receptor (TCR) found in transgenic 2C mouse T-cells (Udaka, K., Wiesmuller, K. H., Kienle, S., Jung, G. & Walden, P. Self-MHC-Restricted peptides recognized by an alloreactive T lymphocyte clone. *J. Immunol.* 157, 670-678 (1996); incorporated herein by reference). Cho et al. used a peptide construct with SYRGL and a heat shock fusion protein (hsp) to demonstrate induction of potent $CD8^+$ immune responses in mice using hsp without the use of exogenous adjuvants (Cho et al. A proposed mechanism for the induction of cytotoxic T lymphocyte production by heat shock fusion proteins. *Immunity* 12, 263-272 (2000); incorporated herein by reference). They found that normal B6 mice have naïve T cells that can recognize the SYRGL-$K^b$ complex, however without the hsp fusion partner, this octapeptide was unable to activate dendritic cells or elicit CD8+ immune responses. Given this evidence, the SYRGL peptide (which so far as is known, does not occur in nature) is not highly immunogenic by itself, and is unable to mediate immune stimulation in B6 mice. Using a pCMV-SYRGL expression construct without a hsp fusion partner, we compared a conventional PLGA delivery system and naked DNA vaccinations to Poly-1 containing microparticles in B6 mice following the schedule represented in FIG. 32A. After only 2 vaccinations with formulations containing Poly-1, significant inhibition of tumor growth was seen, and 30% of the tumors demonstrated complete regression despite the inherent low immunogenicity of the target antigen. This strategy illustrates a dramatic improvement over PLGA microparticle systems and represents a step toward obtaining the potency needed to implement non-viral genetic vaccine formulations in tumor therapies.

This carrier may potentially be widely applicable as a platform for delivery in circumstances where the antigen of interest is not immunogenic enough for plasmid DNA vaccination alone, as in the case of B-cell malignancies or in individuals with weakened or tolerized immune capacity (Savelyeva, N., Munday, R., Spellerberg, M. B., Lomonossoff, G. P. & Stevenson, F. K. Plant viral genes in DNA idiotypic vaccines activate linked CD4(+) T-cell mediated immunity against B-cell malignancies. *Nat. Biotechnol.* 19, 760-764 (2001); incorporated herein by reference). The presence of immunogenicity as a innate property of the carrier bypasses adverse implications of systemic release when using cytokines or adjuvants to augment the immune reaction (O'Hagan, D. T., MacKichan, M. L. & Singh, M. Recent developments in adjuvants for vaccines against infectious diseases. *Biomol Eng* 18, 69-85. (2001); incorporated herein by reference). This property along with increased delivery efficiency also allows the carrier to compliment other new technologies for increasing vaccine efficiency such as: 1) inclusion of plasmid encoding cytokine vaccinations (Luo, Y. P. et al. Plasmid DNA encoding human carcinoembryonic antigen (CEA) adsorbed onto cationic microparticles induces protective immunity against colon cancer in CEA-transgenic mice. *Vaccine* 21, 1938-1947 (2003); incorporated herein by reference), 2) incorporation of immunogenic fusion constructs (Cho, B. K. et al. A proposed mechanism for the induction of cytotoxic T lymphocyte production by heat shock fusion proteins. *Immunity* 12, 263-272 (2000); Savelyeva, N., Munday, R., Spellerberg, M. B., Lomonossoff, G. P. & Stevenson, F. K. Plant viral genes in DNA idiotypic vaccines activate linked CD4(+) T-cell mediated immunity against B-cell malignancies. *Nat. Biotechnol.* 19, 760-764 (2001); each of which is incorporated herein by reference), and 3) addition of APC specific antibodies to the microparticle surface (Kempf, M. et al. Improved stimulation of human dendritic cells by receptor engagement with surface-modified microparticles. *J. Drug Target.* 11, 11-18 (2003); incorporated herein by reference). We are currently exploring third generation microparticle formulations including similar complimentary technologies that even further enhance vaccine potency. Finally, the intracellular delivery capacity of Poly-1 microparticles may have implications for delivery of other drugs to antigen presenting cells, such as in the case of lysosomal storage disorders, where targeted, effective delivery to macrophages is the key to successful enzyme replacement therapy.

Materials and Methods

Materials. Poly(d,l-lactic-co-glycolic acid) polymer (PLGA, RG502H Resomer 50:50) was purchased from Boehringer Ingelheim (Ingelheim, Germany). Poly-1 was synthesized as previously reported ($M_n \approx 5$ kD) (Lynn, D. M., Amiji, M. M. & Langer, R. pH-responsive polymer microspheres: Rapid release of encapsulated material within the range of intracellular pH. *Angew. Chem.-Int. Edit.* 40, 1707-1710 (2001); incorporated herein by reference). Plasmid DNA encoding firefly luciferase (pCMV-Luc), β-galactosidase, and SIYRYYGL peptide (pCMV-SYRGL which expresses a protein construct including SYRGL and β-gal in the place of hsp) were obtained from Elim Biopharmaceuticals (Hayward, Calif.). Dextran conjugated tetramethyl rhodamine ($M_n \approx 70$ kD) was purchased from Molecular Probes (Eugene, Oreg.).

Cells and cell lines. P388D1 macrophage and JawsII dendritic antigen presenting cell lines were obtained from ATCC (Manassas, Va.). P388D1 cells were cultured in RPMI 1640 media (Gibco Life Technologies; Carlsbad, Calif.) containing 10% FBS, 0.1M HEPES, 1 mM Sodium Pyruvate, and 100 U/ml Penecillin/Streptomyocin. Jaws II cells were cultured with α-MEM media (Sigma; Minneapolis, Minn.) containing 20% FBS, 2 μM $Na_2CO_3$, 1 mM Sodium Pyruvate, and 5 ng/ml murine GM-CSF (Sigma). Leukopaks were obtained from Massachusetts General Hospital and human peripheral mononuclear cells (hPBMC) were isolated by adherence as previously described (Romani, N. et al. Proliferating Dendritic Cell Progenitors in Human Blood. *J. Exp. Med.* 180, 83-93 (1994); Thurner, B. et al. Generation of large numbers of fully mature and stable dendritic cells from leukopheresis products for clinical application. *J. Immunol. Methods* 223, 1-15 (1999); each of which is incorporated herein by reference). Human dendritic cells were differentiated in IMDM including 1% human serum (Valley Biomedical; Winchester, Va.) along with 50 ng/ml GM-CSF and 20 ng/ml IL-4 (RnD Systems; Minneapolis, Minn.). EL-4 murine thymoma cells and a transduced SYRGL expressing EL-4 cell line (DP-1) were cultured in RPMI-1640 with 10% FCS and 1 mg/ml G418 (Gibco).

Mice. C57BL/6 (B6, H-2 $K^b$) mice (6-10 weeks) were purchased from (Taconic; Germantown, N.Y.) and housed at the MIT animal facility. All animal experiments were performed in compliance with the MIT Committee on Animal Care guidelines.

Preparation of microspheres. Plasmid containing microspheres were prepared by the following modification of the double emulsion technique previously described (Odonnell, P. B. & McGinity, J. W. Preparation of microspheres by the solvent evaporation technique. *Adv. Drug Deliv. Rev.* 28, 25-42 (1997); incorporated herein by reference). Varying amounts of PLGA blended with Poly-1 (structure shown in FIGS. 1A & B, respectively) were explored in microsphere formulations due to some cellular toxicity observed in 100% Poly-1 formulations. An aqueous solution (100 μL) of EDTA (1 mM), D(+)-Lactose (300 mM) was added to 1 mg of lyophilized plasmid DNA. This solution was then emulsified with an organic solution of PLGA and poly(β-amino ester) at varying degrees of composition (200 mg) in $CH_2Cl_2$ (4 ml) using a probe sonicator (Sonics Danbury, Conneticut). The resulting emulsion was then immediately added to a homogenized solution of poly(vinyl alcohol) (50 ml, 5% PVA (w/w), 5000 rpm) and NaCl (0.1M). After 30 seconds, the final water-oil-water mixture was added to a second PVA solution (100 ml, 1% PVA, (w/w)) and allowed to stir for 3 hours at room temperature and then 1 hour at 4° C. Microspheres were washed and centrifuged 4× (rcf<150×g) to remove PVA prior to lyophilization for 48 hours. Yields were commonly 50-75% by weight of a white, fluffy powder. Fluorescent microspheres for imaging purposes were prepared using the same technique as stated above but using an aqueous solution of dextran tetramethyl-rhodamine (200 ul, 1 mg/ml) in the primary emulsion to yield a pink, fluffy powder. Microspheres and polymers were stored at −20° C. in a desiccated chamber. All in vitro cellular assays and in vivo tumor challenge experiments were performed by normalizing the amount of microspheres administered to a standard dosage of plasmid DNA due to variances in plasmid loading.

Characterization of microspheres. Encapsulation efficiency of the DNA Microspheres was determined by dissolving the microspheres in $CH_2Cl_2$ and performing an extraction into 1×TAE buffer (pH=8.0) over a 2 hour period. DNA concentration was detected using PicoGreen (Molecular Probes) and the Mithras plate reading fluorimeter (Berthold Technologies; Bad Wilbad, Germany). DNA integrity was determined using standard gel electrophoresis (1% agarose) and comparing sample band integrity with unprocessed plasmid DNA standards using Image J software. Microsphere size distributions were measured via volume displacement impedance using a Multisizer 3 (Beckman Coulter Miami, Fla.). Zeta potentials were obtained using a ZetaPALS analyzer (Brookhaven Instruments; Holtsville, N.Y.). Morphology of microsphere surfaces were imaged using scanning electron microscopy (SEM).

3D imaging of antigen presenting cells. Antigen presenting cells were seeded on fibronectin coated coverslips (BD Biosciences San Jose, Calif.) at $4 \times 10^5$ cells/well in 6 well plates and allowed to incubate overnight. Media was then replaced with a suspension of fluorescent microspheres (50 µg/ml cell media) and allowed to incubate for 4-6 hours. Cells were then washed, fixed with 3.2% paraformaldehyde solution in PBS, and permeated using 0.2% triton×100 (Sigma). Actin filaments and nuclear materials were labeled using Alexa 488 conjugated phalloidin and Hoechst, respectively (Molecular Probes).

Cells were imaged using the Zeiss Axiovert fluorescent microscope with an Apochromat 100× oil immersion lens (Göttingen, Germany). Vertical slices were recorded in 0.2 µm slices from top to bottom for each of the three fluorescent labels used. Images were deconvoluted using Openlab software (Improvision; Lexington, Mass.) using the nearest 3 upper and lower layers and then rendered to a 3D image.

Reporter gene transfection. To obtain a full expression profile for the P388D1 macrophage cell line, we modified the 6-well plate protocol used by Hedley et al. to a 96 well plate format (Hedley, M. L., Curley, J. & Urban, R. Microspheres containing plasmid-encoded antigens elicit cytotoxic T-cell responses. Nat. Med. 4, 365-368 (1998); incorporated herein by reference). Briefly, P388D1 macrophages were seeded at $1 \times 10^4$ cells/well in fibronectin coated, white polystyrene 96 well plates and allowed to achieve 75% confluence. Media was then replaced with a suspension of pCMV-Luc plasmid DNA containing microspheres (50 µg/ml) in cell media and allowed to incubate for 20 hours. A titration of the soluble, lipid-based transfection agent Lipofectamine 2000 (Invitrogen) was prepared with DNA as a positive control. At several time points, the media was aspirated from the samples and cells were washed with PBS. Glo Lysis Buffer (Promega, 100 µl, 1×) was added to each well and plates were allowed to incubate for 10 minutes to allow total cell lysis to occur. The wells were then analyzed for luciferase protein content using the Bright Glo Luciferase Assay System (Promega) and a Mithras plate reading luminometer (Berthold Technologies).

Total well protein content was determined using a micro-BCA assay system (Pierce Biotechnology Rockford, Ill.) in tandem with the bioluminescence assay. After the lysis step, BCA reagents were added and the cells were incubated for 3 hours at 37° C. and absorption was read at 562 nm using the Spectra Max 384 Plus multi-well plate reader (Molecular Devices; Sunnyvale, Calif.).

Flow cytometry analysis of fluorescent surface markers. Dendritic cells were plated at $5 \times 10^5$ cells/well in fibronectin coated 6 well plates (BD Biosciences) and allowed to incubate overnight. Media was then replaced with a suspension of microspheres (50 µg/ml) and incubated for varying times. Negative controls were prepared by leaving cells untreated. Positive controls were prepared by adding cell culture media containing murine If-γ (100 U/ml), TNF-α (50 U/ml), and IL-4 (100 U/ml) (R&D Systems Minneapolis, Minn.). At several time points, cells were trypsinized and collected by centrifugation. Monoclonal antibodies for mMHC Class II (clone AF6-120.1 I-$A^b$, FITC, 0.5 µg/$10^6$ cells, Pharmingen San Jose, Calif.), mF4/80 (clone CI:A3-1, PE, 0.25 µg/$10^6$ cells Caltag, Calif.), hCD40 (clone HB14, FITC, 5 µl/$10^6$ cells, Caltag) hCD83 (clone HB15a, FITC, 20 µl/$10^6$ cells, Immunotech, Miami, Fla.), hCD11c (clone BU15, PE, 20 µl/$10^6$ cells, Immunotech), and hCD14 (clone RMO52, APC, 10 µl/$10^6$ cells, Immunotech) were added to the cells in a solution of Hanks Balanced Salt Solution containing 1% BSA and incubated at 4° C. for 30 minutes. Cells were then washed and incubated with Propidium Iodide (5 µg/ml, Sigma) HBSS-BSA before quantitating fluorescence with a FACScan flow cytometer (Benton Dickenson; San Jose, Calif.).

Immunization and Lethal Tumor Challenge. Mice were challenged with tumor cells and measured for their cytotoxic T-cell response as previously described (Cho, B. K., Rao, V. P., Ge, Q., Eisen, H. N. & Chen, J. Z. Homeostasis-stimulated proliferation drives naive T cells to differentiate directly into memory T cells. J. Exp. Med. 192, 549-556 (2000); incorporated herein by reference). Briefly, B6 mice (5 mice per group) were immunized intradermally as described (Davis, H. L. in DNA Vaccines: Methods and Protocols. (ed. D.B.a.W. Lowrie, R. G.) 529 (Humana Press, Totowa, N.J.; 1999); incorporated herein by reference) twice at 2 week intervals using formulations suspended in 1% carboxymethylcellulose (w/w, Sigma) in sterile PBS consisting of 1) no formulation control, 2) naked pCMV-βgal-SYRGL plasmid (10 µg), 3) 502H PLGA encapsulated pCMV-βgal-SYRGL microspheres, 4,5) poly-β amino ester/502H PLGA (15% and 25% w/w poly-β amino ester) hybrid encapsulated pCMV-βgal-SYRGL microspheres. 6) poly-β amino ester/502H PLGA (25% w/w poly-β amino ester) microspheres with no encapsulated plasmid. One week following the last immunization, mice were challenged subcutaneously with lethal doses ($3 \times 10^6$) of EL-4 cells on the right flank and DP-1 cells on the left flank. A week later, tumor size was measured with a caliper every other day in two dimensions for 9 days. Statistics were performed by comparative ANOVA (samples to control) using a Dunnett's error confidence interval of 99%.

Example 8

Formulation and Characterization of Poly-Beta Amino Ester Microparticles for Genetic Vaccine Delivery The microparticulate delivery system fabricated from PLGA and a pH dependant, cationic charge inducible poly β-amino ester (PBAE) capable of offering substantial increases in plasmid delivery efficiency along with the ability to activate primary dendritic cells in vitro is described herein. Using a model antigen system, these particles were capable of inducing antigen-specific tumor regression in vivo while conventional naked plasmid and PLGA microencapsulated plasmid systems failed to exhibit this effect (Little et al. Poly-B amino ester-containing microparticles enhance the activity of nonviral genetic vaccines. *Proceedings of the National Academy of Sciences of the United States of America* 101: 9534-9539 (2004); incorporated herein by reference). The formulation and characterization of these microparticles is, of course, critical to their successful use and it is these issues that are examined in this Example.

Materials and Methods

Materials

Poly(d,l-lactic-co-glycolic acid) polymer (PLGA, RG502H Resomer 50:50) was purchased from Boehringer Ingelheim (Ingelheim, Germany). Poly-β amino ester (PBAE) was synthesized as previously reported ($M_n \approx 5$ kD) (Lynn et al. pH-responsive polymer microspheres: Rapid release of encapsulated material within the range of intracellular pH. *Angewandte Chemie-International Edition* 40: 1707-1710 (2001); incorporated herein by reference). Plasmid DNA encoding firefly luciferase (pCMV-Luc) was obtained from Elim Biopharmaceuticals (Hayward, Calif.).

Cells

The P388D1 macrophage cell line was obtained from ATCC (Manassas, Va.). Cells were cultured in RPMI 1640 media (Gibco Life Technologies; Carlsbad, Calif.) containing 10% FBS, 0.1 M HEPES, 1 mM Sodium Pyruvate, and 100 U/ml Penecillin/Streptomyocin.

Preparation of Microparticles

Plasmid containing microparticles were prepared by the following modification of the double emulsion technique previously described (Odonnelland et al. Preparation of microspheres by the solvent evaporation technique. *Advanced Drug Delivery Reviews* 28: 25-42 (1997); incorporated herein by reference). Varying amounts of PLGA blended with PBAE were explored in microsphere formulations to determine optimal payload release. Lyophilized plasmid DNA (1 mg) was added to an aqueous solution (100 μL) of EDTA (1 mM) and D(+)-Lactose (300 mM). This solution was then emulsified with an organic solution of PLGA and PBAE at varying degrees of composition (200 mg) in $CH_2Cl_2$ (4 ml) using a probe sonicator (Sonics and Materials Inc; Danbury, Conn.). The resulting emulsion was then immediately added to a homogenized solution of poly(vinyl alcohol) (50 ml, 5% PVA (w/w), 5000 rpm) and NaCl. After 30 seconds, the final water-oil-water mixture was added to a second PVA solution (100 ml, 1% PVA, (w/w)) and allowed to stir for 3 hours at room temperature and then 1 hour at 4° C. Microspheres were washed and centrifuged 4× (rcf<150×g) to remove PVA prior to lyophilization for 48 hours. Yields were commonly 50-75% by weight of a white, fluffy powder. Microparticles and polymers were stored at −20° C. in a desiccated chamber.

Characterization of Microparticles

Encapsulation efficiency of the DNA microparticles was determined by dissolution in $CH_2Cl_2$ and extraction into 1×TAE buffer (pH=8.0) over a 2 hour period. DNA concentration was detected using PicoGreen (Molecular Probes) and the Mithras plate reading fluorimeter (Berthold Technologies; Bad Wilbad, Germany). DNA integrity was determined using standard gel electrophoresis (1% agarose) comparing sample band integrity with unprocessed plasmid DNA standards using Image J software. Osmolality of the internal aqueous phase (i.e. solution with the same concentrations of EDTA, lactose, and plasmid used for the internal aqueous phase during the double emulsion procedure) and external aqueous phase (i.e. solution with the same concentrations of PVA and NaCl used for the external aqueous phase during the double emulsion procedure) was determined using a Vapro vapor pressure osmometer (Wescor: Logan, Utah) via vapor pressure depression. Microsphere size distributions were measured via volume displacement impedance using a Multisizer 3 using 30-200 μm orifice tubes (Beckman Coulter; Miami, Fla.). Zeta potentials were obtained using a Zeta-PALS analyzer (Brookhaven Instruments; Holtsville, N.Y.) with 10 mM HEPES buffer at pH=7.4. Morphology of microsphere surfaces was imaged using scanning electron microscopy (SEM). Microparticle samples were certified low endotoxin level (<0.50 EU/mg) by the Cambrex LAL testing service (Walkersville, Md.).

pH Microenvironment Measurements

Internal hydrogen ion concentration was determined as previously described (Shenderova et al. The acidic microclimate in poly(lactide-co-glycolide) microspheres stabilizes camptothecins. *Pharm Res* 16: 241-8 (1999); incorporated herein by reference). Briefly, varying weights of microparticles were carefully weighed out into pre-weighed microcentrifuge tubes. Particles were incubated with 1 ml of 50 μM HEPES (pH=7.4) for 24 or 72 hours. Tubes were centrifuged at 5000 rpm for 10 minutes, the supernatants were discarded, and the total weight of the microparticles and aqueous microenvironment was determined. Particles were then dissolved in acetonitrile (ACN) by vigorous vortexing. Tubes were centrifuged a second time to remove any remaining material and 0.7 ml of this ACN solution was added to 0.175 ml of deionized water prior to pH measurement using a micro probe reader. This measurement determines the total number of moles of free hydrogen ion in the microenvironment, and along with the total weight of water, the pH of the microclimate could be estimated.

Release Profiles

Microparticles were incubated in Tris HCl (pH 7.5) at 37° C. for 24 hours in triplicate. The samples were centrifuged briefly and the supernatant was transferred to a new tube and stored at −80° C. to prevent DNA degradation. Fresh Tris HCl was added to the pelleted spheres and the tube vortexed gently to resuspend particles. This process was repeated for Days 2-7. On Day 7 following the above process, each sample tube from each day was analyzed for double stranded DNA content using Pico Green fluorescence in a black, polypropylene 96 well plate and a fluorescence plate reader at 488 nm (Berthold Technologies). Concentrations were determined with the use of a standard curve.

Reporter Gene Transfection

To obtain a full expression profile for the P388D1 macrophage cell line, we modified the 6-well plate protocol used by Hedley et al. to a 96 well plate format (Hedley et al. Microspheres containing plasmid-encoded antigens elicit cytotoxic T-cell responses. *Nature Medicine* 4: 365-368 (1998); incorporated herein by reference). Briefly, P388D1 macrophages were seeded at $5 \times 10^4$ cells/well in fibronectin coated, white polystyrene 96 well plates and allowed to achieve 75% confluence. Media was then replaced with a suspension of pCMV-Luc plasmid DNA containing microspheres (50 μg/ml) in cell media and allowed to incubate for 20 hours. A titration of the soluble, lipid-based transfection agent, Lipofectamine 2000 (Invitrogen), was prepared with DNA as a positive control. At several time points, the media was aspirated from the samples and cells were washed with PBS. The cells were lysed by incubation for 10 minutes at room temperature with Glo Lysis Buffer (Promega, 100 μl, 1×). The wells were then analyzed for luciferase protein content using the Bright Glo Luciferase Assay System (Promega) and a Mithras plate reading luminometer (Berthold Technologies). Alternatively, cells were treated with Cytochalasin-D (10 μm, Sigma) to inhibit phagocytosis along with transfection agents. Groups were compared using ANOVA and t-test analysis for significance (α=0.05).

Total well protein content was determined using a micro-BCA assay (Pierce Biotechnology; Rockford, Ill.) in tandem with the bioluminescence assay. After the lysis step, BCA reagents were added and the cells were incubated for 3 hours at 37° C. and absorption was read at 562 nm using the Spectra Max 384 Plus multi-well plate reader (Molecular Devices; Sunnyvale, Calif.).

Toxicity

Microparticle toxicity was determined by using a standard MTT assay (ATCC) using P388D1 macrophages. Briefly, 50,000 cells were plated into a 96 well plate and allowed to recover overnight. Supernatants were removed and replaced with a suspension of microparticles or DNA/Lipofectamine complexes in P388D1 media. Non-treated wells were used as controls and were titrated to give optimal signal as suggested in manufacturer's instructions. After 24 hours of incubation with formulations, cells were assayed for metabolic activity after addition of reagent, lysis buffer, and measuring absorbance at 570 nm with a plate reading spectrophotometer (Molecular Devices).

Results

Effect of the Incorporation of PBAE on Particle Formation

Figure 33:
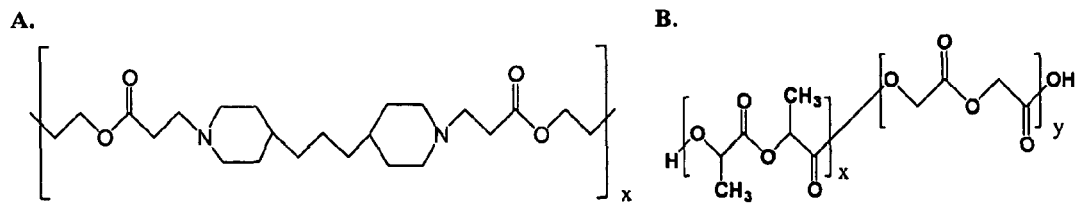
FIG. 33 shows the molecular structure of the poly(beta-amino ester) (PBAE) used in the study (A) and the molecular structure of poly(lactic-glycolic acid) (PLGA) (B).
Figure 34:
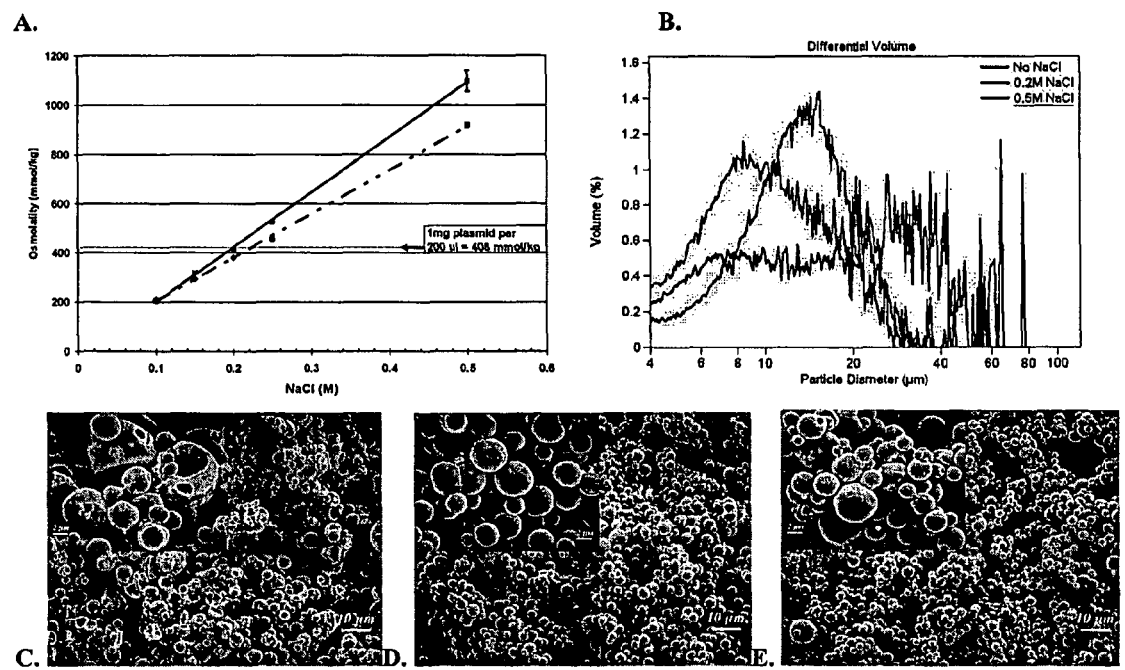
FIG. 34 shows the effect of osmolality balance during fabrication of 25% PBAE microparticles. A. The osmolality (mmol/kg) of the outer aqueous phases (5% PVA w/v=bold line, 2.3% PVA w/v=dashed line), with varying amounts of NaCl. The osmolality of the internal aqueous phase was recorded at 408±3 mmol/kg which corresponds to approximately 0.2M NaCl in the PVA solutions. B. The effect of salt addition to the outer aqueous phase on aggregation during microparticle fabrication. Microparticles that were prepared using an outer aqueous phase which osmotically matched the internal aqueous phase had the lowest diameter measured during fabrication when particles are partially swollen with solvent (blue line). In contrast, particles fabricated using no salt in the external aqueous phase generated slightly more swollen particles. Particles made with 0.5 M salt in the external aqueous phase were smaller, but heavily aggregated. Scanning Electron Micrographs of microparticles were taken after lyophilization and are represented above for use of (C.) 0 M salt (D.) 0.2 M salt, and (E.) 0.5 M salt. Magnifications are 1000× (body) and 5000× (inset) and size bars are included. Encapsulation efficiencies were 55% for 0M salt, 92% for 0.2M salt, and 73% for 0.5M salt.

As described here, and in previous work (Lynn et al. pH-responsive polymer microspheres: Rapid release of encapsulated material within the range of intracellular pH. *Angewandte Chemie-International Edition* 40: 1707-1710 (2001)), addition of PBAE (structure shown in FIG. 1A) into the microparticle formulation with PLGA (structure shown in FIG. 33B), although greatly increasing the plasmid delivery capacity of the particle (Little et al. Poly-B amino ester-containing microparticles enhance the activity of nonviral genetic vaccines. *Proceedings of the National Academy of Sciences of the United States of America* 101: 9534-9539 (2004)), introduces several issues that need to be addressed during fabrication. PBAE is generally tackier than PLGA polymers and high speed centrifugation at temperatures above 4° C. can cause the fusing of particles and extensive aggregation (Lynn et al. pH-responsive polymer microspheres: Rapid release of encapsulated material within the range of intracellular pH. *Angewandte Chemie-International Edition* 40: 1707-1710 (2001)). Another caveat to the addition of PBAE is its sensitivity to differences in internal vs. external aqueous phase osmolality. To demonstrate this effect, the osmolality of the internal aqueous phase (drug compartment) was determined along with the outer aqueous phase for the homogenization step and stirring step (including PVA) using a titration of NaCl (0.1-0.5M) (FIG. 34A). This data suggest that approximately 0.2 M provides osmotic balance.

To demonstrate the resulting effect on microparticle integrity and loading, particles were prepared using pCMV-Luc plasmid using 0, 0.2, and 0.5 M NaCl. Determination of total amount of plasmid encapsulation using $CH_2Cl_2$/TAE buffer extraction and Pico-Green detection indicate that 0.2 M (92%) and 0.5 M NaCl (73%) in the external aqueous phase provides greater encapsulation than no salt at all (55%). SEM analysis of microparticle surface integrity demonstrates the effect of osmotic imbalance when PBAE is present in the microparticle polymer matrix. The surface of particles fabricated in the presence of 0.2 or 0.5 M salt in the external aqueous phase is of high integrity with very little flaws while the surface of particles prepared with no NaCl is covered with large cavities, presumably due to rupture of the polymer matrix above the internal aqueous compartments due to water influx (FIG. 34C-E). However, upon increasing salt concentration to 0.5 M, aggregation of particles was apparent after stirring. This aggregation was greater than in the case of particles prepared using 0 and 0.2 M NaCl (FIG. 34B).

Physical Properties

The physical properties of lyophilized microparticles prepared from PBAE and PLGA were examined to determine if they were compatible with targeted delivery of plasmid DNA to phagocytic antigen presenting cells. Diameters obtained by volume displacement for all microparticle formulations were between 1 and 10 µm allowing for a passive targeting by phagocytosis. There did not seem to be a correlation between size or aggregation and PBAE content when using refrigerated washing and stirring processing steps.

Quality and quantity of plasmid DNA content seemed to favor formulations with PBAE included when compared to PLGA alone. On average, PLGA loadings were below 50% efficiency, while particles prepared from 15-50% PBAE had much higher encapsulation of plasmid (Table 8-1). Supercoiled content directly after the encapsulation and lyophilization process was also generally higher for microparticles with PBAE in the formulation (Table 8-1). Plasmid integrity after incubation in buffer at 37° C. is discussed below.

Zeta potential analysis indicated that particles prepared with PLGA alone had slightly negative values due to residual PVA as previously reported (Sahoo et al. Residual polyvinyl alcohol associated with poly(D,L-lactide-co-glycolide) nanoparticles affects their physical properties and cellular uptake. *Journal of Controlled Release* 82: 105-114 (2002); incorporated herein by reference). Interestingly, particles prepared from 5% PBAE exhibited more negative zeta potentials than pure PLGA microparticles. In general, particles prepared with 5% to 50% PBAE had zeta potentials proportional to the amount of charge inducible PBAE in the structure with a leveling off between 35 and 50% (Table 8-1).

TABLE 8-1

Properties of microparticles containing varying amounts of PBAE with respect to PLGA. All particles shown were prepared with 0.2 M salt in the external aqueous phase. Values for the physical properties of microparticles are shown above for dry, lyophilized formulations resuspended in buffer at physiologic pH. Some values for PLGA, 15% PBAE, 25% PBAE, and 25% PBAE no DNA are taken from a previous work describing these particles (Little et al. Poly-B amino ester-containing microparticles enhance the activity of nonviral genetic vaccines. Proceedings of the National Academy of Sciences of the United States of America 101: 9534-9539 (2004)).

| Formulation (% by weight) | Volume % Mean Diameter (µm) ± σ | Encapsulation Efficiency ± 10% | % Supercoiled Content | Mean Zeta Potential (mV) ± σ |
|---|---|---|---|---|
| 100% PLGA | 4.35 ± 2.34 | 40% | 36 ± 8% | −3.76 ± 0.40 |
| 5% PBAE/ 95% PLGA | 7.90 ± 2.36 | 50% | N/A | −8.90 ± 0.48 |
| 15% PBAE/ 85% PLGA | 6.01 ± 2.06 | 68% | 72 ± 5% | −0.86 ± 0.62 |
| 25% PBAE/ 75% PLGA | 5.53 ± 2.31 | 78% | 68 ± 5% | 0.46 ± 0.38 |
| 25% PBAE/ 75% PLGA No DNA | 5.12 ± 2.20 | — | — | 0.41 ± 0.36 |
| 35% PBAE/ 65% PLGA | 7.11 ± 2.06 | 84% | N/A | 1.41 ± 0.71 |
| 50% PBAE/ 50% PLGA | 4.81 ± 2.10 | 74% | N/A | 1.41 ± 0.68 |

Effect of pH Microclimate

To observe the effect of PBAE buffering on internal microclimate pH, we utilized a previously described procedure in which particles were incubated at 37° C. in buffer followed by dissolution in acetonitrile and physical measurement of pH to calculate the resulting microclimate (Shenderova et al. The acidic microclimate in poly(lactide-co-glycolide) microspheres stabilizes camptothecins. *Pharm Res* 16: 241-8 (1999); incorporated herein by reference). We determined that 24 hour (FIG. 35A) and 72 hour (FIG. 35B) incubation of microparticles resulted in a significantly lower microclimate pH for 100% PLGA microparticles when compared to PBAE microparticles. This effect was especially pronounced at 72 hours where the pH of PLGA microparticles was approximately 2.75 while PBAE buffered the microclimate to pH>4.

Plasmid DNA was extracted from these microparticles after aqueous incubation using the same technique described above. The integrity of the extracted plasmid was examined using 0.8% agarose gels (24 hours, FIG. 35C and 72 hours, FIG. 35D). Integrity of plasmid encapsulated in PBAE microparticles was found to be substantially higher when compared to plasmid extracted from particles prepared from PLGA alone, especially after 72 hours (3-4× greater), corresponding to the data obtained for the low microclimate pH at this time. Supercoiled DNA content did not decrease greatly from 24 hours to 72 hours for 15 and 25% PBAE microparticles.

Plasmid Release

Figure 36:
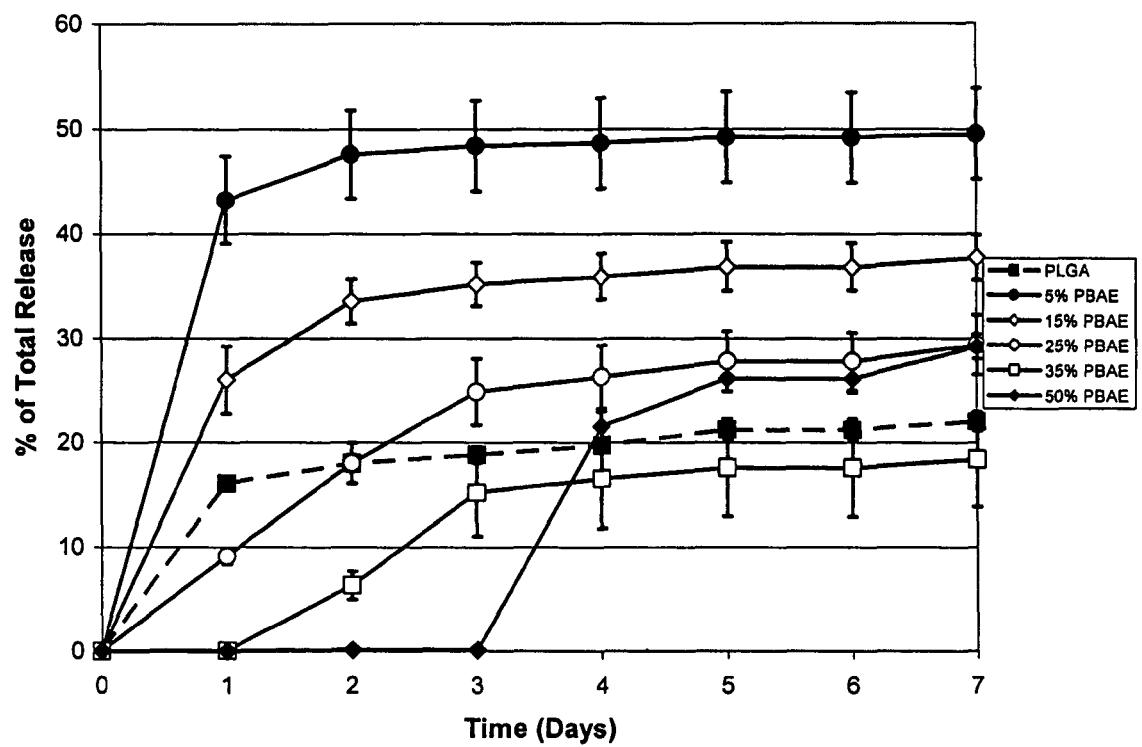
FIG. 36 shows the release of plasmid DNA from PBAE/PLGA microparticle formulations. Microparticles were incubated for 1 week with supernatants removed and replaced every 24 hours. Supernatants were tested for DNA concentration using Pico Green fluorescence in a plate reading fluorimeter and standard curves were used to generate DNA concentration shown above as % of total release from the microparticle sample. Release is shown above for PLGA (■, dashed line), 5% PBAE (●), 15% PBAE (◇), 25% PBAE, (○), 35% PBAE (□), 50% PBAE (◆). Error bars represent standard error at each timepoint (n=3).

To determine the effect of increasing amounts of PBAE on release of plasmid, particles were incubated in buffer for 1-7 days and supernatants were removed daily to be assayed for plasmid concentration using Pico Green. Particles prepared with the lower amounts of PBAE (5%, 15%) exhibited a larger burst phase than those composed of PLGA alone (FIG. 36). PBAE content of 15% and 25% most closely resembled that of 100% PLGA. Larger amounts of PBAE (35% and 50%) seemed to delay release of plasmid for several days before burst phase release. Plasmid release studies were also attempted in which the pH of the media was reduced to 4.7, simulating the low pH environment in phagosomes. However, dissolution of PBAE causes extensive binding to the DNA resulting in a failure to detect plasmid using Pico Green, which yields no signal, and standard UV detection, which yields abnormally high signals possibly due to contribution by PBAE to the absorption at 260 nm.

Trasfection of P388D1 Macrophages Using pCMV-Luc Containing Microparticles

Varying amounts of PBAE in microparticles were tested for the ability to enhance transfection in a P388D1 macrophage cell line. These cells were chosen as they have previously been shown to be amenable to transfection by PLGA as to compare relative magnitudes (Hedley et al. Microspheres containing plasmid-encoded antigens elicit cytotoxic T-cell responses. *Nature Medicine* 4: 365-368 (1998); incorporated herein by reference). Lipofectamine 2000 was used as a positive control. It was found that increasing the amount of PBAE in the particle makeup increased transfection of up to 5 orders of magnitude for 25% PBAE. Increasing the levels further to 35 and 50% PBAE caused a decrease in detected transfection. Optimal formulations of 25% PBAE performed equivalently to 1 log unit below that of an optimal formulation of Lipofectamine 2000 despite the 20× greater level of plasmid needed for this level of transfection with Lipofectamine. With 35% and 50% PBAE microparticles, the observed transfection was greatest across the board with lower microparticle concentrations, especially at the later time points. However, 15% PBAE microparticles achieved the highest transfection at the higher microparticle concentrations.

Figure 38:
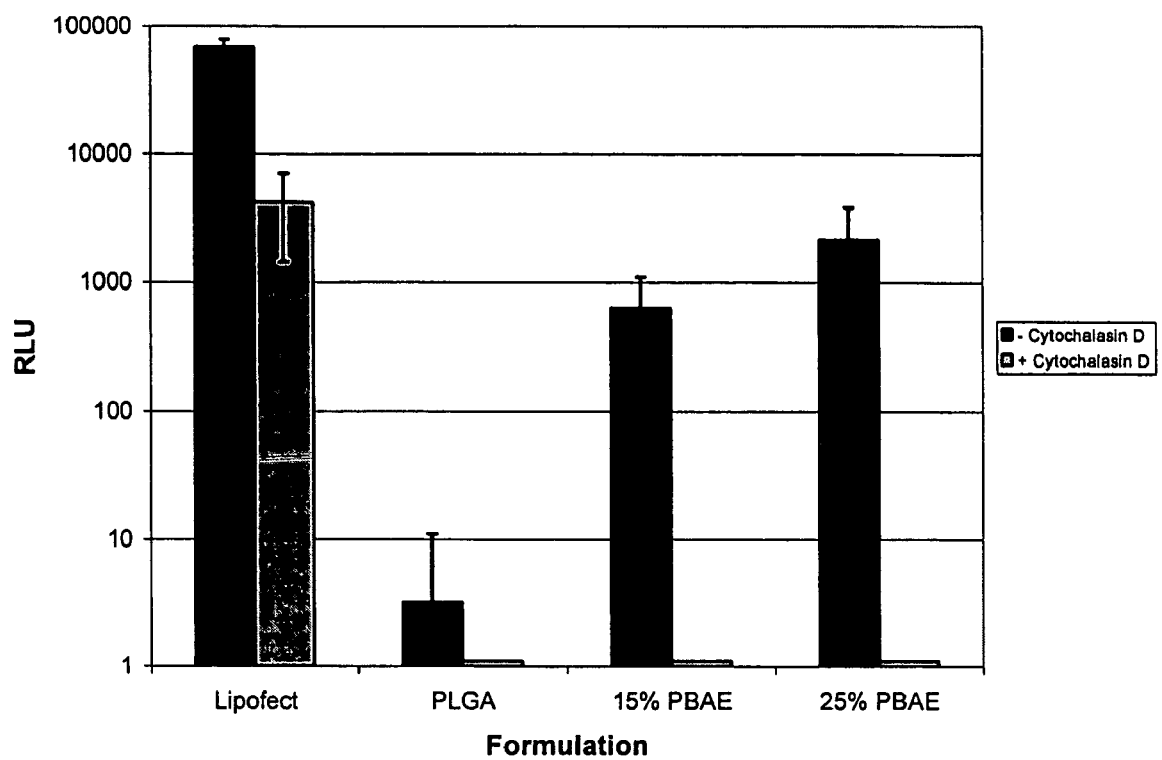
FIG. 38 shows the effect of cytochalasin-D on transfection of phagocytic cell line. Results shown above indicate luciferase transfection after 1 day incubation with microparticles containing pCMV-Luc, with or without the presence of Cytochalasin D (10 μM) in the media to inhibit actin mediated phagocytosis. Data is representative of four averaged experiments with included standard deviation bars.

Transfection of these cells should be mostly due to phagocytosis of the particles if they are to passively target APCs in a complex in vivo cellular milieu. To verify this was the case in our system, we transfected P388D1 macrophages in the presence of cytochalasin-D to inhibit phagocytosis but not endocytosis. Addition of 10 µM cytochalasin-D completely abolished transfection of macrophages using all microparticle formulations tested (FIG. 38). However, Lipofectamine 2000 transfection of P388D1's were only slightly decreased. This effect may have been due to some additional toxicity associated with incubation of cells with cytochalasin-D for 24 hours.

Toxicity of PBAE Microparticles

Toxicity associated with larger amounts of PBAE may be partially responsible for the observed decrease in transfection using larger amounts of particles. An MTT assay was employed to examine this effect on the P388D1 line. Non-treated cells were used as a negative control and Lipofectamine 2000 was used as a positive control for toxicity. Cells were incubated for 24 hours with microparticle formulations, or Lipofectamine 2000, and then tested for metabolic activity.

Figure 39:
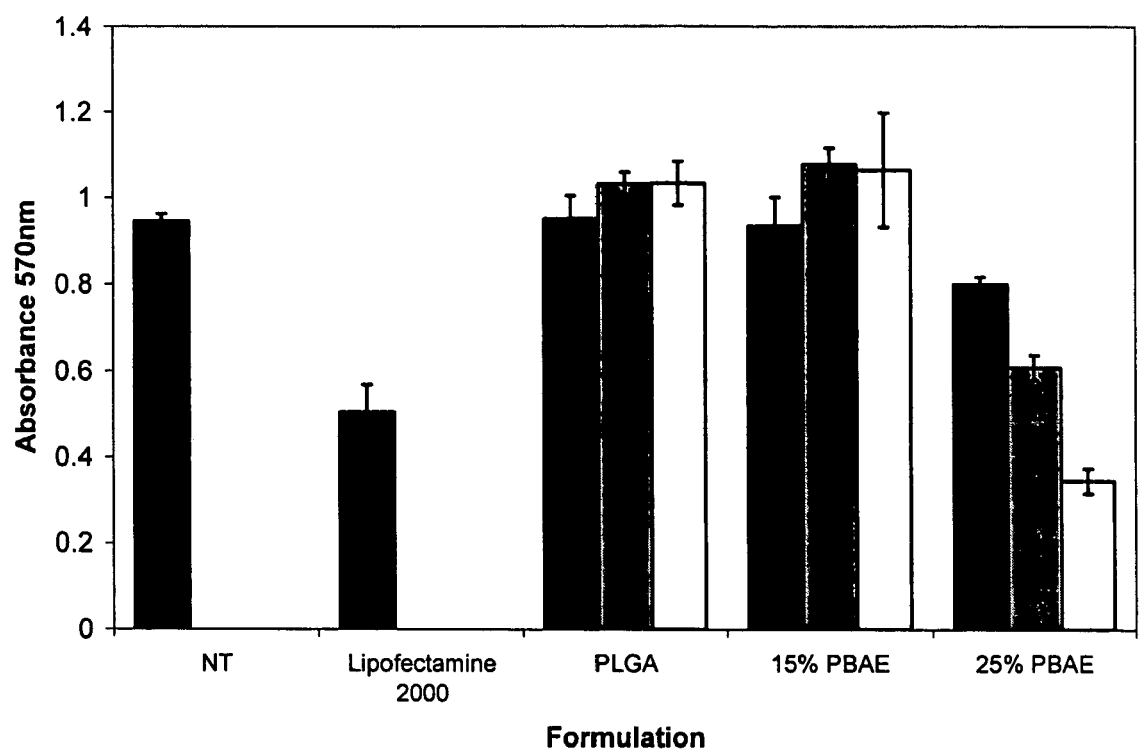
FIG. 39 demonstrates the toxicity of PBAE microparticles. P388D1 macrophages were incubated with microparticle formulations for 24 hours and then analyzed for viability using a standard MTT assay. Results above show absorbance at 570 nm of a solubilized precipitate indicating level of metabolic activity for microparticle concentrations of 10 μg/ml (black), 50 μg/ml (grey), and 100 μg/ml (white).

It was confirmed that addition of PBAE to microparticles increased toxicity as did increasing total dosage of particle to cells in the case of 25% PBAE particles (FIG. 39). Lipofectamine 2000 also demonstrated significant toxicity as expected. However, both PLGA and 15% PBAE showed no detectable levels of toxicity in all dosages used.

Discussion

Disadvantages to using PLGA in plasmid containing microparticles have prompted investigation into additives and replacements which are better suited for the delivery of genetic vaccines (McKeever et al. Protective immune responses elicited in mice by immunization with formulations of poly(lactide-co-glycolide) microparticles. *Vaccine* 20: 1524-1531 (2002); Singh et al. Cationic microparticles: A potent delivery system for DNA vaccines. *Proc Natl Acad Sci USA* 97: 811-6 (2000); Wang et al. Molecularly engineered poly(ortho ester) microspheres for enhanced delivery of DNA vaccines. *Nat. Mater.* 3: 190-6 (2004); Walterand et al. Microparticle-mediated transfection of non-phagocytic cells in vitro. *Journal of Drug Targeting* 10: 11-21 (2002); Luo et al. Plasmid DNA encoding human carcinoembryonic antigen (CEA) adsorbed onto cationic microparticles induces protective immunity against colon cancer in CEA-transgenic mice. *Vaccine* 21: 1938-1947 (2003); each of which is incorporated herein by reference). It is thought that these systems are more appropriate because they either deliver the DNA in a fashion which is timelier to the induction of an immune response or in a form which is more amenable to the transfection of targeted cells. However, switching from a pure, biocompatible and FDA approved material may introduce undesirable side effects such as cellular toxicity, which may or may not be avoidable if the system is to be highly efficient. Therefore, it is imperative that new systems are investigated to allow for optimization of immunogenicity afforded by a delivery system with low toxicity. We recently employed a pH sensitive PBAE polymer which has shown to greatly increase the gene delivery capacity of PLGA formulations while adding adjuvancy (Little et al. Poly-B amino ester-containing microparticles enhance the activity of nonviral genetic vaccines. *Proceedings of the National Academy of Sciences of the United States of America* 101: 9534-9539 (2004); incorporated herein by reference). This system has also been shown to have minimal toxicity at low amounts (Lynn et al. Degradable poly(beta-amino esters): Synthesis, characterization, and self-assembly with plasmid DNA. *Journal of the American Chemical Society* 122: 10761-10768 (2000); incorporated herein by reference), however microparticles require the use of larger amounts of this polymer per unit mass of DNA. Here, we consider the formulation and characterization of polymer microparticles prepared with varying amounts of PBAE added to PLGA in a microparticle encapsulating plasmid DNA.

The physical properties of PBAE require that it be treated differently during the microparticle fabrication procedure (Lynn et al. pH-responsive polymer microspheres: Rapid release of encapsulated material within the range of intracellular pH. *Angewandte Chemie-International Edition* 40: 1707-1710 (2001); incorporated herein by reference). As stated before, refrigerated centrifugation steps are required to minimize aggregation and particle deformation when PBAE is present in microparticle formulations. Another special consideration when using PBAE is the osmotic balance between the internal versus external aqueous phases during homogenization and solvent evaporation steps. This may be particularly pronounced in this system due to PBAE being partially charged in contact with an aqueous phase and therefore more conducive to water influx in the presence of an osmotic gradient (higher semi-permeable membrane effect). The presence of a high osmolality in the microparticle interior and a low osmolality in the outer stirring phases may cause an influx of water and the bursting of compartments. This would lead to the escape of entrapped plasmid and low effective loading. Pico green analysis of DNA extracted from lyophilized 25% PBAE microparticles confirms that particles prepared with no osmotic matching exhibit lower encapsulation efficiencies and cavities in the microparticle surface (FIG. 34C-E). In contrast, particles prepared using salt in the exterior stirring phase had higher encapsulation efficiencies and smooth surfaces. However, too much salt in the stirring phase caused extensive aggregation of the particles (FIG. 34B). It is possible that large amounts of salt may diminish any surface charge repulsion between particles which would tend to reduce such aggregation.

In general, addition of PBAE into the microparticle formulations seemed to increase the integrity and quantity of encapsulated DNA along with creating a more positive zeta potential (Table 8-1). The more positive zeta potentials associated with PBAE may be responsible for the larger encapsulation efficiencies due to a reduction in hydrophobicity resulting from charged tertiary amines present in the polymer backbone which would interact with anionic DNA more favorably. The highly hydrophobic environment present in pure PLGA microparticles would not serve as an optimal retention environment for DNA during microparticle fabrication. The association of the negatively charged plasmid with either free PBAE in the particle interior or a positively charged particle surface may also be responsible for the higher integrity of plasmid DNA following fabrication. High shear stresses are present during sonication and homogenization which can diminish the amount of plasmid in a supercoiled form (Ando et al. PLGA microspheres containing plasmid DNA: Preservation of supercoiled DNA via cryopreparation and carbohydrate stabilization. *Journal of Pharmaceutical Sciences* 88: 126-130 (1999); incorporated herein by reference). The complexation or association of plasmid with PBAE may serve to reduce this effect. It is unknown as to why the zeta potential for 5% PBAE is lower than that of PLGA. One possible explanation is an increased amount of plasmid DNA or PVA residing on the surface of these microparticles after the addition of partially cationic PBAE to the formulation.

Figure 35:
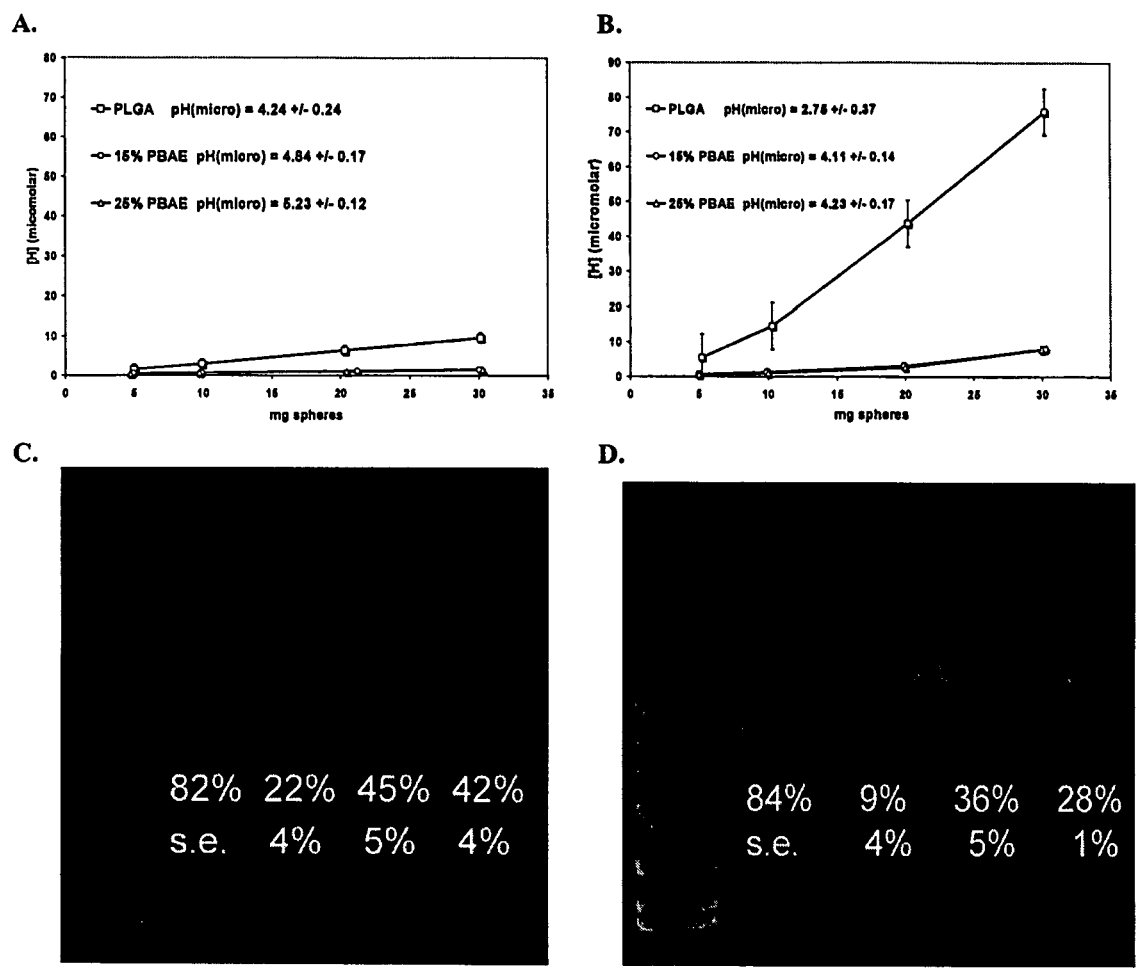
FIG. 35 shows the effect of pH microenvironment on PLGA and PBAE microparticles containing plasmid DNA. Microparticle samples were carefully weighed and incubated for A. 24 hours and B. 72 hours at physiological pH. Samples were centrifuged and supernatants removed to allow weighing of the pellet followed by addition of acetonitrile:water (0.7 ml:0.175 ml) and measurement of pH. Plots represent measured hydrogen ion concentration vs. amount of microparticles incubated and then dissolved in $ACN:H_2O$. Calculated microenvironment pH [pH(micro)] is reported in the legends. Supercoiled DNA content of the microparticles are shown for C. 24 hour incubation, and D. 72 hour incubation for microparticle samples composed entirely of PLGA (Lane 3), 15% PBAE (Lane 4), or 25% PBAE (Lane 5). A DNA ladder (Lane 1) and unprocessed plasmid DNA (Lane 2) were used as controls. Supercoiled plasmid percentages are shown for each lane of the representative gel with standard errors for comparison (n=3).

We previously mentioned that the tertiary amines in PBAE (FIG. 33A) may be responsible in several ways for the increased delivery capacity of microparticles containing this polymer (Little et al. Poly-B amino ester-containing microparticles enhance the activity of nonviral genetic vaccines. *Proceedings of the National Academy of Sciences of the United States of America* 101: 9534-9539 (2004); incorporated herein by reference). One of these gene delivery functions involves the absorption of protons in the acidic endosome which eventually could release the plasmid payload into the cytoplasm of a cell by a proton sponge mechanism (Little et al. Poly-B amino ester-containing microparticles enhance the activity of nonviral genetic vaccines. *Proceedings of the National Academy of Sciences of the United States of America* 101: 9534-9539 (2004); incorporated herein by reference). Furthermore, we hypothesized that the tertiary amines in PBAE (which are absent in PLGA (FIG. 33B) may also act as a weak base, absorbing the protons present in the pH microclimate originating from degradation of ester bonds. This effect was first demonstrated by Shenderova et al who determined that PLGA particle microclimate pH can be as low as 1.8 (Shenderova et al. The acidic microclimate in poly(lactide-co-glycolide) microspheres stabilizes camptothecins. *Pharm Res* 16: 241-8 (1999); incorporated herein by reference). Our data suggest that PBAE significantly buffers the acidic microclimate effect caused by ester degradation (FIG. 3). This effect is particularly pronounced after 3 days of incubation. Measurements obtained at a three day time point indicate that that microclimate pH for PLGA microparticles is approximately 2.75. The higher values obtained here than in previous results (Shenderova et al. The acidic microclimate in poly(lactide-co-glycolide) microspheres stabilizes camptothecins. *Pharm Res* 16: 241-8 (1999)) may be due the larger sizes of the particles used in these studies which would hinder diffusion of acid from the interior even more so than a smaller particle. Microclimate pH after 3 days was measured at 4.11 and 4.23 for 15% and 25% PBAE, respectively. This is important because reduction of pH below 4 has been shown to severely reduce the supercoiled content and transfection activity of plasmid DNA (Walter et al. Microencapsulation of DNA using poly(DL-lactide-co-glycolide): stability issues and release characteristics. *Journal of Controlled Release* 61: 361-374 (1999); incorporated herein by reference). Our data suggest that the supercoiled DNA content of PLGA microparticles is substantially lower than PBAE microparticles after 1 day of aqueous incubation and drastically lower after 3 days of incubation (FIG. 35C-D). Although the buffering of pH microclimate by PBAE is most likely responsible for this stabilization, it cannot be ruled out that plasmid complexation by free or microparticle associated PBAE could be involved with higher levels of supercoiled plasmid.

Release data obtained from microparticles containing PBAE indicates that the amount of partially cationic polymer determines the release of plasmid. Data obtained for the release from PLGA particles correlates well with prior studies on a similar system (Hsu et al. Comparison of process parameters for microencapsulation of plasmid DNA in poly (D,L-lactic-co-glycolic) acid microspheres. *J Drug Target* 7: 313-23 (1999); incorporated herein by reference). Low amounts of PBAE, 5% and 15%, seemed to exhibit a larger burst phase than PLGA alone (FIG. 36). This may be due to a higher amount of plasmid residence on the surface of the particle as suspected earlier to explain zeta potential data. This burst phase could be diminished upon the addition of more cationic polymer which may more tightly bind anionic plasmid. Correspondingly, our data shows that upon increasing the amount of PBAE in the microparticle composition, this burst phase was reduced, and in the case of 35% and 50% PBAE, there is a delay of any release of up to 3 days. This delayed release associated with larger amounts of PBAE may be beneficial in smaller particle systems aimed at targeting destructive genes to cancer cells as to avoid release before uptake.

Figure 37:
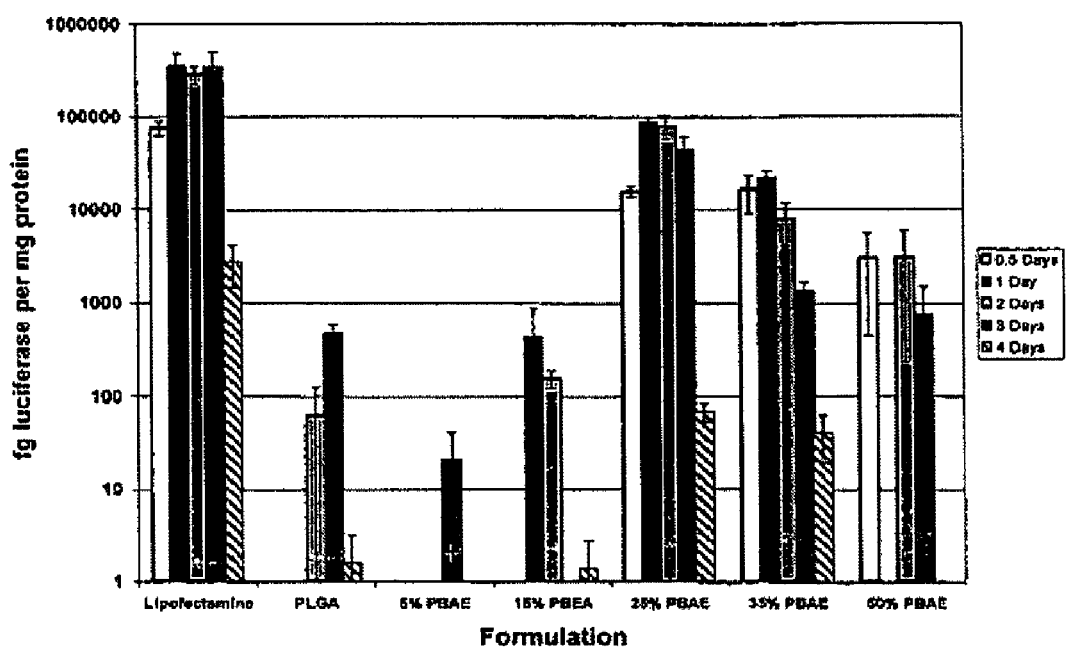
FIG. 37 shows the transfection of P388D1 macrophages using microparticles with increasing amounts of PBAE. P388D1 macrophages were incubated with microparticle formulations containing pCMV-Luc in a 96 well plate for up to 4 days at suspended microparticle concentrations of A. 10 μg/ml, B. 30 μg/ml, C. 100 μg/ml. Wells were analyzed for luminescence after adding luciferin and ATP and were normalized using total protein content in each well by BCA assay. Results show expression levels of luciferase after 0.5 days (white), 1 day (black), 2 days (light grey), 3 days (dark grey), and 4 days (diagonal striped). Values for previously reported microparticle formulations (Little et al. Poly-B amino ester-containing microparticles enhance the activity of nonviral genetic vaccines. *Proceedings of the National Academy of Sciences of the United States of America* 101: 9534-9539 (2004); incorporated herein by reference) are included for comparison. Standard deviations are included (n=4).
Figure 37:
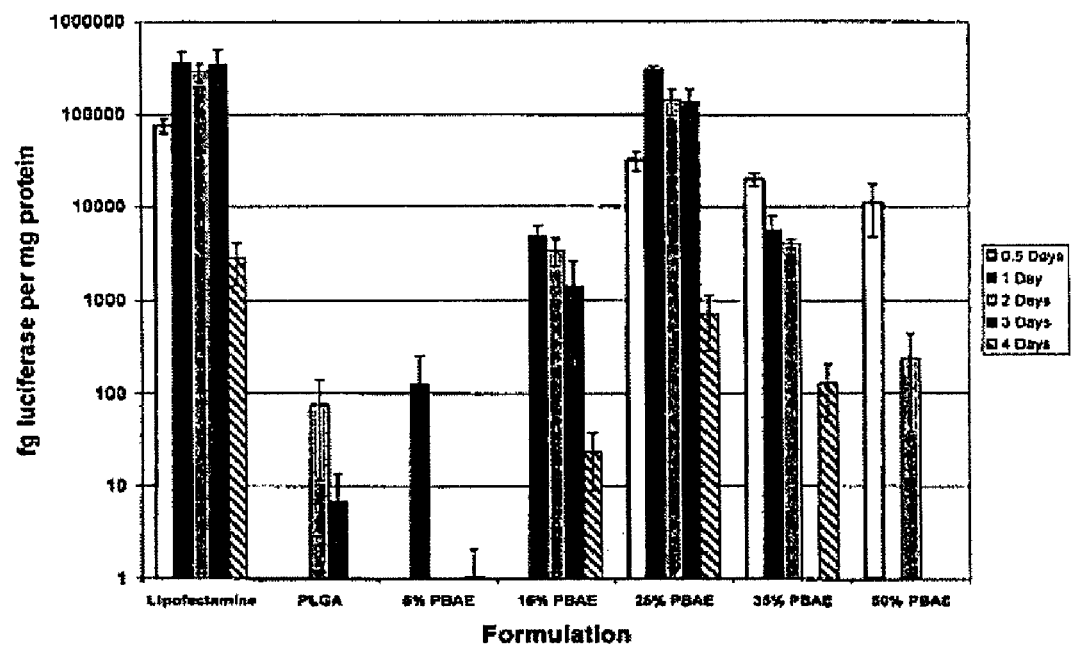

Transfection of P388D1 macrophages was substantially increased upon addition of up to 25% PBAE (FIG. 37). This effect was less pronounced with 15% PBAE but was still 1-2 orders of magnitude greater at most time points. Larger amounts of PBAE seemed to decrease the transfection levels seen with 25% PBAE, and this effect was even more apparent using larger amounts of microparticles in the cell supernatant. This decrease in observed transfection is most likely due to toxicity associated with this amount of PBAE. However, it seems that at least some level of PBAE needs to be present for significantly enhanced transfection as in the case of 15% PBAE where lower levels of microparticles were not as effective as higher doses (FIG. 37). The toxicity effect of larger amounts of PBAE is apparent using 25% formulations which had toxicity equivalent to Lipofectamine 2000 above 50 µg/ml. In contrast, formulations containing 15% PBAE had no observable toxicity in any of the dosages tested, as did 100% PLGA formulations.

CONCLUSION

Due to strong adjuvancy and increased delivery capacity afforded by the addition of PBAE into microparticle formulations, it is desirable to investigate these formulations further in antigen specific models. Formulations containing 25% PBAE seem to have the strongest adjuvancy and transfection efficiency, however stronger toxicity is associated with these particles. Although to a lesser extent, 15% PBAE formulations also exhibit these desirable genetic vaccine properties along with the same pH buffering effect, but without the inherent toxicity of 25% PBAE. Furthermore, our previous vaccination data suggests that 15% PBAE is just as effective as 25% PBAE as a DNA vaccine delivery vector in vivo (Little et al. Poly-B amino ester-containing microparticles enhance the activity of nonviral genetic vaccines. *Proceedings of the National Academy of Sciences of the United States of America* 101: 9534-9539 (2004); incorporated herein by reference). Therefore, we conclude that 15% PBAE is the most logical candidate as a delivery system for disease specific genetic vaccine models.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A particle suitable for drug delivery to an animal comprising
    at least one agent to be delivered;
    a pH triggering agent wherein the pH triggering agent is a poly(beta-amino ester); and
    a synthetic polymer;
    wherein the particle releases the agent to be delivered at pH less than 7 by the dissolution or disruption of the particle; and
    wherein the agent, the pH triggering agent, and the synthetic polymer are distributed throughout the particle.

2. The particle of claim 1 wherein the particle is suitable for delivery to antigen presenting cells.

3. The particle of claim 1 wherein the particle is immunostimulatory.

4. The particle of claim 1 wherein the particle is suitable for intracellular delivery to antigen presenting cells.

5. The particle of claim 1 wherein the particle is suitable for delivery of an antigen for vaccination.

6. The particle of claim 1 wherein the particle is suitable for delivery of DNA vaccines.

7. The particle of claim 1 wherein the particle is suitable for delivery of enzymes.

8. The particle of claim 1 wherein the agent to be delivered is released at pH less than 6.

9. The particle of claim 1 wherein the agent to be delivered is released at pH less than 6.5.

10. The particle of claim 1 wherein the agent to be delivered is released at pH less than 5.

11. The particle of claim 1, wherein the polymer is selected from the group consisting of polyesters, polyanhydrides, polyethers, polyamides, polyacrylates, polymethacrylates, polycarbamates, polycarbonates, polyureas, polyamines, poly(beta-amino esters), and polythioethers.

12. The particle of claim 1, wherein the polymer does not include proteins, lipids, and polysaccharides.

13. The particle of claim 1, wherein the particle does not include polyacrylates or polymethacrylates.

14. The particle of claim 1, wherein the polymer is biodegradable and biocompatible.

15. The particle of claim 1, wherein the largest diameter of the particle is less than 10 micrometers.

16. The particle of claim 1, wherein the largest diameter of the particle ranges from 1 micrometer to 10 micrometers.

17. The particle of claim 1, wherein the particle further comprises an adjuvant.

18. The particle of claim 1, wherein the particle further comprises a targeting agent.

19. A pharmaceutical composition comprising the particles of claim 1, and a pharmaceutically acceptable excipient.

20. The particle of claim, wherein the weight percent of the pH triggering agent is between 1% and 25%.

21. The particle of claim 1, wherein the weight percent of the pH triggering agent is between 1% and 5%.

22. The particle of claim 1, wherein the weight percent of the pH triggering agent is between 10% and approximately 30%.

23. The particle of claim 1, wherein the weight percent of the pH triggering agent is between 15% and approximately 25%.

24. The particle of claim 1, wherein the weight percent of the pH triggering agent is approximately 15%.

* * * * *

UNITED STATES PATENT AND TRADEMARK OFFICE
CERTIFICATE OF CORRECTION

| | | |
|---|---|---|
| PATENT NO. | : 7,943,179 B2 | Page 1 of 1 |
| APPLICATION NO. | : 11/002542 | |
| DATED | : May 17, 2011 | |
| INVENTOR(S) | : Steven R. Little et al. | |

It is certified that error appears in the above-identified patent and that said Letters Patent is hereby corrected as shown below:

In claim 1 at column 115, after line 57, please insert the following line:

--wherein the weight percent of the pH triggering agent is between 1% and 30%;--

In claim 20 at column 116, line 44, please amend claim 20 to depend from claim 1 as follows:

20. The particle of claim 1, wherein the weight percent of the pH triggering agent is between 1% and 25%.

Signed and Sealed this
Fifth Day of July, 2011

David J. Kappos
*Director of the United States Patent and Trademark Office*